United States Patent
Frudakis et al.

(10) Patent No.: US 6,586,570 B1
(45) Date of Patent: Jul. 1, 2003

(54) COMPOSITIONS AND METHODS FOR THE TREATMENT AND DIAGNOSIS OF BREAST CANCER

(75) Inventors: Tony N. Frudakis, Sarasota, FL (US); Steven G. Reed, Bellevue, WA (US); John M. Smith, Everett, WA (US); Lynda Misher, Seattle, WA (US)

(73) Assignee: Corixa Corporation, Seattle, WA (US)

(*) Notice: Subject to any disclaimer, the term of this patent is extended or adjusted under 35 U.S.C. 154(b) by 0 days.

(21) Appl. No.: 09/289,198

(22) Filed: Apr. 9, 1999

Related U.S. Application Data

(63) Continuation-in-part of application No. 09/062,451, filed on Apr. 17, 1998, now Pat. No. 6,344,550, which is a continuation-in-part of application No. 08/991,789, filed on Dec. 11, 1997, now Pat. No. 6,225,054, which is a continuation-in-part of application No. 08/838,762, filed on Apr. 9, 1997, now abandoned, which is a continuation-in-part of application No. PCT/US97/00485, filed on Jan. 10, 1997, which is a continuation-in-part of application No. 08/700,014, filed on Aug. 20, 1996, now abandoned, which is a continuation-in-part of application No. 08/585,392, filed on Jan. 11, 1996, now abandoned.

(51) Int. Cl.$^7$ ............................................... C07K 14/00
(52) U.S. Cl. ........................ 530/350; 536/23.1; 435/6; 435/7.1; 514/2
(58) Field of Search ..................... 530/350; 536/23.1; 435/6; 514/2

(56) References Cited

U.S. PATENT DOCUMENTS

| | | | |
|---|---|---|---|
| 5,231,012 A | 7/1993 | Mosmann et al. | 435/69.52 |
| 5,428,145 A | 6/1995 | Okamoto et al. | 536/23.72 |
| 5,516,650 A | 5/1996 | Foster et al. | 435/68.1 |
| 5,523,225 A | 6/1996 | Kraus | 435/240.1 |
| 5,585,270 A | 12/1996 | Grotendorst et al. | 435/252.3 |
| 5,811,535 A | 9/1998 | Adamou et al. | 536/23.5 |
| 5,872,237 A | 2/1999 | Feder et al. | 536/23.5 |
| 5,912,143 A * | 6/1999 | Bandman et al. | 435/69.1 |

FOREIGN PATENT DOCUMENTS

| | | |
|---|---|---|
| GB | 2 273 099 A | 6/1994 |
| WO | WO 91/02062 | 2/1991 |
| WO | WO 95/10777 | 4/1995 |
| WO | WO 95/19369 | 7/1995 |
| WO | WO 95/32311 | 11/1995 |
| WO | WO 96/38463 | 12/1996 |
| WO | WO 97/06256 | 2/1997 |
| WO | WO 97/25426 | 7/1997 |
| WO | WO 97/25431 | 7/1997 |
| WO | WO 98/45328 | 10/1998 |
| WO | WO 00/61753 | 10/2000 |

OTHER PUBLICATIONS

Burgess et al. J. Cell Biol. 11: 2129–2138, 1990.*
Gura. Science, 278:1041–1042, 1997.*
Jaris. Sci. Amer. 271:58–65, 1994.*
Curti Crit. Rev Oncol/Hematol. 14:29–39, 1993.*
Hartwell. Science, 278:1064–1068, 1997.*
Kazar. Mol & Cell Biol. 8:1247–1252, 1988.*
Tao. J. Immunol. 163(8):2595–2601, 1989.*
Gillies. Human Antibod & Hybridomas 1(1):47–54, 1990.*
Frudakis et al. GenBank Accession No. V68996, 1998.*
NCI–CGAP. GenBank Accession No. AI804733, 1997.*
Johnstone et al. Furan Chemistry in Bacteria, 2nd ed. Blackwell Scientific Pub., Oxford, p. 49–50, 1987.*
Boon et al. Adv Cancer Res. 58:177–210, 1992.*
Drexler et al. Leukemia & Lymphoma, 9:1–25, 1993.*
Embleton et al. Immunol. Ser. 23:181–207, 1984.*
Hsu–Tu: Tissue Cult Methods & Application, Kruse & Patterson, Eds, Academic Press, N.Y., abstract, p. 764.*
Freshney. Culture of Animal Cells, A Manual of Basic Tech., Alan R. Liss, Inc, N.Y, p. 4, 1983.*
Dermer, Bio/Tech. 12:320, 1994.*
Charnock–Jones et al., "Extension of incomplete cDNAs (ESTs) by biotin/streptavidin–mediated walking using polymerase chain reaction," *J. Biotechno.* 35:205–215, Jun. 1994.
Venter et al., "Genome sequence analysis: Scientific objectives and practical strategies," *Trends Biotechnol.* 10(1–2):8–11, Jan. 1992.
Ahn and Kunkel, "The structural and functional diversity of dystrophin," *Nat. Genet.* 3(4):283–291, Apr. 1993.
Cawthon et al., "cDNA sequence and genomic structure of EV12B, a gene lying within an intron of the neurofibromatosis type 1 gene," *Genomics* 9(3):446–460, Mar. 1991.
Harris et al., "Polycystic kidney disease. 1: Identification and analysis of the primary defect," *J. Am. Soc. Nephrol.* 6(4):1125–1133, Oct. 1995.
Adams et al., Genbank Accession No. Q60347, 1993.
Adams et al., Genbank Accession No. Q61250, 1993.
Anderson et al., "Sequence and organization of the human mitochondrial genome," *Nature* 290:457–465, 1981.
Bauer et al., "Identification of differentially expressed mRNA species by an improved display technique (DDRT–PCR)," *Nucleic Acids Research* 21(18):4272–4280, 1993.

(List continued on next page.)

*Primary Examiner*—Susan Ungar
*Assistant Examiner*—Minh Tam Davis
(74) *Attorney, Agent, or Firm*—Seed Intellectual Property Law Group PLLC

(57) ABSTRACT

Compositions and methods for the detection and therapy of breast cancer are disclosed. The compounds provided include nucleotide sequences that are preferentially expressed in breast tumor tissue, as well as polypeptides encoded by such nucleotide sequences. Vaccines and pharmaceutical compositions comprising such compounds are also provided and may be used, for example, for the prevention and treatment of breast cancer. The polypeptides may also be used for the production of antibodies, which are useful for diagnosing and monitoring the progression of breast cancer in a patient.

2 Claims, 19 Drawing Sheets

OTHER PUBLICATIONS

Bernard et al., "Cloning and Sequencing of Pro–α1(XI) Collagen cDNA Demonstrates That Type XI Belongs to the Fibrillar Class of Collagens and Reveals That the Expression of the Gene Is Not Restricted to Cartilagenous Tissue," *J. Biol. Chem.* 263(32):17159–17166, 1988.

Bratthauer et al., "Expression of LINE–1 Retrotransposons in Human Breast Cancer," *Cancer* 73:2333–2336, 1994.

Byrne et al., "A Screening Method to Identify Genes Commonly Overexpressed in Carcinomas and the Identification of a Novel Complementary DNA Sequence," *Cancer Research* 55:2869–2903, 1995.

Chai et al., Genbank Accession No. U03644, 1994.

Chen and Sager, "Differential Expression of Human Tissue Factor in Normal Mammary Epithelial Cells and in Carcinomas," *Molecular Medicine* 1(2):153–160, 1995.

Hillier et al., Genbank Accession No. R60426, 1995.

Hillier et al., Genbank Accession No. T83348, 1995.

Hillier et al., Genbank Accession No. R35308, 1995.

Keydar et al., "Properties of retrovirus–like particles produced by a human breast carcinoma cell line: Immunobiological relationship with mouse mammary tumor virus proteins," *Proc. Natl. Acad. Sci. USA* 81:4188–92, 1984.

Leib–Mösch and Seifarth, "Evolution and Biological Significance of Human Retroelements," *Virus Genes* 11(2/3):133–145, 1996.

Leib–Mösch et al., "Endogenous Retroviral Elements in Human DNA," *Cancer Research* 50:5636s–5642s, 1994.

Leib–Mösch et al., "Genomic Distribution and Transcription of Solitary HERV–K LTRs," *Genomics* 18:261–269, 1993.

Liang et al., "Differential Display of Eukaryotic Messenger RNA by Means of the Polymerase Chain Reaction," *Science* 257:967–971, 1992.

Matsubara et al., Genbank Accession No. T24124, 1995.

Wang et al., "Detection of Mammary Tumor Virus ENV Gene–like Sequences in Human Breast Cancer," *Cancer Research* 55:5173–5179, 1995.

Watson and Fleming, "Isolation of Differentially Expressed Sequence Tags from Human Breast Cancer," *Cancer Research* 54(17):4598–4602, 1994.

Werner et al., "S71 Is a Phylogenetically Distinct Human Endogenous Retroviral Element with Structural and Sequence Homology to Simian Sarcoma Virus (SSV)," *Virology* 174:225–238, 1990.

Yoshioka et al., "Pro–α1(XI) Collagen. Structure Of The Amino–Terminal Propeptide And Expression Of The Gene In Tumor Cell Lines," *J. Biol. Chem.* 265(11):6423–6426, 1990.

Critical Snyergy: The Biotechnology Industry and Intellectual Property Protection, Presentation of the Intellectual Property Committee of the Biotechnology Industry Organization at the Oct. 17, 1994, Hearing of the U.S. Patent and Trademark Office, San Diego, CA, published by the Biotechnology Industry Organization, Washington, D.C., pp. 75, 100–107.

* cited by examiner

NUCLEOTIDE SEQUENCE OF THE REPRESENTATIVE
BREAST-TUMOR SPECIFIC cDNA B18Ag1

```
TTA GAG ACC CAA TTG GGA CCT AAT TGG GAC CCA AAT TTC TCA AGT GGA    48
Leu Glu Thr Gln Leu Gly Pro Asn Trp Asp Pro Asn Phe Ser Ser Gly
 1           5                   10                  15

GGG AGA ACT TTT GAC GAT TTC CAC CGG TAT CTC CTC GTG GGT ATT CAG    96
Gly Arg Thr Phe Asp Asp Phe His Arg Tyr Leu Leu Val Gly Ile Gln
            20                  25                  30

GGA GCT GCC CAG AAA CCT ATA AAC TTG TCT AAG GCG ATT GAA GTC GTC   144
Gly Ala Ala Gln Lys Pro Ile Asn Leu Ser Lys Ala Ile Glu Val Val
        35                  40                  45

CAG GGG CAT GAT GAG TCA CCA GGA GTG TTT TTA GAG CAC CTC CAG GAG   192
Gln Gly His Asp Glu Ser Pro Gly Val Phe Leu Glu His Leu Gln Glu
    50                  55                  60

GCT TAT CGG ATT TAC ACC CCT TTT GAC CTG GCA GCC CCC GAA AAT AGC   240
Ala Tyr Arg Ile Tyr Thr Pro Phe Asp Leu Ala Ala Pro Glu Asn Ser
65                  70                  75                  80

CAT GCT CTT AAT TTG GCA TTT GTG GCT CAG GCA GCC CCA GAT AGT AAA   288
His Ala Leu Asn Leu Ala Phe Val Ala Gln Ala Ala Pro Asp Ser Lys
            85                  90                  95

AGG AAA CTC CAA AAA CTA GAG GGA TTT TGC TGG AAT GAA TAC CAG TCA   336
Arg Lys Leu Gln Lys Leu Glu Gly Phe Cys Trp Asn Glu Tyr Gln Ser
            100                 105                 110

GCT TTT AGA GAT AGC CTA AAA GGT TTT                               363
Ala Phe Arg Asp Ser Leu Lys Gly Phe
        115                 120
```

*Fig. 6*

NUCLEOTIDE SEQUENCE OF THE REPRESENTATIVE
BREAST-TUMOR SPECIFIC cDNA B17Ag1

```
GC TGGGCACAGT GGCTCATACC TGTAATCCTG ACCGTTCAG AGGCTCAGGT    60

CG CTTGAGCCCA AGATTTCAAG ACTAGTCTGG GTAACATAGT GAGACCCTAT   120

AA AAATAAAAAA ATGAGCCTGG TGTAGTGGCA CACACCAGCT GAGGAGGGAG   180

CT AGGAGA                                                  196
```

*Fig. 7*

NUCLEOTIDE SEQUENCE OF THE REPRESENTATIVE
BREAST-TUMOR SPECIFIC cDNA B17Ag2

GC TTGGGGGCTC TGACTAGAAA TTCAAGGAAC CTGGGATTCA AGTCCAACTG    60

AC TTACACTGTG GNCTCCAATA AACTGCTTCT TTCCTATTCC CTCTCTATTA   120

AA GGAAAACGAT GTCTGTGTAT AGCCAAGTCA GNTATCCTAA AAGGAGATAC   180

AT TAAATATCAG AATGTAAAAC CTGGGAACCA GGTTCCCAGC CTGGGATTAA   240

CA AGAAGACTGA ACAGTACTAC TGTGAAAAGC CCGAAGNGGC AATATGTTCA   300

TT GAAGGATGGC TGGGAGAATG AATGCTCTGT CCCCCAGTCC CAAGCTCACT   360

CT CCTTTATAGC CTAGGAGA                                     388

*Fig. 8*

NUCLEOTIDE SEQUENCE OF THE REPRESENTATIVE
BREAST-TUMOR SPECIFIC cDNA B13Ag2a

GC CTATAATCAT GTTTCTCATT ATTTTCACAT TTTATTAACC AATTTCTGTT    60

AA AATATGAGGG AAATATATGA AACAGGGAGG CAATGTTCAG ATAATTGATC   120

TG ATTTCTACAT CAGATGCTCT TTCCTTTCCT GTTTATTTCC TTTTTATTTC   180

GG TCGAATGTAA TAGCTTTGTT TCAAGAGAGA GTTTTGGCAG TTTCTGTAGC   240

CT GCTCATGTCT CCAGGCATCT ATTTGCACTT TAGGAGGTGT CGTGGGAGAC   300

CT ATTTTTTCCA TATTTGGGCA ACTACTA                           337

*Fig. 9*

NUCLEOTIDE SEQUENCE OF THE REPRESENTATIVE BREAST-TUMOR SPECIFIC cDNA B13Ag1b

```
GC CATACAGTGC CTTTCCATTT ATTTAACCCC CACCTGAACG GCATAAACTG    60

GC TGGTGTTTTT TACTGTAAAC AATAAGGAGA CTTTGCTCTT CATTTAAACC   120

AT TTCATATTTT ACGCTCGAGG GTTTTTACCG GTTCCTTTTT ACACTCCTTA   180

TT TAAGTCGTTT GGAACAAGAT ATTTTTTCTT TCCTGGCAGC TTTTAACATT   240

TT TGTGTCTGGG GGACTGCTGG TCACTGTTTC TCACAGTTGC AAATCAAGGC   300

CC AAGAAAAAAA AATTTTTTTG TTTTATTTGA AACTGGACCG GATAAACGGT   360

CG GCTGCTGTAT ATAGTTTTAA ATGGTTTATT GCACCTCCTT AAGTTGCACT   420

GG GGGGNTTTTG NATAGAAAGT NTTTANTCAC ANAGTCACAG GGACTTTTNT   480

NA CTGAGCTAAA AAGGGCTGNT TTTCGGGTGG GGGCAGATGA AGGCTCACAG   540

TC TCTTAGAGGG GGGAACTNCT A                                  571
```

*Fig. 10*

NUCLEOTIDE SEQUENCE OF THE REPRESENTATIVE BREAST-TUMOR SPECIFIC cDNA B13Ag1a

```
TA ATAACTTAAA TATATTTTGA TCACCCACTG GGGTGATAAG ACAATAGATA    60

TT TCCAAAAAGC ATAAAACCAA AGTATCATAC CAAACCAAAT TCATACTGCT   120

CC GCACTGAAAC TTCACCTTCT AACTGTCTAC CTAACCAAAT TCTACCCTTC   180

GG TGCGTGCTCA CTACTCTTTT TTTTTTTTT TTTNTTTGG AGATGGAGTC     240

CA GCCCAGGGGT GGAGTACAAT GGCACAACCT CAGCTCACTG NAACCTCCGC   300

TT CATGAGATTC TCCTGNTTCA GCCTTCCCAG TAGCTGGGAC TACAGGTGTG   360

TG CCTGGNTAAT CTTTTTTNGT TTTNGGGTAG AGATGGGGGT TTTACATGTT   420

TG GTNTCGAACT CCTGACCTCA AGTGATCCAC CCACCTCAGG CTCCCAAAGT   480

TA CAGACATGAG CCACTGNGCC CAGNCCTGGT GCATGCTCAC TTCTCTAGGC   540
```

*Fig. 11*

NUCLEOTIDE SEQUENCE OF THE REPRESENTATIVE BREAST-TUMOR SPECIFIC cDNA B11Ag1

```
TG CACATGCAGA ATATTCTATC GGTACTTCAG CTATTACTCA TTTTGATGGC    60

AG CCTATCCTCA AGATGAGTAT TTAGAAAGAA TTGATTTAGC GATAGACCAA   120

GC ACTCTGACTA CACGAAATTG TTCAGATGTG ATGGATTTAT GACAGTTGAT   180

GA GATTATTAAG TGATTATTTT AAAGGGAATC CATTAATTCC AGAATATCTT   240

TC AAGATGATAT AGAAATAGAA CAGAAAGAGA CTACAAATGA AGATGTATCA   300

TA TTGAAGAGCC TATAGTAGAA AATGAATTAG CTGCATTTAT TAGCCTTACA   360

TT TTCCTGATGA ATCTTATATT CAGCCATCGA CATAGCATTA CCTGATGGGC   420

GA ATAATAGAAA CTGGGTGCGG GGCTATTGAT GAATTCATCC NCAGTAAATT   480

AC AAAATATAAC TCGATTGCAT TTGGATGATG GAATACTAAA TCTGGCAAAA   540

GG AGCTACTAGT AACCTCTCTT TTTGAGATGC AAAATTTTCT TTAGGGTTT    600

CT ACTTTACGGA TATTGGAGCA TAACGGGA                           638
```

*Fig. 12*

NUCLEOTIDE SEQUENCE OF THE REPRESENTATIVE
BREAST-TUMOR SPECIFIC cDNA B3CA3c

```
ACTGATGGAT GTCGCCGGAG GCGAGGGGCC TTATCTGATG CTCGGCTGCC TGTTCGTGAT    60
GTGCGCGGCG ATTGGGCTGT TTATCTCAAA CACCGCCACG GCGGTGCTGA TGGCGCCTAT   120
TGCCTTAGCG GCGGCGAAGT CAATGGGCGT CTCACCCTAT CCTTTTGCCA TGGTGGTGGC   180
GATGGCGGCT TCGGCGGCGT TTATGACCCC GGTCTCCTCG CCGGTTAACA CCCTGGTGCT   240
TGGCCCTGGC AAGTACTCAT TTAGCGATTT TGTCAAAATA GGCGTG                  286
```

*Fig. 13*

NUCLEOTIDE SEQUENCE OF THE REPRESENTATIVE
BREAST-TUMOR SPECIFIC cDNA B9CG1

```
AG CAGCCCCTTC TTCTCAATTT CATCTGTCAC TACCCTGGTG TAGTATCTCA     60

CA TTTTTATAGC CTCCTCCCTG GTCTGTCTTT TGATTTTCCT GCCTGTAATC    120

AC ATAACTGCAA GTAAACATTT CTAAAGTGTG GTTATGCTCA TGTCACTCCT    180

AA ATAGTTTCCA TTACCGTCTT AATAAAATTC GGATTTGTTC TTTNCTATTN    240

CA CCTATGACCG AA                                             262
```

*Fig. 14*

NUCLEOTIDE SEQUENCE OF THE REPRESENTATIVE
BREAST-TUMOR SPECIFIC cDNA B9CG3

| | |
|---|---|
| AG CAAAGCCAGT GGTTTGAGCT CTCTACTGTG TAAACTCCTA AACCAAGGCC | 60 |
| TA AATGGTGGCA GGATTTTTAT TATAAACATG TACCCATGCA AATTTCCTAT | 120 |
| GA TATATTCTTC TACATTTAAA CAATAAAAAT AATCTATTTT TAAAAGCCTA | 180 |
| AG TTAGGTAAGA GTGTTTAATG AGAGGGTATA AGGTATAAAT CACCAGTCAA | 240 |
| TG CCTATGACCG A | 261 |

*Fig. 15*

NUCLEOTIDE SEQUENCE OF THE REPRESENTATIVE
BREAST-TUMOR SPECIFIC cDNA B2CA2

| | |
|---|---|
| GG GCATGGACGC AGACGCCTGA CGTTTGGCTG AAAATCTTTC ATTGATTCGT | 60 |
| AT AGGAAAATTC CCAAAGAGGG AATGTCCTGT TGCTCGCCAG TTTTTNTGTT | 120 |
| GG ANAAGGCAAN GAGCTCTTCA GACTATTGGN ATTNTCGTTC GGTCTTCTGC | 180 |
| CG NCTTGCNANG ATCTTCAT | 208 |

*Fig. 16*

NUCLEOTIDE SEQUENCE OF THE REPRESENTATIVE
BREAST-TUMOR SPECIFIC cDNA B3CA1

GG GCATGGACGC AGACGCCTGA CGTTTGGCTG AAAATCTTTC ATTGATTCGT  60

AT AGGAAAATTC CCAAAGAGGG AATGTCCTGT TGCTCGCCAG TTTTTNTGTT  120

GG ANAAGGCAAN GAGCTCTTCA GACTATTGGN ATTNTCGTTC GGTCTTCTGC  180

CG NCTTGCNANG ATCTTCAT                              208

*Fig. 17*

NUCLEOTIDE SEQUENCE OF THE REPRESENTATIVE
BREAST-TUMOR SPECIFIC cDNA B3CA2

GG GCATGGACGC AGACGCCTGA CGTTTGGCTG AAAATCTTTC ATTGATTCGT  60

AT AGGAAAATTC CCAAAGAGGG AATGTCCTGT TGCTCGCCAG TTTTTNTGTT  120

GG ANAAGGCAAN GAGCTCTTCA GACTATTGGN ATTNTCGTTC GGTCTTCTGC  180

CG NCTTGCNANG ATCTTCAT                              208

*Fig. 18*

NUCLEOTIDE SEQUENCE OF THE REPRESENTATIVE
BREAST-TUMOR SPECIFIC cDNA B3CA3

AG GGAGCAAGGA GAAGGCATGG AGAGGCTCAN GCTGGTCCTG GCCTACGACT  60

CT GTCGCCGGGG ATGGTGGAGA ACTGAAGCGG GACCTCCTCG AGGTCCTCCG  120

TC NCCGTCCAGG AGGAGGGTCT TTCCGTGGTC TNGGAGGAGC GGGGGGAGAA  180

TC ATGGTCNACA TCCC                              204

*Fig. 19*

NUCLEOTIDE SEQUENCE OF THE REPRESENTATIVE
BREAST-TUMOR SPECIFIC cDNA B4CA1

```
TC AGGAGCGGGT AGAGTGGCAC CATTGAGGGG ATATTCAAAA ATATTATTTT     60

TG ATAGTTGCTG AGTTTTTCTT TGACCCATGA GTTATATTGG AGTTTATTTT    120

CC AATCGCATGG ACATGTTAGA CTTATTTTCT GTTAATGATT NCTATTTTTA    180

GA TTTGAGAAAT TGGTTNTTAT TATATCAATT TTTGGTATTT GTTGAGTTTG    240

GC TTAGTATGTG ACCA                                           264
```

*Fig. 20*

COMPOSITIONS AND METHODS FOR THE TREATMENT AND DIAGNOSIS OF BREAST CANCER

CROSS REFERENCE TO RELATED APPLICATIONS

This application is a continuation-in-part of U.S. patent application Ser. No. 09/062,451, filed Apr. 17, 1998, patented, now U.S. Pat. No. 6,344,550, which is a continuation in part of U.S. patent application Ser. No. 08/991,789, filed Dec. 11, 1997, patented, now U.S. Pat. No. 6,225,054, which is a continuation-in-part of U.S. patent application Ser. No. 08/838,762, filed Apr. 9, 1997 now abandoned, which claims priority as a continuation-in-part from International Patent Application No. PCT/US97/00485, filed Jan. 10, 1997, and is a continuation-in-part of U.S. patent application Ser. No. 08/700,014, filed Aug. 20, 1996, now abandoned, which is a continuation-in-part of U.S. patent application Ser. No. 08/585,392, filed Jan. 11, 1996 now abandoned.

TECHNICAL FIELD

The present invention relates generally to the detection and therapy of breast cancer. The invention is more specifically related to nucleotide sequences that are preferentially expressed in breast tumor tissue and to polypeptides encoded by such nucleotide sequences. The nucleotide sequences and polypeptides may be used in vaccines and pharmaceutical compositions for the prevention and treatment of breast cancer. The polypeptides may also be used for the production of compounds, such as antibodies, useful for diagnosing and monitoring the progression of breast cancer in a patient.

BACKGROUND OF THE INVENTION

Breast cancer is a significant health problem for women in the United States and throughout the world. Although advances have been made in detection and treatment of the disease, breast cancer remains the second leading cause of cancer-related deaths in women, affecting more than 180,000 women in the United States each year. For women in North America, the life-time odds of getting breast cancer are now one in eight.

No vaccine or other universally successful method for the prevention or treatment of breast cancer is currently available. Management of the disease currently relies on a combination of early diagnosis (through routine breast screening procedures) and aggressive treatment, which may include one or more of a variety of treatments such as surgery, radiotherapy, chemotherapy and hormone therapy. The course of treatment for a particular breast cancer is often selected based on a variety of prognostic parameters, including an analysis of specific tumor markers. See, e.g., Porter-Jordan and Lippman, *Breast Cancer* 8:73–100 (1994). However, the use of established markers often leads to a result that is difficult to interpret, and the high mortality observed in breast cancer patients indicates that improvements are needed in the treatment, diagnosis and prevention of the disease.

Accordingly, there is a need in the art for improved methods for therapy and diagnosis of breast cancer. The present invention fulfills these needs and further provides other related advantages.

SUMMARY OF THE INVENTION

Briefly stated, the subject invention provides compositions and methods for the diagnosis and therapy of breast cancer. In one aspect, isolated polynucleotides are provided, comprising (a) a nucleotide sequence preferentially expressed in breast cancer tissue, relative to normal tissue; (b) a variant of such a sequence, as defined below; or (c) a nucleotide sequence encoding an epitope of a polypeptide encoded by at least one of the above sequences. In one embodiment, the isolated polynucleotide comprises a human endogenous retroviral sequence recited in SEQ ID NO:1. In other embodiments, the isolated polynucleotide comprises a sequence recited in any one of SEQ ID NO: 3–26, 28–77, 142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284, 288, 291–298, 301–303 and 307.

In related embodiments, the isolated polynucleotide encodes an epitope of a polypeptide, wherein the polypeptide is encoded by a nucleotide sequence that: (a) hybridizes to a sequence recited in any one of SEQ ID NO: 1, 3–26, 28–77, 142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284, 288, 291–298, 301–303 and 307 under stringent conditions; and (b) is at least 80% identical to a sequence recited in any one of SEQ ID NO: 1, 3–26, 28–77, 142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284, 288, 291–298, 301–303 and 307.

In another embodiment, the present invention provides an isolated polynucleotide encoding an epitope of a polypeptide, the polypeptide being encoded by: (a) a nucleotide sequence transcribed from the sequence of SEQ ID NO: 141; or (b) a variant of said nucleotide sequence that contains one or more nucleotide substitutions deletions, insertions and/or modifications at no more than 20% of the nucleotide positions, such that the antigenic and/or immunogenic properties of the polypeptide encoded by the nucleotide sequence are retained. Isolated DNA and RNA molecules comprising a nucleotide sequence complementary to a polynucleotide as described above are also provided.

In related aspects, the present invention provides recombinant expression vectors comprising a polynucleotide as described above and host cells transformed or transfected with such expression vectors.

In further aspects, polypeptides comprising an amino acid sequence encoded by a polynucleotide as described above, and monoclonal antibodies that bind to such polypeptides are provided. In certain embodiments, the inventive polypeptides comprise an amino acid sequence selected from the group consisting of SEQ ID NO: 299, 200 and 304–306, and variants thereof as defined below.

In yet another aspect, methods are provided for determining the presence of breast cancer in a patient. In one embodiment, the method comprises detecting, within a biological sample, a polypeptide as described above. In another embodiment, the method comprises detecting, within a biological sample, an RNA molecule encoding a polypeptide as described above. In yet another embodiment, the method comprises (a) intradermally injecting a patient with a polypeptide as described above; and (b) detecting an immune response on the patient's skin and therefrom detecting the presence of breast cancer in the patient. In further embodiments, the present invention provides methods for determining the presence of breast cancer in a patient as described above wherein the polypeptide is encoded by a nucleotide sequence selected from the group consisting of SEQ ID NO: 78–86, 144, 145, 153, 167, 177, 193, 199, 205, 208, 215, 217, 220, 241, 242, 246, 248, 249, 252, 256, 267, 270, 274, 277, 279, 282, 283, 285–287, 289, 290 and sequences that hybridize thereto under stringent conditions.

In a related aspect, diagnostic kits useful in the determination of breast cancer are provided. The diagnostic kits generally comprise either one or more monoclonal antibodies as described above, or one or more monoclonal antibodies that bind to a polypeptide encoded by a nucleotide sequence selected from the group consisting of sequences provided in SEQ ID NO: 78–86, 144, 145, 153, 167, 177, 193, 199, 205, 208, 215, 217, 220, 241, 242 and 246, 248, 249, 252, 256, 267, 270, 274, 277, 279, 282, 283, 285–287, 289, 290 and a detection reagent.

Diagnostic kits are also provided that comprise a first polymerase chain reaction primer and a second polymerase chain reaction primer, at least one of the primers being specific for a polynucleotide described herein. In one embodiment, at least one of the primers comprises at least about 10 contiguous nucleotides of a polynucleotide as described above, or a polynucleotide encoding a polypeptide encoded by a sequence selected from the group consisting of SEQ ID NO: 78–86, 144, 145, 153, 167, 177, 193, 199, 205, 208, 215, 217, 220, 241, 242 246, 248, 249, 252, 256, 267, 270, 274, 277, 279, 282, 283, 285–287, 289 and 290.

Within another related aspect, the diagnostic kit comprises at least one oligonucleotide probe, the probe being specific for a polynucleotide described herein. In one embodiment, the probe comprises at least about 15 contiguous nucleotides of a polynucleotide as described above, or a polynucleotide selected from the group consisting of SEQ ID NO: 78–86, 144, 145, 153, 167, 177, 193, 199, 205, 208, 215, 217, 220, 241, 242 246, 248, 249, 252, 256, 267, 270, 274, 277, 279, 282, 283, 285–287, 289 and 290.

In another related aspect, the present invention provides methods for monitoring the progression of breast cancer in a patient. In one embodiment, the method comprises: (a) detecting an amount, in a biological sample, of a polypeptide as described above at a first point in time; (b) repeating step (a) at a subsequent point in time; and (c) comparing the amounts of polypeptide detected in steps (a) and (b), and therefrom monitoring the progression of breast cancer in the patient. In another embodiment, the method comprises (a) detecting an amount, within a biological sample, of an RNA molecule encoding a polypeptide as described above at a first point in time; (b) repeating step (a) at a subsequent point in time; and (c) comparing the amounts of RNA molecules detected in steps (a) and (b), and therefrom monitoring the progression of breast cancer in the patient. In yet other embodiments, the present invention provides methods for monitoring the progression of breast cancer in a patient as described above wherein the polypeptide is encoded by a nucleotide sequence selected from the group consisting of SEQ ID NO: 78–86, 144, 145, 153, 167, 177, 193, 199, 205, 208, 215, 217, 220, 241, 242, 246, 248, 249, 252, 256, 267, 270, 274, 277, 279, 282, 283, 285–287, 289, 290 and sequences that hybridize thereto under stringent conditions.

In still other aspects, pharmaceutical compositions, which comprise a polypeptide as described above in combination with a physiologically acceptable carrier, and vaccines, which comprise a polypeptide as described above in combination with an immune response enhancer or adjuvant, are provided. In yet other aspects, the present invention provides pharmaceutical compositions and vaccines comprising a polypeptide encoded by a nucleotide sequence selected from the group consisting of SEQ ID NO: 78–86, 144, 145, 153, 167, 177, 193, 199, 205, 208, 215, 217, 220, 241, 242 and 246, 248, 249, 252, 256, 267, 270, 274, 277, 279, 282, 283, 285–287, 289, 290 and sequences that hybridize thereto under stringent conditions.

In related aspects, the present invention provides methods for inhibiting the development of breast cancer in a patient, comprising administering to a patient a pharmaceutical composition or vaccine as described above.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 6 shows the nucleotide sequence of the representative breast tumor-specific cDNA B18Ag1 (SEQ ID NO: 1).

FIG. 7 shows the nucleotide sequence of the representative breast tumor-specific cDNA B17Ag1 (SEQ ID NO: 11).

FIG. 8 shows the nucleotide sequence of the representative breast tumor-specific cDNA B17Ag2 (SEQ ID NO: 12).

FIG. 9 shows the nucleotide sequence of the representative breast tumor-specific cDNA B13Ag2a (SEQ ID NO: 13).

FIG. 10 shows the nucleotide sequence of the representative breast tumor-specific cDNA B13Ag1b (SEQ ID NO: 14).

FIG. 11 shows the nucleotide sequence of the representative breast tumor-specific cDNA B13Ag1a (SEQ ID NO: 15).

FIG. 12 shows the nucleotide sequence of the representative breast tumor-specific cDNA B11Ag1 (SEQ ID NO: 16).

FIG. 13 shows the nucleotide sequence of the representative breast tumor-specific cDNA B3CA3c (SEQ ID NO: 17).

FIG. 14 shows the nucleotide sequence of the representative breast tumor-specific cDNA B9CG1 (SEQ ID NO: 18).

FIG. 15 shows the nucleotide sequence of the representative breast tumor-specific cDNA B9CG3 (SEQ ID NO: 19).

FIG. 16 shows the nucleotide sequence of the representative breast tumor-specific cDNA B2CA2 (SEQ ID NO: 20).

FIG. 17 shows the nucleotide sequence of the representative breast tumor-specific cDNA B3CA1 (SEQ ID NO: 21).

FIG. 18 shows the nucleotide sequence of the representative breast tumor-specific cDNA B3CA2 (SEQ ID NO: 22).

FIG. 19 shows the nucleotide sequence of the representative breast tumor-specific cDNA B3CA3 (SEQ ID NO: 23).

FIG. 20 shows the nucleotide sequence of the representative breast tumor-specific cDNA B4CA1 (SEQ ID NO: 24).

DETAILED DESCRIPTION OF THE INVENTION

Figure 1:
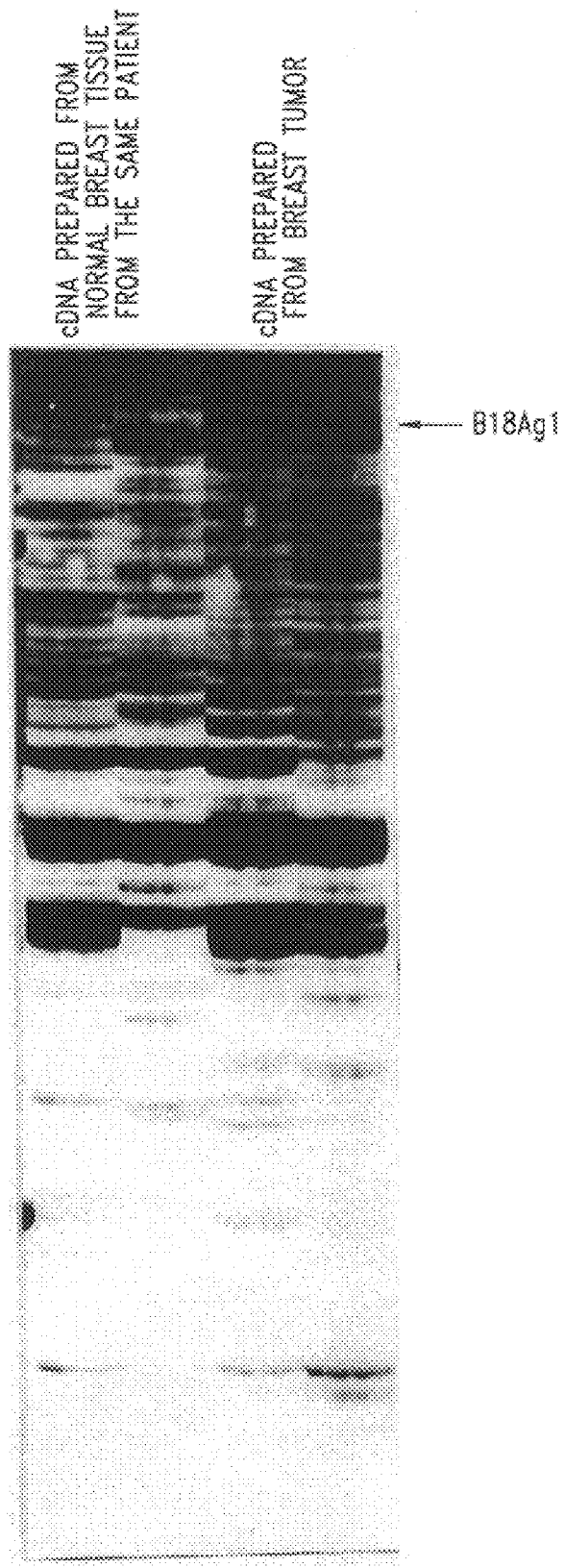
FIG. 1 shows the differential display PCR products, separated by gel electrophoresis, obtained from cDNA prepared from normal breast tissue (lanes 1 and 2) and from cDNA prepared from breast tumor tissue from the same patient (lanes 3 and 4). The arrow indicates the band corresponding to B18Ag1.

As noted above, the present invention is generally directed to compositions and methods for the diagnosis, monitoring and therapy of breast cancer. The compositions described herein include polypeptides, polynucleotides and antibodies. Polypeptides of the present invention generally comprise at least a portion of a protein that is expressed at a greater level in human breast tumor tissue than in normal breast tissue (i.e., the level of RNA encoding the polypeptide is at least 2-fold higher in tumor tissue). Such polypeptides are referred to herein as breast tumor-specific polypeptides, and cDNA molecules encoding such polypeptides are referred to as breast tumor-specific cDNAs. Polynucleotides of the subject invention generally comprise a DNA or RNA sequence that encodes all or a portion of a polypeptide as described above, or that is complementary to such a sequence. Antibodies are generally immune system proteins, or fragments thereof, that are capable of binding to a portion of a polypeptide as described above. Antibodies can be produced by cell culture techniques, including the generation of monoclonal antibodies as described herein, or via transfection of antibody genes into suitable bacterial or mammalian cell hosts, in order to allow for the production of recombinant antibodies.

Polypeptides within the scope of this invention include, but are not limited to, polypeptides (and epitopes thereof) encoded by a human endogenous retroviral sequence, such as the sequence designated B18Ag1 (FIG. 5 and SEQ ID NO:1). Also within the scope of the present invention are polypeptides encoded by other sequences within the retroviral genome containing B18Ag1 (SEQ ID NO: 141). Such sequences include, but are not limited to, the sequences recited in SEQ ID NO:3–SEQ ID NO:10. B18Ag1 has homology to the gag p30 gene of the endogenous human retroviral element S71, as described in Werner et al., *Virology* 174:225–238 (1990) and also shows homology to about thirty other retroviral gag genes. As discussed in more detail below, the present invention also includes a number of additional breast tumor-specific polypeptides, such as those encoded by the nucleotide sequences recited in SEQ ID NO: 11–26, 28–77, 142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284, 288, 291–298, 301–303 and 307.

As used herein, the term "polypeptide" encompasses amino acid chains of any length, including full length proteins containing the sequences recited herein. A polypeptide comprising an epitope of a protein containing a sequence as described herein may consist entirely of the epitope, or may contain additional sequences. The additional sequences may be derived from the native protein or may be heterologous, and such sequences may (but need not) possess immunogenic or antigenic properties.

An "epitope," as used herein is a portion of a polypeptide that is recognized (i.e., specifically bound) by a B-cell and/or T-cell surface antigen receptor. Epitopes may generally be identified using well known techniques, such as those summarized in Paul, *Fundamental Immunology*, 3rd ed., 243–247 (Raven Press, 1993) and references cited therein. Such techniques include screening polypeptides derived from the native polypeptide for the ability to react with antigen-specific antisera and/or T-cell lines or clones. An epitope of a polypeptide is a portion that reacts with such antisera and/or T-cells at a level that is similar to the reactivity of the full length polypeptide (e.g., in an ELISA and/or T-cell reactivity assay). Such screens may generally be performed using methods well known to those of ordinary skill in the art, such as those described in Harlow and Lane, *Antibodies: A Laboratory Manual*, Cold Spring Harbor Laboratory, 1988. B-cell and T-cell epitopes may also be predicted via computer analysis. Polypeptides comprising an epitope of a polypeptide that is preferentially expressed in a tumor tissue (with or without additional amino acid sequence) are within the scope of the present invention.

The term "polynucleotide(s)," as used herein, means a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a DNA molecule in a generally one-to-one manner. An mRNA molecule corresponds to an HnRNA and DNA molecule from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments.

The compositions and methods of the present invention also encompass variants of the above polypeptides and polynucleotides.

A polypeptide "variant," as used herein, is a polypeptide that differs from the recited polypeptide only in conservative substitutions and/or modifications, such that the antigenic properties of the polypeptide are retained. In a preferred embodiment, variant polypeptides differ from an identified sequence by substitution, deletion or addition of five amino acids or fewer. Such variants may generally be identified by modifying one of the above polypeptide sequences, and evaluating the antigenic properties of the modified polypeptide using, for example, the representative procedures described herein. Polypeptide variants preferably exhibit at least about 70%, more preferably at least about 90% and most preferably at least about 95% identity (determined as described below) to the identified polypeptides.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

A nucleotide "variant" is a sequence that differs from the recited nucleotide sequence in having one or more nucleotide deletions, substitutions or additions. Such modifications may be readily introduced using standard mutagenesis techniques, such as oligonucleotide-directed site-specific mutagenesis as taught, for example, by Adelman et al. (*DNA*, 2:183, 1983). Nucleotide variants may be naturally occurring allelic variants, or non-naturally occurring variants. Variant nucleotide sequences preferably exhibit at least about 70%, more preferably at least about 80% and most preferably at least about 90% identity (determined as described below) to the recited sequence.

The breast tumor antigens provided by the present invention include variants that are encoded by DNA sequences which are substantially homologous to one or more of the DNA sequences specifically recited herein. "Substantial homology," as used herein, refers to DNA sequences that are capable of hybridizing under moderately stringent conditions. Suitable moderately stringent conditions include prewashing in a solution of 5×SSC, 0.5% SDS, 1.0 mM EDTA (pH 8.0); hybridizing at 50° C.–65° C., 5×SSC, overnight or, in the event of cross-species homology, at 45° C. with 0.5×SSC; followed by washing twice at 65° C. for 20 minutes with each of 2×, 0.5× and 0.2×SSC containing 0.1% SDS. Such hybridizing DNA sequences are also within the scope of this invention, as are nucleotide sequences that, due to code degeneracy, encode an immunogenic polypeptide that is encoded by a hybridizing DNA sequence.

Two nucleotide or polypeptide sequences are said to be "identical" if the sequence of nucleotides or amino acid residues in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Resarch Foundaiton, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) Fast and sensitive multiple sequence alignments on a microcomputer *CABIOS* 5:151–153; Myers, E. W. and Muller W. (1988) Optimal alignments in linear space *CABIOS* 4:11–17; Robinson, E. D. (1971) *Comb. Theor* 11:105; Santou, N. Nes, M. (1987) The neighbor joining method. A new method for reconstructing phylogenetic trees *Mol. Biol. Evol.* 4:406–425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) Rapid similarity searches of nucleic acid and protein data banks *Proc. Natl. Acad. Sci. USA* 80:726–730.

Preferably, the "percentage of sequence identity" is determined by comparing two optimally aligned sequences over a window of comparison of at least 20 positions, wherein the portion of the polynucleotide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

In general, polynucleotides encoding all or a portion of the polypeptides described herein may be prepared using any of several techniques. For example, cDNA molecules encoding such polypeptides may be cloned on the basis of the breast tumor-specific expression of the corresponding mRNAs, using differential display PCR. This technique compares the amplified products from RNA template prepared from normal and breast tumor tissue. cDNA may be prepared by reverse transcription of RNA using a $(dT)_{12}AG$ primer. Following amplification of the cDNA using a random primer, a band corresponding to an amplified product specific to the tumor RNA may be cut out from a silver stained gel and subcloned into a suitable vector (e.g., the T-vector, Novagen, Madison, Wis.). Polynucleotides encoding all or a portion of the breast tumor-specific polypeptides disclosed herein may be amplified from cDNA prepared as described above using the random primers shown in SEQ ID NO.:87–125.

Alternatively, a polynucleotide encoding a polypeptide as described herein (or a portion thereof) may be amplified from human genomic DNA, or from breast tumor cDNA, via polymerase chain reaction. For this approach, B18Ag1 sequence-specific primers may be designed based on the sequence provided in SEQ ID NO:1, and may be purchased or synthesized. One suitable primer pair for amplification from breast tumor cDNA is (5'ATG GCT ATT TTC GGG GGC TGA CA) (SEQ ID NO:126) and (5'CCG GTA TCT CCT CGT GGG TAT T) (SEQ ID NO:127). An amplified portion of B18Ag1 may then be used to isolate the full length gene from a human genomic DNA library or from a breast tumor cDNA library, using well known techniques, such as those described in Sambrook et al., *Molecular Cloning: A Laboratory Manual*, Cold Spring Harbor Laboratories, Cold Spring Harbor, N.Y. (1989). Other sequences within the retroviral genome of which B18Ag1 is a part may be similarly prepared by screening human genomic libraries using B18Ag1-specific sequences as probes. Nucleotides translated into protein from the retroviral genome shown in SEQ ID NO: 141 may then be determined by cloning the corresponding cDNAs, predicting the open reading frames and cloning the appropriate cDNAs into a vector containing a viral promoter, such as T7. The resulting constructs can be employed in a translation reaction, using techniques known to those of skill in the art, to identify nucleotide sequences which result in expressed protein. Similarly, primers specific for the remaining breast tumor-specific polypeptides described herein may be designed based on the nucleotide sequences provided in SEQ ID NO:11–86, 142–298, 301–303 and 307.

Recombinant polypeptides encoded by the DNA sequences described above may be readily prepared from the DNA sequences. For example, supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

In general, any of a variety of expression vectors known to those of ordinary skill in the art may be employed to express recombinant polypeptides of this invention. Expression may be achieved in any appropriate host cell that has been transformed or transfected with an expression vector containing a polynucleotide that encodes a recombinant polypeptide. Suitable host cells include prokaryotes, yeast and higher eukaryotic cells. Preferably, the host cells employed are *E. coli*, yeast or a mammalian cell line such as COS or CHO.

Such techniques may also be used to prepare polypeptides comprising epitopes or variants of the native polypeptides. For example, variants of a native polypeptide may generally be prepared using standard mutagenesis techniques, such as oligonucleotide-directed site-specific mutagenesis, and sections of the DNA sequence may be removed to permit preparation of truncated polypeptides. Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146 (1963). Equipment for automated synthesis of polypeptides is commercially available from suppliers such as Perkin Elmer/Applied BioSystems Division, Foster City, Calif., and may be operated according to the manufacturer's instructions.

In specific embodiments, polypeptides of the present invention encompass amino acid sequences encoded by a polynucleotide having a sequence recited in any one of SEQ ID NO:1, 3–26, 28–77, 142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284, 288, 291–298, 301–303 and 307, and variants of such polypeptides. Polypeptides within the scope of the present invention also include polypeptides (and epitopes thereof) encoded by DNA sequences that hybridize to a sequence recited in any one of SEQ ID NO:1, 3–26, 28–77, 142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284, 288, 291–298, 301–303 and 307 under stringent conditions, wherein the DNA sequences are at least 80% identical in overall sequence to a recited sequence and wherein RNA corresponding to the nucleotide sequence is expressed at a greater level in human breast tumor tissue than in normal breast tissue. As used herein, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C. Polynucleotides according to the present invention include molecules that encode any of the above polypeptides.

In another aspect of the present invention, antibodies are provided. Such antibodies may be prepared by any of a variety of techniques known to those of ordinary skill in the art. See, e.g., Harlow and Lane, *Antibodies: A Laboratory Manual*, Cold Spring Harbor Laboratory, 1988. In one such technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511–519 (1976), and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Antibodies may be used, for example, in methods for detecting breast cancer in a patient. Such methods involve using an antibody to detect the presence or absence of a breast tumor-specific polypeptide as described herein in a suitable biological sample. As used herein, suitable biological samples include tumor or normal tissue biopsy, mastectomy, blood, lymph node, serum or urine samples, or other tissue, homogenate, or extract thereof obtained from a patient.

There are a variety of assay formats known to those of ordinary skill in the art for using an antibody to detect polypeptide markers in a sample. See, e.g., Harlow and Lane, *Antibodies: A Laboratory Manual, Cold Spring Harbor Laboratory*, 1988. For example, the assay may be performed in a Western blot format, wherein a protein preparation from the biological sample is submitted to gel electrophoresis, transferred to a suitable membrane and allowed to react with the antibody. The presence of the antibody on the membrane may then be detected using a suitable detection reagent, as described below.

In another embodiment, the assay involves the use of antibody immobilized on a solid support to bind to the polypeptide and remove it from the remainder of the sample. The bound polypeptide may then be detected using a second antibody or reagent that contains a reporter group. Alternatively, a competitive assay may be utilized, in which a polypeptide is labeled with a reporter group and allowed to bind to the immobilized antibody after incubation of the antibody with the sample. The extent to which components of the sample inhibit the binding of the labeled polypeptide to the antibody is indicative of the reactivity of the sample with the immobilized antibody, and as a result, indicative of the concentration of polypeptide in the sample.

The solid support may be any material known to those of ordinary skill in the art to which the antibody may be attached. For example, the solid support may be a test well in a microtiter plate or a nitrocellulose filter or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The antibody may be immobilized on the solid support using a variety of techniques known to those in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the antibody, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of antibody ranging from about 10 ng to about 1 µg, and preferably about 100–200 ng, is sufficient to immobilize an adequate amount of polypeptide.

Covalent attachment of antibody to a solid support may also generally be achieved by first reacting the support with a bifunctional reagent that will react with both the support and a functional group, such as a hydroxyl or amino group, on the antibody. For example, the antibody may be covalently attached to supports having an appropriate polymer coating using benzoquinone or by condensation of an aldehyde group on the support with an amine and an active hydrogen on the binding partner (see, e.g., Pierce Immunotechnology Catalog and Handbook (1991) at A12–A13).

In certain embodiments, the assay for detection of polypeptide in a sample is a two-antibody sandwich assay. This assay may be performed by first contacting an antibody that has been immobilized on a solid support, commonly the well of a microtiter plate, with the biological sample, such that the polypeptide within the sample are allowed to bind to the immobilized antibody. Unbound sample is then removed from the immobilized polypeptide-antibody complexes and a second antibody (containing a reporter group) capable of binding to a different site on the polypeptide is added. The amount of second antibody that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is that period of time that is sufficient to detect the presence of polypeptide within a sample obtained from an individual with breast cancer. Preferably, the contact time is sufficient to achieve a level of binding that is at least 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include enzymes (such as horseradish peroxidase), substrates, cofactors, inhibitors, dyes, radionuclides, luminescent groups, fluorescent groups and biotin. The conjugation of antibody to reporter group may be achieved using standard methods known to those of ordinary skill in the art.

The second antibody is then incubated with the immobilized antibody-polypeptide complex for an amount of time sufficient to detect the bound polypeptide. An appropriate amount of time may generally be determined by assaying the level of binding that occurs over a period of time. Unbound second antibody is then removed and bound second antibody is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of breast cancer, the signal detected from the reporter group that remains bound to the solid support is generally compared to a signal that corresponds to a predetermined cut-off value established from non-tumor tissue. In one preferred embodiment, the cut-off value is the average mean signal obtained when the immobilized antibody is incubated with samples from patients without breast cancer. In general, a sample generating a signal that is three standard deviations above the predetermined cut-off value may be considered positive for breast cancer. In an alternate preferred embodiment, the cut-off value is determined using a Receiver Operator Curve, according to the method of Sackett et al., *Clinical Epidemiology: A Basic Science for Clinical Medicine*, p. 106–7 (Little Brown and Co., 1985). Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for breast cancer.

In a related embodiment, the assay is performed in a flow-through or strip test format, wherein the antibody is immobilized on a membrane, such as nitrocellulose. In the flow-through test, the polypeptide within the sample bind to the immobilized antibody as the sample passes through the membrane. A second, labeled antibody then binds to the antibody-polypeptide complex as a solution containing the second antibody flows through the membrane. The detection of bound second antibody may then be performed as described above. In the strip test format, one end of the membrane to which antibody is bound is immersed in a solution containing the sample. The sample migrates along the membrane through a region containing second antibody and to the area of immobilized antibody. Concentration of second antibody at the area of immobilized antibody indicates the presence of breast cancer. Typically, the concentration of second antibody at that site generates a pattern, such as a line, that can be read visually. The absence of such a pattern indicates a negative result. In general, the amount of antibody immobilized on the membrane is selected to generate a visually discernible pattern when the biological sample contains a level of polypeptide that would be sufficient to generate a positive signal in the two-antibody sandwich assay, in the format discussed above. Preferably, the amount of antibody immobilized on the membrane ranges from about 25 ng to about 1 $\mu$g, and more preferably from about 50 ng to about 1 $\mu$g. Such tests can typically be performed with a very small amount of biological sample.

The presence or absence of breast cancer in a patient may also be determined by evaluating the level of mRNA encoding a breast tumor-specific polypeptide as described herein within the biological sample (e.g., a biopsy, mastectomy and/or blood sample from a patient) relative to a predetermined cut-off value. Such an evaluation may be achieved using any of a variety of methods known to those of ordinary skill in the art such as, for example, in situ hybridization and amplification by polymerase chain reaction.

For example, polymerase chain reaction may be used to amplify is sequences from cDNA prepared from RNA that is isolated from one of the above biological samples. Sequence-specific primers for use in such amplification may be designed based on the sequences provided in any one of SEQ ID NO: 1, 11–86, 142–298 301–303 and 307, and may be purchased or synthesized. In the case of B18Ag1, as noted herein, one suitable primer pair is B18Ag1-2 (5'ATG GCT ATT TTC GGG GGC TGA CA) (SEQ ID NO:126) and B18Ag1-3 (5'CCG GTA TCT CCT CGT GGG TAT T) (SEQ ID NO:127). The PCR reaction products may then be separated by gel electrophoresis and visualized according to methods well known to those of ordinary skill in the art. Amplification is typically performed on samples obtained from matched pairs of tissue (tumor and non-tumor tissue from the same individual) or from unmatched pairs of tissue (tumor and non-tumor tissue from different individuals). The amplification reaction is preferably performed on several dilutions of cDNA spanning two orders of magnitude. A two-fold or greater increase in expression in several dilutions of the tumor sample as compared to the same dilution of the non-tumor sample is considered positive.

As used herein, the term "primer/probe specific for a polynucleotide" means an oligonucleotide sequence that has at least about 80% identity, preferably at least about 90% and more preferably at least about 95%, identity to the polynucleotide in question, or an oligonucleotide sequence that is anti-sense to a sequence that has at least about 80% identity, preferably at least about 90% and more preferably at least about 95%, identity to the polynucleotide in question. Primers and/or probes which may be usefully employed in the inventive diagnostic methods preferably have at least about 10–40 nucleotides. In a preferred embodiment, the polymerase chain reaction primers comprise at least about 10 contiguous nucleotides of a polynucleotide that encodes one of the polypeptides disclosed herein or that is anti-sense to a sequence that encodes one of the polypeptides disclosed herein. Preferably, oligonucleotide probes for use in the inventive diagnostic methods comprise at least about 15 contiguous oligonucleotides of a polynucleotide that encodes one of the polypeptides disclosed herein or that is anti-sense to a sequence that encodes one of the polypeptides disclosed herein. Techniques for both PCR based assays and in situ hybridization assays are well known in the art.

Conventional RT-PCR protocois using agarose and ethidium bromide staining, while important in defining gene specificity, do not lend themselves to diagnostic kit development because of the time and effort required in making them quantitative (i.e., construction of saturation and/or titration curves), and their sample throughput. This problem is overcome by the development of procedures such as real time RT-PCR which allows for assays to be performed in single tubes, and in turn can be modified for use in 96 well plate formats. Instrumentation to perform such methodologies are available from Perkin Elmer/Applied Biosystems Division. Alternatively, other high throughput assays using labeled probes (e.g., digoxygenin) in combination with labeled (e.g., enzyme fluorescent, radioactive) antibodies to such probes can also be used in the development of 96 well plate assays.

In yet another method for determining the presence or absence of breast cancer in a patient, one or more of the breast tumor-specific polypeptides described may be used in a skin test. As used herein, a "skin test" is any assay performed directly on a patient in which a delayed-type hypersensitivity (DTH) reaction (such as swelling, reddening or dermatitis) is measured following intradermal injection of one or more polypeptides as described above. Such injection may be achieved using any suitable device sufficient to contact the polypeptide or polypeptides with dermal cells of the patient, such as a tuberculin syringe or 1 mL syringe. Preferably, the reaction is measured at least 48 hours after injection, more preferably 48–72 hours.

The DTH reaction is a cell-mediated immune response, which is greater in patients that have been exposed previously to a test antigen (i.e., an immunogenic portion of a polypeptide employed, or a variant thereof). The response may measured visually, using a ruler. In general, a response that is greater than about 0.5 cm in diameter, preferably greater than about 5.0 cm in diameter, is a positive response, indicative of breast cancer.

The breast tumor-specific polypeptides described herein are preferably formulated, for use in a skin test, as pharmaceutical compositions containing at least one polypeptide and a physiologically acceptable carrier, such as water, saline, alcohol, or a buffer. Such compositions typically contain one or more of the above polypeptides in an amount ranging from about 1 μg to 100 μg, preferably from about 10 μg to 50 μg in a volume of 0.1 mL. Preferably, the carrier employed in such pharmaceutical compositions is a saline solution with appropriate preservatives, such as phenol and/or Tween 80™.

In other aspects of the present invention, the progression and/or response to treatment of a breast cancer may be monitored by performing any of the above assays over a period of time, and evaluating the change in the level of the response (i.e., the amount of polypeptide or mRNA detected or, in the case of a skin test, the extent of the immune response detected). For example, the assays may be performed every month to every other month for a period of 1 to 2 years. In general, breast cancer is progressing in those patients in whom the level of the response increases over time. In contrast, breast cancer is not progressing when the signal detected either remains constant or decreases with time.

In further aspects of the present invention, the compounds described herein may be used for the immunotherapy of breast cancer. In these aspects, the compounds (which may be polypeptides, antibodies or polynucleotides) are preferably incorporated into pharmaceutical compositions or vaccines. Pharmaceutical compositions comprise one or more such compounds and a physiologically acceptable carrier. Vaccines may comprise one or more such compounds and an immune response enhancer, such as an adjuvant or a liposome (into which the compound is incorporated). Pharmaceutical compositions and vaccines may additionally contain a delivery system, such as biodegradable microspheres as disclosed, for example, in U.S. Pat. Nos. 4,897,268 and 5,075,109. Pharmaceutical compositions and vaccines within the scope of the present invention may also contain other compounds, including one or more separate polypeptides.

Alternatively, a vaccine may contain DNA encoding one or more of the polypeptides as described above, such that the polypeptide is generated in situ. In such vaccines, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Techniques for incorporating DNA into such expression systems are well known to those of ordinary skill in the art. The DNA may also be "naked," as described, for example, in Ulmer et al., *Science* 259:1745–1749 (1993), and reviewed by Cohen, *Science* 259:1691–1692 (1993). The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration; any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.), Merck Adjuvant 65 (Merck and Company, Inc., Rahway, N.J.), alum, biodegradable microspheres, monophosphoryl lipid A and quil A. Cytokines, such as GM-CSF or interleukin-2, -7, or -12. may also be used as adjuvants.

The above pharmaceutical compositions and vaccines may be used, for example, for the therapy of breast cancer in a patient. As used herein, a "patient" refers to any warm-blooded animal, preferably a human. A patient may or may not be afflicted with breast cancer. Accordingly, the above pharmaceutical compositions and vaccines may be used to prevent the development of breast cancer or to treat a patient afflicted with breast cancer. In a preferred embodiment, the compounds are administered either prior to or following surgical removal of primary tumors and/or treatment by administration of radiotherapy and conventional chemotherapeutic drugs. To prevent or slow the development of breast cancer, a pharmaceutical composition or vaccine comprising one or more polypeptides as described herein may be administered to a patient. Alternatively, naked DNA or plasmid or viral vector encoding the polypeptide may be administered. For treating a patient with breast cancer, the pharmaceutical composition or vaccine may comprise one or more polypeptides, antibodies or polynucleotides complementary to DNA encoding a polypeptide as described herein (e.g., antisense RNA or antisense deoxyribonucleotide oligonucleotides).

Routes and frequency of administration, as well as dosage, will vary from individual to individual. In general, the pharmaceutical compositions and vaccines may be administered by injection (e.g., intracutaneous, intramuscular, intravenous or subcutaneous), intranasally (e.g., by aspiration) or orally. Between 1 and 10 doses may be administered for a 52-week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 100 $\mu$g to 5 mg. Suitable dose sizes will vary with the size of the patient, but will typically range from about 0.1 mL to about 5 mL.

Polypeptides disclosed herein may also be employed in adoptive immunotherapy for the treatment of cancer. Adoptive immunotherapy may be broadly classified into either active or passive immunotherapy. In active immunotherapy, treatment relies on the in vivo stimulation of the endogenous host immune system to react against tumors with the administration of immune response-modifying agents (for example, tumor vaccines, bacterial adjuvants, and/or cytokines).

In passive immunotherapy, treatment involves the delivery of biologic reagents with established tumor-immune reactivity (such as effector cells or antibodies) that can directly or indirectly mediate antitumor effects and does not necessarily depend on an intact host immune system. Examples of effector cells include T lymphocytes (for example, CD8+ cytotoxic T-lymphocyte, CD4+ T-helper, tumor-infiltrating lymphocytes), killer cells (Natural Killer cells, lymphokine-activated killer cells), B cells, or antigen presenting cells (such as dendritic cells and macrophages) expressing the disclosed antigens. The polypeptides disclosed herein may also be used to generate antibodies or anti-idiotypic antibodies (as in U.S. Pat. No. 4,918,164), for passive immunotherapy.

The predominant method of procuring adequate numbers of T-cells for adoptive immunotherapy is to grow immune T-cells in vitro. Culture conditions for expanding single antigen-specific T-cells to several billion in number with retention of antigen recognition in vivo are well known in the art. These in vitro culture conditions typically utilize intermittent stimulation with antigen, often in the presence of cytokines, such as IL-2, and non-dividing feeder cells. As noted above, the immunoreactive polypeptides described herein may be used to rapidly expand antigen-specific T cell cultures in order to generate sufficient number of cells for immunotherapy. In particular, antigen-presenting cells, such as dendritic, macrophage or B-cells, may be pulsed with immunoreactive polypeptides or transfected with a polynucleotide sequence(s), using standard techniques well known in the art. For cultured T-cells to be effective in therapy, the cultured T-cells must be able to grow and distribute widely and to survive long term in vivo. Studies have demonstrated that cultured T-cells can be induced to grow in vivo and to survive long term in substantial numbers by repeated stimulation with antigen supplemented with IL-2 (see, for example, Cheever et al. Ibid).

The polypeptides disclosed herein may also be employed to generate and/or isolate tumor-reactive T-cells, which can then be administered to the patient. In one technique, antigen-specific T-cell lines may be generated by in vivo immunization with short peptides corresponding to immunogenic portions of the disclosed polypeptides. The resulting antigen specific CD8+ CTL clones may be isolated from the patient, expanded using standard tissue culture techniques, and returned to the patient.

Alternatively, peptides corresponding to immunogenic portions of the polypeptides may be employed to generate tumor reactive T cell subsets by selective in vitro stimulation and expansion of autologous T cells to provide antigen-specific T cells which may be subsequently transferred to the patient as described, for example, by Chang et al. (*Crit. Rev. Oncol. Hematol.*, 22(3), 213, 1996).

In another embodiment, syngeneic or autologous dendritic cells may be pulsed with peptides corresponding to at least an immunogenic portion of a polypeptide disclosed herein. The resulting antigen-specific dendritic cells may either be transferred into a patient, or employed to stimulate T cells to provide antigen-specific T cells which may, in turn, be administered to a patient. The use of peptide-pulsed dendritic cells to generate antigen-specific T cells and the subsequent use of such antigen-specific T cells to eradicate tumors in a murine model has been demonstrated by Cheever et al. ("Therapy With Cultured T Cells: Principles Revisited," *Immunological Reviews*, 157:177, 1997).

Additionally vectors expressing the disclosed polynucleotides may be introduced into stem cells taken from the patient and clonally propagated in vitro for autologous transplant back into the same patient. In one embodiment, cells of the immune system, such as T cells, may be isolated from the peripheral blood of a patient, using a commercially available cell separation system, such as CellPro Incorporated's (Bothell, Wash.) CEPRATE™ system (see U.S. Pat. Nos. 5,240,856; 5,215,926; WO 89/06280; WO 91/16116 and WO 92/07243). The separated cells are stimulated with one or more of the immunoreactive polypeptides contained within a delivery vehicle, such as a microsphere, to provide antigen-specific T cells. The population of tumor antigen-specific T cells is then expanded using standard techniques and the cells are administered back to the patient.

The following Examples are offered by way of illustration and not by way of limitation.

EXAMPLES

Example 1

Preparation of Breast Tumor-Specific cDNAs Using Differential Display RT-PCR

This Example illustrates the preparation of cDNA molecules encoding breast tumor-specific polypeptides using a differential display screen.

A. Preparation of B18Ag1 cDNA and Characterization of mRNA Expression

Tissue samples were prepared from breast tumor and normal tissue of a patient with breast cancer that was confirmed by pathology after removal from the patient. Normal RNA and tumor RNA was extracted from the samples and mRNA was isolated and converted into cDNA using a $(dT)_{12}AG$ (SEQ ID NO:130) anchored 3' primer. Differential display PCR was then executed using a randomly chosen primer (CTTCAACCTC) (SEQ ID NO:103). Amplification conditions were standard buffer containing 1.5 mM $MgCl_2$, 20 pmol of primer, 500 pmol dNTP, and 1 unit of Taq DNA polymerase (Perkin-Elmer, Branchburg, N.J.). Forty cycles of amplification were performed using 94° C. denaturation for 30 seconds, 42° C. annealing for 1 minute, and 72° C. extension for 30 seconds. An RNA fingerprint containing 76 amplified products was obtained. Although the RNA fingerprint of breast tumor tissue was over 98% identical to that of the normal breast tissue, a band was repeatedly observed to be specific to the RNA fingerprint pattern of the tumor. This band was cut out of a silver stained gel, subcloned into the T-vector (Novagen, Madison, Wis.) and sequenced.

The sequence of the cDNA, referred to as B18Ag1, is provided in SEQ ID NO:1. A database search of GENBANK and EMBL revealed that the B18Ag1 fragment initially cloned is 77% identical to the endogenous human retroviral element S71, which is a truncated retroviral element homologous to the Simian Sarcoma Virus (SSV). S71 contains an incomplete gag gene, a portion of the pol gene and an LTR-like structure at the 3' terminus (see Werner et al., *Virology* 174:225–238 (1990)). B18Ag1 is also 64% identical to SSV in the region corresponding to the P30 (gag) locus. B18Ag1 contains three separate and incomplete reading frames covering a region which shares considerable homology to a wide variety of gag proteins of retroviruses which infect mammals. In addition, the homology to S71 is not just within the gag gene, but spans several kb of sequence including an LTR.

Figure 2:
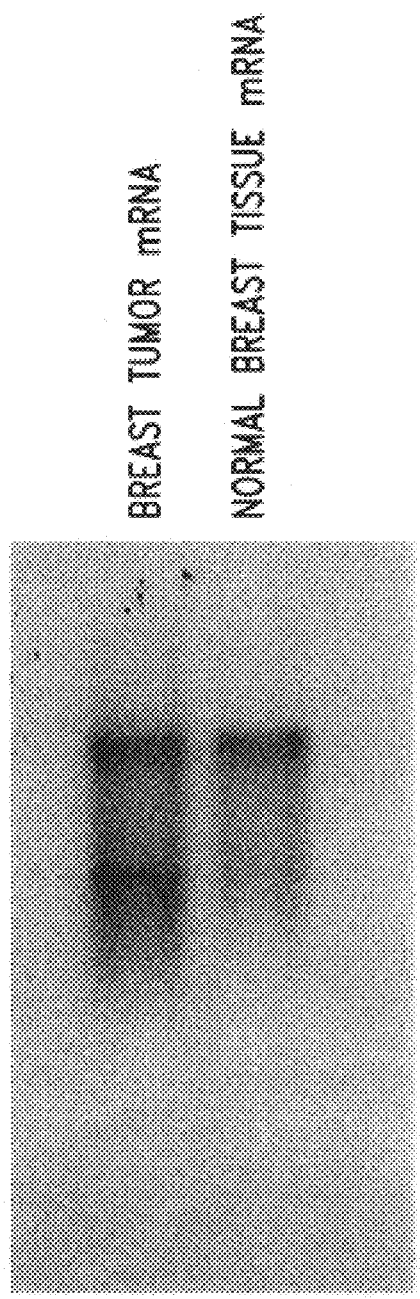
FIG. 2 is a northern blot comparing the level of B18Ag1 mRNA in breast tumor tissue (lane 1) with the level in normal breast tissue.

B18Ag1-specific PCR primers were synthesized using computer analysis guidelines. RT-PCR amplification (94° C., 30 seconds; 60° C.→42° C., 30 seconds; 72° C., 30 seconds for 40 cycles) confirmed that B18Ag1 represents an actual mRNA sequence present at relatively high levels in the patient's breast tumor tissue. The primers used in amplification were B18Ag1-1 (CTG CCT GAG CCA CAA ATG) (SEQ ID NO:128) and B18Ag1-4 (CCG GAG GAG GAA GCT AGA GGA ATA) (SEQ ID NO:129) at a 3.5 mM magnesium concentration and a pH of 8.5, and B18Ag1-2 (ATG GCT ATT TTC GGG GCC TGA CA) (SEQ ID NO:126) and B18Ag1-3 (CCG GTA TCT CCT CGT GGG TAT T) (SEQ ID NO:127) at 2 mM magnesium at pH 9.5. The same experiments showed exceedingly low to nonexistent levels of expression in this patient's normal breast tissue (see FIG. 1). RT-PCR experiments were then used to show that B18Ag1 mRNA is present in nine other breast tumor samples (from Brazilian and American patients) but absent in, or at exceedingly low levels in, the normal breast tissue corresponding to each cancer patient. RT-PCR analysis has also shown that the B18Ag1 transcript is not present in various normal tissues (including lymph node, myocardium and liver) and present at relatively low levels in PBMC and lung tissue. The presence of B18Ag1 mRNA in breast tumor samples, and its absence from normal breast tissue, has been confirmed by Northern blot analysis, as shown in FIG. 2.

Figure 3:
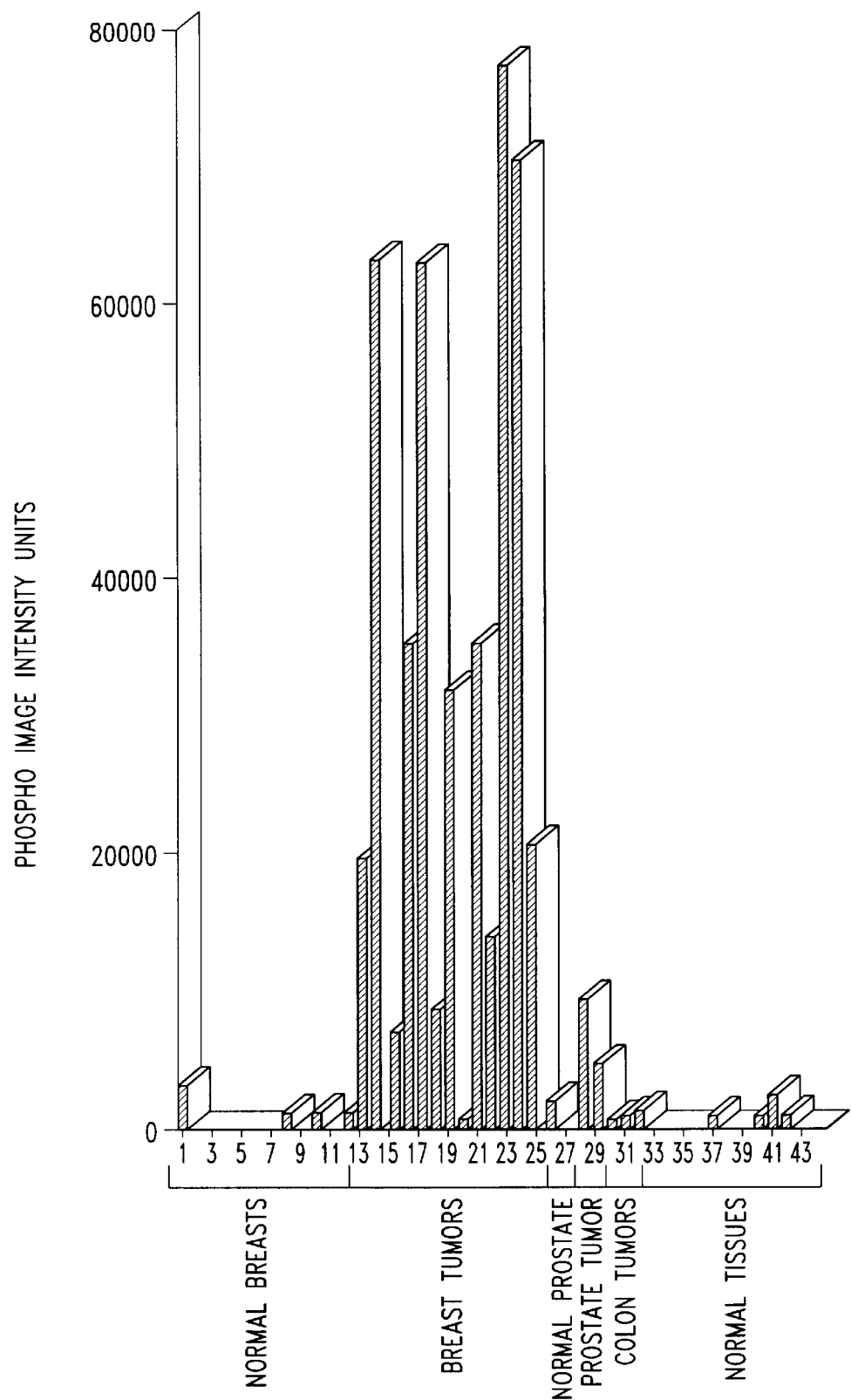
FIG. 3 shows the level of B18Ag1 mRNA in breast tumor tissue compared to that in various normal and non-breast tumor tissues as determined by RNase protection assays.

The differential expression of B18Ag 1 in breast tumor tissue was also confirmed by RNase protection assays. FIG. 3 shows the level of B18Ag1 mRNA in various tissue types as determined in four different RNase protection assays. Lanes 1–12 represent various normal breast tissue samples, lanes 13–25 represent various breast tumor samples; lanes 26–27 represent normal prostate samples; lanes 28–29 represent prostate tumor samples; lanes 30–32 represent colon tumor samples; lane 33 represents normal aorta; lane 34 represents normal small intestine; lane 35 represents normal skin, lane 36 represents normal lymph node; lane 37 represents normal ovary; lane 38 represents normal liver; lane 39 represents normal skeletal muscle; lane 40 represents a first normal stomach sample, lane 41 represents a second normal stomach sample; lane 42 represents a normal lung; lane 43 represents normal kidney; and lane 44 represents normal pancreas. Interexperimental comparison was facilitated by including a positive control RNA of known β-actin message abundance in each assay and normalizing the results of the different assays with respect to this positive control.

Figure 4:
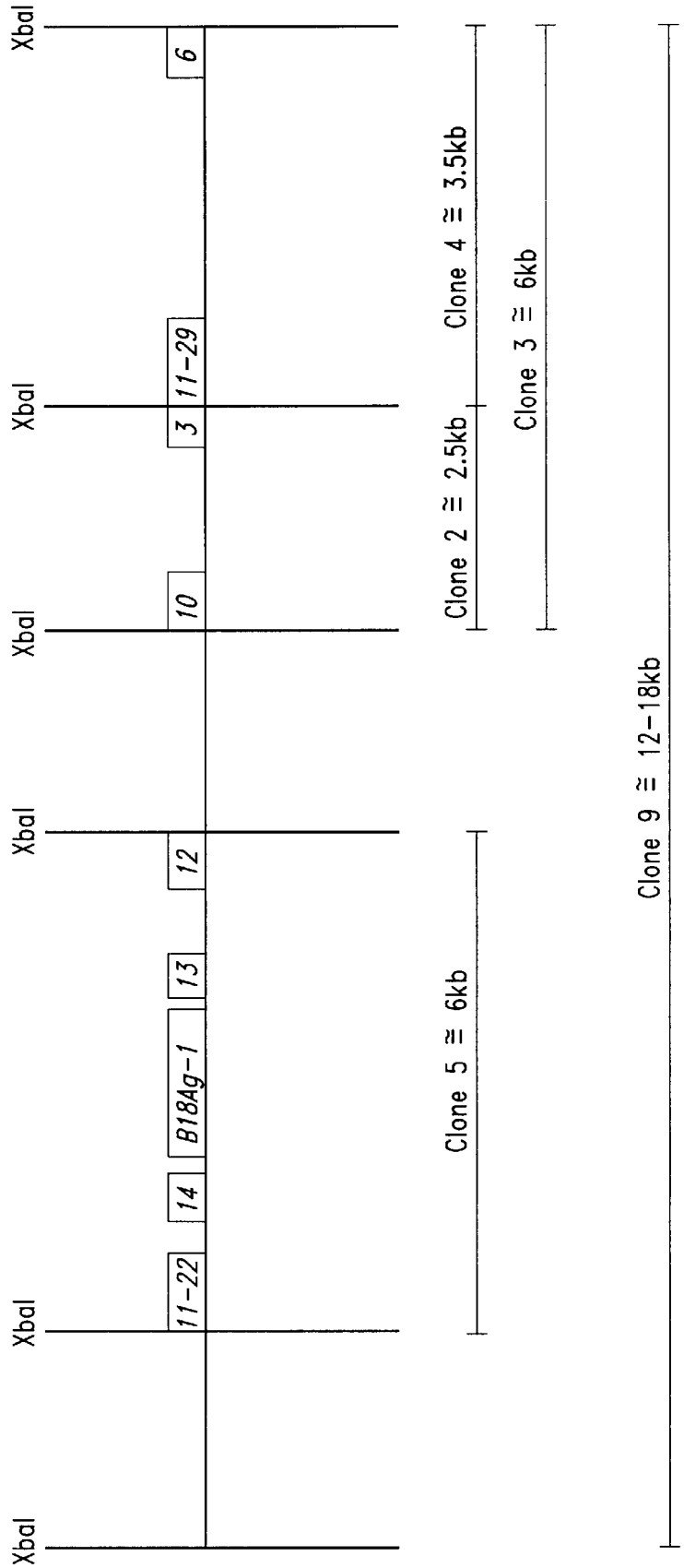
FIG. 4 is a genomic clone map showing the location of additional retroviral sequences obtained from ends of XbaI restriction digests (provided in SEQ ID NO:3–SEQ ID NO:10) relative to B18Ag1.

RTF-PCR and Southern Blot analysis has shown the B18Ag1 locus to be present in human genomic DNA as a single copy endogenous retroviral element. A genomic clone of approximately 12–18 kb was isolated using the initial B18Ag1 sequence as a probe. Four additional subclones were also isolated by XbaI digestion. Additional retroviral sequences obtained from the ends of the XbaI digests of these clones (located as shown in FIG. 4) are shown as SEQ ID NO:3–SEQ ID NO:10, where SEQ ID NO:3 shows the location of the sequence labeled 10 in FIG. 4, SEQ ID NO:4 shows the location of the sequence labeled 11–29, SEQ ID NO:5 shows the location of the sequence labeled 3, SEQ ID NO:6 shows the location of the sequence labeled 6, SEQ ID NO:7 shows the location of the sequence labeled 12, SEQ ID NO:8 shows the location of the sequence labeled 13, SEQ ID NO:9 shows the location of the sequence labeled 14 and SEQ ID NO:10 shows the location of the sequence labeled 11–22.

Figures 5A, 5B:
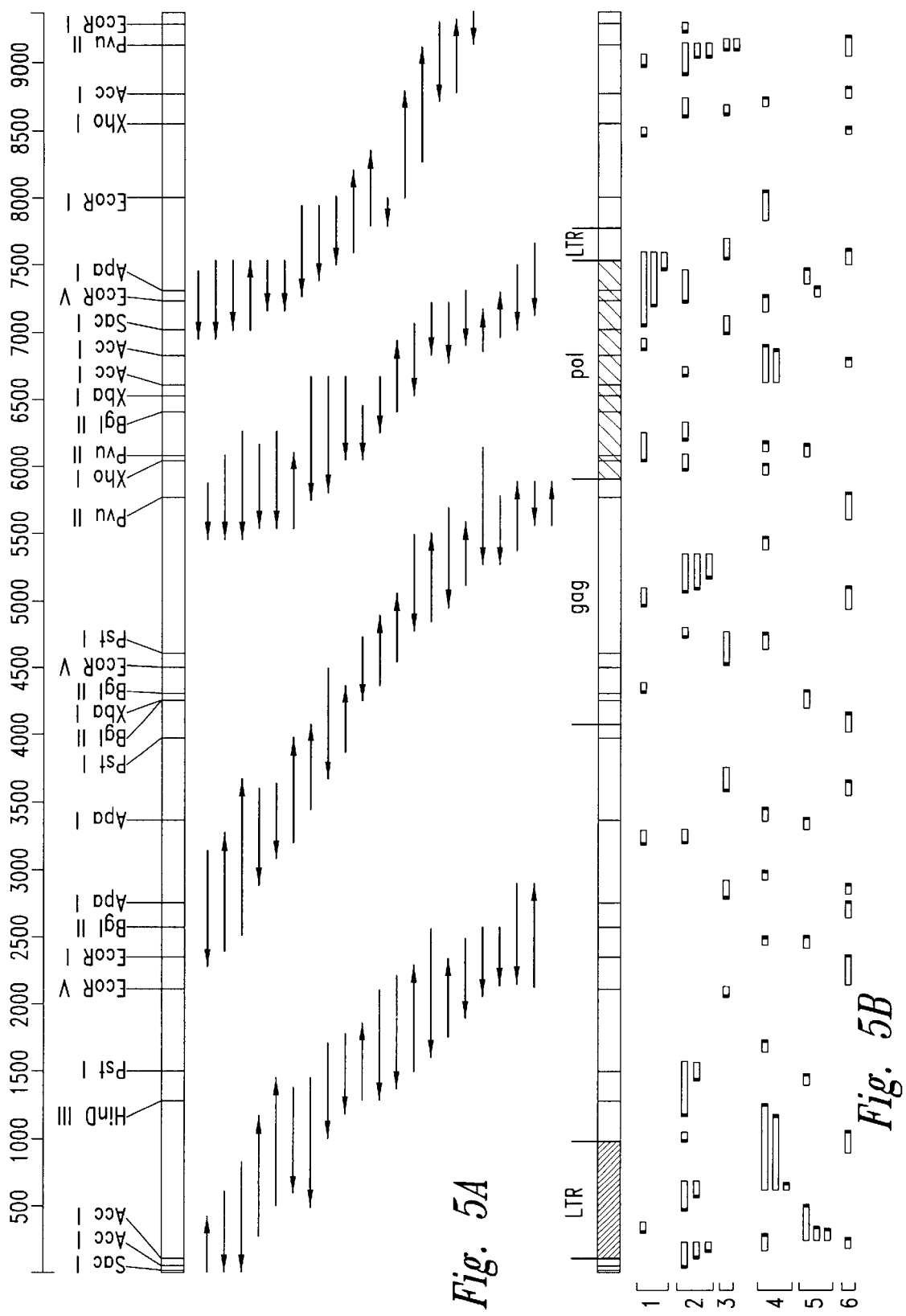
FIGS. 5A and 5B show the sequencing strategy, genomic organization and predicted open reading frame for the retroviral element containing B18Ag1.
Figure 21A:
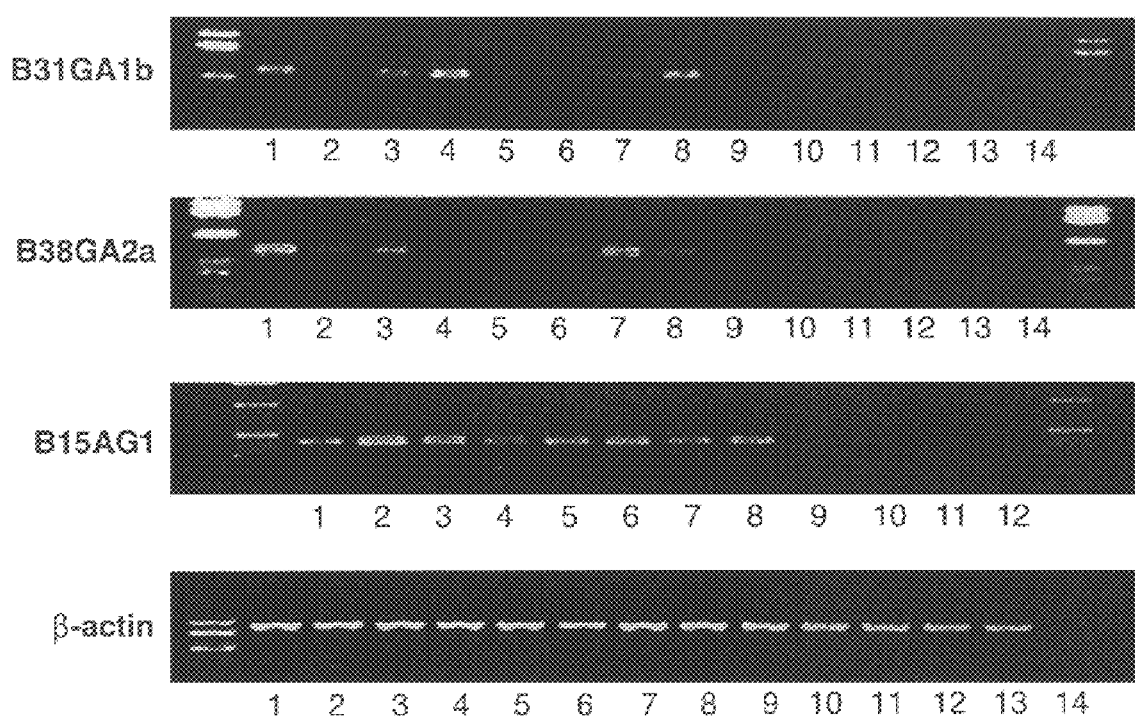
FIG. 21A depicts RT-PCR analysis of breast tumor genes in breast tumor tissues (lanes 1–8) and normal breast tissues (lanes 9–13) and H$_2$O (lane 14).
Figure 21B:
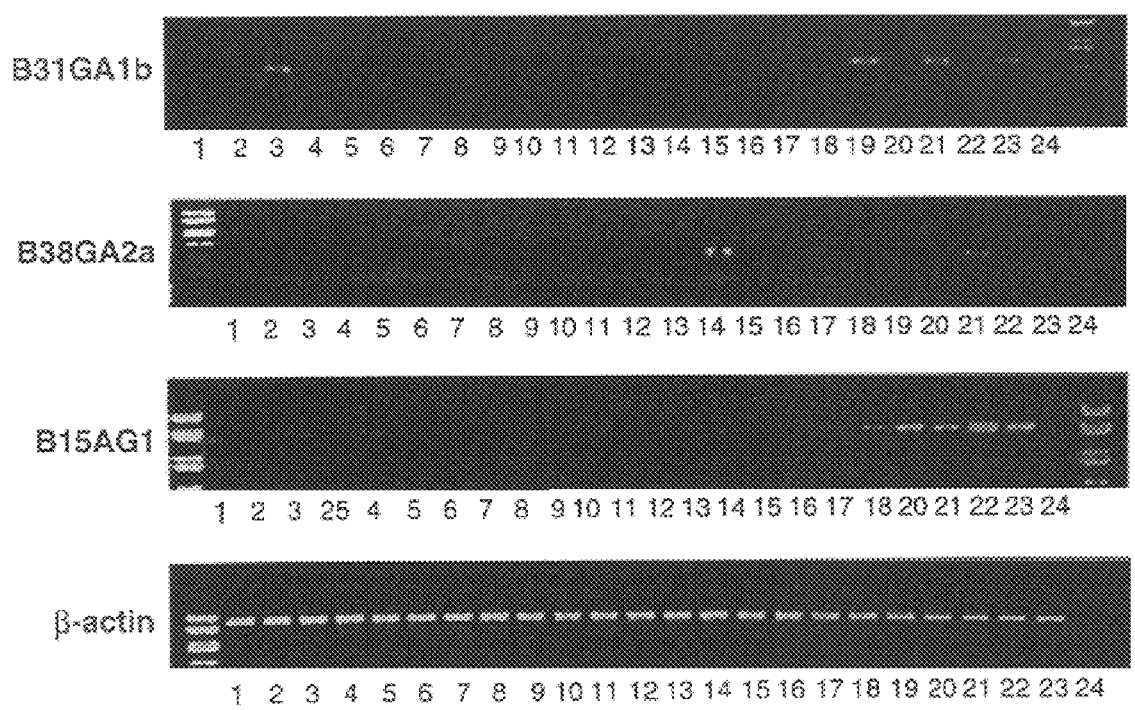
FIG. 21B depicts RT-PCR analysis of breast tumor genes in prostate tumors (lane 1, 2), colon tumors (lane 3), lung tumor (lane 4), normal prostate (lane 5), normal colon (lane 6), normal kidney (lane 7), normal liver (lane 8), normal lung (lane 9), normal ovary (lanes 10, 18), normal pancreases (lanes 11, 12), normal skeletal muscle (lane 13), normal skin (lane 14), normal stomach (lane 15), normal testes (lane 16), normal small intestine (lane 17), HBL-100 (lane 19), MCF-12A (lane 20), breast tumors (lanes 21–23), H$_2$O (lane 24), and colon tumor (lane 25).
Figure 22:
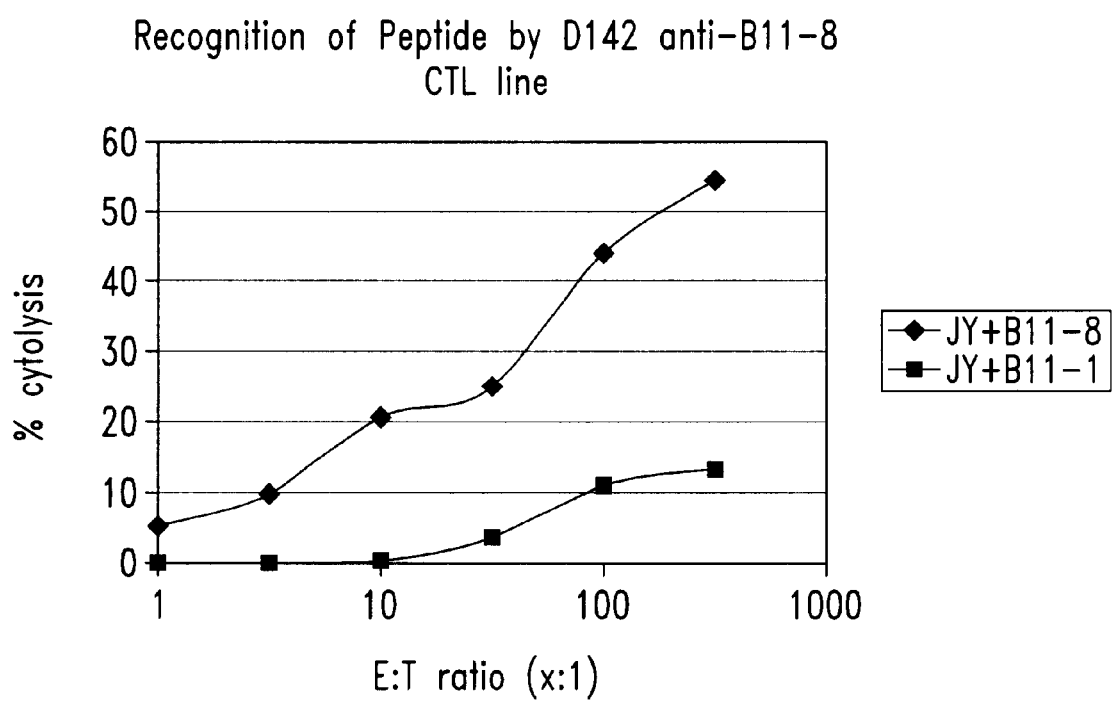
FIG. 22 shows the recognition of a B11Ag1 peptide (referred to as B11-8) by an anti-B11-8 CTL line.
Figure 23:
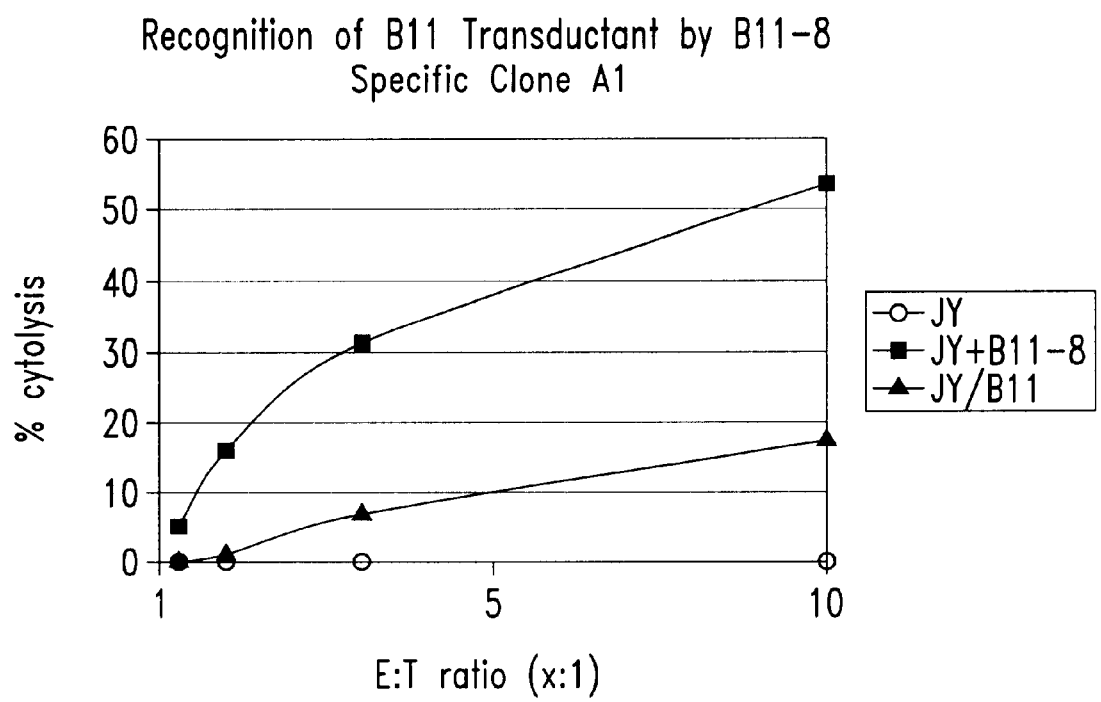
FIG. 23 shows the recognition of a cell line transduced with the antigen B11Ag1 by the B11-8 specific clone A1.
Figure 24:
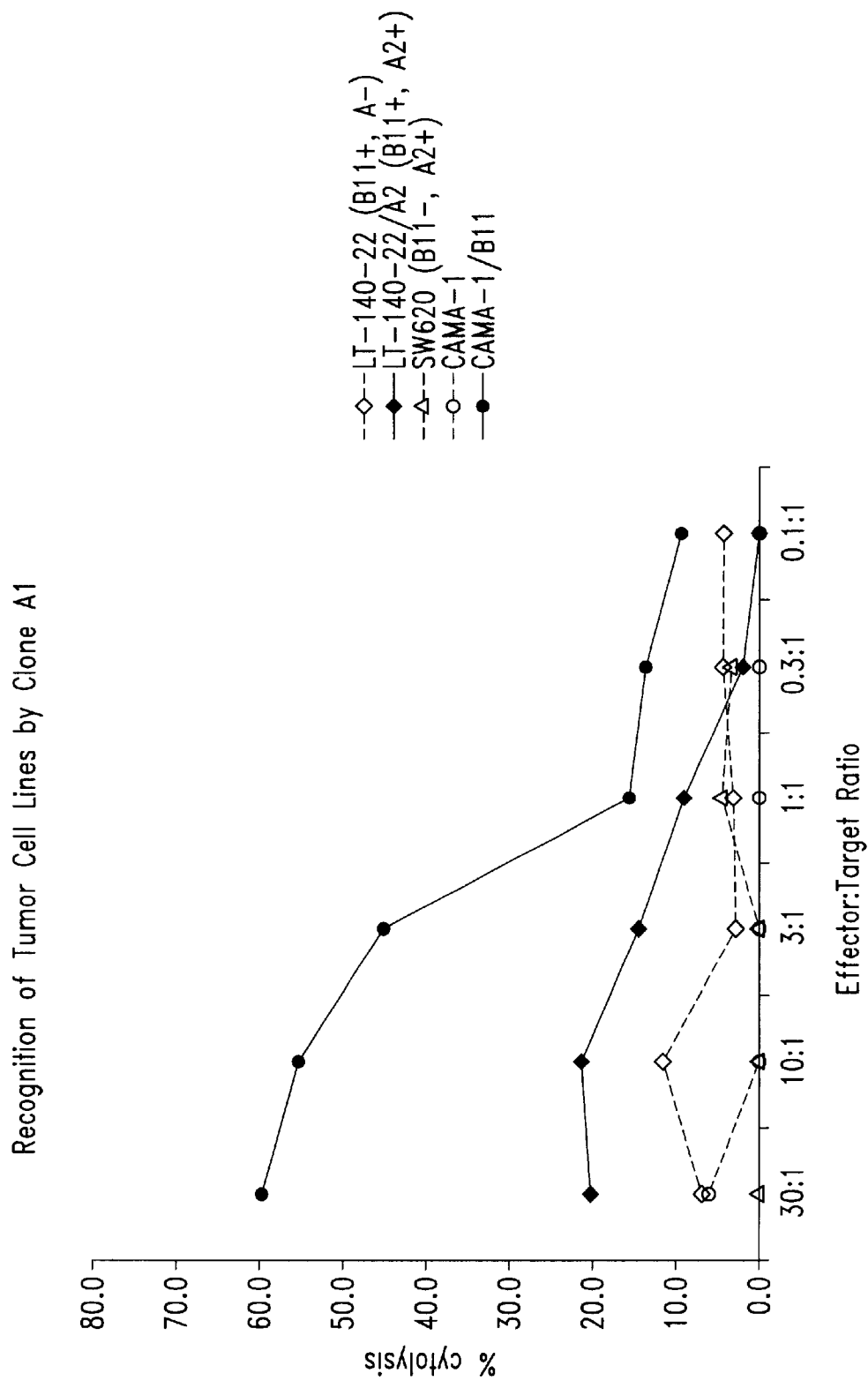
FIG. 24 shows recognition of a lung adenocarcinoma line (LT-140-22) and a breast adenocarcinoma line (CAMA-1) by the B11-8 specific clone A1.

Subsequent studies demonstrated that the 12–18 kb genomic clone contains a retroviral element of about 7.75 kb, as shown in FIGS. 5A and 5B. The sequence of this retroviral element is shown in SEQ ID NO: 141. The numbered line at the top of FIG. 5A represents the sense strand sequence of the retroviral genomic clone. The box below this line shows the position of selected restriction sites. The arrows depict the different overlapping clones used to sequence the retroviral element. The direction of the arrow shows whether the single-pass subclone sequence corresponded to the sense or anti-sense strand. FIG. 5B is a schematic diagram of the retroviral element containing B18Ag1 depicting the organization of viral genes within the element. The open boxes correspond to predicted reading frames, starting with a methionine, found throughout the element. Each of the six likely reading frames is shown, as indicated to the left of the boxes, with frames 1–3 corresponding to those found on the sense strand.

Using the cDNA of SEQ ID NO:1 as a probe, a longer cDNA was obtained (SEQ ID NO:227) which contains minor nucleotide differences (less than 1%) compared to the genomic sequence shown in SEQ ID NO:141.

B. Preparation of cDNA Molecules Encoding Other Breast Tumor-Specific Polypeptides Normal RNA and tumor RNA was prepared and mRNA was isolated and converted into cDNA using a $(dT)_{12}AG$ anchored 3' primer, as described above. Differential display PCR was then executed using the randomly chosen primers of SEQ ID NO: 87–125. Amplification conditions were as noted above, and bands observed to be specific to the RNA fingerprint pattern of the tumor were cut out of a silver stained gel, subcloned into either the T-vector (Novagen, Madison, Wis.) or the pCRII vector (Invitrogen, San Diego, Calif.) and sequenced. The sequences are provided in SEQ ID NO:11–SEQ ID NO:86. Of the 79 sequences isolated, 67 were found to be novel (SEQ ID NO:11–26 and 28–77) (see also FIGS. 6–20).

An extended DNA sequence (SEQ ID NO: 290) for the antigen B15Ag1 (originally identified partial sequence provided in SEQ ID NO: 27) was obtained in further studies. Comparison of the sequence of SEQ ID NO: 290 with those in the gene bank as described above, revealed homology to the known human β-A activin gene. Further studies led to the isolation of the full-length cDNA sequence for the antigen B21GT2 (originally identified partial cDNA sequence provided in SEQ ID NO: 56). The full-length sequence is provided in SEQ ID NO: 307.

Subsequent studies identified an additional 146 sequences (SEQ ID NOS:142–289), of which 115 appeared to be novel (SEQ ID NOS:142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284, 288 and 291). To the best of the inventors' knowledge none of the previously identified sequences have heretofore been shown to be expressed at a greater level in human breast tumor tissue than in normal breast tissue.

In further studies, several different splice forms of the antigen B11Ag1 (also referred to as B305D) were isolated, with each of the various splice forms containing slightly different versions of the B11Ag1 coding frame. Splice junction sequences define individual exons which, in various patterns and arrangements, make up the various splice forms. Primers were designed to examine the expression pattern of each of the exons using RT-PCR as described below. Each exon was found to show the same expression pattern as the original B11Ag1 clone, with expression being breast tumor-, normal prostate- and normal testis-specific. The determined cDNA sequences for the isolated protein coding exons are provided in SEQ ID NO: 292–298, respectively. The predicted amino acid sequences corresponding to the sequences of SEQ ID NO: 292 and 298 are provided in SEQ ID NO: 299 and 300. Additional studies using rapid amplification of cDNA ends (RACE), a 5' specific primer to one of the splice forms of B11Ag1 provided above and a breast adenocarcinoma, led to the isolation of three additional, related, splice forms referred to as isoforms B11C-15, B11C-8 and B11C-9,16. The determined cDNA sequences for these isoforms are provided in SEQ ID NO: 301–303, with the corresponding predicted amino acid sequences being provided in SEQ ID NO: 304–306.

Example 2

Preparation of B18Ag1 DNA from Human Genomic DNA

This Example illustrates the preparation of B18Ag1 DNA by amplification from human genomic DNA.

B18Ag1 DNA may be prepared from 250 ng human genomic DNA using 20 pmol of B18Ag1 specific primers, 500 pmol dNTPS and 1 unit of Taq DNA polymerase (Perkin Elmer, Branchburg, N.J.) using the following amplification parameters: 94° C. for 30 seconds denaturing, 30 seconds 60° C. to 42° C. touchdown annealing in 2° C. increments every two cycles and 72° C. extension for 30 seconds. The last increment (a 42° C. annealing temperature) should cycle 25 times. Primers were selected using computer analysis. Primers synthesized were B18Ag1-1, B18Ag1-2, B18Ag1-3, and B18Ag1-4. Primer pairs that may be used are 1+3, 1+4, 2+3, and 2+4.

Following gel electrophoresis, the band corresponding to B18Ag1 DNA may be excised and cloned into a suitable vector.

Example 3

Preparation of B18Ag1 from Breast Tumor cDNA

This Example illustrates the preparation of B18Ag1 DNA by amplification from human breast tumor cDNA.

First strand cDNA is synthesized from RNA prepared from human breast tumor tissue in a reaction mixture containing 500 ng poly A+ RNA, 200 pmol of the primer $(T)_{12}AG$ (i.e., TTT TTT TTT TTT AG) (SEQ ID NO: 130), 1× first strand reverse transcriptase buffer, 6.7 mM DTT, 500 mmol dNTPs, and 1 unit AMV or MMLV reverse transcriptase (from any supplier, such as Gibco-BRL (Grand Island, N.Y.)) in a final volume of 30 μl. After first strand synthesis, the cDNA is diluted approximately 25 fold and 1 μl is used for amplification as described in Example 2. While some primer pairs can result in a heterogeneous population of transcripts, the primers B18Ag1-2 (5'ATG GCT ATT TTC GGG GGC TGA CA) (SEQ ID NO: 126) and B18Ag1-3 (5'CCG GTA TCT CCT CGT GGG TAT T) (SEQ ID NO: 127) yield a single 151 bp amplification product.

Example 4

Identification of B-cell and T-cell Epitopes of B18Ag1

This Example illustrates the identification of B18Ag1 epitopes.

The B18Ag1 sequence can be screened using a variety of computer algorithms. To determine B-cell epitopes, the sequence can be screened for hydrophobicity and hydrophilicity values using the method of Hopp, *Prog. Clin. Biol. Res.* 172B:367–77 (1985) or, alternatively, Cease et al., *J. Exp. Med.* 164:1779–84 (1986) or Spouge et al., *J. Immunol.* 138:204–12 (1987). Additional Class II MHC (antibody or B-cell) epitopes can be predicted using programs such as AMPHI (e.g., Margalit et al., *J. Immunol.* 138:2213 (1987)) or the methods of Rothbard and Taylor (e.g., *EMBO J.* 7:93 (1988)).

Once peptides (15–20 amino acids long) are identified using these techniques, individual peptides can be synthesized using automated peptide synthesis equipment (available from manufacturers such as Perkin Elmer/ Applied Biosystems Division, Foster City, Calif.) and techniques such as Merrifield synthesis. Following synthesis, the peptides can used to screen sera harvested from either normal or breast cancer patients to determine whether patients with breast cancer possess antibodies reactive with the peptides. Presence of such antibodies in breast cancer patient would confirm the immunogenicity of the specific B-cell epitope in question. The peptides can also be tested for their ability to generate a serologic or humoral immune in animals (mice, rats, rabbits, chimps etc.) following immunization in vivo. Generation of a peptide-specific antiserum following such immunization further confirms the immunogenicity of the specific B-cell epitope in question.

To identify T-cell epitopes, the B18Ag1 sequence can be screened using different computer algorithms which are useful in identifying 8–10 amino acid motifs within the B18Ag1 sequence which are capable of binding to HLA Class I MHC molecules. (see, e.g., Rammensee et al.,

*Immunogenetics* 41:178–228 (1995)). Following synthesis such peptides can be tested for their ability to bind to class I MHC using standard binding assays (e.g., Sette et al., *J. Immunol.* 153:5586–92 (1994)) and more importantly can be tested for their ability to generate antigen reactive cytotoxic T-cells following in vitro stimulation of patient or normal peripheral mononuclear cells using, for example, the methods of Bakker et al., *Cancer Res.* 55:5330–34 (1995); Visseren et al., *J. Immunol.* 154:3991–98 (1995); Kawakami et al., *J. Immunol.* 154:3961–68 (1995); and Kast et al., *J. Immunol.* 152:3904–12 (1994). Successful in vitro generation of T-cells capable of killing autologous (bearing the same Class I MHC molecules) tumor cells following in vitro peptide stimulation further confirms the immunogenicity of the B18Ag1 antigen. Furthermore, such peptides may be used to generate murine peptide and B18Ag1 reactive cytotoxic T-cells following in vivo immunization in mice rendered transgenic for expression of a particular human MHC Class I haplotype (Vitiello et al., *J. Exp. Med.* 173:1007–15 (1991).

A representative list of predicted B18Ag1 B-cell and T-cell epitopes, broken down according to predicted HLA Class I MHC binding antigen, is shown below:

Predicted Th Motifs (B-cell epitopes) (SEQ ID NOS.: 131–133)

SSGGRTFDDFHRYLLVGI

QGAAQKPINLSKXIEVVQGHDE

SPGVFLEHLQEAYRIYTPFDLSA

Predicted HLA A2.1 Motifs (T-cell epitopes) (SEQ ID NOS.: 134–140)

YLLVGIQGA

GAAQKPINL

NLSKXIEVV

EVVQGHDES

HLQEAYRIY

NLAFVAQAA

FVAQAAPDS

Example 5

Identification of T-cell Epitopes of B11Ag1

This Example illustrates the identification of B11Ag1 (also referred to as B305D) epitopes. Four peptides, referred to as B11-8, B11-1, B11-5 and B11-12 (SEQ ID NO: 309–312, respectfully) were derived from the B11Ag1 gene.

Human CD8 T cells were primed in vitro to the peptide B11-8 using dendritic cells according to the protocol of Van Tsai et al. (*Critical Reviews in Immunology* 18:65–75, 1998). The resulting CD8 I cell cultures were tested for their ability to recognize the B11-8 peptide or a negative control peptide, presented by the B-LCL line, JY. Briefly, T cells were incubated with autologous monocytes in the presence of 10 ug/ml peptide, 10 ng/ml IL-7 and 10 ug/ml IL-2, and assayed for their ability to specifically lyse target cells in a standard 51-Cr release assay. As shown in FIG. 22, the bulk culture line demonstrated strong recognition of the B11-8 peptide with weaker recognition of the peptide B11-1.

A clone from this CTL line was isolated following rapid expansion using the monoclonal antibody OKT3 and human IL-2. As shown in FIG. 23, this clone (referred to as A1), in addition to being able to recognize specific peptide, recognized JY LCL transduced with the B11Ag1 gene. This data demonstrates that B11-8 is a naturally processed epitope of the B11Ag1 gene. In addition these T cells were further found to recognize and lyse, in an HLA-A2 restricted manner, an established tumor cell line naturally expressing B11Ag1 (FIG. 24). The T cells strongly recognize a lung adenocarcinoma (LT-140-22) naturally expressing B11Ag1 transduced with HLA-A2, as well as an A2+ breast carcinoma (CAMA-1) transduced with B11Ag1, but not untransduced lines or another negative tumor line (SW620).

These data clearly demonstrate that these human T cells recognize not only B11-specific peptides but also transduced cells, as well as naturally expressing tumor lines.

CTL lines raised against the antigens B11-5 and B11-12, using the procedures described above, were found to recognize corresponding peptide-coated targets.

Example 6

Characterization of Breast Tumor Genes Discovered by Differential Display PCR

The specificity and sensitivity of the breast tumor genes discovered by differential display PCR were determined using RT-PCR. This procedure enabled the rapid evaluation of breast tumor gene mRNA expression semiquantitatively without using large amounts of RNA. Using gene specific primers, mRNA expression levels in a variety of tissues were examined, including 8 breast tumors, 5 normal breasts, 2 to prostate tumors, 2 colon tumors, 1 lung tumor, and 14 other normal adult human tissues, including normal prostate, colon, kidney, liver, lung, ovary, pancreas, skeletal muscle, skin, stomach and testes.

To ensure the semiquantitative nature of the RT-PCR, β-actin was used is internal control for each of the tissues examined. Serial dilutions of the first strand cDNAs were prepared and RT-PCR assays performed using β-actin specific primers. A dilution was then selected that enabled the linear range amplification of β-actin template, and which was sensitive enough to reflect the difference in the initial copy number. Using this condition, the β-actin levels were determined for each reverse transcription reaction from each tissue. DNA contamination was minimized by DNase treatment and by assuring a negative result when using first strand cDNA that was prepared without adding reverse transcriptase.

Using gene specific primers, the mRNA expression levels were determined in a variety of tissues. To date, 38 genes have been successfully examined by RT-PCR, five of which exhibit good specificity and sensitivity for breast tumors (B15AG-1, B31GA1b, B38GA2a, B11A1a and B18AG1a). FIGS. 21A and 21B depict the results for three of these genes: B15AG-1 (SEQ ID NO:27), B31GA1b (SEQ ID NO:148) and B38GA2a (SEQ ID NO. 157). Table I summarizes the expression level of all the genes tested in normal breast tissue and breast tumors, and also in other tissues.

TABLE I

Percentage of Breast Cancer Antigens that are Expressed in Various Tissues

| | | |
|---|---|---|
| Breast Tissues | Over-expressed in Breast Tumors | 84% |
| | Equally Expressed in Normals and Tumor | 16% |
| Other Tissues | Over-expressed in Breast Tumors but not in any Normal Tissues | 9% |
| | Over-expressed in Breast Tumors but Expressed in Some Normal Tissues | 30% |
| | Over-expressed in Breast Tumors but Equally Expressed in All Other Tissues | 61% |

From the foregoing, it will be appreciated that, although specific embodiments of the invention have been described herein for the purpose of illustration, various modifications may be made without deviating from the spirit and scope of the invention.

What is claimed is:

1. An isolated polypeptide comprising SEQ ID NO:304.
2. A composition comprising a polypeptide according to claim 1 in combination with a physiologically acceptable carrier.

* * * * *

UNITED STATES PATENT AND TRADEMARK OFFICE
CERTIFICATE OF CORRECTION

PATENT NO. : 6,586,570 B1
DATED : July 1, 2003
INVENTOR(S) : Tony N. Frudakis et al.

It is certified that error appears in the above-identified patent and that said Letters Patent is hereby corrected as shown below:

<u>Title page,</u>
Item [56], References Cited, OTHER PUBLICATIONS, the following should be listed:
-- Cordonnier et al., "Isolation of Novel Human Endogenous Retrovirus-Like Elements with Foamy Virus-Related *pol* Sequence," *Journal of Virology 69*(9):5890-5897, 1995

Databank Genebank Accession No. Z34289, 1995.

Ezzell, "Cancer "Vaccines": An Idea Whose Time Has Come?," *The Journal of NIH Research 7*:46-49, 1995.

Frank et al., Genbank Accession No. Q70049, 1994.

Haltmeier et al. "Identification of S71-Related Human Endogenous Retroviral Sequences with Full-Length *pol* Genes," *Virology 209*:550-560, 1995.

Hillier et al., Genbank Accession No. H80165, 1995.

Hillier et al., Genbank Accession No. R19532, 1995.

Hillier et al., Genbank Accession No. R55637, 1995. --

Signed and Sealed this

Twenty-third Day of March, 2004

JON W. DUDAS
*Acting Director of the United States Patent and Trademark Office*

SEQUENCE LISTING

<160> NUMBER OF SEQ ID NOS: 312

<210> SEQ ID NO 1
<211> LENGTH: 363
<212> TYPE: DNA
<213> ORGANISM: Homo sapien

<400> SEQUENCE: 1

```
ttagagaccc aattgggacc taattgggac ccaaatttct caagtggagg gagaactttt      60
gacgatttcc accggtatct cctcgtgggt attcagggag ctgcccagaa acctataaac     120
ttgtctaagg cgattgaagt cgtccagggg catgatgagt caccaggagt gttttagag      180 cacctccagg aggcttatcg gatttacacc ccttttgacc tggcagcccc cgaaaatagc     240
catgctctta atttggcatt tgtggctcag gcagccccag atagtaaaag gaaactccaa     300
aaactagagg gattttgctg gaatgaatac cagtcagctt ttagagatag cctaaaaggt     360
ttt                                                                    363
```

<210> SEQ ID NO 2
<211> LENGTH: 121
<212> TYPE: PRT
<213> ORGANISM: Homo sapien

<400> SEQUENCE: 2

```
Leu Glu Thr Gln Leu Gly Pro Asn Trp Asp Pro Asn Phe Ser Ser Gly
  1               5                  10                  15

Gly Arg Thr Phe Asp Asp Phe His Arg Tyr Leu Leu Val Gly Ile Gln
             20                  25                  30

Gly Ala Ala Gln Lys Pro Ile Asn Leu Ser Lys Ala Ile Glu Val Val
         35                  40                  45

Gln Gly His Asp Glu Ser Pro Gly Val Phe Leu His Leu Gln Glu
     50                  55                  60

Ala Tyr Arg Ile Tyr Thr Pro Phe Asp Leu Ala Ala Pro Glu Asn Ser
 65                  70                  75                  80

His Ala Leu Asn Leu Ala Phe Val Ala Gln Ala Ala Pro Asp Ser Lys
                 85                  90                  95

Arg Lys Leu Gln Lys Leu Glu Gly Phe Cys Trp Asn Glu Tyr Gln Ser
            100                 105                 110

Ala Phe Arg Asp Ser Leu Lys Gly Phe
            115                 120
```

<210> SEQ ID NO 3
<211> LENGTH: 1080
<212> TYPE: DNA
<213> ORGANISM: Homo sapien
<220> FEATURE:
<221> NAME/KEY: misc_feature
<222> LOCATION: (1)...(1080)
<223> OTHER INFORMATION: n = A,T,C or G

<400> SEQUENCE: 3

```
tcttagaatc ttcataccc gaactcttgg gaaaacttta atcagtcacc tacagtctac       60
cacccattta ggaggagcaa agctacctca gctcctccgg agccgtttta agatccccca     120
tcttcaaagc ctaacagatc aagcagctct ccggtgcaca acctgcgccc aggtaaatgc     180 caaaaaggt cctaaaccca gcccaggcca ccgtctccaa gaaaactcac caggagaaaa      240
gtgggaaatt gactttacag aagtaaaacc acaccgggct gggtacaaat accttctagt    300
```

```
actggtagac accttctctg gatggactga agcatttgct accaaaaacg aaactgtcaa    360
tatggtagtt aagtttttac tcaatgaaat catccctcga cgtgggctgc ctgttgccat    420
agggtctgat aatggaacgg ccttcgcctt gtctatagtt taatcagtca gtaaggcgtt    480
aaacattcaa tggaagctcc attgtgccta tcgacccaga gctctgggca agtagaacgc    540
atgaactgca ccctaaaaaa acactcttac aaaattaatc ttaaaaaccg gtgttaattg    600
tgttagtctc cttcccttag ccctacttag agttaaggtg caccccttac tgggctgggt    660
tctttacctt ttgaaatcat ntttnggaag gggctgccta tctttnctta actaaaaaan    720
gcccatttgg caaaaatttc ncaactaatt tntacgtncc tacgtctccc caacaggtan    780
aaaaatctnc tgccctttc aaggaaccat cccatccatt cctnaacaaa aggcctgccn    840
ttcttccccc agttaactnt tttttnttaa aattcccaaa aaangaaccn cctgctggaa    900 aaacncccc ctccaancccc cggccnaagn ggaaggttcc cttgaatccc nccccncna    960 anggcccgga accnttaaan tngttccngg gggtnnggcc taaaagnccn atttggtaaa   1020
cctanaaatt ttttcttttn taaaaaccac nntttnnttt tcttaaaca aaaccctntt   1080
```

<210> SEQ ID NO 4
<211> LENGTH: 1087
<212> TYPE: DNA
<213> ORGANISM: Homo sapien
<220> FEATURE:
<221> NAME/KEY: misc_feature
<222> LOCATION: (1)...(1087)
<223> OTHER INFORMATION: n = A,T,C or G

<400> SEQUENCE: 4

```
tctagagctg cgcctggatc ccgccacagt gaggagacct gaagaccaga gaaaacacag     60
caagtaggcc ctttaaacta ctcacctgtg ttgtcttcta atttattctg ttttatttg    120 tttccatcat tttaaggggt taaaatcatc ttgttcagac ctcagcatat aaaatgaccc    180
atctgtagac ctcaggctcc aaccataccc caagagttgt ctggttttgt ttaaattact    240 gccaggttc agctgcagat atccctggaa ggaatattcc agattcctg agtagtttcc     300 aggttaaaat cctataggct tcttctgttt tgaggaagag ttcctgtcag agaaaaacat    360
gattttggat ttttaacttt aatgcttgtg aaacgctata aaaaaaattt tctaccccta    420
gctttaaagt actgttagtg agaaattaaa attccttcag gaggattaaa ctgccatttc    480
agttacccta attccaaatg ttttggtggt tagaatcttc tttaatgttc ttgaagaagt    540
gttttatatt ttcccatcna gataaaattct ctcncnccttt nnttttntnt ctnntttttt    600
aaaacggant cttgctccgt tgtccangct gggaatttt ttttggccaa tctccgctnc     660
cttgcaanaa tnctgcntcc caaaattacc nccttttcc cacctccacc ccnnggaatt    720
acctggaatt anaggccccc nccccccccc cggctaattt gttttgttt ttagtaaaaa    780 acgggttcc tgttttagtt aggatggccc anntctgacc ccntatcnt ccccctcngc     840 cctcnaatnt tnggnntang gcttaccccc cccngnngtt ttcctccat tnaaattttc    900 tntggantct tgaatnncgg gttttccctt ttaaaccnat ttttttttn nnccccccan    960 ttttncctcc cccntntnta anggggttt ccaaccgg gtccncccc angtcccaa       1020 ttttctcccc ccccctctt tttctttnc cccaaaantc ctatctttc ctnnaaatat    1080 cnantnt                                                             1087
```

<210> SEQ ID NO 5

<211> LENGTH: 1010
<212> TYPE: DNA
<213> ORGANISM: Homo sapien
<220> FEATURE:
<221> NAME/KEY: misc_feature
<222> LOCATION: (1)...(1010)
<223> OTHER INFORMATION: n = A,T,C or G

<400> SEQUENCE: 5

| | | | | | |
|---|---|---|---|---|---|
| tctagaccaa | gaaatgggag | gattttagag | tgactgatga | tttctctatc | atctgcagtt | 60 |
| agtaaacatt | ctccacagtt | tatgcaaaaa | gtaacaaaac | cactgcagat | gacaaacact | 120 |
| aggtaacaca | catactatct | cccaaatacc | tacccacaag | ctcaacaatt | ttaaactgtt | 180 |
| aggatcactg | gctctaatca | ccatgacatg | aggtcaccac | caaaccatca | agcgctaaac | 240 |
| agacagaatg | tttccactcc | tgatccactg | tgtgggaaga | agcaccgaac | ttacccactg | 300 |
| gggggcctgc | ntcanaanaa | aagcccatgc | ccccgggtnt | nccttnaac | cggaacgaat | 360 |
| naacccacca | tccccacanc | tcctctgttc | ntgggccctg | catcttgtgg | cctcntntnc | 420 |
| tttngggan | acntggggaa | ggtaccccat | ttcnttgacc | ccncnanaaa | accccngtgg | 480 |
| cccctttgccc | tgattcncnt | gggccttttc | tcttttccct | tttggttgt | ttaaattccc | 540 |
| aatgtcccn | gaaccctctc | cntnctgccc | aaaacctacc | taaattnctc | nctangnntt | 600 |
| ttcttggtgt | tncttttcaa | aggtnacctt | ncctgttcan | ncccnacnaa | aatttnttcc | 660 |
| ntatnntggn | cccnnaaaaa | nnnatcnncc | cnaattgccc | gaattggttn | ggttttttcct | 720 |
| nctggggaa | acccttttaaa | tttccccctt | ggccggcccc | cctttttcc | cccctttnga | 780 |
| aggcaggngg | ttcttcccga | acttccaatt | ncaacagccn | tgcccattgn | tgaaaccctt | 840 |
| ttcctaaaat | taaaaaatan | ccggttnngg | nnggcctctt | tcccctccng | gngggnngng | 900 |
| aaantcctta | ccccnaaaaa | ggttgcttag | ccccngtcc | ccactccccc | nggaaaaatn | 960 |
| aaccttttcn | aaaaaaggaa | tataantttn | ccactccttn | gttctcttcc | | 1010 |

<210> SEQ ID NO 6
<211> LENGTH: 950
<212> TYPE: DNA
<213> ORGANISM: Homo sapien
<220> FEATURE:
<221> NAME/KEY: misc_feature
<222> LOCATION: (1)...(950)
<223> OTHER INFORMATION: n = A,T,C or G

<400> SEQUENCE: 6

| | | | | | |
|---|---|---|---|---|---|
| tctagagctc | gcggccgcga | gctctaatac | gactcactat | agggcgtcga | ctcgatctca | 60 |
| gctcactgca | atctctgccc | ccggggtcat | gcgattctcc | tgcctcagcc | ttccaagtag | 120 |
| ctgggattac | aggcgtgcaa | caccacaccc | ggctaatttt | gtattttaa | tagagatggg | 180 |
| gttttcccctt | gttggccann | atggtctcna | acccctgacc | tcnngtgatc | ccccncccn | 240 |
| nganctcnna | ctgctgggga | tnccgnnnn | nnncctcccn | ncncnnnnnn | ncncnntccn | 300 |
| tnntccttnc | tcnnnnnnnn | cnntcnntcc | nncttctcnc | cnnntnttnt | cnncnnccnn | 360 |
| cnnnccncnt | ncccncnnnt | tcncntncnn | tntccnncnn | nntcnncnnn | cnnnncntnn | 420 |
| ccnntacntc | ntnnncnnnt | cctctntnn | cctcnncnnt | cnctcncncnt | tntctccctcn | 480 |
| ntnnnnnnct | ccnnnnntct | cntcncnncn | tncctcnntn | nccncncccc | ncctcncnnc | 540 |
| ctnntttnnn | cnncnnntcc | ntncnttcn | nntccnntnn | cnncntcncn | nncnttnttc | 600 |
| ccncnnttc | cttncncntn | nnntcnnn | cncntcnntc | ntttctcct | nnntccnnc | 660 |
| tcnnttcncc | cnnntccncc | cccncnnctnt | ctctcncccn | nntnnntntn | nnncntcccnc | 720 |

| | | | | |
|---|---|---|---|---|
| tntcncnttc | ntcnntncnt | tnctntcnnc | nncnntncnc | tnccntntnt ctnnntcncn 780 |
| tcncntntcn | ccntccnttn | ctntctcctn | tntccttccc | ctncctnct cnttcnccnc 840 |
| ccnntntntn | tnncnccnnt | nctnnncnnc | cntcntttcn | tctctnctnn nnntnnccctc 900 |
| nncccntncc | ctnntncnct | nctnntaccn | tnctncntccn | tcttccttcc 950 |

<210> SEQ ID NO 7
<211> LENGTH: 1086
<212> TYPE: DNA
<213> ORGANISM: Homo sapien
<220> FEATURE:
<221> NAME/KEY: misc_feature
<222> LOCATION: (1)...(1086)
<223> OTHER INFORMATION: n = A,T,C or G

<400> SEQUENCE: 7

| | | | | | |
|---|---|---|---|---|---|
| tctagagctc | gcggccgcga | gctcaattaa | ccctcactaa | agggagtcga | ctcgatcaga 60 |
| ctgttactgt | gtctatgtag | aaagaagtag | acataagaga | ttccattttg | ttctgtacta 120 |
| agaaaaattc | ttctgccttg | agatgctgtt | aatctgtaac | cctagcccca | accctgtgct 180 |
| cacagagaca | tgtgctgtgt | tgactcaagg | ttcaatggat | ttagggctat | gctttgttaa 240 |
| aaaagtgctt | gaagataata | tgcttgttaa | aagtcatcac | cattctctaa | tctcaagtac 300 |
| ccagggacac | aatacactgc | ggaaggccgc | agggacctct | gtctaggaaa | gccaggtatt 360 |
| gtccaagatt | tctccccatg | tgatagcctg | agatatggcc | tcatgggaag | ggtaagacct 420 |
| gactgtcccc | cagcccgaca | tcccccagcc | cgacatcccc | cagcccgaca | cccgaaaagg 480 |
| gtctgtgctg | aggaagatta | ntaaaagagg | aaggctcttt | gcattgaagt | aagaagaagg 540 |
| ctctgtctcc | tgctcgtccc | tgggcaataa | aatgtcttgg | tgttaaaccc | gaatgtatgt 600 |
| tctacttact | gagaatagga | gaaaacatcc | ttagggctgg | aggtgagaca | ccctggcggc 660 |
| atactgctct | ttaatgcacg | agatgtttgt | ntaattgcca | tccagggcca | nccccttttcc 720 |
| ttaactttt | atganacaaa | aactttgttc | ncttttcctg | cgaacctctc | ccctattan 780 |
| cctattggcc | tgcccatccc | ctccccaaan | ggtgaaaana | tgttcntaaa | tncgagggaa 840 |
| tccaaaacnt | tttcccgttg | gtcccctttc | caaccccgtc | cctgggccnn | tttcctcccc 900 |
| aacntgtccc | ggntccttcn | ttcccncccc | cttcccngan | aaaaaacccc | gtntganggn 960 |
| gcccccctcaa | attataaacct | ttccnaaaca | aannggttcn | aaggtggttt | gnttccggtg 1020 |
| cggctggcct | tgaggtcccc | cctncacccc | aatttggaan | ccngttttt | ttattgcccn 1080 |
| ntcccc | | | | | 1086 |

<210> SEQ ID NO 8
<211> LENGTH: 1177
<212> TYPE: DNA
<213> ORGANISM: Homo sapien
<220> FEATURE:
<221> NAME/KEY: misc_feature
<222> LOCATION: (1)...(1177)
<223> OTHER INFORMATION: n = A,T,C or G

<400> SEQUENCE: 8

| | | | | | |
|---|---|---|---|---|---|
| nccntttaga | tgttgacaan | ntaaacaagc | ngctcaggca | gctgaaaaaa | gccactgata 60 |
| aagcatcctg | gagtatcaga | gtttactgtt | agatcagcct | catttgactt | cccctcccac 120 |
| atggtgttta | aatccagcta | cactacttcc | tgactcaaac | tccactattc | ctgttcatga 180 |
| ctgtcaggaa | ctgttggaaa | ctactgaaac | tggccgacct | gatcttcaaa | atgtgcccct 240 |

-continued

| | |
|---|---|
| aggaaaggtg gatgccaccg tgttcacaga cagtaccncc ttcctcgaga agggactacg | 300 |
| aggggccggt gcanctgtta ccaaggagac tnatgtgttg tgggctcagg ctttaccanc | 360 |
| aaacacctca ncncnnaagg ctgaattgat cgccctcact caggctctcg gatgggtaa | 420 |
| gggatattaa cgttaacact gacagcaggt acgcctttgc tactgtgcat gtacgtggag | 480 |
| ccatctacca ggagcgtggg ctactcactc ggcaggtggc tgtnatccac tgtaaangga | 540 |
| catcaaaagg aaaacnnggc tgttgcccgt ggtaaccana aanctgatcn ncagctcnaa | 600 |
| gatgctgtgt tgactttcac tcncncctct taaacttgct gcccacantc tcctttccca | 660 |
| accagatctg cctgacaatc cccatactca aaaaaaaaan aanactggcc ccgaacccna | 720 |
| accaataaaa acggggangg tnggtnganc nncctgaccc aaaaataatg gatccccgg | 780 |
| gctgcaggaa ttcaattcan ccttatcnat accccaacn nggngggggg ggccngtncc | 840 |
| cattnccct ntattnattc tttnnccccc ccccggcnt ccttttnaa ctcgtgaaag | 900 |
| ggaaaacctg ncttaccaan ttatcncctg gaccntcccc ttccncggtn gnttanaaaa | 960 |
| aaaagcccnc antcccntcc naaatttgca cngaaaggna aggaatttaa cctttatttt | 1020 |
| ttnntcctt antttgtnnn ccccctttta cccaggcgaa cngccatcnt ttaanaaaaa | 1080 |
| aaanagaang tttattttc cttngaacca tcccaatana aancacccgc ngggggaacgg | 1140 |
| ggnggnaggc cnctcacccc ctttntgtng gnggnc | 1177 |

<210> SEQ ID NO 9
<211> LENGTH: 1146
<212> TYPE: DNA
<213> ORGANISM: Homo sapien
<220> FEATURE:
<221> NAME/KEY: misc_feature
<222> LOCATION: (1)...(1146)
<223> OTHER INFORMATION: n = A,T,C or G

<400> SEQUENCE: 9

| | |
|---|---|
| nccnnttnnt gatgttgtct ttttggcctc tctttggata ctttccctct cttcagaggt | 60 |
| gaaaagggtc aaaaggagct gttgacagtc atcccaggtg ggccaatgtg tccagagtac | 120 |
| agactccatc agtgaggtca aagcctgggg cttttcagag aagggaggat tatgggtttt | 180 |
| ccaattatac aagtcagaag tagaaagaag ggacataaac caggaagggg gtggagcact | 240 |
| catcacccag agggacttgt gcctctctca gtggtagtag aggggctact tcctcccacc | 300 |
| acggttgcaa ccaagaggca atgggtgatg agcctacagg gacatancc gaggagacat | 360 |
| gggatgaccc taagggagta ggctggtttt aaggcggtgg gactgggtga gggaaactct | 420 |
| cctcttcttc agagagaagc agtacagggc gagctgaacc ggctgaaggt cgaggcgaaa | 480 |
| acacggtctg gctcaggaag accttggaag taaaattatg aatggtgcat gaatggagcc | 540 |
| atggaagggg tgctcctgac caaactcagc cattgatcaa tgttagggaa actgatcagg | 600 |
| gaagccggga atttcattaa caacccgcca cacagcttga acattgtgag gttcagtgac | 660 |
| ccttcaaggg gccactccac tccaactttg gccattctac tttgcnaaat ttccaaaact | 720 |
| tcctttttta aggccgaatc cntantccct naaaaacnaa aaaaaatctg cnccctattct | 780 |
| ggaaaaggcc canccttac caggctggaa gaaattttnc cttttttttt ttttgaagg | 840 |
| cntttnttaa attgaacctn aattcnccc cccaaaaaaa aacccnccng ggggcggat | 900 |
| ttccaaaaac naattccctt accaaaaaac aaaaaccnc ccttnttccc ttccnccctn | 960 |
| ttcttttaat tagggagaga tnaagccccc caatttccng gnctngatnn gtttccccc | 1020 |
| ccccccatttt ccnaaaacttt ttcccancna ggaanccncc ctttttttng gtcngattna | 1080 |

```
ncaaccttcc aaaccatttt tccnnaaaaa ntttgntngg ngggaaaaan acctnntttt    1140 atagan                                                              1146

<210> SEQ ID NO 10
<211> LENGTH: 545
<212> TYPE: DNA
<213> ORGANISM: Homo sapien

<400> SEQUENCE: 10
cttcattggg tacgggcccc ctcgaggtcg acggtatcga taagcttgat atcgaattcc     60
tgcagcccgg gggatccact agttctagag tcaggaagaa ccaccaacct tcctgatttt    120
tattggctct gagttctgag gccagttttc ttcttctgtt gagtatgcgg gattgtcagg    180
cagatctggc tgtggaaagg agactgtggg cagcaagttt agaggcgtga ctgaaagtca    240
cactgcatct tgagctgctg aatcagcttt ctggttacca cggcaacag ccgtgttttc     300 cttttgatgt cctttacagt ggattacagc cacctgctga ggtgagtagc ccacgctcct    360
ggtagatggc tccacgtaca tgcacagtag caaaggcgta cctgctgtca gtgttaacgt    420
taatatcctt accccatcgg agagcctgag tgagggcgat caattcagcc cttttgtgct    480
gaggtgtttg ctggttaagc cctgaaccca caacacatct gtctccatgg taacagctgc    540
accgg                                                                545

<210> SEQ ID NO 11
<211> LENGTH: 196
<212> TYPE: DNA
<213> ORGANISM: Homo sapien

<400> SEQUENCE: 11
tctcctaggc tgggcacagt ggctcatacc tgtaatcctg accgtttcag aggctcaggt     60 gggggatcg cttgagccca agatttcaag actagtctgg gtaacatagt gagaccctat     120
ctctacgaaa aaataaaaaa atgagcctgg tgtagtggca cacaccagct gaggagggag    180
aatcgagcct aggaga                                                   196

<210> SEQ ID NO 12
<211> LENGTH: 388
<212> TYPE: DNA
<213> ORGANISM: Homo sapien
<220> FEATURE:
<221> NAME/KEY: misc_feature
<222> LOCATION: (1)...(388)
<223> OTHER INFORMATION: n = A,T,C or G

<400> SEQUENCE: 12
tctcctaggc ttgggggctc tgactagaaa ttcaaggaac ctgggattca agtccaactg     60
tgacaccaac ttcactgtg gnctccaata aactgcttct ttcctattcc ctctctatta     120
aataaaataa ggaaaacgat gtctgtgtat agccaagtca gntatcctaa aaggagatac    180
taagtgacat taaatatcag aatgtaaaac ctgggaacca ggttcccagc ctgggattaa    240
actgacagca agaagactga acagtactac tgtgaaaagc ccgaagnggc aatatgttca    300
ctctaccgtt gaaggatggc tgggagaatg aatgctctgt ccccagtcc caagctcact     360 tactatacct cctttatagc ctaggaga                                       388

<210> SEQ ID NO 13
<211> LENGTH: 337
<212> TYPE: DNA
```

<213> ORGANISM: Homo sapien

<400> SEQUENCE: 13

| | | | | | |
|---|---|---|---|---|---|
| tagtagttgc | ctataatcat | gtttctcatt | attttcacat | tttattaacc | aatttctgtt | 60 |
| taccctgaaa | aatatgaggg | aaatatatga | acagggagg | caatgttcag | ataattgatc | 120 |
| acaagatatg | atttctacat | cagatgctct | ttcctttcct | gtttatttcc | tttttatttc | 180 |
| ggttgtgggg | tcgaatgtaa | tagctttgtt | tcaagagaga | gttttggcag | tttctgtagc | 240 |
| ttctgacact | gctcatgtct | ccaggcatct | atttgcactt | taggaggtgt | cgtgggagac | 300 |
| tgagaggtct | attttttcca | tatttgggca | actacta | | | 337 |

<210> SEQ ID NO 14
<211> LENGTH: 571
<212> TYPE: DNA
<213> ORGANISM: Homo sapien
<220> FEATURE:
<221> NAME/KEY: misc_feature
<222> LOCATION: (1)...(571)
<223> OTHER INFORMATION: n = A,T,C or G

<400> SEQUENCE: 14

| | | | | | |
|---|---|---|---|---|---|
| tagtagttgc | catacagtgc | ctttccattt | atttaaccccc | cacctgaacg | gcataaactg | 60 |
| agtgttcagc | tggtgttttt | tactgtaaac | aataaggaga | ctttgctctt | catttaaacc | 120 |
| aaaatcatat | ttcatatttt | acgctcgagg | gttttttaccg | gttccttttt | acactcctta | 180 |
| aaacagtttt | taagtcgttt | ggaacaagat | atttttttctt | tcctggcagc | ttttaacatt | 240 |
| atagcaaatt | tgtgtctggg | ggactgctgg | tcactgtttc | tcacagttgc | aaatcaaggc | 300 |
| atttgcaacc | aagaaaaaaa | aatttttttg | ttttatttga | aactggaccg | gataaacggt | 360 |
| gtttggagcg | gctgctgtat | atagttttaa | atggtttatt | gcacctcctt | aagttgcact | 420 |
| tatgtggggg | gggnttttg | natagaaagt | ntttantcac | anagtcacag | ggacttttnt | 480 |
| cttttggnna | ctgagctaaa | aagggctgnt | tttcgggtgg | gggcagatga | aggctcacag | 540 |
| gaggcctttc | tcttagaggg | gggaactnct | a | | | 571 |

<210> SEQ ID NO 15
<211> LENGTH: 548
<212> TYPE: DNA
<213> ORGANISM: Homo sapien
<220> FEATURE:
<221> NAME/KEY: misc_feature
<222> LOCATION: (1)...(548)
<223> OTHER INFORMATION: n = A,T,C or G

<400> SEQUENCE: 15

| | | | | | |
|---|---|---|---|---|---|
| tatatattta | ataacttaaa | tatattttga | tcacccactg | gggtgataag | acaatagata | 60 |
| taaaagtatt | tccaaaaagc | ataaaaccaa | agtatcatac | caaaccaaat | tcatactgct | 120 |
| tcccccaccc | gcactgaaac | ttcaccttct | aactgtctac | ctaaccaaat | tctacccttc | 180 |
| aagtctttgg | tgcgtgctca | ctactctttt | tttttttttt | tttntttttgg | agatggagtc | 240 |
| tggctgtgca | gcccagggt | ggagtacaat | ggcacaacct | cagctcactg | naacctccgc | 300 |
| ctcccaggtt | catgagattc | tcctgnttca | gccttcccag | tagctgggac | tacaggtgtg | 360 |
| catcaccatg | cctggntaat | ctttttttngt | tttngggtag | agatgggggt | tttacatgtt | 420 |
| ggccaggntg | gtntcgaact | cctgacctca | agtgatccac | ccacctcagg | ctcccaaagt | 480 |
| gctaggatta | cagacatgag | ccactgngcc | cagncctggt | gcatgctcac | ttctctaggc | 540 |
| aactacta | | | | | | 548 |

<210> SEQ ID NO 16
<211> LENGTH: 638
<212> TYPE: DNA
<213> ORGANISM: Homo sapien
<220> FEATURE:
<221> NAME/KEY: misc_feature
<222> LOCATION: (1)...(638)
<223> OTHER INFORMATION: n = A,T,C or G

<400> SEQUENCE: 16

```
ttccgttatg cacatgcaga atattctatc ggtacttcag ctattactca ttttgatggc      60
gcaatccgag cctatcctca agatgagtat ttagaaagaa ttgatttagc gatagaccaa     120
gctggtaagc actctgacta cacgaaattg ttcagatgtg atggatttat gacagttgat     180
ctttggaaga gattattaag tgattatttt aaagggaatc cattaattcc agaatatctt     240
ggtttagctc aagatgatat agaaatagaa cagaaagaga ctacaaatga agatgtatca     300
ccaactgata ttgaagagcc tatagtagaa atgaattag ctgcatttat tagccttaca      360
catagcgatt ttcctgatga atcttatatt cagccatcga catagcatta cctgatgggc     420
aaccttacga ataatagaaa ctgggtgcgg ggctattgat gaattcatcc ncagtaaatt     480
tggatatnac aaaatataac tcgattgcat ttggatgatg gaatactaaa tctggcaaaa     540
gtaactttgg agctactagt aacctctctt tttgagatgc aaaattttct tttagggttt     600
cttattctct actttacgga tattggagca taacggga                            638
```

<210> SEQ ID NO 17
<211> LENGTH: 286
<212> TYPE: DNA
<213> ORGANISM: Homo sapien

<400> SEQUENCE: 17

```
actgatggat gtcgccggag gcgaggggcc ttatctgatg ctcggctgcc tgttcgtgat      60
gtgcgcggcg attgggctgt ttatctcaaa caccgccacg gcggtgctga tggcgccta     120 tgccttagcg gcggcgaagt caatgggcgt ctcaccctat ccttttgcca tggtggtggc     180
gatggcggct tcggcggcgt ttatgacccc ggtctcctcg ccggttaaca ccctggtgct     240
tggccctggc aagtactcat ttagcgattt tgtcaaaata ggcgtg                   286
```

<210> SEQ ID NO 18
<211> LENGTH: 262
<212> TYPE: DNA
<213> ORGANISM: Homo sapien
<220> FEATURE:
<221> NAME/KEY: misc_feature
<222> LOCATION: (1)...(262)
<223> OTHER INFORMATION: n = A,T,C or G

<400> SEQUENCE: 18

```
tcggtcatag cagcccttc ttctcaattt catctgtcac taccctggtg tagtatctca       60
tagccttaca tttttatagc ctcctccctg gtctgtcttt tgattttcct gcctgtaatc     120
catatcacac ataactgcaa gtaaacattt ctaaagtgtg gttatgctca tgtcactcct     180
gtgncaagaa atagtttcca ttaccgtctt aataaaattc ggatttgttc tttnctattn     240
tcactcttca cctatgaccg aa                                             262
```

<210> SEQ ID NO 19
<211> LENGTH: 261
<212> TYPE: DNA

<213> ORGANISM: Homo sapien

<400> SEQUENCE: 19

| tcggtcatag caaagccagt ggtttgagct ctctactgtg taaactccta aaccaaggcc | 60 |
| atttatgata aatggtggca ggatttttat tataaacatg tacccatgca aatttcctat | 120 |
| aactctgaga tatattcttc tacatttaaa caataaaaat aatctatttt taaaagccta | 180 |
| atttgcgtag ttaggtaaga gtgtttaatg agagggtata aggtataaat caccagtcaa | 240 |
| cgtttctctg cctatgaccg a | 261 |

<210> SEQ ID NO 20
<211> LENGTH: 294
<212> TYPE: DNA
<213> ORGANISM: Homo sapien
<220> FEATURE:
<221> NAME/KEY: misc_feature
<222> LOCATION: (1)...(294)
<223> OTHER INFORMATION: n = A,T,C or G

<400> SEQUENCE: 20

| tacaacgagg cgacgtcggt aaaatcggac atgaagccac cgctggtctt ttcgtccgag | 60 |
| cgataggcgc cggccagcca gcggaacggt tgcccggatg gcgaagcgag ccggagttct | 120 |
| tcggactgag tatgaatctt gttgtgaaaa tactcgccgc cttcgttcga cgacgtcgcg | 180 |
| tcgaaatctt cganctcctt acgatcgaag tcttcgtggg cgacgatcgc ggtcagttcc | 240 |
| gccccaccga aatcatggtt gagccggatg ctgnccccga agncctcgtt tgtn | 294 |

<210> SEQ ID NO 21
<211> LENGTH: 208
<212> TYPE: DNA
<213> ORGANISM: Homo sapien
<220> FEATURE:
<221> NAME/KEY: misc_feature
<222> LOCATION: (1)...(208)
<223> OTHER INFORMATION: n = A,T,C or G

<400> SEQUENCE: 21

| ttggtaaagg gcatggacgc agacgcctga cgtttggctg aaaatctttc attgattcgt | 60 |
| atcaatgaat aggaaaattc ccaaagaggg aatgtcctgt tgctcgccag tttttntgtt | 120 |
| gttctcatgg anaaggcaan gagctcttca gactattggn attntcgttc ggtcttctgc | 180 |
| caactagtcg ncttgcnang atcttcat | 208 |

<210> SEQ ID NO 22
<211> LENGTH: 287
<212> TYPE: DNA
<213> ORGANISM: Homo sapien
<220> FEATURE:
<221> NAME/KEY: misc_feature
<222> LOCATION: (1)...(287)
<223> OTHER INFORMATION: n = A,T,C or G

<400> SEQUENCE: 22

| nccnttgagc tgagtgattg agatntgtaa tggttgtaag ggtgattcag gcggattagg | 60 |
| gtggcgggtc acccggcagt gggtctcccg acaggccagc aggatttggg gcaggtacgg | 120 |
| ngtgcgcatc gctcgactat atgctatggc aggcgagccg tggaaggngg atcaggtcac | 180 |
| ggcgctggag ctttccacgg tccatgnatt gngatggctg ttctaggcgg ctgttgccaa | 240 |
| gcgtgatggt acgctggctg gagcattgat ttctggtgcc aaggtgg | 287 |

<210> SEQ ID NO 23
<211> LENGTH: 204
<212> TYPE: DNA
<213> ORGANISM: Homo sapien
<220> FEATURE:
<221> NAME/KEY: misc_feature
<222> LOCATION: (1)...(204)
<223> OTHER INFORMATION: n = A,T,C or G

<400> SEQUENCE: 23
ttgggtaaag ggagcaagga gaaggcatgg agaggctcan gctggtcctg gcctacgact    60
gggccaagct gtcgccgggg atggtggaga actgaagcgg gacctcctcg aggtcctccg   120
ncgttacttc nccgtccagg aggagggtct ttccgtggtc tnggaggagc gggggggagaa  180 gatnctcctc atggtcnaca tccc                                         204

<210> SEQ ID NO 24
<211> LENGTH: 264
<212> TYPE: DNA
<213> ORGANISM: Homo sapien
<220> FEATURE:
<221> NAME/KEY: misc_feature
<222> LOCATION: (1)...(264)
<223> OTHER INFORMATION: n = A,T,C or G

<400> SEQUENCE: 24
tggattggtc aggagcgggt agagtggcac cattgagggg atattcaaaa atattatttt    60
gtcctaaatg atagttgctg agttttcttt gacccatga gttatattgg agtttatttt   120
ttaactttcc aatcgcatgg acatgttaga cttattttct gttaatgatt nctatttta   180 ttaaattgga tttgagaaat tggttnttat tatatcaatt tttggtattt gttgagtttg   240
acattatagc ttagtatgtg acca                                         264

<210> SEQ ID NO 25
<211> LENGTH: 376
<212> TYPE: DNA
<213> ORGANISM: Homo sapien
<220> FEATURE:
<221> NAME/KEY: misc_feature
<222> LOCATION: (1)...(376)
<223> OTHER INFORMATION: n = A,T,C or G

<400> SEQUENCE: 25
ttacaacgag gggaaactcc gtctctacaa aaattaaaaa attagccagg tgtggtggtg    60
tgcacccgca atcccagcta cttgggaggt tgagacacaa gantcaccta natgtgggag   120
gtcaaggttg catgagtcat gattgtgcca ctgcactcca gcctgggtga cagaccgaga   180
ccctgcctca anaganaang aataggaagt tcagaaatcn tggntgtggn gcccagcaat   240
ctgcatctat ncaacccctg caggcaangc tgatgcagcc tangttcaag agctgctgtt   300
tctggaggca gcagttnggg cttccatcca gtatcacggc cacactcgca cnagccatct   360
gtcctccgtn tgtnac                                                  376

<210> SEQ ID NO 26
<211> LENGTH: 372
<212> TYPE: DNA
<213> ORGANISM: Homo sapien
<220> FEATURE:
<221> NAME/KEY: misc_feature
<222> LOCATION: (1)...(372)
<223> OTHER INFORMATION: n = A,T,C or G

<400> SEQUENCE: 26

```
ttacaacgag gggaaactcc gtctctacaa aaattaaaaa attagccagg tgtggtggtg      60
tgcacctgta atcccagcta cttgggcggc tgagacacaa gaaccaccta aatgtgggag     120
ggtcaaggtt gcatgagtca tgatcgcgcc actgcactcc agcctgggtg acagactgag     180
accctgcctc aaaagaaaaa gaataggaag ttcagaaacc ctgggtgtgg ngcccagcaa     240
tctgcattta aacaatccct gcaggcaatg ctgatgcagc ctaagttcaa gagctgctgt     300
tctggaggca gnagtaaggg cttccatcca gcatcacggn caacactgca aaagcacctg     360
tcctcgttgg ta                                                        372

<210> SEQ ID NO 27
<211> LENGTH: 477
<212> TYPE: DNA
<213> ORGANISM: Homo sapien

<400> SEQUENCE: 27
ttctgtccac atctacaagt tttatttatt ttgtgggttt tcagggtgac taagtttttc      60
cctacattga aaagagaagt tgctaaaagg tgcacaggaa atcattttt taagtgaata     120 tgataatatg ggtccgtgct taatacaact gagacatatt tgttctctgt tttttagag     180 tcacctctta aagtccaatc ccacaatggt gaaaaaaaa tagaaagtat ttgttctacc     240
tttaaggaga ctgcagggat tctccttgaa aacggagtat ggaatcaatc ttaaataaat     300
atgaaattgg ttggtcttct gggataagaa attcccaact cagtgtgctg aaattcacct     360
gacttttttt gggaaaaaat agtcgaaaat gtcaatttgg tccataaaat acatgttact     420
attaaaagat atttaaagac aaattctttc agagctctaa gattggtgtg gacagaa        477

<210> SEQ ID NO 28
<211> LENGTH: 438
<212> TYPE: DNA
<213> ORGANISM: Homo sapien
<220> FEATURE:
<221> NAME/KEY: misc_feature
<222> LOCATION: (1)...(438)
<223> OTHER INFORMATION: n = A,T,C or G

<400> SEQUENCE: 28
tctncaacct cttgantgtc aaaaaccttn taggctatct ctaaaagctg actggtattc      60
attccagcaa aatccctcta gtttttggag tttcctttta ctatctgggg ctgcctgagc     120
cacaaatgcc aaattaagag catggctatt tcgggggct gacaggtcaa aagggggtgta     180 aatccgataa gcctcctgga ggtgctctaa aaacactcct ggtgactcat catgcccctg     240
gacgacttca atcgncttag acaagtttat aggtttctgg gcagctccct gaatacccac     300
gaggagatac cggtggaaat cgtcaaaagt tctccctcca cttgagaaat ttgggtccca     360
attaggtccc aattgggtct ctaatcacta ttcctctagc ttcctcctcc ggnctattgg     420
ttgatgtgag gttgaaga                                                  438

<210> SEQ ID NO 29
<211> LENGTH: 620
<212> TYPE: DNA
<213> ORGANISM: Homo sapien
<220> FEATURE:
<221> NAME/KEY: misc_feature
<222> LOCATION: (1)...(620)
<223> OTHER INFORMATION: n = A,T,C or G

<400> SEQUENCE: 29
aagagggtac cagcccccaag ccttgacaac ttccataggg tgtcaagcct gtgggtgcac      60
```

| agaagtcaaa | aattgagttt | tgggatcctc | agcctagatt | tcagaggata | taaagaaaca | 120 |
| cctaacacct | agatattcag | acaaaagttt | actacaggga | tgaagctttc | acggaaaacc | 180 |
| tctactagga | aagtacagaa | gagaaatgtg | ggtttggagc | ccccaaacag | aatcccctct | 240 |
| agaacactgc | ctaatgaaac | tgtgagaaga | tggccactgt | catccagaca | ccagaatgat | 300 |
| agacccacca | aaaacttatg | ccatattgcc | tataaaacct | acagacactc | aatgccagcc | 360 |
| ccatgaaaaa | aaaactgaga | agaagactgt | ncccctacaat | gccaccggag | cagaactgcc | 420 |
| ccaggccatg | gaagcacagc | tcttatatca | atgtgacctg | gatgttgaga | catggaatcc | 480 |
| nangaaatcn | ttttaanact | tccacggttn | aatgactgcc | ctattanatt | cngaacttan | 540 |
| atccnggcct | gtgacctctt | tgctttggcc | attccccctt | tttggaatgg | ctntttttt | 600 |
| cccatgcctg | tncctctta | | | | | 620 |

<210> SEQ ID NO 30
<211> LENGTH: 100
<212> TYPE: DNA
<213> ORGANISM: Homo sapien

<400> SEQUENCE: 30

| ttacaacgag | ggggtcaatg | tcataaatgt | cacaataaaa | caatctcttc | tttttttttt | 60 |
| tttttttttt | tttttttttt | tttttttttt | tttttttttt | | | 100 |

<210> SEQ ID NO 31
<211> LENGTH: 762
<212> TYPE: DNA
<213> ORGANISM: Homo sapien
<220> FEATURE:
<221> NAME/KEY: misc_feature
<222> LOCATION: (1)...(762)
<223> OTHER INFORMATION: n = A,T,C or G

<400> SEQUENCE: 31

| tagtctatgc | gccggacaga | gcagaattaa | attggaagtt | gccctccgga | ctttctaccc | 60 |
| acactcttcc | tgaaaagaga | aagaaaagag | gcaggaaaga | ggttaggatt | tcattttcaa | 120 |
| gagtcagcta | attaggagag | cagagtttag | acagcagtag | gcaccccatg | atacaaacca | 180 |
| tggacaaagt | ccctgtttag | taactgccag | acatgatcct | gctcaggttt | tgaaatctct | 240 |
| ctgcccataa | aagatggaga | gcaggagtgc | catccacatc | aacacgtgtc | caagaaagag | 300 |
| tctcagggag | acaagggtat | caaaaaacaa | gattcttaat | gggaaggaaa | tcaaaccaaa | 360 |
| aaattagatt | tttctctaca | tatatataat | atacagatat | ttaacacatt | attccagagg | 420 |
| tggctccagt | ccttggggct | tgagagatgg | tgaaaacttt | tgttccacat | taacttctgc | 480 |
| tctcaaattc | tgaagtatat | cagaatggga | caggcaatgt | tttgctccac | actggggcac | 540 |
| agacccaaat | ggttctgtgc | cgaagaaga | gaagcccgaa | agacatgaag | gatgcttaag | 600 |
| gggggttggg | aaagccaaat | tggtantatc | ttttcctcct | gcctgtgttc | cngaagtctc | 660 |
| cnctgaagga | attcttaaaa | ccctttgtga | ggaaatgccc | ccttaccatg | acaantggtc | 720 |
| ccattgcttt | tagggngatg | gaaacaccaa | gggttttgat | cc | | 762 |

<210> SEQ ID NO 32
<211> LENGTH: 276
<212> TYPE: DNA
<213> ORGANISM: Homo sapien

<400> SEQUENCE: 32

```
tagtctatgc gtgtattaac ctcccctccc tcagtaacaa ccaaagaggc aggagctgtt      60
attaccaacc ccatttttaca gatgcatcaa taatgacaga gaagtgaagt gacttgcgca    120
cacaaccagt aaaattggcag agtcagattt gaatccatgg agtctggtct gcactttcaa    180
tcaccgaata cccttctaa gaacgtgtg ctgaatgagt gcatggataa atcagtgtct       240
actcaacatc tttgcctaga tatcccgcat agacta                               276
```

<210> SEQ ID NO 33
<211> LENGTH: 477
<212> TYPE: DNA
<213> ORGANISM: Homo sapien

<400> SEQUENCE: 33

```
tagtagttgc caaatatttg aaaatttacc cagaagtgat tgaaaacttt ttggaaacaa      60
aaacaaataa agccaaaagg taaaataaaa atatctttgc actctcgtta ttacctatcc    120
ataacttttt caccgtaagc tctcctgctt gttagtgtag tgtggttata ttaaactttt    180
tagttattat ttttttattca cttttccact agaaagtcat tattgattta gcacacatgt   240
tgatctcatt tcatttttc tttttatagg caaaatttga tgctatgcaa caaaaatact     300
caagcccatt atcttttttc ccccgaaat ctgaaaattg caggggacag agggaagtta     360
tcccattaaa aaattgtaaa tatgttcagt ttatgtttaa aaatgcacaa aacataagaa     420
aattgtgttt acttgagctg ctgattgtaa gcagttttat ctcagggca actacta        477
```

<210> SEQ ID NO 34
<211> LENGTH: 631
<212> TYPE: DNA
<213> ORGANISM: Homo sapien

<400> SEQUENCE: 34

```
tagtagttgc caattcagat gatcagaaat gctgctttcc tcagcattgt cttgttaaac      60
cgcatgccat ttggaacttt ggcagtgaga agccaaaagg aagaggtgaa tgacatatat    120
atatatatat attcaatgaa agtaaaatgt atatgctcat atactttcta gttatcagaa    180
tgagttaagc tttatgccat tgggctgctg catatttaa tcagaagata aagaaaatc      240 tgggcatttt tagaatgtga tacatgtttt tttaaaactg ttaaatatta tttcgatatt    300
tgtctaagaa ccggaatgtt cttaaaattt actaaaacag tattgtttga ggaagagaaa    360
actgtactgt ttgccattat tacagtcgta caagtgcatg tcaagtcacc cactctctca    420
ggcatcagta tccacctcat agctttacac attttgacgg ggaatattgc agcatcctca    480
ggcctgacat ctgggaaagg ctcagatcca cctactgctc cttgctcgtt gatttgtttt    540
aaaatattgt gcctggtgtc acttttaagc cacagccctg cctaaaagcc agcagagaac    600
agaacccgca ccattctata ggcaactact a                                   631
```

<210> SEQ ID NO 35
<211> LENGTH: 578
<212> TYPE: DNA
<213> ORGANISM: Homo sapien

<400> SEQUENCE: 35

```
tagtagttgc catcccatat tacagaaggc tctgtataca tgacttattt ggaagtgatc      60
tgttttctct ccaaacccat ttatcgtaat tcaccagtc ttggatcaat cttggttttcc    120 actgatacca tgaaacctac ttggagcaga cattgcacag ttttctgtgg taaaaactaa    180
aggtttattt gctaagctgt catcttatgc ttagtatttt tttttttacag tggggaattg   240
```

```
ctgagattac attttgttat tcattagata ctttgggata acttgacact gtcttctttt      300
tttcgctttt aattgctatc atcatgcttt tgaaacaaga acacattagt cctcaagtat      360
tacataagct tgcttgttac gcctggtggt ttaaaggact atctttggcc tcaggttcac      420
aagaatgggc aaagtgtttc cttatgttct gtagttctca ataaaagatt gccagggggcc     480 gggtactgtg gctcgcactg taatcccagc actttgggaa gctgaggctg gcggatcatg      540
ttagggcagg tgttcgaaac cagcctgggc aactacta                              578

<210> SEQ ID NO 36
<211> LENGTH: 583
<212> TYPE: DNA
<213> ORGANISM: Homo sapien

<400> SEQUENCE: 36
tagtagttgc ctgtaatccc agcaactcag gaggctgggg caggagaatc agttgaacct       60
gggaggcaga agttgtaatt agcaaagatc gcaccattgc acttcagcct gggcaacaag      120
agtgagattc catctcaaaa acaaaaaaaa gaaaagaaa  agaaaaggaa aaaacgtata      180
aacccagcca aacaaaatg atcattcttt taataagcaa gactaattta atgtgtttat       240
ttaatcaaag cagttgaatc ttctgagtta ttggtgaaaa tacccatgta gttaatttag      300
ggttcttact tgggtgaacg tttgatgttc acaggttata aaatggttaa caaggaaaat      360
gatgcataaa gaatcttata aactactaaa ataaataaa  atataaatgg ataggtgcta      420
tggatggagt ttttgtgtaa tttaaaatct tgaagtcatt ttggatgctc attggttgtc      480
tggtaatttc cattaggaaa aggttatgat atggggaaac tgtttctgga aattgcggaa      540
tgtttctcat ctgtaaaatg ctagtatctc agggcaacta cta                       583

<210> SEQ ID NO 37
<211> LENGTH: 716
<212> TYPE: DNA
<213> ORGANISM: Homo sapien
<220> FEATURE:
<221> NAME/KEY: misc_feature
<222> LOCATION: (1)...(716)
<223> OTHER INFORMATION: n = A,T,C or G

<400> SEQUENCE: 37
gatctactag tcatntggat tctatccatg gcagctaagc ctttctgaat ggattctact       60
gctttcttgt tctttaatcc agaccctat  atatgtttat gttcacaggc agggcaatgt      120
ttagtgaaaa caattctaaa ttttttattt tgcattttca tgctaatttc cgtcacactc      180
cagcaggctt cctgggagaa taaggagaaa tacagctaaa gacattgtcc ctgcttactt      240
acagcctaat ggtatgcaaa accacttcaa taaagtaaca ggaaaagtac taaccaggta      300
gaatggacca aaactgatat agaaaaatca gaggaagaga ggaacaaata tttactgagt      360
cctagaatgt acaaggcttt ttaattacat attttatgta aggcctgcaa aaaacaggtg      420
agtaatcaac atttgtccca ttttacatat aaggaaactg aagcttaaat tgaataattt      480
aatgcataga ttttatagtt agaccatgtt caggtcccta tgttatactt actagctgta      540
tgaatatgag aaaataattt tgttattttc ttggcatcag tattttcatc tgcaaaataa      600
agctaaagtt atttagcaaa cagtcagcat agtgcctgat acatagtagg tgctccaaac      660
atgattacnc tantattngg tattanaaaa atccaatata ggcntggata aaaccg         716

<210> SEQ ID NO 38
```

<211> LENGTH: 688
<212> TYPE: DNA
<213> ORGANISM: Homo sapien
<220> FEATURE:
<221> NAME/KEY: misc_feature
<222> LOCATION: (1)...(688)
<223> OTHER INFORMATION: n = A,T,C or G

<400> SEQUENCE: 38

```
ttctgtccac atatcatccc actttaattg ttaatcagca aactttcaa tgaaaaatca      60
tccattttaa ccaggatcac accaggaaac tgaaggtgta ttttttttta ccttaaaaaa     120
aaaaaaaaaa accaaacaaa ccaaaacaga ttaacagcaa agagttctaa aaaatttaca    180
tttctcttac aactgtcatt cagagaacaa tagttcttaa gtctgttaaa tcttggcatt    240
aacagagaaa cttgatgaan agttgtactt ggaatattgt ggatttttt ttttgtctaa    300
tctcccccta ttgttttgcc aacagtaatt taagtttgtg tggaacatcc ccgtagttga    360
agtgtaaaca atgtatagga aggaatatat gataagatga tgcatcacat atgcattaca    420
tgtagggacc ttcacaactt catgcactca gaaaacatgc ttgaagagga ggagaggacg    480
gcccagggtc accatccagg tgccttgagg acagagaatg cagaagtggc actgttgaaa    540
tttagaagac catgtgtgaa tggtttcagg cctgggatgt ttgccaccaa gaagtgcctc    600
cgagaaattt ctttcccatt tggaatacag ggtggcttga tgggtacggt gggtgaccca    660
acgaagaaaa tgaaattctg ccctttcc                                       688
```

<210> SEQ ID NO 39
<211> LENGTH: 585
<212> TYPE: DNA
<213> ORGANISM: Homo sapien
<220> FEATURE:
<221> NAME/KEY: misc_feature
<222> LOCATION: (1)...(585)
<223> OTHER INFORMATION: n = A,T,C or G

<400> SEQUENCE: 39

```
tagtagttgc cgcnnaccta aaanttggaa agcatgatgt ctaggaaaca tantaaaata      60
gggtatgcct atgtgctaca gagagatgtt agcatttaaa gtgcatantt ttatgtattt    120
tgacaaatgc atatncctct ataatccaca actgattacg aagctattac aattaaaaag    180
tttggccggg cgtggtgggc ggtggctgac gcctgtaatc ccagcacttt gggaggccga    240
ggcacgcgga tcacgaggtc gggagttcaa gaccatcctg gctaacacgg tgaaagtcca    300
tctctactaa aaatacgaaa aaattacccc ggcgtggtgg cgggcgcctg tagtcccagc    360
tactccggag gctgaggcag gagaatggcg tgaacccagg acacggagct tgcagtgtgc    420
caacatcacg tcactgccct ccagcctggg ggacaggaac aagantcccg tcctcanaaa    480
agaaaaatac tactnatant ttcnacttta ttttaantta cacagaactn cctcttggta    540
ccccccttacc attcatctca cccacctcct ataggggcacn nctaa                   585
```

<210> SEQ ID NO 40
<211> LENGTH: 475
<212> TYPE: DNA
<213> ORGANISM: Homo sapien

<400> SEQUENCE: 40

```
tctgtccaca ccaatcttag aagctctgaa aagaatttgt ctttaaatat cttttaatag      60
taacatgtat tttatggacc aaattgacat ttcgactgt tttttccaaa aaagtcaggt    120
gaatttcagc acactgagtt gggaatttct tatcccagaa gaccaaccaa tttcatattt    180
```

```
atttaagatt gattccatac tccgttttca aggagaatcc ctgcagtctc cttaaaggta      240
gaacaaatac ttcctatttt tttttcacca ttgtgggatt ggactttaag aggtgactct      300
aaaaaaacag agaacaaata tgtctcagtt gtattaagca cggacccata ttatcatatt      360
cacttaaaaa aatgatttcc tgtgcacctt ttggcaactt ctcttttcaa tgtagggaaa      420
aacttagtca ccctgaaaac ccacaaaata ataaaaactt gtagatgtgg acaga           475
```

<210> SEQ ID NO 41
<211> LENGTH: 423
<212> TYPE: DNA
<213> ORGANISM: Homo sapien

<400> SEQUENCE: 41

```
taagagggta catcgggtaa gaacgtaggc acatctagag cttagagaag tctggggtag       60
gaaaaaaatc taagtattta tagggtata ggtaacattt aaaagtaggg ctagctgaca       120
ttatttagaa agaacacata cggagagata agggcaaagg actaagacca gaggaacact      180
aatatttagt gatcacttcc attcttggta aaaatagtaa cttttaagtt agcttcaagg      240 aagattttg gccatgatta gttgtcaaaa gttagttctc ttgggtttat attactaatt       300
ttgttttaag atccttgtta gtgctttaat aaagtcatgt tatatcaaac gctctaaaac      360
attgtagcat gttaaatgtc acaatatact taccatttgt tgtatatggc tgtaccctct      420
cta                                                                   423
```

<210> SEQ ID NO 42
<211> LENGTH: 527
<212> TYPE: DNA
<213> ORGANISM: Homo sapien
<220> FEATURE:
<221> NAME/KEY: misc_feature
<222> LOCATION: (1)...(527)
<223> OTHER INFORMATION: n = A,T,C or G

<400> SEQUENCE: 42

```
tctcctaggc taatgtgtgt gtttctgtaa aagtaaaaag ttaaaaattt taaaaataga       60
aaaaagctta tagaataaga atatgaagaa agaaaatatt tttgtacatt tgcacaatga      120
gtttatgttt taagctaagt gttattacaa aagagccaaa aaggttttaa aaattaaaac      180
gtttgtaaag ttacagtacc cttatgttaa tttataattg aagaaagaaa aacttttttt      240
tataaatgta gtgtagccta agcatacagt atttataaag tctggcagtg ttcaataatg      300
tcctaggcct tcacattcac tcactgactc acccagagca acttccagtc ctgtaagctc      360
cattcgtggt aagtgcccta tacaggtgca ccatttattt tacagtattt ttactgtacc      420
ttctctatgt ttccatatgt ttcgatatac aaataccact ggttactatn gcccnacagg      480
taattccagt aacacggcct gtatacgtct ggtancccta gngaaga                   527
```

<210> SEQ ID NO 43
<211> LENGTH: 331
<212> TYPE: DNA
<213> ORGANISM: Homo sapien

<400> SEQUENCE: 43

```
tcttcaacct cgtaggacaa ctctcatatg cctgggcact attttaggt tactaccttg        60 gctgcccttc tttaagaaaa aaaaaagaag aaaaagaac ttttccacaa gtttctcttc      120
ctctagttgg aaaattagag aaatcatgtt tttaattttg tgttatttca gatcacaaat      180
```

| | |
|---|---|
| tcaaacactt gtaaacatta agcttctgtt caatccctg ggaagaggat tcattctgat | 240 |
| atttacggtt caaaagaagt tgtaatattg tgcttggaac acagagaacc agttattaac | 300 |
| ttcctactac tattatataa taaataataa c | 331 |

<210> SEQ ID NO 44
<211> LENGTH: 592
<212> TYPE: DNA
<213> ORGANISM: Homo sapien
<220> FEATURE:
<221> NAME/KEY: misc_feature
<222> LOCATION: (1)...(592)
<223> OTHER INFORMATION: n = A,T,C or G

<400> SEQUENCE: 44

| | |
|---|---|
| ggcttagtag ttgccaggca aaatarcgtt gattctcctc aggagccacc cccaacaccc | 60 |
| ctgtttgctt ctagacctat acctagacta aagtcccagc agaccctag aggtgaggtt | 120 |
| cagagtgacc cttgaggaga tgtgctacac tagaaaagaa ctgcttgagt tttctaattt | 180 |
| atataagcag aaatctggag aagagtcata ggaatggata ttaagggtgt gagataatgg | 240 |
| cggaaggaat atagagttgg atcaggctgg acttattgat ttgaacccac taagtagaga | 300 |
| ttctgctttt gatgttgcag ctcagggagt taaaaaaggt tttaatggtt ctaatagttt | 360 |
| atttgcttgg ttagctgaaa tatggataaa agatggccca ctgtgagcaa gctggaaatg | 420 |
| cctgatctct ctcagtttaa tgtagaggaa gggatccaaa agtttaggga ganttggatg | 480 |
| ctggraktgg attggtcact ttgrgaccta cccwtcccag ctgggagggt ccagaagata | 540 |
| caccccttgac caacgcttg cgaaatggat ttgtgatggc ggcaactact aa | 592 |

<210> SEQ ID NO 45
<211> LENGTH: 567
<212> TYPE: DNA
<213> ORGANISM: Homo sapien
<220> FEATURE:
<221> NAME/KEY: misc_feature
<222> LOCATION: (1)...(567)
<223> OTHER INFORMATION: n = A,T,C or G

<400> SEQUENCE: 45

| | |
|---|---|
| ggcttagtag ttgccattgc gagtgcttgc tcaacgagcg ttgaacatgg cggattgtct | 60 |
| agattcaacg gatttgagtt ttaccagcaa agcgaaccaa gcgcggccca gagaattatg | 120 |
| ggttggttgg ctttgaaaag atggaaatcc tgtaggccta gtcagaaaag ccttcttgca | 180 |
| gaacagttgg ttctcgggcg aacgctcatc aagatgccca ttggaaaggc tagcgtgtat | 240 |
| ttgggagagc ctgatagcgt gtcttctgat gatgtttgtg cttggacagt gacaaaagat | 300 |
| atgcaaagca gtccgaact agacgtcaag cttcgtgagc aaattattgt agactcctac | 360 |
| ttatactgtg aggaatgata gccaagggtg gggactttaa gactaaggtg gtttgtactt | 420 |
| gcgccgatga tcccaggcag aaagamctga tcgctagttt tatacgggca actactaagc | 480 |
| cgaattccag cacactggcg gccgttacta attggatccg anctcggtac cagcttgatg | 540 |
| catascttga gttwtctata ntgtcnc | 567 |

<210> SEQ ID NO 46
<211> LENGTH: 908
<212> TYPE: DNA
<213> ORGANISM: Homo sapien
<220> FEATURE:
<221> NAME/KEY: misc_feature
<222> LOCATION: (1)...(908)
<223> OTHER INFORMATION: n = A,T,C or G

<400> SEQUENCE: 46

```
gagcgaaaga ccgagggcag ngnntangng cgangaagcg gagagggcca aaaagcaacc        60
gctttccccg gggggtgccg attcattaag gcaggtggag gacaggtttc ccgatggaag       120
gcggcagggg cgcaagcaat taatgtgagt aggccattca ttagcacccg ggcttaacat       180
ttaagcttcg ggttggtatg tggtgggaat tgtgagcgga taacaatttc acacaggaaa       240
cagctatgac catgattacg ccaagctatt taggtgacat tatagaataa ctcaagttat       300
gcatcaagct tggtaccgag ttcggatcca ctagtaacgc cgccagtgt gtggaattcg        360
gcttagtagt tgccgaccat ggagtgctac ctaggctaga atacctgagy tcctccctag       420
cctcactcac attaaattgt atcttttcta cattagatgt cctcagcgcc ttatttctgc       480
tggacwatcg ataaattaat cctgatagga tgatagcagc agattaatta ctgagagtat       540
gttaatgtgt catccctcct atataacgta tttgcatttt aatggagcaa ttctggagat       600
aatccctgaa ggcaaaggaa tgaatcttga gggtgagaaa gccagaatca gtgtccagct       660
gcagttgtgg gagaaggtga tattatgtat gtctcagaag tgacaccata tgggcaacta       720
ctaagcccga attccagcac actggcgggc gttactaatg gatccgagct cggtaccaag       780
cttgatgcat agcttgagta tctatagtgt cactaaatag cctggcgtta tcatggtcat       840
agctgtttcc tgtgtgaaat tgttatccgc tcccaattcc ccccaccata cgagccggaa       900
cataaagt                                                                908
```

<210> SEQ ID NO 47
<211> LENGTH: 480
<212> TYPE: DNA
<213> ORGANISM: Homo sapien
<220> FEATURE:
<221> NAME/KEY: misc_feature
<222> LOCATION: (1)...(480)
<223> OTHER INFORMATION: n = A,T,C or G

<400> SEQUENCE: 47

```
tgccaacaag gaaagtttta aatttcccct tgaggattct tggtgatcat caaattcagt        60
ggttttttaag gttgttttct gtcaaataac tctaacttta agccaaacag tatatggaag      120
cacagataka atattacaca gataaaagag gagttgatct aaagtaraga tagttggggg       180
ctttaatttc tggaacctag gtctccccat cttcttctgt gctgaggaac ttcttggaag       240
cggggattct aaagttcttt ggaagacagt ttgaaaacca ccatgttgtt ctcagtacct       300
ttatttttaa aaagtaggtg aacattttga gagagaaaag ggcttggttg agatgaagtc       360
cccccccccc cttttttttt ttttagctga aatagatacc ctatgttnaa rgaarggatt       420
attatttacc atgccaytar scacatgctc tttgatgggc nyctccstac cctccttaag       480
```

<210> SEQ ID NO 48
<211> LENGTH: 591
<212> TYPE: DNA
<213> ORGANISM: Homo sapien

<400> SEQUENCE: 48

```
aagagggtac cgagtggaat tccgcttca ctagtctggt gtggctagtc ggtttcgtgg         60
tggccaacat tacgaacttc caactcaacc gttcttggac gttcaagcgg gagtaccggc       120
gaggatggtg gcgtgaattc tggcctttct ttgccgtggg atcggtagcc gccatcatcg       180
gtatgtttat caagatcttc tttactaacc cgacctctcc gatttacctg cccgagccgt       240
```

```
ggtttaacga ggggaggggg atccagtcac gcgagtactg gtcccagatc ttcgccatcg    300
tcgtgacaat gcctatcaac ttcgtcgtca ataagttgtg gaccttccga acggtgaagc    360
actccgaaaa cgtccggtgg ctgctgtgcg gtgactccca aaatcttgat aacaacaagg    420
taaccgaatc gcgctaagga accccggcat ctcgggtact ctgcatatgc gtacccctta    480
agccgaattc cagcacactg gcggccgtta ctaattggat ccgaactccg taaccaagcc    540
tgatgcgtaa cttgagttat tctatagtgt ccctaaaata acctggcgtt a             591
```

<210> SEQ ID NO 49
<211> LENGTH: 454
<212> TYPE: DNA
<213> ORGANISM: Homo sapien

<400> SEQUENCE: 49

```
aagagggtac ctgccttgaa atttaaatgt ctaaggaaar tgggagatga ttaagagttg     60
gtgtggcyta gtcacaccaa aatgtattta ttacatcctg ctccttteta gttgacagga    120 aagaaagctg ctgtgggaa aggagggata aatactgaag ggatttacta aacaaatgtc     180
catcacagag ttttcctttt ttttttttg agacagagtc ttgctctgtc acccaggctg     240
gaatgaagwg gtatgatctc agttgaatgc aacctctacc tcctaggttc aagcgattct    300
catgcctcag cctcctgagc agctgggact ataggcgcat gctaccatgc caggctaatt    360
tttatatttt tattagagac ggggtgttgc catgttggcc aggcaggtct cgaactcctg    420
ggcctcagat gatctgcccc accgtaccct ctta                                454
```

<210> SEQ ID NO 50
<211> LENGTH: 463
<212> TYPE: DNA
<213> ORGANISM: Homo sapien

<400> SEQUENCE: 50

```
aagagggtac caaaaaaaag aaaaaggaaa aaagaaaaa caacttgtat aaggctttct      60
gctgcataca gcttttttttt tttaaataaa tggtgccaac aaatgttttt gcattcacac    120
caattgctgg ttttgaaatc gtactcttca aaggtatttg tgcagatcaa tccaatagtg    180
atgccccgta ggttttgtgg actgcccacg ttgtctacct tctcatgtag gagccattga    240
gagactgttt ggacatgcct gtgttcatgt agccgtgatg tccgggggcc gtgtacatca    300
tgttaccgtg gggtggggtc tgcattggct gctgggcata tggctgggtg cccatcatgc    360
ccatctgcat ctgcataggg tattgggggcg tttgatccat atagccatga ttgctgtggt   420
agccactgtt catcattggc tgggacatgc tgttaccctc tta                      463
```

<210> SEQ ID NO 51
<211> LENGTH: 399
<212> TYPE: DNA
<213> ORGANISM: Homo sapien

<400> SEQUENCE: 51

```
cttcaacctc ccaaagtgct gggattacag gactgagcca ccacgctcag cctaagcctc     60
tttttcacta ccctctaagc gatctaccac agtgatgagg ggctaaagag cagtgcaatt    120
tgattacaat aatggaactt agatttatta attaacaatt tttccttagc atgttggttc    180
cataattatt aagagtatgg acttacttag aaatgagctt tcattttaag aatttcatct    240
ttgaccttct ctattagtct gagcagtatg acactatacg tattttattt aactaaccta    300
ccttgagcta ttacttttta aaaggctata tacatgaatg tgtattgtca actgtaaagc    360
```

```
cccacagtat ttaattatat catgatgtct ttgaggttg                               399
```

<210> SEQ ID NO 52
<211> LENGTH: 392
<212> TYPE: DNA
<213> ORGANISM: Homo sapien

<400> SEQUENCE: 52

```
cttcaacctc aatcaacctt ggtaattgat aaaatcatca cttaactttc tgatataatg    60
gcaataatta tctgagaaaa aaagtggtg aaagattaaa cttgcatttc tctcagaatc    120
ttgaaggata tttgaataat tcaaaagcgg aatcagtagt atcagccgaa gaaactcact   180
tagctagaac gttggaccca tggatctaag tccctgccct tccactaacc agctgattgg   240
ttttgtgtaa acctcctaca cgcttgggct tggtcgcctc atttgtcaaa gtaaaggctg   300
aaataggaag ataatgaacc gtgtctttt ggtctctttt ccatccatta ctctgatttt    360
acaaagaggc ctgtattccc ctggtgaggt tg                                  392
```

<210> SEQ ID NO 53
<211> LENGTH: 179
<212> TYPE: DNA
<213> ORGANISM: Homo sapien
<220> FEATURE:
<221> NAME/KEY: misc_feature
<222> LOCATION: (1)...(179)
<223> OTHER INFORMATION: n = A,T,C or G

<400> SEQUENCE: 53

```
ttcgggtgat gcctcctcag gctacagtga agactggatt acagaaaggt gccagcgaga    60
tttcagattc ctgtaaacct ctaaagaaaa ggagtcgcgc ctcaactgat gtagaaatga   120
ctagttcagc atacngagac acntctgact ccgattctag aggactgagt gacctgcan    179
```

<210> SEQ ID NO 54
<211> LENGTH: 112
<212> TYPE: DNA
<213> ORGANISM: Homo sapien
<220> FEATURE:
<221> NAME/KEY: misc_feature
<222> LOCATION: (1)...(112)
<223> OTHER INFORMATION: n = A,T,C or G

<400> SEQUENCE: 54

```
ttcgggtgat gcctcctcag gctacatcat natagaagca aagtagaana atcnngtttg    60
tgcattttcc cacanacaaa attcaaatga ntggaagaaa ttggganagt at           112
```

<210> SEQ ID NO 55
<211> LENGTH: 225
<212> TYPE: DNA
<213> ORGANISM: Homo sapien

<400> SEQUENCE: 55

```
tgagcttccg cttctgacaa ctcaatagat aatcaaagga caactttaac agggattcac    60
aaggagtat atccaaatgc caataaacat ataaaaagga attcagcttc atcatcatca   120
gaagwatgca aattaaaacc ataatgaaa accactatgt cccactagaa tagataaaat    180
cttaaaagac tggtaaaacc aagtgttggt aaggcaagag gagca                   225
```

<210> SEQ ID NO 56
<211> LENGTH: 175
<212> TYPE: DNA

<213> ORGANISM: Homo sapien

<400> SEQUENCE: 56

| gctcctcttg ccttaccaac acattctcaa aaacctgtta gagtcctaag cattctcctg | 60 |
| ttagtattgg gattttaccc ctgtcctata aagatgttat gtaccaaaaa tgaagtggag | 120 |
| ggccataccc tgagggaggg gagggatctc tagtgttgtc agaagcggaa gctca | 175 |

<210> SEQ ID NO 57
<211> LENGTH: 223
<212> TYPE: DNA
<213> ORGANISM: Homo sapien

<400> SEQUENCE: 57

| agccatttac cacccatgga tgaatggatt ttgtaattct agctgttgta ttttgtgaat | 60 |
| ttgttaattt tgttgttttt ctgtgaaaca catacattgg atatgggagg taaaggagtg | 120 |
| tcccagttgc tcctggtcac tcctttata gccattactg tcttgtttct tgtaactcag | 180 |
| gttaggtttt ggtctctctt gctccactgc aaaaaaaaaa aaa | 223 |

<210> SEQ ID NO 58
<211> LENGTH: 211
<212> TYPE: DNA
<213> ORGANISM: Homo sapien

<400> SEQUENCE: 58

| gttcgaaggt gaacgtgtag gtagcggatc tcacaactgg ggaactgtca agacgaatt | 60 |
| aactgacttg gatcaatcaa atgtgactga ggaaacacct gaaggtgaag aacatcatcc | 120 |
| agtggcagac actgaaaata aggagaatga agttgaagag gtaaaagagg agggtccaaa | 180 |
| agagatgact ttggatgggt ggtaaatggc t | 211 |

<210> SEQ ID NO 59
<211> LENGTH: 208
<212> TYPE: DNA
<213> ORGANISM: Homo sapien

<400> SEQUENCE: 59

| gctcctcttg cctaccaac tttgcaccca tcatcaacca tgtggccagg tttgcagccc | 60 |
| aggctgcaca tcagggact gcctcgcaat acttcatgct gttgctgctg actgatggtg | 120 |
| ctgtgacgga tgtggaagcc acacgtgagg ctgtggtgcg tgcctcgaac ctgcccatgt | 180 |
| cagtgatcat tatgggtggt aaatggct | 208 |

<210> SEQ ID NO 60
<211> LENGTH: 171
<212> TYPE: DNA
<213> ORGANISM: Homo sapien

<400> SEQUENCE: 60

| agccatttac cacccatact aaattctagt tcaaactcca acttcttcca taaaacatct | 60 |
| aaccactgac accagttggc aatagcttct tccttcttta acctcttaga gtatttatgg | 120 |
| tcaatgccac acatttctgc aactgaataa agttggtaag gcaagaggag c | 171 |

<210> SEQ ID NO 61
<211> LENGTH: 134
<212> TYPE: DNA
<213> ORGANISM: Homo sapien
<220> FEATURE:
<221> NAME/KEY: misc_feature
<222> LOCATION: (1)...(134)
<223> OTHER INFORMATION: n = A,T,C or G

<400> SEQUENCE: 61
cgggtgatgc ctcctcaggc tttggtgtgt ccactcnact cactggcctc ttctccagca    60
actggtgaan atgtcctcan gaaaancncc acacgcngct cagggtgggg tgggaancat   120
canaatcatc nggc                                                    134

<210> SEQ ID NO 62
<211> LENGTH: 145
<212> TYPE: DNA
<213> ORGANISM: Homo sapien

<400> SEQUENCE: 62
agagggtaca tatgcaacag tatataaagg aagaagtgca ctgagaggaa cttcatcaag    60
gccatttaat caataagtga tagagtcaag gctcaaccca ggtgtgacgg attccaggtc   120
ccaagctcct tactggtacc ctctt                                        145

<210> SEQ ID NO 63
<211> LENGTH: 297
<212> TYPE: DNA
<213> ORGANISM: Homo sapien

<400> SEQUENCE: 63
tgcactgaga ggaattcaaa gggtttatgc caaagaacaa accagtcctc tgcagcctaa    60
ctcatttgtt tttgggctgc gaagccatgt agagggcgat caggcagtag atggtccctc   120
ccacagtcag cgccatggtg gtccggtaaa gcatttggtc aggcaggcct cgtttcaggt   180
agacgggcac acatcagctt tctggaaaaa cttttgtagc tctggagctt tgttttttcc   240
agcataatca tacactgtgg aatcggaggt cagtttagtt ggtaaggcaa gaggagc      297

<210> SEQ ID NO 64
<211> LENGTH: 300
<212> TYPE: DNA
<213> ORGANISM: Homo sapien

<400> SEQUENCE: 64
gcactgagag gaacttccaa tactatgttg aataggagtg gtgagagagg gcatccttgt    60
cttgtgccgg ttttcaaagg gaatgcttcc agcttttgcc cattcagtat aatattaaag   120
aatgttttac cattttctgt cttgcctgtt tttctgtgtt tttgttggtc tcttcattct   180
ccatttttag gcctttacat gttaggaata tatttctttt aatgatactt cacctttggt   240
atcttttgtg agactctact catagtgtga taagcactgg gttggtaagg caagaggagc   300

<210> SEQ ID NO 65
<211> LENGTH: 203
<212> TYPE: DNA
<213> ORGANISM: Homo sapien

<400> SEQUENCE: 65
gctcctcttg ccttaccaac tcacccagta tgtcagcaat tttatcrgct ttacctacga    60
aacagcctgt atccaaacac ttaacacact cacctgaaaa gttcaggcaa caatcgcctt   120
ctcatgggtc tctctgctcc agttctgaac cttttctcttt tcctagaaca tgcatttarg   180
tcgatagaag ttcctctcag tgc                                          203

<210> SEQ ID NO 66

```
<211> LENGTH: 344
<212> TYPE: DNA
<213> ORGANISM: Homo sapien

<400> SEQUENCE: 66
tacggggacc cctgcattga gaaagcgaga ctcactctga agctgaaatg ctgttgccct    60
tgcagtgctg gtagcaggag ttctgtgctt tgtgggctaa ggctcctgga tgacccctga   120
catggagaag gcagagttgt gtgccccttc tcatggcctc gtcaaggcat catggactgc   180
cacacacaaa atgccgtttt tattaacgac atgaaattga aggagagaac acaattcact   240
gatgtggctc gtaaccatgg atatggtcac atacagaggt gtgattatgt aaaggttaat   300
tccacccacc tcatgtggaa actagcctca atgcagggt ccca                    344

<210> SEQ ID NO 67
<211> LENGTH: 157
<212> TYPE: DNA
<213> ORGANISM: Homo sapien

<400> SEQUENCE: 67
gcactgagag gaacttcgta gggaggttga actggctgct gaggaggggg aacaacaggg    60
taaccagact gatagccatt ggatggataa tatggtggtt gaggagggac actacttata   120
gcagagggtt gtgtatagcc tgaggaggca tcacccg                            157

<210> SEQ ID NO 68
<211> LENGTH: 137
<212> TYPE: DNA
<213> ORGANISM: Homo sapien

<400> SEQUENCE: 68
gcactgagag gaacttctag aaagtgaaag tctagacata aataaaata aaatttaaa     60 actcaggaga gacagcccag cacggtggct cacgcctgta atcccagaac tttgggagcc   120
tgaggaggca tcacccg                                                  137

<210> SEQ ID NO 69
<211> LENGTH: 137
<212> TYPE: DNA
<213> ORGANISM: Homo sapien

<400> SEQUENCE: 69
cgggtgatgc ctcctcaggc tgtattttga agactatcga ctggacttct tatcaactga    60
agaatccgtt aaaaatacca gttgtattat ttctacctgt caaaatccat ttcaaatgtt   120
gaagttcctc tcagtgc                                                  137

<210> SEQ ID NO 70
<211> LENGTH: 220
<212> TYPE: DNA
<213> ORGANISM: Homo sapien
<220> FEATURE:
<221> NAME/KEY: misc_feature
<222> LOCATION: (1)...(220)
<223> OTHER INFORMATION: n = A,T,C or G

<400> SEQUENCE: 70
agcatgttga gcccagacac gcaatctgaa tgagtgtgca cctcaagtaa atgtctacac    60
gctgcctggt ctgacatggc acaccatcnc gtggagggca casctctgct cngcctacwa   120
cgagggcant ctcatwgaca ggttccaccc accaaactgc aagaggctca nnaagtactr   180
ccagggtmya sggacmasgg tgggaytyca ycacwcatct                         220
```

<210> SEQ ID NO 71
<211> LENGTH: 353
<212> TYPE: DNA
<213> ORGANISM: Homo sapien
<220> FEATURE:
<221> NAME/KEY: misc_feature
<222> LOCATION: (1)...(353)
<223> OTHER INFORMATION: n = A,T,C or G

<400> SEQUENCE: 71

| | | | | | |
|---|---|---|---|---|---|
| cgttagggtc | tctatccact | gctaaaccat | acacctgggt | aaacagggac | catttaacat | 60 |
| tcccanctaa | atatgccaag | tgacttcaca | tgtttatctt | aaagatgtcc | aaaacgcaac | 120 |
| tgattttctc | ccctaaacct | gtgatggtgg | gatgattaan | cctgagtggt | ctacagcaag | 180 |
| ttaagtgcaa | ggtgctaaat | gaangtgacc | tgagatacag | catctacaag | gcagtacctc | 240 |
| tcaacncagg | gcaactttgc | ttctcanagg | gcatttagca | gtgtctgaag | taatttctgt | 300 |
| attacaactc | acgggcggg | gggtgaatat | ctantggana | gnagaccta | acg | 353 |

<210> SEQ ID NO 72
<211> LENGTH: 343
<212> TYPE: DNA
<213> ORGANISM: Homo sapien

<400> SEQUENCE: 72

| | | | | | |
|---|---|---|---|---|---|
| gcactgagag | gaacttccaa | tacyatkatc | agagtgaaca | rgcarccyac | agaacaggag | 60 |
| aaaatgttyg | caatctctcc | atctgacaaa | aggctaatat | ccagawtcta | awaggaactt | 120 |
| aaacaaattt | atgagaaaag | aacaracaac | ctcawcaaaa | agtgggtgaa | ggawatgcts | 180 |
| aaargaagac | atytattcag | ccagtaaaca | yatgaaaaaa | aggctcatsa | tcactgawca | 240 |
| ttagagaaat | gcaaatcaaa | accacaatga | gataccatct | yayrccagtt | agaayggtga | 300 |
| tcattaaaar | stcaggaaac | aacagatgct | ggacaaggtg | tca | | 343 |

<210> SEQ ID NO 73
<211> LENGTH: 321
<212> TYPE: DNA
<213> ORGANISM: Homo sapien
<220> FEATURE:
<221> NAME/KEY: misc_feature
<222> LOCATION: (1)...(321)
<223> OTHER INFORMATION: n = A,T,C or G

<400> SEQUENCE: 73

| | | | | | |
|---|---|---|---|---|---|
| gcactgagag | gaacttcaga | gagagagaga | gagttccacc | ctgtacttgg | ggagagaaac | 60 |
| agaaggtgag | aaagtctttg | gttctgaagc | agcttctaag | atcttttcat | ttgcttcatt | 120 |
| tcaaagttcc | catgctgcca | aagtgccatc | ctttggggta | ctgttttctg | agctccagtg | 180 |
| ataactcatt | tatacaaggg | agatacccag | aaaaaaagtg | agcaaatctt | aaaaggtgg | 240 |
| cttgagttca | gccttaaata | ccatcttgaa | atgacacaga | gaaagaanga | tgttgggtgg | 300 |
| gagtggatag | agaccctaac | g | | | | 321 |

<210> SEQ ID NO 74
<211> LENGTH: 321
<212> TYPE: DNA
<213> ORGANISM: Homo sapien

<400> SEQUENCE: 74

| | | | | | |
|---|---|---|---|---|---|
| gcactgagag | gaacttcaga | gagagagaga | gagttccacc | ctgtacttgg | ggagagaaac | 60 |

-continued

```
agaaggtgag aaagtctttg gttctgaagc agcttctaag atcttttcat ttgcttcatt    120
tcaaagttcc catgctgcca aagtgccatc ctttggggta ctgttttctg agctccagtg    180
ataactcatt tatacaaggg agatacccag aaaaaaagtg agcaaatctt aaaaaggtgg    240
cttgagttca gycttaaata ccatcttgaa atgamacaga gaaagaagga tgttgggtgg    300
gagtggatag agaccctaac g                                              321
```

<210> SEQ ID NO 75
<211> LENGTH: 317
<212> TYPE: DNA
<213> ORGANISM: Homo sapien

<400> SEQUENCE: 75

```
gcactgagag gaacttccac atgcactgag aaatgcatgt tcacaaggac tgaagtctgg     60
aactcagttt ctcagttcca atcctgattc aggtgtttac cagctacaca acctaagca     120 agtcagataa ccttagcttc ctcatatgca aaatgagaat gaaaagtact catcgctgaa    180
ttgttttgag gattagaaaa acatctggca tgcagtagaa attcaattag tattcatttt    240
cattcttcta aattaaacaa ataggatttt tagtggtgga acttcagaca ccagaaatgg    300
gagtggatag agaccct                                                   317
```

<210> SEQ ID NO 76
<211> LENGTH: 244
<212> TYPE: DNA
<213> ORGANISM: Homo sapien

<400> SEQUENCE: 76

```
cgttagggtc tctatccact cccactactg atcaaactct atttatttaa ttatttttat    60
catactttaa gttctgggat acacgtgcag catgcgcagg tttgttgcat aggtatacac    120
ttgccatggt ggtttgctgc acccatcagt ccatcatcta cattaggtat ttctcctaat    180
gctatccctc ccctagcccc ttacaccccc aacaggctct agtgtgtgaa gttcctctca    240
gtgc                                                                 244
```

<210> SEQ ID NO 77
<211> LENGTH: 254
<212> TYPE: DNA
<213> ORGANISM: Homo sapien

<400> SEQUENCE: 77

```
cgttagggtc tctatccact gaaatctgaa gcacaggagg aagagaagca gtyctagtga     60
gatggcaagt tcwtttacca cactctttaa catttygttt agttttaacc tttatttatg    120
gataataaag gttaatatta ataatgattt atttttaaggc attcccraat ttgcataatt    180
ctccttttgg agatacccct ttatctccag tgcaagtctg gatcaaagtg atasamagaa    240
gttcctctca gtgc                                                      254
```

<210> SEQ ID NO 78
<211> LENGTH: 355
<212> TYPE: DNA
<213> ORGANISM: Homo sapien
<220> FEATURE:
<221> NAME/KEY: misc_feature
<222> LOCATION: (1)...(355)
<223> OTHER INFORMATION: n = A,T,C or G

<400> SEQUENCE: 78

```
ttcgatacag gcaaacatga actgcaggag ggtggtgacg atcatgatgt tgccgatggt     60
```

```
ccggatggnc acgaagacgc actggancac gtgcttacgt ccttttgctc tgttgatggc      120
cctgagggga cgcaggaccc ttatgaccct cagaatcttc acaacgggag atggcactgg      180
attgantccc antgacacca gagacacccc aaccaccagn atatcantat attgatgtag      240
ttcctgtaga nggccccctt gtggaggaaa gctccatnag ttggtcatct tcaacaggat      300
ctcaacagtt tccgatggct gtgatgggca tagtcatant taaccntgtn tcgaa           355

<210> SEQ ID NO 79
<211> LENGTH: 406
<212> TYPE: DNA
<213> ORGANISM: Homo sapien

<400> SEQUENCE: 79
taagagggta ccagcagaaa ggttagtatc atcagatagc atcttatacg agtaatatgc       60
ctgctatttg aagtgtaatt gagaaggaaa attttagcgt gctcactgac ctgcctgtag      120
ccccagtgac agctaggatg tgcattctcc agccatcaag agactgagtc aagttgttcc      180
ttaagtcaga acagcagact cagctctgac attctgattc gaatgacact gttcaggaat      240
cggaatcctg tcgattagac tggacagctt gtggcaagtg aatttgcctg taacaagcca      300 gatttttttaa aatttatatt gtaaataatg tgtgtgtgtg tgtgtgtata tatatatata      360
tgtacagtta tctaagttaa tttaaaagtt gtttggtacc tctctta                    406

<210> SEQ ID NO 80
<211> LENGTH: 327
<212> TYPE: DNA
<213> ORGANISM: Homo sapien

<400> SEQUENCE: 80
tttttttttt tttactcggc tcagtctaat ccttttttgta gtcactcata ggccagactt      60
agggctagga tgatgattaa taagagggat gacataacta ttagtggcag gttagttgtt      120
tgtagggctc atggtagggg taaaaggagg gcaatttcta gatcaaataa taagaaggta      180
atagctacta agaagaattt tatggagaaa gggacgcggg cggggatat agggtcgaag       240 ccgcactcgt aagggtgga tttttctatg tagccgttga gttgtggtag tcaaaatgta       300
ataattatta gtagtaagcc taggaga                                          327

<210> SEQ ID NO 81
<211> LENGTH: 318
<212> TYPE: DNA
<213> ORGANISM: Homo sapien

<400> SEQUENCE: 81
tagtctatgc ggttgattcg gcaatccatt atttgctgga ttttgtcatg tgttttgcca       60
attgcattca taatttatta tgcatttatg cttgtatctc ctaagtcatg gtatataatc      120
catgcttttt atgttttgtc tgacataaac tcttatcaga gccctttgca cacagggatt      180
caataaatat taacacagtc tacatttatt tggtgaatat tgcatatctg ctgtactgaa      240
agcacattaa gtaacaaagg caagtgagaa gaatgaaaag cactactcac aacagttatc      300
atgattgcgc atagacta                                                    318

<210> SEQ ID NO 82
<211> LENGTH: 338
<212> TYPE: DNA
<213> ORGANISM: Homo sapien
```

```
<400> SEQUENCE: 82
tcttcaacct ctactcccac taatagcttt ttgatgactt ctagcaagcc tcgctaacct      60
cgccttaccc cccactatta acctactggg agaactctct gtgctagtaa ccacgttctc     120
ctgatcaaat atcactctcc tacttacagg actcaacata ctagtcacag ccctatactc     180
cctctacata tttaccacaa cacaatgggg ctcactcacc caccacatta acaacataaa     240
accctcattc acacgagaaa acaccctcat gttcatacac ctatccccca ttctcctcct     300
atccctcaac cccgacatca ttaccgggtt ttcctctt                             338

<210> SEQ ID NO 83
<211> LENGTH: 111
<212> TYPE: DNA
<213> ORGANISM: Homo sapien

<400> SEQUENCE: 83
agccatttac cacccatcca caaaaaaaaa aaaaaaaag aaaatatca aggaataaaa      60
atagactttg aacaaaaagg aacatttgct ggcctgagga ggcatcaccc g             111

<210> SEQ ID NO 84
<211> LENGTH: 224
<212> TYPE: DNA
<213> ORGANISM: Homo sapien

<400> SEQUENCE: 84
tcgggtgatg cctcctcagg ccaagaagat aaagcttcag accctaaca catttccaaa      60
aaggaagaaa ggagaaaaaa gggcatcatc cccgttccga agggtcaggg aggaggaaat    120
tgaggtggat tcacgagttg cggacaactc ctttgatgcc aagcgaggtg cagccggaga    180
ctggggagag cgagccaatc aggttttgaa gttcctctca gtgc                     224

<210> SEQ ID NO 85
<211> LENGTH: 348
<212> TYPE: DNA
<213> ORGANISM: Homo sapien

<400> SEQUENCE: 85
gcactgagag gaacttcgtt ggaaacgggt ttttttcatg taaggctaga cagaagaatt      60
ctcagtaact tccttgtgtt gtgtgtattc aactcacasa gttgaacgat cctttacaca    120
gagcagactt gtaacactct twttgtggaa tttgcaagtg gagatttcag scgctttgaa    180
gtsaaggta gaaaaggaaa tatcttccta taaaaactag acagaatgat tctcagaaac     240
tcctttgtga tgtgtgcgtt caactcacag agtttaacct ttcwtttcat agaagcagtt    300
aggaaacact ctgtttgtaa agtctgcaag tggatagaga ccctaacg                 348

<210> SEQ ID NO 86
<211> LENGTH: 293
<212> TYPE: DNA
<213> ORGANISM: Homo sapien

<400> SEQUENCE: 86
gcactgagag gaacttcytt gtgwtgtktg yattcaactc acagagttga asswtsmttt      60
acabagwkca ggcttkcaaa cactctttt gtmgaatytg caagwggaka tttsrrccrc     120
tttgwggycw wysktmgaaw mggrwatatc ttcwyatmra amctagacag aaksattctc    180
akaawstyyy ytgtgawgws tgcrttcaac tcacagagkt kaacmwtyct kytsatrgag    240
cagttwkgaa actctmtttc tttggattct gcaagtggat agagaccta acg            293
```

<210> SEQ ID NO 87
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 87
ctcctaggct                                                           10

<210> SEQ ID NO 88
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 88
agtagttgcc                                                           10

<210> SEQ ID NO 89
<211> LENGTH: 11
<212> TYPE: DNA
<213> ORGANISM: Artificial Sequence
<220> FEATURE:
<223> OTHER INFORMATION: Primer for amplification from breast tumor cDNA

<400> SEQUENCE: 89
ttccgttatg c                                                         11

<210> SEQ ID NO 90
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 90
tggtaaaggg                                                           10

<210> SEQ ID NO 91
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 91
tcggtcatag                                                           10

<210> SEQ ID NO 92
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 92
tacaacgagg                                                           10

<210> SEQ ID NO 93
<211> LENGTH: 10
<212> TYPE: DNA
<213> ORGANISM: Artificial Sequence
<220> FEATURE:

<223> OTHER INFORMATION: Primer for amplification from breast tumor cDNA

<400> SEQUENCE: 93
tggattggtc                                                              10

<210> SEQ ID NO 94
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 94
ctttctaccc                                                              10

<210> SEQ ID NO 95
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 95
ttttggctcc                                                              10

<210> SEQ ID NO 96
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 96
ggaaccaatc                                                              10

<210> SEQ ID NO 97
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 97
tcgatacagg                                                              10

<210> SEQ ID NO 98
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 98
ggtactaagg                                                              10

<210> SEQ ID NO 99
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 99
agtctatgcg                                                              10

<210> SEQ ID NO 100
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 100
ctatccatgg                                                            10

<210> SEQ ID NO 101
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 101
tctgtccaca                                                            10

<210> SEQ ID NO 102
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 102
aagagggtac                                                            10

<210> SEQ ID NO 103
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 103
cttcaacctc                                                            10

<210> SEQ ID NO 104
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 104
gctcctcttg ccttaccaac                                                 20

<210> SEQ ID NO 105
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 105
gtaagtcgag cagtgtgatg                                                 20

<210> SEQ ID NO 106
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 106
gtaagtcgag cagtctgatg                                           20

<210> SEQ ID NO 107
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 107
gacttagtgg aaagaatgta                                           20

<210> SEQ ID NO 108
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 108
gtaattccgc caaccgtagt                                           20

<210> SEQ ID NO 109
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 109
atggttgatc gatagtggaa                                           20

<210> SEQ ID NO 110
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 110
acggggaccc ctgcattgag                                           20

<210> SEQ ID NO 111
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 111
tattctagac cattcgctac                                           20

<210> SEQ ID NO 112
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 112
acataaccac tttagcgttc                                           20

<210> SEQ ID NO 113
<211> LENGTH: 20

```
<212> TYPE: DNA
<213> ORGANISM: Artificial Sequence
<220> FEATURE:
<223> OTHER INFORMATION: Primer for amplification from breast tumor cDNA

<400> SEQUENCE: 113
cgggtgatgc ctcctcaggc                                              20

<210> SEQ ID NO 114
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 114
agcatgttga gcccagacac                                              20

<210> SEQ ID NO 115
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 115
gacaccttgt ccagcatctg                                              20

<210> SEQ ID NO 116
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 116
tacgctgcaa cactgtggag                                              20

<210> SEQ ID NO 117
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 117
cgttagggtc tctatccact                                              20

<210> SEQ ID NO 118
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 118
agactgactc atgtccccta                                              20

<210> SEQ ID NO 119
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 119
```

```
tcatcgctcg gtgactcaag                                                  20

<210> SEQ ID NO 120
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 120
caagattcca taggctgacc                                                  20

<210> SEQ ID NO 121
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 121
acgtactggt cttgaaggtc                                                  20

<210> SEQ ID NO 122
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 122
gacgcttggc cacttgacac                                                  20

<210> SEQ ID NO 123
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 123
gtatcgacgt agtggtctcc                                                  20

<210> SEQ ID NO 124
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 124
tagtgacatt acgacgctgg                                                  20

<210> SEQ ID NO 125
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 125
cgggtgatgc ctcctcaggc                                                  20

<210> SEQ ID NO 126
<211> LENGTH: 23
<212> TYPE: DNA
<213> ORGANISM: Artificial Sequence
```

```
<220> FEATURE:
<223> OTHER INFORMATION: Primer for amplification from breast tumor cDNA

<400> SEQUENCE: 126
atggctattt tcgggggctg aca                                              23

<210> SEQ ID NO 127
<211> LENGTH: 22
<212> TYPE: DNA
<213> ORGANISM: Artificial Sequence
<220> FEATURE:
<223> OTHER INFORMATION: Primer for amplification from breast tumor cDNA

<400> SEQUENCE: 127
ccggtatctc ctcgtgggta tt                                               22

<210> SEQ ID NO 128
<211> LENGTH: 18
<212> TYPE: DNA
<213> ORGANISM: Artificial Sequence
<220> FEATURE:
<223> OTHER INFORMATION: Primer for amplification from breast tumor cDNA

<400> SEQUENCE: 128
ctgcctgagc cacaaatg                                                    18

<210> SEQ ID NO 129
<211> LENGTH: 24
<212> TYPE: DNA
<213> ORGANISM: Artificial Sequence
<220> FEATURE:
<223> OTHER INFORMATION: Primer for amplification from breast tumor cDNA

<400> SEQUENCE: 129
ccggaggagg aagctagagg aata                                             24

<210> SEQ ID NO 130
<211> LENGTH: 14
<212> TYPE: DNA
<213> ORGANISM: Artificial Sequence
<220> FEATURE:
<223> OTHER INFORMATION: Primer

<400> SEQUENCE: 130
tttttttttt ttag                                                        14

<210> SEQ ID NO 131
<211> LENGTH: 18
<212> TYPE: PRT
<213> ORGANISM: Artificial Sequence
<220> FEATURE:
<223> OTHER INFORMATION: Predicited Th Motifs (B-cell epitopes)

<400> SEQUENCE: 131

Ser Ser Gly Gly Arg Thr Phe Asp Asp Phe His Arg Tyr Leu Leu Val
 1               5                  10                  15

Gly Ile

<210> SEQ ID NO 132
<211> LENGTH: 22
<212> TYPE: PRT
<213> ORGANISM: Artificial Sequence
<220> FEATURE:
<223> OTHER INFORMATION: Predicited Th Motifs (B-cell epitopes)
<220> FEATURE:
<221> NAME/KEY: VARIANT
```

```
<222> LOCATION: (1)...(22)
<223> OTHER INFORMATION: Xaa = Any Amino Acid

<400> SEQUENCE: 132

Gln Gly Ala Ala Gln Lys Pro Ile Asn Leu Ser Lys Xaa Ile Glu Val
  1               5                  10                  15

Val Gln Gly His Asp Glu
            20

<210> SEQ ID NO 133
<211> LENGTH: 23
<212> TYPE: PRT
<213> ORGANISM: Artificial Sequence
<220> FEATURE:
<223> OTHER INFORMATION: Predicited Th Motifs (B-cell epitopes)

<400> SEQUENCE: 133

Ser Pro Gly Val Phe Leu Glu His Leu Gln Glu Ala Tyr Arg Ile Tyr
  1               5                  10                  15

Thr Pro Phe Asp Leu Ser Ala
            20

<210> SEQ ID NO 134
<211> LENGTH: 9
<212> TYPE: PRT
<213> ORGANISM: Artificial Sequence
<220> FEATURE:
<223> OTHER INFORMATION: Predicted HLA A2.1 Motifs (T-cell epitopes)

<400> SEQUENCE: 134

Tyr Leu Leu Val Gly Ile Gln Gly Ala
  1               5

<210> SEQ ID NO 135
<211> LENGTH: 9
<212> TYPE: PRT
<213> ORGANISM: Artificial Sequence
<220> FEATURE:
<223> OTHER INFORMATION: Predicted HLA A2.1 Motifs (T-cell epitopes)

<400> SEQUENCE: 135

Gly Ala Ala Gln Lys Pro Ile Asn Leu
  1               5

<210> SEQ ID NO 136
<211> LENGTH: 9
<212> TYPE: PRT
<213> ORGANISM: Artificial Sequence
<220> FEATURE:
<223> OTHER INFORMATION: Predicted HLA A2.1 Motifs (T-cell epitopes)
<220> FEATURE:
<221> NAME/KEY: VARIANT
<222> LOCATION: (1)...(9)
<223> OTHER INFORMATION: Xaa = Any Amino Acid

<400> SEQUENCE: 136

Asn Leu Ser Lys Xaa Ile Glu Val Val
  1               5

<210> SEQ ID NO 137
<211> LENGTH: 9
<212> TYPE: PRT
<213> ORGANISM: Artificial Sequence
<220> FEATURE:
<223> OTHER INFORMATION: Predicted HLA A2.1 Motifs (T-cell epitopes)

<400> SEQUENCE: 137
```

Glu Val Val Gln Gly His Asp Glu Ser
1               5

<210> SEQ ID NO 138
<211> LENGTH: 9
<212> TYPE: PRT
<213> ORGANISM: Artificial Sequence
<220> FEATURE:
<223> OTHER INFORMATION: Predicted HLA A2.1 Motifs (T-cell epitopes)

<400> SEQUENCE: 138

His Leu Gln Glu Ala Tyr Arg Ile Tyr
1               5

<210> SEQ ID NO 139
<211> LENGTH: 9
<212> TYPE: PRT
<213> ORGANISM: Artificial Sequence
<220> FEATURE:
<223> OTHER INFORMATION: Predicted HLA A2.1 Motifs (T-cell epitopes)

<400> SEQUENCE: 139

Asn Leu Ala Phe Val Ala Gln Ala Ala
1               5

<210> SEQ ID NO 140
<211> LENGTH: 9
<212> TYPE: PRT
<213> ORGANISM: Artificial Sequence
<220> FEATURE:
<223> OTHER INFORMATION: Predicted HLA A2.1 Motifs (T-cell epitopes)

<400> SEQUENCE: 140

Phe Val Ala Gln Ala Ala Pro Asp Ser
1               5

<210> SEQ ID NO 141
<211> LENGTH: 9388
<212> TYPE: DNA
<213> ORGANISM: Homo sapien

<400> SEQUENCE: 141
gctcgcggcc gcgagctcaa ttaaccctca ctaaagggag tcgactcgat cagactgtta      60
ctgtgtctat gtagaaagaa gtagacataa gagattccat tttgttctgt actaagaaaa     120
attcttctgc cttgagatgc tgttaatctg taaccctagc cccaaccctg tgctcacaga     180
gacatgtgct gtgttgactc aaggttcaat ggatttaggg ctatgctttg ttaaaaaagt     240
gcttgaagat aatatgcttg ttaaaagtca tcaccattct ctaatctcaa gtacccaggg     300
acacaataca ctgcggaagg ccgcagggac ctctgtctag gaaagccagg tattgtccaa     360
gatttctccc catgtgatag cctgagatat ggcctcatgg gaagggtaag acctgactgt     420
cccccagccc gacatccccc agcccgacat ccccagccc gacacccgaa agggtctgt      480
gctgaggagg attagtaaaa gaggaaggcc tctttgcagt tgaggtaaga ggaaggcatc     540
tgtctcctgc tcgtccctgg gcaatagaat gtcttggtgt aaaacccgat tgtatgttct     600
acttactgag ataggagaaa acatccttag ggctggaggt gagacacgct ggcggcaata     660
ctgctcttta atgcaccgag atgtttgtat aagtgcacat caaggcacag cacctttcct     720
taaacttatt tatgacacag agacctttgt tcacgttttc ctgctgaccc tctcccact      780
attaccctat tggcctgcca catccccctc tccgagatgg tagagataat gatcaataaa     840

```
tactgaggga actcagagac cagtgtccct gtaggtcctc cgtgtgctga gcgccggtcc      900
cttgggctca cttttctttc tctatacttt gtctctgtgt ctctttcttt tctcagtctc      960
tcgttccacc tgacgagaaa tacccacagg tgtggagggg caggccaccc cttcaataat     1020
ttactagcct gttcgctgac aacaagactg gtggtgcaga aggttgggtc ttggtgttca     1080
ccgggtggca ggcatgggcc agtgtgggag gtctccagcg cctggtgcaa atctccaaga     1140
aagtgcagga aacagcacca agggtgattg taaattttga tttggcgcgg caggtagcca     1200
ttccagcgca aaaatgcgca ggaaagcttt tgctgtgctt gtaggcaggt aggcccaag      1260
cacttcttat tggctaatgt ggagggaacc tgcacatcca ttggctgaaa tctccgtcta     1320
tttgaggctg actgagcgcg ttcctttctt ctgtgttgcc tggaaacgga ctgtctgcct     1380
agtaacatct gatcacgttt cccattggcc gccgtttccg gaagcccgcc ctcccatttc     1440
cggaagcctg cgcaaggtt ggtctgcagg tggcctccag gtgcaaagtg ggaagtgtga      1500
gtcctcagtc ttgggctatt cggccacgtg cctgccggac atgggacgct ggagggtcag     1560
cagcgtggag tcctggcctt ttgcgtccac gggtgggaaa ttggccattg ccacggcggg     1620
aactgggact caggctgccc cccggccgtt tctcatccgt ccaccggact cgtgggcgct     1680
cgcactggcg ctgatgtagt ttcctgacct ctgacccgta ttgtctccag attaaaggta     1740
aaaacgggc tttttcagcc cactcgggta aaacgccttt tgatttctag gcaggtgttt      1800
tgttgcacgc ctgggaggga gtgacccgca ggttgaggtt tattaaaata cattcctggt     1860
ttatgttatg tttataataa agcaccccaa cctttacaaa atctcacttt tgccagttg      1920
tattatttag tggactgtct ctgataagga cagccagtta aaatggaatt tgttgttgc      1980
taattaaacc aattttagt tttggtgttt gtcctaatag caacaacttc tcaggcttta      2040
taaaaccata tttcttgggg gaaatttctg tgtaaggcac agcgagttag tttggaattg     2100
ttttaaagga agtaagttcc tggttttgat atcttagtag tgtaatgccc aacctggttt     2160
ttactaaccc tgttttaga ctctcccttt ccttaaatca cctagccttg tttccacctg      2220
aattgactct cccttagcta agagcgccag atggactcca tcttggctct ttcactggca     2280
gcccttcct caaggactta acttgtgcaa gctgactccc agcacatcca agaatgcaat      2340
taactgttaa gatactgtgg caagctatat ccgcagttcc gaggaattca tccgattgat     2400
tatgcccaaa agccccgcgt ctatcacctt gtaataatct taaagcccct gcacctggaa     2460
ctattaactt tcctgtaacc atttatcctt ttaactttt tgcttacttt atttctgtaa      2520
aattgtttta actagacctc ccctcccctt tctaaaccaa agtataaaag aagatctagc     2580
cccttcttca gagcggagag aattttgagc attagccatc tcttggcggc cagctaaata     2640
aatggacttt taatttgtct caaagtgtgg cgttttctct aactcgctca ggtacgacat     2700
ttggaggccc cagcgagaaa cgtcaccggg agaaacgtca ccgggcgaga gccgggcccg     2760
ctgtgtgctc ccccggaagg acagccagct tgtaggggg agtgccacct gaaaaaaaaa     2820
tttccaggtc cccaaagggt gaccgtcttc cggaggacag cggatcgact accatgcggg     2880
tgcccaccaa aattccacct ctgagtcctc aactgctgac cccgggtca ggtaggtcag      2940
atttgacttt ggttctggca gagggaagcg accctgatga gggtgtccct cttttgactc     3000
tgcccatttc tctaggatgc tagagggtag agccctggtt ttctgttaga cgcctctgtg     3060
tctctgtctg ggagggaagt ggccctgaca ggggccatcc cttgagtcag tccacatccc     3120
aggatgctgg gggactgagt cctggtttct ggcagactgg tctctctctc tctcttttt     3180
tatctctaat ctttccttgt tcaggtttct tggagaatct ctgggaaaga aaaaagaaaa     3240
```

```
actgttataa actctgtgtg aatggtgaat gaatggggga ggacaagggc ttgcgcttgt    3300
cctccagttt gtagctccac ggcgaaagct acggagttca agtgggccct cacctgcggt    3360
tccgtggcga cctcataagg cttaaggcag catccggcat agctcgatcc gagccggggg    3420
tttataccgg cctgtcaatg ctaagaggag cccaagtccc ctaaggggga gcggccaggc    3480
gggcatctga ctgatcccat cacgggaccc cctccccttg tttgtctaaa aaaaaaaaa    3540 gaagaaactg tcataactgt ttacatgccc tagggtcaac tgtttgtttt atgtttattg    3600
ttctgttcgg tgtctattgt cttgtttagt ggttgtcaag gttttgcatg tcaggacgtc    3660
gatattgccc aagacgtctg ggtaagaact tctgcaaggt ccttagtgct gatttttgt    3720 cacaggaggt taaatttctc atcaatcatt taggctggcc accacagtcc tgtcttttct    3780
gccagaagca agtcaggtgt tgttacggga atgagtgtaa aaaacattc gcctgattgg    3840 gatttctggc accatgatgg ttgtatttag attgtcatac cccacatcca ggttgattgg    3900
acctcctcta aactaaactg gtggtgggtt caaacagcc accctgcaga tttccttgct    3960
cacctctttg gtcattctgt aacttttcct gtgcccttaa atagcacact gtgtagggaa    4020
acctaccctc gtactgcttt acttcgttta gattcttact ctgttcctct gtggctactc    4080
tcccatctta aaaacgatcc aagtggtcct tttcctcctc cctgccccct accccacaca    4140
tctcgttttc cagtgcgaca gcaagttcag cgtctccagg acttggctct gctctcactc    4200
cttgaaccct taaagaaaa agctgggttt gagctatttg cctttgagtc atggagacac    4260
aaaaggtatt tagggtacag atctagaaga agagagagaa cacctagatc caactgaccc    4320
aggagatctc gggctggcct ctagtcctcc tccctcaatc ttaaagctac agtgatgtgg    4380
caagtggtat ttagctgttg tggttttttct gctctttctg gtcatgttga ttctgttctt    4440
tcgatactcc agcccccccag gggagtgagtt tctctgtctg tgctgggttt gatatctatg    4500
ttcaaatctt attaaattgc cttcaaaaaa aaaaaaaaaa gggaaacact tcctcccagc    4560
cttgtaaggg ttggagccct ctccagtata tgctgcagaa ttttctctc ggtttctcag    4620 aggattatgg agtccgcctt aaaaaaggca agctctggac actctgcaaa gtagaatggc    4680
caaagtttgg agttgagtgg cccccttgaag ggtcactgaa cctcacaatt gttcaagctg    4740
tgtggcgggt tgttactgaa actcccggcc tccctgatca gtttccctac attgatcaat    4800
ggctgagttt ggtcaggagc accccttcca tggctccact catgcaccat tcataatttt    4860
acctccaagg tcctcctgag ccagaccgtg ttttcgcctc gaccctcagc cggttcagct    4920
cgccctgtac tgcctctctc tgaagaagag gagagtctcc ctcacccagt cccaccgcct    4980
taaaaccagc ctactccctt agggtcatcc catgtctcct cggctatgtc ccctgtaggc    5040
tcatcaccca ttgcctcttg gttgcaaccg tggtgggagg aagtagcccc tctactacca    5100
ctgagagagg cacaagtccc tctgggtgat gagtgctcca cccccttcct ggtttatgtc    5160
ccttctttct acttctgact tgtataattg gaaacccat aatcctccct tctctgaaaa    5220
gccccaggct ttgacctcac tgatggagtc tgtactctgg acacattggc ccacctggga    5280
tgactgtcaa cagctccttt tgacccttt cacctctgaa gagagggaaa gtatccaaag    5340
agaggccaaa aagtacaacc tcacatcaac caataggccg gaggaggaag ctagaggaat    5400
agtgattaga gacccaattg ggacctaatt gggacccaaa tttctcaagt ggagggagaa    5460
cttttgacga tttccaccgg tatctcctcg tgggtattca gggagctgct cagaaaccta    5520
taaacttgtc taaggcgact gaagtcgtcc agggcatga tgagtcacca ggagtgtttt    5580
```

-continued

```
tagagcacct ccaggaggct tatcggattt acaccccttt tgacctggca gccccgaaa     5640 atagccatgc tcttaatttg gcatttgtgg ctcaggcagc cccagatagt aaaaggaaac    5700
tccaaaaact agagggattt tgctggaatg aataccagtc agcttttaga gatagcctaa    5760 aaggttttg acagtcaaga ggttgaaaaa caaaaacaag cagctcaggc agctgaaaaa     5820
agccactgat aaagcatcct ggagtatcag agtttactgt tagatcagcc tcatttgact   5880 tccctccca catggtgttt aaatccagct acactactc ctgactcaaa ctccactatt     5940
cctgttcatg actgtcagga actgttggaa actactgaaa ctggccgacc tgatcttcaa   6000
aatgtgcccc taggaaaggt ggatgccacc gtgttcacag acagtagcag cttcctcgag   6060
aagggactac gaaaggccgg tgcagctgtt accatggaga cagatgtgtt gtgggctcag   6120
gctttaccag caaacacctc agcacaaaag gctgaattga tcgccctcac tcaggctctc   6180
cgatggggta aggatattaa cgttaacact gacagcaggt acgcctttgc tactgtgcat   6240
gtacgtggag ccatctacca ggagcgtggg ctactcacct cagcaggtgg ctgtaatcca   6300
ctgtaaagga catcaaaagg aaaacacggc tgttgcccgt ggtaaccaga aagctgattc   6360
agcagctcaa gatgcagtgt gactttcagt cacgcctcta aacttgctgc ccacagtctc   6420 cttccacag ccagatctgc ctgacaatcc cgcatactca acagaagaag aaaactggcc    6480
tcagaactca gagccaataa aaatcaggaa ggttggtgga ttcttcctga ctctagaatc   6540
ttcatacccc gaactcttgg gaaaacttta atcagtcacc tacagtctac cacccattta   6600
ggaggagcaa agctacctca gctcctccgg agccgtttta agatccccca tcttcaaagc   6660
ctaacagatc aagcagctct ccggtgcaca acctgcgccc aggtaaatgc caaaaaaggt   6720
cctaaaccca gcccaggcca ccgtctccaa gaaaactcac caggagaaaa gtgggaaatt   6780
gactttacag aagtaaaacc acaccggggct gggtacaaat accttctagt actggtagac  6840
accttctctg gatggactga agcatttgct accaaaaacg aaactgtcaa tatggtagtt   6900 aagttttac tcaatgaaat catccctcga cgtgggctgc ctgttgccat agggtctgat    6960
aatggaccgg ccttcgcctt gtctatagtt tagtcagtca gtaaggcgtt aaacattcaa   7020
tggaagctcc attgtgccta tcgaccccag agctctgggc aagtagaacg catgaactgc   7080
accctaaaaa acactcttac aaaattaatc ttagaaaccg gtgtaaattg tgtaagtctc   7140
cttcctttag ccctacttag agtaaggtgc acccttact gggctgggtt cttaccttt    7200 gaaatcatgt atgggagggc gctgcctatc ttgcctaagc taagagatgc ccaattggca   7260
aaaatatcac aaactaattt attacagtac ctacagtctc cccaacaggt acaagatatc   7320
atcctgccac ttgttcgagg aacccatccc aatccaattc ctgaacagac agggccctgc   7380
cattcattcc cgccaggtga cctgttgttt gttaaaaagt tccagagaga aggactccct   7440
cctgcttgga agagacctca caccgtcatc acgatgccaa cggctctgaa ggtggatggc   7500
attcctgcgt ggattcatca ctcccgcatc aaaaaggcca acggagccca actagaaaca   7560 tgggtccccca gggctgggtc aggccccctta aaactgcacc taagttgggt gaagccatta   7620
gattaattct ttttcttaat tttgtaaaac aatgcatagc ttctgtcaaa cttatgtatc    7680
ttaagactca atataacccc cttgttataa ctgaggaatc aatgatttga ttccccaaaa    7740
acacaagtgg ggaatgtagt gtccaacctg gttttttacta accctgtttt tagactctcc   7800 cttttccttta atcactcagc cttgtttcca cctgaattga ctctcccttg gctaagagcg    7860
ccagatggac tccatcttgg ctctttcact ggcagccgct tcctcaagga cttaacttgt   7920
gcaagctgac tcccagcaca tccaagaatg caattaactg ataagatact gtggcaagct   7980
```

```
atatccgcag ttcccaggaa ttcgtccaat tgattacacc caaaagcccc gcgtctatca    8040
ccttgtaata atcttaaagc ccctgcacct ggaactatta acgttcctgt aaccattttat   8100 cctttaact tttttgccta ctttatttct gtaaaattgt tttaactaga cccccctct     8160 cctttctaaa ccaaagtata aaagcaaatc tagccccttc ttcaggccga gagaatttcg    8220
agcgttagcc gtctcttggc caccagctaa ataaacggat tcttcatgtg tctcaaagtg    8280
tggcgttttc tctaactcgc tcaggtacga ccgtggtagt attttcccca acgtcttatt    8340
tttagggcac gtatgtagag taacttttat gaaagaaacc agttaaggag gttttgggat    8400
ttcctttatc aactgtaata ctggttttga ttatttattt atttatttat ttttttttgag   8460 aaggagtttc actcttgttg cccaggctgg agtgcaatgg tgcgatcttg gctcactgca    8520
acttccgcct cccaggttca agcgattctc ctgcctcagc ctcgagagta gctgggatta    8580
taggcatgcg ccaccacacc cagctaattt tgtatttta gtaaagatgg ggtttcttca    8640
tgttggtcaa gctggtctgg aactccccgc ctcgggtgat ctgcccgcct cggcctccga    8700
aagtgctggg attacaggtg tgatccacca cacccagccg atttatatgt atataaatca    8760
cattcctcta accaaaatgt agtgtttcct tccatcttga atataggctg tagacccgt    8820 gggtatggga cattgttaac agtgagacca cagcagtttt tatgtcatct gacagcatct    8880
ccaaatagcc ttcatggttg tcactgcttc ccaagacaat tccaaataac acttcccagt    8940
gatgacttgc tacttgctat tgttacttaa tgtgttaagg tggctgttac agacactatt    9000
agtatgtcag gaattacacc aaaatttagt ggctcaaaca atcattttat tatgtatgtg    9060
gattctcatg gtcaggtcag gatttcagac agggcacaag ggtagcccac ttgtctctgt    9120
ctatgatgtc tggcctcagc acaggagact caacagctgg ggtctgggac catttggagg    9180
cttgttccct cacatctgat acctggcttg ggatgttgga agagggggtg agctgagact    9240
gagtgcctat atgtagtgtt tccatatggc cttgacttcc ttacagcctg gcagcctcag    9300
ggtagtcaga attcttagga ggcacagggc tccagggcag atgctgaggg gtcttttatg    9360
aggtagcaca gcaaatccac ccaggatc                                      9388
```

<210> SEQ ID NO 142
<211> LENGTH: 419
<212> TYPE: DNA
<213> ORGANISM: Homo sapien

<400> SEQUENCE: 142

```
tgtaagtcga gcagtgtgat ggaaggaatg gtctttggag agagcatatc catctcctcc     60
tcactgcctc ctaatgtcat gaggtacact gagcagaatt aaacagggta gtcttaacca   120
cactattttt agctaccttg tcaagctaat ggttaaagaa cactttggt ttacacttgt    180 tgggtcatag aagttgcttt ccgccatcac gcaataagtt tgtgtgtaat cagaaggagt    240
taccttatgg tttcagtgtc attctttagt taacttggga gctgtgtaat ttaggctttg    300
cgtattattt cacttctgtt ctccacttat gaagtgattg tgtgttcgcg tgtgtgtgcg    360
tgcgcatgtg cttccggcag ttaacataag caaatacccca acatcacact gctcgactt    419
```

<210> SEQ ID NO 143
<211> LENGTH: 402
<212> TYPE: DNA
<213> ORGANISM: Homo sapien

<400> SEQUENCE: 143

```
tgtaagtcga gcagtgtgat gtccactgca gtgtgttgct gggaacagtt aatgagcaaa    60
ttgtatacaa tggctagtac attgaccggg atttgttgaa gctggtgagt gttatgactt   120
agcctgttag actagtctat gcacatggct ctggtcaact accgctctct catttctcca   180
gataaatccc ccatgcttta tattctcttc caaacatact atcctcatca ccacatagtt   240
cctttgttaa tgctttgttc tagactttcc cttttctgtt ttcttattca aacctatatc   300
tctttgcata gattgtaaat tcaaatgccc tcagggtgca ggcagttcat gtaagggagg   360
gaggctagcc agtgagatct gcatcacact gctcgactta ca                      402
```

<210> SEQ ID NO 144
<211> LENGTH: 224
<212> TYPE: DNA
<213> ORGANISM: Homo sapien

<400> SEQUENCE: 144

```
tcgggtgatg cctcctcagg ccaagaagat aaagcttcag acccctaaca catttccaaa    60
aaggaagaaa ggagaaaaaa gggcatcatc cccgttccga agggtcaggg aggaggaaat   120
tgaggtggat tcacgagttg cggacaactc ctttgatgcc aagcgaggtg cagccggaga   180
ctggggagag cgagccaatc aggttttgaa gttcctctca gtgc                    224
```

<210> SEQ ID NO 145
<211> LENGTH: 111
<212> TYPE: DNA
<213> ORGANISM: Homo sapien

<400> SEQUENCE: 145

```
agccatttac cacccatcca caaaaaaaaa aaaaaaaag aaaatatca aggaataaaa      60 atagactttg aacaaaaagg aacatttgct ggcctgagga ggcatcaccc g            111
```

<210> SEQ ID NO 146
<211> LENGTH: 585
<212> TYPE: DNA
<213> ORGANISM: Homo sapien

<400> SEQUENCE: 146

```
tagcatgttg agcccagaca cttgtagaga gaggaggaca gttagaagaa gaagaaaagt    60
ttttaaatgc tgaaagttac tataagaaag ctttggcttt ggatgagact tttaaagatg   120
cagaggatgc tttgcagaaa cttcataaat atatgcaggt gattccttat ttcctcctag   180
aaatttagtg atatttgaaa taatgcccaa acttaatttt ctcctgagga aaactattct   240
acattactta agtaaggcat tatgaaaagt ttcttttag gtatagtttt tcctaattgg    300
gtttgacatt gcttcatagt gcctctgttt ttgtccataa tcgaaagtaa agatagctgt   360
gagaaaacta ttacctaaat ttggtatgtt gttttgagaa atgtccttat agggagctca   420
cctggtggtt tttaaattat tgttgctact ataattgagc taattataaa aacctttttg   480
agacatattt taaattgtct tttcctgtaa tactgatgat gatgttttct catgcatttt   540
cttctgaatt gggaccattg ctgctgtgtc tgggctcaca tgcta                  585
```

<210> SEQ ID NO 147
<211> LENGTH: 579
<212> TYPE: DNA
<213> ORGANISM: Homo sapien
<220> FEATURE:
<221> NAME/KEY: misc_feature
<222> LOCATION: (1)...(579)
<223> OTHER INFORMATION: n = A,T,C or G

<400> SEQUENCE: 147

```
tagcatgttg agcccagaca ctgggcagcg ggggtggcca cggcagctcc tgccgagccc      60
aagcgtgttt gtctgtgaag gaccctgacg tcacctgcca ggctagggag gggtcaatgt     120
ggagtgaatg ttcaccgact ttcgcaggag tgtgcagaag ccaggtgcaa cttggtttgc     180
ttgtgttcat caccccctcaa gatatgcaca ctgctttcca aataaagcat caactgtcat     240
ctccagatgg ggaagacttt ttctccaacc agcaggcagg tccccatcca ctcagacacc     300
agcacgtcca ccttctcggg cagcaccacg tcctccacct tctgctggta cacggtgatg     360
atgtcagcaa agccgttctg cangaccagc tgccccgtgt gctgtgccat ctcactggcc     420
tccaccgcgt acaccgctct aggccgcgca tantgtgcac agaanaaatg atgatccagt     480
cccacagccc acgtccaaga ngactttatc cgtcagggat tctttattct gcaggatgac     540
ctgtggtatt aattgttcgt gtctgggctc aacatgcta                           579
```

<210> SEQ ID NO 148
<211> LENGTH: 249
<212> TYPE: DNA
<213> ORGANISM: Homo sapien

<400> SEQUENCE: 148

```
tgacaccttg tccagcatct gcaagccagg aagagagtcc tcaccaagat ccccaccccg      60
ttggcaccag gatcttggac ttccaatctc cagaactgtg agaaataagt atttgtcgct     120
aaataaatct ttgtggtttc agatatttag ctatagcaga tcaggctgac taagagaaac     180
cccataagag ttacatactc attaatctcc gtctctatcc ccaggtctca gatgctggac     240
aaggtgtca                                                            249
```

<210> SEQ ID NO 149
<211> LENGTH: 255
<212> TYPE: DNA
<213> ORGANISM: Homo sapien

<400> SEQUENCE: 149

```
tgacaccttg tccagcatct gctattttgt gactttttaa taatagccat tctgactggt      60
gtgagatggt aactcattgt gggtttggtc tgcatttctc taatgatcag tgatattaag     120 cttttttttaa atatgcttgt tgaccacatg tatatcatct tttgagaagt gtctgttcat     180
atcctttgcc cacttttttaa ttttttttatc ttgtaaatttt gtttaatttc cttacagatg     240
ctggacaagg tgtca                                                    255
```

<210> SEQ ID NO 150
<211> LENGTH: 318
<212> TYPE: DNA
<213> ORGANISM: Homo sapien

<400> SEQUENCE: 150

```
ttacgctgca acactgtgga ggccaagctg ggatcacttc ttcattctaa ctggagagga      60
gggaagttca agtccagcag agggtgggtg ggtagacagt ggcactcaga aatgtcagct     120
ggacccctgt ccccgcatag gcaggacagc aaggctgtgg ctctccaggg ccagctgaag     180
aacaggacac tgtctccgct gccacaaagc gtcagagact cccatctttg aagcacggcc     240
ttcttggtct tcctgcactt ccctgttctg ttagagacct ggttatagac aaggcttctc     300
cacagtgttg cagcgtaa                                                  318
```

<210> SEQ ID NO 151
<211> LENGTH: 323
<212> TYPE: DNA
<213> ORGANISM: Homo sapien
<220> FEATURE:
<221> NAME/KEY: misc_feature
<222> LOCATION: (1)...(323)
<223> OTHER INFORMATION: n = A,T,C or G

<400> SEQUENCE: 151

| | | | | | | |
|---|---|---|---|---|---|---|
| tnacgcngcn | acnntgtaga | ganggnaagg | cnttccccac | attnccctt | catnanagaa | 60 |
| ttattcnacc | aagnntgacc | natgccnttt | atgacttaca | tgcnnactnc | ntaatctgtn | 120 |
| tcnngcctta | aaagcnnntc | cactacatgc | ntcancactg | tntgtgtnac | ntcatnaact | 180 |
| gtcngnaata | ggggcncata | actacagaaa | tgcanttcat | actgcttcca | ntgccatcng | 240 |
| cgtgtggcct | tncctactct | tcttntattc | caagtagcat | ctctggantg | cttccccact | 300 |
| ctccacattg | ttgcagcnat | aat | | | | 323 |

<210> SEQ ID NO 152
<211> LENGTH: 311
<212> TYPE: DNA
<213> ORGANISM: Homo sapien

<400> SEQUENCE: 152

| | | | | | | |
|---|---|---|---|---|---|---|
| tcaagattcc | ataggctgac | cagtccaagg | agagttgaaa | tcatgaagga | gagtctatct | 60 |
| ggagagagct | gtagttttga | gggttgcaaa | gacttaggat | ggagttggtg | ggtgtggtta | 120 |
| gtctctaagg | ttgattttgt | tcataaattt | catgccctga | atgccttgct | tgcctcaccc | 180 |
| tggtccaagc | cttagtgaac | acctaaaagt | ctctgtcttc | ttgctctcca | aacttctcct | 240 |
| gaggatttcc | tcagattgtc | tacattcaga | tcgaagccag | ttggcaaaca | agatgcagtc | 300 |
| cagagggtca | g | | | | | 311 |

<210> SEQ ID NO 153
<211> LENGTH: 332
<212> TYPE: DNA
<213> ORGANISM: Homo sapien

<400> SEQUENCE: 153

| | | | | | | |
|---|---|---|---|---|---|---|
| caagattcca | taggctgacc | aggaggctat | tcaagatctc | tggcagttga | ggaagtctct | 60 |
| ttaagaaaat | agtttaaaca | atttgttaaa | attttctgt | cttacttcat | ttctgtagca | 120 |
| gttgatatct | ggctgtcctt | tttataatgc | agagtgggaa | ctttccctac | catgtttgat | 180 |
| aaatgttgtc | caggctccat | tgccaataat | gtgttgtcca | aaatgcctgt | ttagttttta | 240 |
| aagacggaac | tccacccttt | gcttggtctt | aagtatgtat | ggaatgttat | gataggacat | 300 |
| agtagtagcg | gtggtcagcc | tatggaatct | tg | | | 332 |

<210> SEQ ID NO 154
<211> LENGTH: 345
<212> TYPE: DNA
<213> ORGANISM: Homo sapien
<220> FEATURE:
<221> NAME/KEY: misc_feature
<222> LOCATION: (1)...(345)
<223> OTHER INFORMATION: n = A,T,C or G

<400> SEQUENCE: 154

| | | | | | | |
|---|---|---|---|---|---|---|
| tcaagattcc | ataggctgac | ctggacagag | atctcctggg | tctggcccag | gacagcaggc | 60 |
| tcaagctcag | tggagaaggt | ttccatgacc | ctcagattcc | cccaaaacctt | ggattgggtg | 120 |

```
acattgcatc tcctcagaga gggaggagat gtangtctgg gcttccacag ggacctggta    180 tttaggatc agggtaccgc tggcctgagg cttggatcat tcanagcctg ggggtggaat    240
ggctggcagc ctgtggcccc attgaaatag gctctgggc actccctctg ttcctanttg    300
aacttgggta aggaacagga atgtggtcan cctatggaat cttga                   345
```

```
<210> SEQ ID NO 155
<211> LENGTH: 295
<212> TYPE: DNA
<213> ORGANISM: Homo sapien
<220> FEATURE:
<221> NAME/KEY: misc_feature
<222> LOCATION: (1)...(295)
<223> OTHER INFORMATION: n = A,T,C or G

<400> SEQUENCE: 155
```

```
gacgcttggc cacttgacac attaaacagt tttgcataat cactancatg tatttctagt    60
ttgctgtctg ctgtgatgcc ctgccctgat tctctggcgt taatgatggc aagcataatc   120
aaacgctgtt ctgttaattc caagttataa ctggcattga ttaaagcatt atctttcaca   180
actaaactgt tcttcatana acagcccata ttattatcaa attaagagac aatgtattcc   240
aatatccttt anggccaata tatttnatgt cccttaatta agagctactg tccgt        295
```

```
<210> SEQ ID NO 156
<211> LENGTH: 406
<212> TYPE: DNA
<213> ORGANISM: Homo sapien
<220> FEATURE:
<221> NAME/KEY: misc_feature
<222> LOCATION: (1)...(406)
<223> OTHER INFORMATION: n = A,T,C or G

<400> SEQUENCE: 156
```

```
gacgcttggc cacttgacac tgcagtggga aaaccagcat gagccgctgc ccccaaggaa    60
cctcgaagcc caggcagagg accagccatc ccagcctgca ggtaaagtgt gtcacctgtc   120
aggtgggctt ggggtgagtg ggtgggggaa gtgtgtgtgc aaaggggtg tnaatgtnta   180 tgcgtgtgag catgagtgat ggctagtgtg actgcatgtc agggagtgtg aacaagcgtg   240 cggggtgtg tgtgcaagtg cgtatgcata tgagaatatg tgtctgtgga tgagtgcatt    300
tgaaagtctg tgtgtgtgcg tgtggtcatg anggtaantt antgactgcg caggatgtgt   360
gagtgtgcat ggaacactca ntgtgtgtgt caagtggccn ancgtc                  406
```

```
<210> SEQ ID NO 157
<211> LENGTH: 208
<212> TYPE: DNA
<213> ORGANISM: Homo sapien
<220> FEATURE:
<221> NAME/KEY: misc_feature
<222> LOCATION: (1)...(208)
<223> OTHER INFORMATION: n = A,T,C or G

<400> SEQUENCE: 157
```

```
tgacgcttgg ccacttgaca cactaaaggg tgttactcat cactttcttc tctcctcggt    60
ggcatgtgag tgcatctatt cacttggcac tcatttgttt ggcagtgact gtaanccana   120
tctgatgcat acaccagctt gtaaattgaa taaatgtctc taatactatg tgctcacaat   180
anggtanggg tgaggagaag gggagaga                                      208
```

```
<210> SEQ ID NO 158
```

<211> LENGTH: 547
<212> TYPE: DNA
<213> ORGANISM: Homo sapien
<220> FEATURE:
<221> NAME/KEY: misc_feature
<222> LOCATION: (1)...(547)
<223> OTHER INFORMATION: n = A,T,C or G

<400> SEQUENCE: 158

| | | | | | | |
|---|---|---|---|---|---|---|
| cttcaacctc | cttcaacctc | cttcaacctc | ctggattcaa | acaatcatcc | cacctcagac | 60 |
| tccttagtag | ctgagactac | agactcacgc | cactacatct | ggctaaattt | ttgtagagat | 120 |
| agggtttcat | catgttgccc | tggctggtct | caaactcctg | acctcaagca | atgtgcccac | 180 |
| ctcagcctcc | caaagtgctg | ggattacagg | cataagccac | catgcccagt | ccatntttaa | 240 |
| tctttcctac | cacattctta | ccacactttc | ttttatgttt | agatacataa | atgcttacca | 300 |
| ttatgataca | attgcccaca | gtattaagac | agtaacatgc | tgcacaggtt | tgtagcctag | 360 |
| gaacagtagg | caataccaca | tagcttaggt | gtgtggtaga | ctataccatc | taggtttgtg | 420 |
| taagttacac | tttatgctgt | ttacacaatg | acaaaaccat | ctaatgatgc | atttctcaga | 480 |
| atgtatcctt | gtcagtaagc | tatgatgtac | agggaacact | gcccaaggac | acagatattg | 540 |
| tacctgt | | | | | | 547 |

<210> SEQ ID NO 159
<211> LENGTH: 203
<212> TYPE: DNA
<213> ORGANISM: Homo sapien

<400> SEQUENCE: 159

| | | | | | | |
|---|---|---|---|---|---|---|
| gctcctcttg | ccttaccaac | tcacccagta | tgtcagcaat | tttatcrgct | ttacctacga | 60 |
| aacagcctgt | atccaaacac | ttaacacact | cacctgaaaa | gttcaggcaa | caatcgcctt | 120 |
| ctcatgggtc | tctctgctcc | agttctgaac | ctttctcttt | tcctagaaca | tgcatttarg | 180 |
| tcgatagaag | ttcctctcag | tgc | | | | 203 |

<210> SEQ ID NO 160
<211> LENGTH: 402
<212> TYPE: DNA
<213> ORGANISM: Homo sapien

<400> SEQUENCE: 160

| | | | | | | |
|---|---|---|---|---|---|---|
| tgtaagtcga | gcagtgtgat | gggtggaaca | gggttgtaag | cagtaattgc | aaactgtatt | 60 |
| taaacaataa | taataatatt | tagcatttat | agagcacttt | atatcttcaa | agtacttgca | 120 |
| aacattayct | aattaaatac | cctctctgat | tataatctgg | atacaaatgc | acttaaactc | 180 |
| aggacagggt | catgagaraa | gtatgcattt | gaaagttggt | gctagctatg | ctttaaaaac | 240 |
| ctatacaatg | atgggraagt | tagagttcag | attctgttgg | actgttttg | tgcatttcag | 300 |
| ttcagcctga | tggcagaatt | agatcatatc | tgcactcgat | gactytgctt | gataacttat | 360 |
| cactgaaatc | tgagtgttga | tcatcacact | gctcgactta | ca | | 402 |

<210> SEQ ID NO 161
<211> LENGTH: 193
<212> TYPE: DNA
<213> ORGANISM: Homo sapien

<400> SEQUENCE: 161

| | | | | | | |
|---|---|---|---|---|---|---|
| agcatgttga | gcccagacac | tgaccaggag | aaaaaccaac | caatagaaac | acgcccagac | 60 |
| actgaccagg | agaaaaacca | accaataaaa | acaggcccgg | acataagaca | aataataaaa | 120 |

```
ttagcggaca aggacatgaa aacagctatt gtaagagcgg atatagtggt gtgtgtctgg      180
gctcaacatg cta                                                        193

<210> SEQ ID NO 162
<211> LENGTH: 147
<212> TYPE: DNA
<213> ORGANISM: Homo sapien

<400> SEQUENCE: 162
tgttgagccc agacactgac caggagaaaa accaaccaat aaaaacaggc ccggacataa      60
gacaaataat aaaattagcg gacaaggaca tgaaaacagc tattgtaaga gcggatatag     120
tggtgtgtgt ctgggctcaa catgcta                                         147

<210> SEQ ID NO 163
<211> LENGTH: 294
<212> TYPE: DNA
<213> ORGANISM: Homo sapien

<400> SEQUENCE: 163
tagcatgttg agcccagaca caaatctttc cttaagcaat aaatcatttc tgcatatgtt      60
tttaaaacca cagctaagcc atgattattc aaaaggacta ttgtattggg tattttgatt     120
tgggttctta tctccctcac attatcttca tttctatcat tgacctctta tcccagagac     180
tctcaaactt ttatgttata caaatcacat tctgtctcaa aaaatatctc acccacttct     240
cttctgtttc tgcgtgtgta tgtgtgtgtg tgtgtgtctg ggctcaacat gcta           294

<210> SEQ ID NO 164
<211> LENGTH: 412
<212> TYPE: DNA
<213> ORGANISM: Homo sapien
<220> FEATURE:
<221> NAME/KEY: misc_feature
<222> LOCATION: (1)...(412)
<223> OTHER INFORMATION: n = A,T,C or G

<400> SEQUENCE: 164
cgggattggc tttgagctgc agatgctgcc tgtgaccgca cccggcgtgg aacagaaagc      60
cacctggctg caagtgcgcc agagccgccc tgactacgtg ctgctgtggg gctggggcgt     120
gatgaactcc accgccctga aggaagccca ggccaccgga taccccgcg acaagatgta     180 cggcgtgtgg tgggccggtg cggagcccga tgtgcgtgac gtgggcgaag cgccaagggg     240
ctacaacgcg ctggctctga cggctacgg cacgcagtcc aaggtgatcc angacatcct     300
gaaacacgtg cacgacaagg gccagggcac ggggcccaaa gacgaagtgg gctcggtgct     360
gtacacccgc ggcgtgatca tccagatgct ggacaaggtg tcaatcacta at             412

<210> SEQ ID NO 165
<211> LENGTH: 361
<212> TYPE: DNA
<213> ORGANISM: Homo sapien

<400> SEQUENCE: 165 ttgacaccttt gtccagcatc tgcatctgat gagagcctca gatggctacc actaatggca      60
gaaggcaaag gagaacaggc attgtatggc aagaaaggaa gaaagagaga ggggagaaag     120
gtgctaggtt cttttcaaca accagttctt gatggaactg agagtaagag ctcaaggcca     180
ggtgtggtga ctccaaccag taatcccaac attttaggag gctgaggcag gcagatgtct     240
```

```
tgacccatg agtttgtgac cagcctgaac aacatcatga gactccatct ctacaataat      300
tacaaaaatt aatcaggcat tgtggtatgc cctgtagtcc cagatgctgg acaaggtgtc      360
a                                                                    361
```

<210> SEQ ID NO 166
<211> LENGTH: 427
<212> TYPE: DNA
<213> ORGANISM: Homo sapien

<400> SEQUENCE: 166

```
twgactgact catgtcccct acacccaact atcttctcca ggtggccagg catgatagaa       60
tctgatcctg acttagggga atattttctt tttacttccc atcttgattc cctgccggtg      120
agtttcctgg ttcagggtaa gaaaggagct caggccaaag taatgaacaa atccatcctc      180
acagacgtac agaataagag aacwtggacw tagccagcag aacmcaaktg aaamcagaac      240
mcttamctag gatracaamc mcrraratar ktgcycmcmc wtataataga aaccaaactt      300
gtatctaatt aaatatttat ccacygtcag ggcattagtg gttttgataa atacgctttg      360
gctaggattc ctgaggttag aatggaaraa caattgcamc gagggtaggg gacatgagtc      420 aktctaa                                                              427
```

<210> SEQ ID NO 167
<211> LENGTH: 500
<212> TYPE: DNA
<213> ORGANISM: Homo sapien
<220> FEATURE:
<221> NAME/KEY: misc_feature
<222> LOCATION: (1)...(500)
<223> OTHER INFORMATION: n = A,T,C or G

<400> SEQUENCE: 167

```
aacgtcgcat gctcccggcc gccatggccg cgggatagac tgactcatgt cccctaagat       60
agaggagaca cctgctaggt gtaaggagaa gatggttagg tctacggagg ctccagggtg      120
ggagtagttc cctgctaagg gagggtagac tgttcaacct gttcctgctc cggcctccac      180
tatagcagat gcgagcagga gtaggagaga gggaggtaag agtcagaagc ttatgttgtt      240
tatgcgggga aacgccrtat cgggggcagc cragttatta ggggacantr tagwyartcw      300
agntagcatc caaagcgngg gagttntccc atatggttgg acctgcaggc ggccgcatta      360
gtgattagca tgtgagcccc agacacgcat agcaacaagg acctaaactc agatcctgtg      420
ctgattactt aacatgaatt attgtattta tttaacaact ttgagttatg aggcatatta      480
ttaggtccat attacctgga                                                 500
```

<210> SEQ ID NO 168
<211> LENGTH: 358
<212> TYPE: DNA
<213> ORGANISM: Homo sapien

<400> SEQUENCE: 168

```
ttcatcgctc ggtgactcaa gcctgtaatc ccagaacttt gggaggccga ggggagcaga       60
tcacctgagg ttgggagttt gagaccagcc tggccaacat ggtgacaacc cgtctctgct      120
aaaaatacaa aaattagcca agcatggtgg catgcacttg taatcccagc tactcgggag      180
gctgaggcag gagaatcact tgaggccagg aggcagaggt tgcagtgagg cagaggttga      240
gatcatgcca ctgcactcca gcctgggcaa cagagtaaga ctccatctca aaaaaaaaa      300 aaaaaagaa tgatcagagc cacaaataca gaaaaccttg agtcaccgag cgatgaaa      358
```

<210> SEQ ID NO 169
<211> LENGTH: 1265
<212> TYPE: DNA
<213> ORGANISM: Homo sapien

<400> SEQUENCE: 169

```
ttctgtccac accaatctta gagctctgaa agaatttgtc tttaaatatc ttttaatagt      60
aacatgtatt ttatggacca aattgacatt ttcgactatt ttttcccaaa aaaagtcagg     120
tgaatttcag cacactgagt tgggaattte ttatcccaga agwcggcacg agcaatttca     180
tatttattta agattgattc catactccgt tttcaaggag aatccctgca gtctccttaa     240
aggtagaaca aatactttct atttttttt caccattgtg ggattggact ttaagaggtg      300
actctaaaaa aacagagaac aaatatgtct cagttgtatt aagcacggac ccatattatc     360
atattcactt aaaaaaatga tttcctgtgc acctttggc aacttctctt ttcaatgtag      420
ggaaaaactt agtcaccctg aaacccaca aataaataa aacttgtaga tgtgggcaga       480
argtttgggg gtggacattg tatgtgttta aattaaaccc tgtatcactg agaagctgtt     540
gtatgggtca gagaaaatga atgcttagaa gctgttcaca tcttcaagag cagaagcaaa     600
ccacatgtct cagctatatt attatttatt ttttatgcat aaagtgaatc atttcttctg     660
tattaatttc caaagggttt taccctctat ttaaatgctt tgaaaaacag tgcattgaca     720
atgggttgat attttctttt aaagaaaaa tataattatg aaagccaaga taatctgaag      780
cctgttttat tttaaaactt tttatgttct gtggttgatg ttgtttgttt gtttgtttct     840
attttgttgg ttttttactt tgttttttgt tttgttttgt tttggttttdg catactacat    900
gcagtttctt taaccaatgt ctgtttggct aatgtaatta aagttgttaa tttatatgag     960
tgcatttcaa ctatgtcaat ggtttcttaa tatttattgt gtagaagtac tggtaatttt    1020
tttatttaca atatgtttaa agagataaca gtttgatatg ttttcatgtg tttatagcag    1080
aagttattta tttctatggc attccagcgg atattttggt gtttgcgagg catgcagtca    1140
atattttgta cagttagtgg acagtattca gcaacgcctg atagcttctt tggccttatg    1200
ttaaataaaa agacctgttt gggatgtaaa aaaaaaaaa aaaaaaaaaa aaaaaaaaa      1260
aaaaa                                                                 1265
```

<210> SEQ ID NO 170
<211> LENGTH: 383
<212> TYPE: DNA
<213> ORGANISM: Homo sapien

<400> SEQUENCE: 170

```
tgtaagtcga gcagtgtgat gacgatattc ttcttattaa tgtggtaatt gaacaaatga      60
tctgtgatac tgatcctgag ctaggaggcg ctgttcagtt aatgggactt cttcgtactc     120
taattgatcc agagaacatg ctggctacaa ctaataaaac cgaaaaaagt gaatttctaa     180
atttttcta caaccattgt atgcatgttc tcacagcacc acttttgacc aatacttcag      240
aagacaaatg tgaaaggat aatatagttg gatcaaacaa aacaacaca atttgtcccg       300
ataattatca acagcacag ctacttgcct taatttttaga gttactcaca ttttgtgtgg     360
aacatcacac tgctcgactt aca                                             383
```

<210> SEQ ID NO 171
<211> LENGTH: 383
<212> TYPE: DNA

<213> ORGANISM: Homo sapien

<400> SEQUENCE: 171

| | | | | | |
|---|---|---|---|---|---|
| tgggcacctt | caatatcgca | agttaaaaat | aatgttgagt | ttattatact | tttgacctgt | 60 |
| ttagctcaac | agggtgaagg | catgtaaaga | atgtggactt | ctgaggaatt | ttcttttaaa | 120 |
| aagaacataa | tgaagtaaca | ttttaattac | tcaaggacta | cttttggttg | aagtttataa | 180 |
| tctagatacc | tctactttt | gtttttgctg | ttcgacagtt | cacaaagacc | ttcagcaatt | 240 |
| tacagggtaa | aatcgttgaa | gtagtggagg | tgaaactgaa | atttaaaatt | attctgtaaa | 300 |
| tactataggg | aaagaggctg | agcttagaat | cttttggttg | ttcatgtgtt | ctgtgctctt | 360 |
| atcatcacac | tgctcgactt | aca | | | | 383 |

<210> SEQ ID NO 172
<211> LENGTH: 699
<212> TYPE: DNA
<213> ORGANISM: Homo sapien
<220> FEATURE:
<221> NAME/KEY: misc_feature
<222> LOCATION: (1)...(699)
<223> OTHER INFORMATION: n = A,T,C or G

<400> SEQUENCE: 172

| | | | | | |
|---|---|---|---|---|---|
| tcgggtgatg | cctcctcagg | cttgtcgtta | gtgtacacag | agctgctcat | gaagcgacag | 60 |
| cggctgcccc | tggcacttca | gaacctcttc | ctctacactt | tggtgcgct | tctgaatcta | 120 |
| ggtctgcatg | ctggcggcgg | ctctggccca | ggcctcctgg | aaagtttctc | aggatgggca | 180 |
| gcactcgtgg | tgctgagcca | ggcactaaat | ggactgctca | tgtctgctgt | catggagcat | 240 |
| ggcagcagca | tcacacgcct | ctttgtggtg | tcctgctcgc | tggtggtcaa | cgccgtgctc | 300 |
| tcagcagtcc | tgctacggct | gcagctcaca | gccgccttct | tcctggccac | attgctcatt | 360 |
| ggcctggcca | tgcgcctgta | ctatggcagc | cgctagtccc | tgacaacttc | caccctgatt | 420 |
| ccggaccctg | tagattgggc | gccaccacca | gatccccctc | ccaggccttc | ctccctctcc | 480 |
| catcagcggc | cctgtaacaa | gtgccttgtg | agaaaagctg | gagaagtgag | ggcagccagg | 540 |
| ttattctctg | gaggttggtg | gatgaagggg | tacccctagg | agatgtgaag | tgtgggtttg | 600 |
| gttaaggaaa | tgcttaccat | cccccacccc | caaccaagtt | nttccagact | aaagaattaa | 660 |
| ggtaacatca | atacctaggc | ctgaggaggc | atcacccga | | | 699 |

<210> SEQ ID NO 173
<211> LENGTH: 701
<212> TYPE: DNA
<213> ORGANISM: Homo sapien

<400> SEQUENCE: 173

| | | | | | |
|---|---|---|---|---|---|
| tcgggtgatg | cctcctcagg | ccagatcaaa | cttggggttg | aaaactgtgc | aaagaaatca | 60 |
| atgtcggaga | agaatttttg | caaaagaaaa | atgcctaatc | agtactaatt | taataggtca | 120 |
| cattagcagt | ggaagaagaa | atgttgatat | tttatgtcag | ctattttata | atcaccagag | 180 |
| tgcttagctt | catgtaagcc | atctcgtatt | cattagaaat | aagaacaatt | ttattcgtcg | 240 |
| gaaagaactt | ttcaatttat | agcatcttaa | ttgctcagga | ttttaaattt | tgataaagaa | 300 |
| agctccactt | ttggcaggag | taggggg cag | ggagagagga | ggctccatcc | acaaggacag | 360 |
| agacaccagg | gccagtaggg | tagctggtgg | ctggatcagt | cacaacggac | tgacttatgc | 420 |
| catgagaaga | aacaacctcc | aaatctcagt | tgcttaatac | aacacaagct | catttcttgc | 480 |
| tcacgttaca | tgtcctatgt | agatcaacag | caggtgactc | agggacccag | gctccatctc | 540 |

| | |
|---|---|
| catatgagct tccatagtca ccaggacacg ggctctgaaa gtgtcctcca tgcagggaca | 600 |
| catgcctctt cctttcattg ggcagagcaa gtcacttatg ccagaagtc acactgcagg | 660 |
| gcagtgccat cctgctgtat gcctgaggag gcatcacccg a | 701 |

<210> SEQ ID NO 174
<211> LENGTH: 700
<212> TYPE: DNA
<213> ORGANISM: Homo sapien
<220> FEATURE:
<221> NAME/KEY: misc_feature
<222> LOCATION: (1)...(700)
<223> OTHER INFORMATION: n = A,T,C or G

<400> SEQUENCE: 174

| | |
|---|---|
| tcgggtgatg cctcctcang cccctaaatc agagtccagg gtcagagcca caggagacag | 60 |
| ggaaagacat agattttaac cggccccctt caggagattc tgaggctcag ttcactttgt | 120 |
| tgcagtttga acagaggcag caaggctagt ggttaggggc acggtctcta aagctgcact | 180 |
| gcctggatct gcctcccagc tctgccagga accagctgcg tggccttgag ctgctgacac | 240 |
| gcagaaagcc ccctgtggac ccagtctcct cgtctgtaag atgaggacag gactctagga | 300 |
| acccttccc ttggtttggc ctcactttca caggctccca tcttgaactc tatctactct | 360 |
| tttcctgaaa ccttgtaaaa gaaaaagtg ctagcctggg caacatggca aaaccctgtc | 420 |
| tctacaaaaa atacaaaaat tagttgggtg tggtggcatg tgcctgtagt cccagccact | 480 |
| tgggaggtgc tgaggtggga ggatcacttg agcccgggag gtggaggttg cagtgagcca | 540 |
| agatcatgcc actgcactcc agcctgagta atagagtaag actctgtctc aaaaacaaca | 600 |
| acaacaacag tgagtgtgcc tctgtttccg ggttggatgg ggcaccacat ttatgcatct | 660 |
| ctcagatttg gacgctgcag cctgaggagg catcacccga | 700 |

<210> SEQ ID NO 175
<211> LENGTH: 484
<212> TYPE: DNA
<213> ORGANISM: Homo sapien
<220> FEATURE:
<221> NAME/KEY: misc_feature
<222> LOCATION: (1)...(484)
<223> OTHER INFORMATION: n = A,T,C or G

<400> SEQUENCE: 175

| | |
|---|---|
| tatagggcga attgggcccg agttgcatgn tcccggccgc catggccgcg ggattcgggt | 60 |
| gatgcctcct caggcttgtc tgccacaagc tacttctctg agctcagaaa gtgcccttg | 120 |
| atgagggaaa atgtcctact gcactgcgaa tttctcagtt ccattttacc tcccagtcct | 180 |
| ccttctaaac cagttaataa attcattcca caagtattta ctgattacct gcttgtgcca | 240 |
| gggactattc tcaggctgaa gaaggtggga ggggagggcg gaacctgagg agccacctga | 300 |
| gccagcttta tatttcaacc atggctggcc catctgagag catctcccca ctctcgccaa | 360 |
| cctatcgggg catagcccag ggatgcccc aggcggccca ggttagatgc gtcccttt gg | 420 |
| cttgtcagtg atgacataca ccttagctgc ttagctggtg ctggcctgag gaggcatcac | 480 |
| ccga | 484 |

<210> SEQ ID NO 176
<211> LENGTH: 432
<212> TYPE: DNA
<213> ORGANISM: Homo sapien

<400> SEQUENCE: 176

```
tcgggtgatg cctcctcagg gctcaaggga tgagaagtga cttctttctg gagggaccgt      60
tcatgccacc caggatgaaa atggataggg acccacttgg aggacttgct gatatgtttg     120
gacaaatgcc aggtagcgga attggtactg gtccaggagt tatccaggat agattttcac    180
ccaccatggg acgtcatcgt tcaaatcaac tcttcaatgg ccatggggga cacatcatgc    240
ctcccacaca atcgcagttt ggagagatgg gaggcaagtt tatgaaaagc cagggctaa    300
gccagctcta ccataaccag agtcaggac tcttatccca gctgcaagga cagtcgaagg     360
atatgccacc tcggttttct aagaaaggac agcttaatgc agatgagatt agcctgagga    420
ggcatcaccc ga                                                         432
```

<210> SEQ ID NO 177
<211> LENGTH: 788
<212> TYPE: DNA
<213> ORGANISM: Homo sapien

<400> SEQUENCE: 177

```
tagcatgttg agcccagaca cagtagcatt tgtgccaatt tctggttgga atggtgacaa      60
catgctggag ccaagtgcta acatgccttg gttcaaggga tggaaagtca cccgtaagga    120
tggcaatgcc agtggaacca cgctgcttga ggctctggac tgcatcctac caccaactcg    180
cccaactgac aagcccttgc gcctgcctct ccaggatgtc tacaaaattg gtggtattgg    240
tactgttcct gttggccgag tggagactgg tgttctcaaa cccggtatgg tggtcacctt    300
tgctccagtc aacgttacaa cggaagtaaa atctgtcgaa atgcaccatg aagctttgag    360
tgaagctctt cctggggaca atgtgggctt caatgtcaag aatgtgtctg tcaaggatgt    420
tcgtcgtggc aacgttgctg gtgacagcaa aaatgaccca ccaatggaag cagctggctt    480
cactgctcag gtgattatcc tgaaccatcc aggccaaata agtgccggct atgcccctgt    540
attggattgc cacacggctc acattgcatg caagtttgct gagctgaagg aaaagattga    600
tcgccgttct ggtaaaaagc tggaagatgg ccctaaattc ttgaagtctg gtgatgctgc    660
cattgttgat atggttcctg gcaagcccat gtgtgttgag agcttctcag actatccacc    720
tttgggtcgc tttgctgttc gtgatatgag acagacagtt gcggtgggtg tctgggctca    780
acatgcta                                                             788
```

<210> SEQ ID NO 178
<211> LENGTH: 786
<212> TYPE: DNA
<213> ORGANISM: Homo sapien

<400> SEQUENCE: 178

```
tagcatgttg agcccagaca cctgtgtttc tgggagctct ggcagtggcg gattcatagg      60
cacttgggct gcactttgaa tgacacactt ggctttatta gattcactag ttttttaaaaa    120
attgttgttc gtttctttc attaaaggtt taatcagaca gatcagacag cataattttg      180
tatttaatga cagaaacgtt ggtacatttc ttcatgaatg agcttgcatt ctgaagcaag    240
agcctacaaa aggcacttgt tataaatgaa agttctggct ctagaggcca gtactctgga    300
gtttcagagc agccagtgat tgttccagtc agtgatgcct agtgatatag aggaggagta    360
cactgtgcac tcttctaggt gtaagggtat gcaactttgg atcttaaaat tctgtacaca    420
tacacacttt atatatatgt atgtatgtat gaaaacatga aattagtttg tcaaatatgt    480
gtgtgtttag tattttagct tagtgcaact atttccacat tatttattaa attgatctaa    540
```

```
gacactttct tgttgacacc ttgaatatta atgttcaagg gtgcaatgtg tattcctttta      600 gattgttaaa gcttaattac tatgatttgt agtaaattaa cttttaaaat gtatttgagc      660
ccttctgtag tgtcgtaggg ctcttacagg gtgggaaaga ttttaattt ccagttgcta       720 attgaacagt atggcctcat tatatatttt gatttatagg agtttgtgtc tgggctcaac      780
atgcta                                                                 786
```

<210> SEQ ID NO 179
<211> LENGTH: 796
<212> TYPE: DNA
<213> ORGANISM: Homo sapien

<400> SEQUENCE: 179

```
tagcatgttg agcccagaca ctggttacaa gaccagacct gcttcctcca tatgtaaaca      60
gcttttaaaa agccagtgaa cctttttaat actttgcaa ccttctttca caggcaaaga      120 acaccccat ccgccccttg tttggagtgc agagtttggc tttggttctt tgccttgcct      180
ggagtatact tctaattcct gttgtcctgc acaagctgaa taccgagcta cccaccgcca      240
cccaggccag gtttccactc atttattact ttatgtttct gttccattgc tggtccacag      300
aaataagttt tccttggag gaatgtgatt atacccttt aatttcctcc ttttgctttt       360
ttttaatatc attggtatgt gtttggccca gaggaaactg aaattcacca tcatcttgac      420
tggcaatccc attaccatgc tttttttaaa aaacgtaatt tttcttgcct tacattggca      480
gagtagccct tcctggctac tggcttaatg tagtcactca gtttctaggt ggcattaggc      540
atgagacctg aagcacagac tgtcttacca caaaggtga caagatctca aaccttagcc       600
aaagggctat gtcaggtttc aatgctatct gcttctgttc ctgctcactg ttctggattt      660
tgtccttctt catccctagc accagaattt cccagtctcc ctccctacct tcccttgttt      720
taattctaat ctatcagcaa ataactttt caaatgtttt aaccggtatc tccatgtgtc      780
tgggctcaac atgcta                                                      796
```

<210> SEQ ID NO 180
<211> LENGTH: 488
<212> TYPE: DNA
<213> ORGANISM: Homo sapien

<400> SEQUENCE: 180

```
ggatgtgctg caaggcgatt aagttgggta acgccagggt tttcccagtc acgacgttgt      60
aaaacgacgg ccagtgaatt gtaatacgac tcactatagg gcgaattggg cccgacgtcg      120
catgctcccg gccgccatgg ccgcgggata gcatgttgag cccagacacc tgcaggtcat      180
ttggagagat ttttcacgtt accagcttga tggtcttttt caggaggaga gacactgagc      240
actcccaagg tgaggttgaa gatttcctct agatagccgg ataagaagac taggagggat      300
gcctagaaaa tgattagcat gcaaatttct acctgccatt tcagaactgt gtgtcagccc      360
acattcagct gcttcttgtg aactgaaaag agagaggtat tgagactttt ctgatggccg      420
ctctaacatt gtaacacagt aatctgtgtg tgtgtgggtg tgtgtgtgtg tctgggctca      480
acatgcta                                                               488
```

<210> SEQ ID NO 181
<211> LENGTH: 317
<212> TYPE: DNA
<213> ORGANISM: Homo sapien -continued

<400> SEQUENCE: 181

| tagcatgttg agcccagaca cggcgacggt acctgatgag tggggtgatg gcacctgtga | 60 |
| aaaggaggaa cgtcatcccc catgatattg gggacccaga tgatgaacca tggctccgcg | 120 |
| tcaatgcata tttaatccat gatactgctg attggaagga cctgaacctg aagtttgtgc | 180 |
| tgcaggttta tcgggactat tacctcacgg gtgatcaaaa cttcctgaag gacatgtggc | 240 |
| ctgtgtgtct agtaagggat gcacatgcag tggccagtgt gccaggggta tggttggtgt | 300 |
| ctgggctcaa catgcta | 317 |

<210> SEQ ID NO 182
<211> LENGTH: 507
<212> TYPE: DNA
<213> ORGANISM: Homo sapien
<220> FEATURE:
<221> NAME/KEY: misc_feature
<222> LOCATION: (1)...(507)
<223> OTHER INFORMATION: n = A,T,C or G

<400> SEQUENCE: 182

| tagcatgttg agcccagaca ctggctgtta gccaaatcct ctctcagctg ctccctgtgg | 60 |
| tttggtgact caggattaca gaggcatcct gtttcaggga acaaaaagat tttagctgcc | 120 |
| agcagagagc accacataca ttagaatggt aaggactgcc acctccttca agaacaggag | 180 |
| tgagggtggt ggtgaatggg aatggaagcc tgcattccct gatgcatttg tgctctctca | 240 |
| aatcctgtct tagtcttagg aaaggaagta agtttcaag gacggttccg aactgctttt | 300 |
| tgtgtctggg ctcaacatgc tatcccgcgg ccatggcggc cgggagcatg cgacgtcggg | 360 |
| cccaattcgc cctatagtga gtcgtattac aattcactgg ccgtcgtttt acaacgtcgt | 420 |
| gactgggaaa accctggcgt tacccaactt aatcgccttg cagcacatcc ccctttccca | 480 |
| gctggcgtaa tancgaaaag gcccgca | 507 |

<210> SEQ ID NO 183
<211> LENGTH: 227
<212> TYPE: DNA
<213> ORGANISM: Homo sapien

<400> SEQUENCE: 183

| gatttacgct gcaacactgt ggaggtagcc ctggagcaag gcaggcatgg atgcttctgc | 60 |
| aatccccaaa tggagcctgg tatttcagcc aggaatctga gcagagcccc ctctaattgt | 120 |
| agcaatgata agttattctc tttgttcttc aaccttccaa tagccttgag cttccagggg | 180 |
| agtgtcgtta atcattacag cctggtctcc acagtgttgc agcgtaa | 227 |

<210> SEQ ID NO 184
<211> LENGTH: 225
<212> TYPE: DNA
<213> ORGANISM: Homo sapien

<400> SEQUENCE: 184

| ttacgctgca acactgtgga gcagattaac atcagacttt tctatcaaca tgactggggt | 60 |
| tactaaaaag acaacaaatc aatggcttca aaagtctaag gaataatttc gatacttcaa | 120 |
| ctttataaaa cctgacaaaa ctatcaatca agcataaaga cagatgaaga acatttccag | 180 |
| attttggcca atcagatatt ttacctccac agtgttgcag cgtaa | 225 |

<210> SEQ ID NO 185
<211> LENGTH: 597

<212> TYPE: DNA
<213> ORGANISM: Homo sapien

<400> SEQUENCE: 185

```
ggcccgacgt cgcatgctcc cggccgccat ggccgcggga ttcgttaggg tctctatcca    60
ctgggaccca taggctagtc agagtattta gagttgagtt cctttctgct tcccagaatt   120
tgaaagaaaa ggagtgaggt gatagagctg agagatcaga tttgcctctg aagcctgttc   180
aagatgtatg tgctcagacc ccaccactgg ggcctgtggg tgaggtcctg ggcatctatt   240
tgaatgaatt gctgaagggg agcactatgc caaggaaggg gaacccatcc tggcactggc   300
acagggtca  ccttatccag tgctcagtgc ttctttgctg ctacctggtt ttctctcata   360
tgtgaggggc aggtaagaag aagtgcccrg tgttgtgcga gttttagaac atctaccagt   420
aagtggggaa gtttcacaaa gcagcagctt tgttttgtgt attttcacct tcagttagaa   480
gaggaaggct gtgagatgaa tgttagttga gtggaaaaga cgggtaagct tagtggatag   540
agaccctaac gaatcactag tgcggccgcc ttgcaggtcg accatatggg agagctc      597
```

<210> SEQ ID NO 186
<211> LENGTH: 597
<212> TYPE: DNA
<213> ORGANISM: Homo sapien

<400> SEQUENCE: 186

```
ggcccgaagt tgcatgttcc cggccgccat ggccgcggga ttcgttaggg tctctatcca    60
ctacctaaaa aatcccaaac atataactga actcctcaca cccaattgga ccaatccatc   120
accccagagg cctacagatc ctcctttgat acataagaaa atttccccaa actacctaac   180
tatatcattt tgcaagattt gttttaccaa attttgatgg cctttctgag cttgtcagtg   240
tgaaccacta ttacgaacga tcggatatta actgcccctc accgtccagg tgtagctggc   300
aacatcaagt gcagtaaata ttcattaagt tttcacctac taaggtgctt aaacacccta   360
gggtgccatg tcggtagcag atcttttgat ttgtttttat ttcccataag ggtcctgttc   420
aaggtcaatc atacatgtag tgtgagcagc tagtcactat cgcatgactt ggagggtgat   480
aatagaggcc tcctttgctg ttaaagaact cttgtcccag cctgtcaaag tggatagaga   540
ccctaacgaa tcactagtgc ggccgcctgc aggtcgacca tatgggagag ctcccaa      597
```

<210> SEQ ID NO 187
<211> LENGTH: 324
<212> TYPE: DNA
<213> ORGANISM: Homo sapien

<400> SEQUENCE: 187

```
tcgttagggt ctctatccac ttgcaggtaa atccaatcc  tgtgtatatc ttatagtctt    60
ccatatgtag tggttcaaga gactgcagtt ccagaaagac tagccgagcc catccatgtc   120
ttccacttaa ccctgctttg ggttacacat cttaactttt ctgttcaagt ttctctgtgt   180
agtttatagc atgagtattg ggawaatgcc ctgaaacctg acatgagatc tgggaaacac   240
aaacttactc aataagaatt tctcccatat ttttatgatg gaaaaatttc acatgcacag   300
aggagtggat agagaccta  acga                                          324
```

<210> SEQ ID NO 188
<211> LENGTH: 178
<212> TYPE: DNA
<220> FEATURE:
<213> ORGANISM: Homo sapien

```
<221> NAME/KEY: misc_feature
<222> LOCATION: (1)...(178)
<223> OTHER INFORMATION: n = A,T,C or G

<400> SEQUENCE: 188 gcgcgggat  tcggggtgat  acctcctcat  gccaaaatac  aacgtntaat  ttcacaactt      60
gccttccaat  ttacgcattt  tcaatttgct  ctccccattt  gttgagtcac  aacaaacacc     120
attgcccaga  aacatgtatt  acctaacatg  cacatactct  taaaactact  catcccctt     178

<210> SEQ ID NO 189
<211> LENGTH: 367
<212> TYPE: DNA
<213> ORGANISM: Homo sapien

<400> SEQUENCE: 189
tgacaccttg  tccagcatct  gacacagtct  tggctcttgg  aaaatattgg  ataaatgaaa      60
atgaatttct  ttagcaagtg  gtataagctg  agaatatacg  tatcacatat  cctcattcta     120
agacacattc  agtgtccctg  aaattagaat  aggacttaca  ataagtgtgt  tcactttctc     180
aatagctgtt  attcaattga  tggtaggcct  taaaagtcaa  agaaatgaga  gggcatgtga     240
aaaaaagctc  aacatcactg  atcattagaa  aacttccatt  caaaccccca  atgagatacc     300
atctcatacc  agtcagaatg  gctattatta  aaaagtcaaa  aataacaga   tgctggacaa     360 ggtgtca                                                                    367

<210> SEQ ID NO 190
<211> LENGTH: 369
<212> TYPE: DNA
<213> ORGANISM: Homo sapien
<220> FEATURE:
<221> NAME/KEY: misc_feature
<222> LOCATION: (1)...(369)
<223> OTHER INFORMATION: n = A,T,C or G

<400> SEQUENCE: 190
gacaccttgt  ccagcatctg  acaacgctaa  cagcctgagg  agatctttat  ttattttattt    60 agttttttact  ctggctaggc  agatggtggc  taaaacattc  atttacccat  ttattcatttt   120 aattgttcct  gcaaggccta  tgatagagt   attgtccagc  actgctctgg  aagctaggag     180 catgggatg   aacaagatag  gctacatcct  gttcccacag  aacttccact  ttagtctggg     240
aaacagatga  tatatacaaa  tatataaatg  aattcaggta  gttttaagta  cgaaaagaat     300
aagaaagcag  agtcatgatt  tanaatgctg  gaaacagggg  ctattgcttg  agatattgaa     360
ggtgcccaa                                                                  369

<210> SEQ ID NO 191
<211> LENGTH: 369
<212> TYPE: DNA
<213> ORGANISM: Homo sapien

<400> SEQUENCE: 191
tgacaccttg  tccagcatct  gcacagggaa  aagaaactat  tatcagagtg  aacaggcaac      60
ctacagaatg  ggagaaaatt  tttgcaatct  atccatctga  caaagggcta  atatccagaa     120
tctacaaaga  acttatacaa  atttacaaga  aacaaacaaa  caaacaactc  ctcaaaaagt     180
gggtgaagga  tgtgaacaga  cacttctcaa  aagaagacat  ttatgggcc   aacaaacata     240 tgaaaaaaag  ctcatcatca  ctggtcacta  gataaatgca  aatcaaaacc  acaatgagat     300
accatctcat  tccagttaga  atggcaatca  ttaaaaagtc  aggaaacaac  agatgctgga     360
``` caaggtgtc                                                                       369

<210> SEQ ID NO 192
<211> LENGTH: 449
<212> TYPE: DNA
<213> ORGANISM: Homo sapien

<400> SEQUENCE: 192
tgacgcttgg ccacttgaca cttcatcttt gcacagaaaa acttctttac agatttaatt      60
caagactggt ctagtgacag tcctccagac atttttcat ttgttccata tacgtggaat     120
tttaaaatca tgtttcatca gtttgaaatg atttgggctg ctaatcaaca caattggatc     180
gactgttcta ctaaacaaca ggaaaatgtg tatctggcag cctgtggaga aacactaaac     240
attgattttt ctttgccttt tacggacttt gttccagcta catgtaatac caagttctct     300
ttaagaggag aagatgttga tcttcatttg tttctaccag actgccaccc tagtaaatat     360
tctttattta tgctggtaaa aaattgccat ccaaataaga tgattcatga tactggtatt     420
cctgctgagt gtcaagtggc caagcgtca                                      449

<210> SEQ ID NO 193
<211> LENGTH: 372
<212> TYPE: DNA
<213> ORGANISM: Homo sapien

<400> SEQUENCE: 193
tgacgcttgg ccacttgaca ccagggatgt akcagttgaa tataatcctg caattgtaca      60
tattggcaat ttcccatcaa acattctaga aagagacaac caggattgct aggccataaa     120
agctgcaata ataactggt aattgcagta atcatttcag gccaattcaa tccagtttgg     180
ctcagaggtg cctttggctg agagaagagg tgagatataa tgtgttttct tgcaacttct     240
tggaagaata actccacaat agtctgagga ctagatacaa acctatttgc cattaaagca     300
ccagagtctg ttaattccag tactgataag tgttggagat tagactccag tgtgtcaagt     360
ggccaagcgt ca                                                         372

<210> SEQ ID NO 194
<211> LENGTH: 309
<212> TYPE: DNA
<213> ORGANISM: Homo sapien
<220> FEATURE:
<221> NAME/KEY: misc_feature
<222> LOCATION: (1)...(309)
<223> OTHER INFORMATION: n = A,T,C or G

<400> SEQUENCE: 194
tgacgcttgg ccacttgaca cttatgtaga atccatcgtg ggctgatgca agcccttat       60
ttaggcttag tgttgtgggc accttcaata tcacactaga gacaaacgcc acaagatctg     120
cagaaacatt cagttctgan cactcgaatg gcaggataac ttttgtgtt gtaatccttc      180
acatatacaa aaacaaactc tgcantctca cgttacaaaa aaacgtactg ctgtaaaata    240
ttaagaaggg gtaaaggata ccatctataa caaagtaact tacaactagt gtcaagtggc     300
caagcgtca                                                             309

<210> SEQ ID NO 195
<211> LENGTH: 312
<212> TYPE: DNA
<213> ORGANISM: Homo sapien
<220> FEATURE:

```
<221> NAME/KEY: misc_feature
<222> LOCATION: (1)...(312)
<223> OTHER INFORMATION: n = A,T,C or G

<400> SEQUENCE: 195
tgacgcttgg ccacttgaca cccaatctcg cacttcatcc tcccagcacc tgatgaagta      60
ggactgcaac tatccccact tcccagatga ggggaccaan gtacacatta ggacccggat     120
gggagcacag atttgtccga tcccagactc caagcactca gcgtcactcc aggacagcgg     180
ctttcagata aggtcacaaa catgaatggc tccgacaacc ggagtcagtc cgtgctgagt     240
taaggcaatg gtgacacgga tgcacgtgtn acctgtaatg gttcatcgta agtgtcaagt     300
ggccaagcgt ca                                                         312

<210> SEQ ID NO 196
<211> LENGTH: 288
<212> TYPE: DNA
<213> ORGANISM: Homo sapien

<400> SEQUENCE: 196
tgtatcgacg tagtggtctc ctcagccatg cagaactgtg actcaattaa acctctttcc      60
tttatgaatt acccaatctc gggtagtgtc tttatagtag tgtgagaatg gactaataca     120
agtacatttt acttagtaat aataataaac aaatatatta cattttttgtg tatttactac   180 accatatttt ttattgttat tgtagtgtac accttctact tattaaaaga aataggcccg     240
aggcgggcag atcacgaggt caggagatgg agaccactac gtcgatac                  288

<210> SEQ ID NO 197
<211> LENGTH: 289
<212> TYPE: DNA
<213> ORGANISM: Homo sapien

<400> SEQUENCE: 197
ttgggcacct tcaatatcat gacaggtgat gtgataacca agaaggctac taagtgatta      60
atgggtgggt aatgtataca gagtaggtac actggacaga ggggtaattc atagccaagg     120
caggagaagc agaatggcaa acatttcat cacactactc aggatagcat gcagtttaaa     180
acctataagt agtttatttt tggaattttc cacttaaatat tttcagactg caggtaacta    240
aactgtggaa cacaagaaca tagataaggg gagaccacta cgtcgatac                 289

<210> SEQ ID NO 198
<211> LENGTH: 288
<212> TYPE: DNA
<213> ORGANISM: Homo sapien

<400> SEQUENCE: 198
gtatcgacgt agtggtctcc caagcagtgg gaagaaaacg tgaaccaatt aaaatgtatc      60 agataccccca agaaaggcg cttgagtaaa gattccaagt gggtcacaat ctcagatctt    120
aaaattcagg ctgtcaaaga gatttgctat gaggttgctc tcaatgactt caggcacagt    180
cggcaggaga ttgaagccct ggccattgtc aagatgaagg agctttgtgc catgtatggc    240
aagaaagacc ccaatgagcg ggactcctgg agaccactac gtcgatac                  288

<210> SEQ ID NO 199
<211> LENGTH: 1027
<212> TYPE: DNA
<213> ORGANISM: Homo sapien
<220> FEATURE:
<221> NAME/KEY: misc_feature
```

<222> LOCATION: (1)...(1027)
<223> OTHER INFORMATION: n = A,T,C or G

<400> SEQUENCE: 199

```
gcttttggg aaaaacncaa ntggggaaa ggggnttnn tngcagggg ataaagggg      60
aancccaggg tttccccatt cagggaggtg taaaaagncg gccagggat tgtaanagga    120
ttcaataata gggggaatgg gcccngaagt tgcaaggttc cngcccgcca tgnccgcggg   180
atttagtgac attacgacgs tggtaataaa gtgggsccaa waaatatttg tgatgtgatt   240
tttsgaccag tgaacccatt gwacaggacc tcatttccty tgagatgrta gccataatca   300
gataaaagrt tagaagtytt tctgcacgtt aacagcatca ttaaatggag tggcatcacc   360
aatttcaccc tttgttagcc gatacettcc ccttgaaggc attcaattaa gtgaccaatc   420
gtcatacgag aggggatggc atgggattg atgatgatat caggggtgat accttcacag    480
gtgaaaggca tatcctcttg tctatactga ataccacaag tacccttttg accatgtcga   540
ctagcaaatt tgtctccaat ctgtgtwatc cctaacagag cgtacccttta ttttacaaaa  600
tttatatcct tcctgattga gagttaccat aacctgatcc acaatgcccg tctcgctwgt   660
tctgagaaaa gtgctacagt ctctcttggt atagcgtcta ttggtgctct ccaattcatc   720
ttcattttc aggcaaggtg aactgttttg cctataataa cmtcatctcc tgatacmcga    780
aacccckgga rctatcaaac catcatcatc cagcgttckt watgtymcta aatccctatt   840
gcggccgcct gcaggtcaac atatnggaaa acccccacc ccttnggagc ntaccttgaa    900
ttttccatat gtcccntaaa ttanctngnc ttanccctggc cntaacctnt tccggtttaa   960
attgtttccg ccccnttcc ccnccttnna accggaaacc ttaattttna accngggtt    1020
cctatcc                                                           1027
```

<210> SEQ ID NO 200
<211> LENGTH: 207
<212> TYPE: DNA
<213> ORGANISM: Homo sapien

<400> SEQUENCE: 200

```
agtgacatta cgacgctggc catcttgaat cctagggcat gaagttgccc caaagttcag    60
cacttggtta agcctgatcc ctctggttta tcacaaagaa taggatggga taagaaagt   120
ggacacttaa ataagctata aattatatgg tccttgtcta gcaggagaca actgcacagg   180
tatactacca gcgtcgtaat gtcacta                                      207
```

<210> SEQ ID NO 201
<211> LENGTH: 209
<212> TYPE: DNA
<213> ORGANISM: Homo sapien

<400> SEQUENCE: 201

```
tgggcaccttt caatatctat taaaagcaca aatactgaag aacacaccaa gactatcaat    60
gaggttacat ctggagtcct cgatatatca ggaaaaatg aagtgaacat tcacagagtt   120
ttacttcttt gggaactcaa atgctagaaa agaaaagggt gccctctttc tctggcttcc   180
tggtcctatc cagcgtcgta atgtcacta                                    209
```

<210> SEQ ID NO 202
<211> LENGTH: 349
<212> TYPE: DNA
<213> ORGANISM: Homo sapien
<220> FEATURE:

<221> NAME/KEY: misc_feature
<222> LOCATION: (1)...(349)
<223> OTHER INFORMATION: n = A,T,C or G

<400> SEQUENCE: 202

| | | | | | |
|---|---|---|---|---|---|
| ntacgctgca | acactgtgga | gccactggtt | tttattcccg | gcaggttatc | cagcaaacag | 60 |
| tcactgaaca | caccgaagac | cgtggtatgg | taaccgttca | cagtaatcgt | tccagtcgtc | 120 |
| tgcgggaccc | cgacgagcgt | cactgggtac | agaccagatt | cagccggaag | agaaagcgcc | 180 |
| gcagggagag | actcgaactc | cactccgctg | gtgagcagcc | ccatgttttc | aactcgaagt | 240 |
| tcaaacggca | ttgggttata | taccatcagc | tgaacttcac | acacatctcc | ttgaacccac | 300 |
| tggaaatcta | ttttcttgtt | ccgctcttct | ccacagtgtt | gcagcgtaa | | 349 |

<210> SEQ ID NO 203
<211> LENGTH: 241
<212> TYPE: DNA
<213> ORGANISM: Homo sapien

<400> SEQUENCE: 203

| | | | | | |
|---|---|---|---|---|---|
| tgctcctctt | gccttaccaa | cccaaagccc | actgtgaaat | atgaagtgaa | tgacaaaatt | 60 |
| cagttttcaa | cgcaatatag | tatagtttat | ctgattcttt | tgatctccag | gacactttaa | 120 |
| acaactgcta | ccaccaccac | caacctaggg | atttaggatt | ctcccagac | cagaaattat | 180 |
| ttctcctttg | agtttcaggc | tcctctggga | ctcctgttca | tcaatgggtg | gtaaatggct | 240 |
| a | | | | | | 241 |

<210> SEQ ID NO 204
<211> LENGTH: 248
<212> TYPE: DNA
<213> ORGANISM: Homo sapien

<400> SEQUENCE: 204

| | | | | | |
|---|---|---|---|---|---|
| tagccattta | ccacccatct | gcaaaccswg | acmwwcargr | cywgwackya | ggcgatttga | 60 |
| agtactggta | atgctctgat | catgttagtt | acataagtgt | ggtcagttta | caaaaattca | 120 |
| cagaactaaa | tactcaatgc | tatgtgttca | tgtctgtgtt | tatgtgtgtg | taatgtttca | 180 |
| attaagtttt | tttaaaaaaa | agagatgatt | tccaaataag | aaagccgtgt | tggtaaggca | 240 |
| agaggagc | | | | | | 248 |

<210> SEQ ID NO 205
<211> LENGTH: 505
<212> TYPE: DNA
<213> ORGANISM: Homo sapien
<220> FEATURE:
<221> NAME/KEY: misc_feature
<222> LOCATION: (1)...(505)
<223> OTHER INFORMATION: n = A,T,C or G

<400> SEQUENCE: 205

| | | | | | |
|---|---|---|---|---|---|
| tacgctgcaa | cactgtggag | ccattcatac | aggtccctaa | ttaaggaaca | agtgattatg | 60 |
| ctacctttgc | acggttaggg | taccgcggcc | gttaaacatg | tgtcactggg | caggcggtgc | 120 |
| ctctaatact | ggtgatgcta | gaggtgatgt | ttttggtaaa | caggcggggt | aagatttgcc | 180 |
| gagttccttt | tactttttttt | aacctttcct | tatgagcatg | cctgtgttgg | gttgacagtg | 240 |
| ggggtaataa | tgacttgttg | gttgattgta | gatattgggc | tgttaattgt | cagttcagtg | 300 |
| ttttaatctg | acgcaggctt | atgcggagga | gaatgttttc | atgttactta | tactaacatt | 360 |
| agttcttcta | tagggtgata | gattggtcca | attgggtgtg | aggagttcag | ttatatgttt | 420 |

```
gggattttttt aggtagtggg tgttganctt gaacgctttc ttaattggtg gctgctttta      480
rgcctactat gggtggtaaa tggct                                             505
```

<210> SEQ ID NO 206
<211> LENGTH: 179
<212> TYPE: DNA
<213> ORGANISM: Homo sapien

<400> SEQUENCE: 206

```
tagactgact catgtcccct accaaagccc atgtaaggag ctgagttctt aaagactgaa       60
gacagactat tctctggaga aaataaaat ggaaattgta ctttaaaaaa aaaaaaaatc       120
ggccgggcat ggtagcacac acctgtaatc ccagctacta ggggacatga gtcagtcta      179
```

<210> SEQ ID NO 207
<211> LENGTH: 176
<212> TYPE: DNA
<213> ORGANISM: Homo sapien

<400> SEQUENCE: 207

```
agactgactc atgtcccta ccccaccttc tgctgtgctg ccgtgttcct aacaggtcac        60
agactggtac tggtcagtgg cctgggggtt ggggacctct attatatggg atacaaattt     120
aggagttgga attgacacga tttagtgact gatgggatat gggtggtaaa tggcta          176
```

<210> SEQ ID NO 208
<211> LENGTH: 196
<212> TYPE: DNA
<213> ORGANISM: Homo sapien

<400> SEQUENCE: 208

```
agactgactc atgtcccta tttaacaggg tctctagtgc tgtgaaaaaa aaaaatgctg        60
aacattgcat ataacttata ttgtaagaaa tactgtacaa tgactttatt gcatctgggt     120
agctgtaagg catgaaggat gccaagaagt ttaaggaata tgggtggtaa atggctaggg     180
gacatgagtc agtcta                                                      196
```

<210> SEQ ID NO 209
<211> LENGTH: 345
<212> TYPE: DNA
<213> ORGANISM: Homo sapien
<220> FEATURE:
<221> NAME/KEY: misc_feature
<222> LOCATION: (1)...(345)
<223> OTHER INFORMATION: n = A,T,C or G

<400> SEQUENCE: 209

```
gacgcttggc cacttgacac ctttatttt ttaaggattc ttaagtcatt tangtnactt        60
tgtaagtttt tcctgtgccc ccataagaat gatagcttta aaaattatgc tggggtagca     120
aagaagatac ttctagcttt agaatgtgta ggtatagcca ggattcttgt gaggagggt      180 gatttagagc aaatttctta ttctccttgc ctcatctgta acatgggat aataatagaa      240 ctggcttgac aaggttggaa ttagtattac atggtaaata catgtaaaat gtttagaatg     300
gtgccaagta tctaggaagt acttgggcat gggtggtaaa tggct                     345
```

<210> SEQ ID NO 210
<211> LENGTH: 178
<212> TYPE: DNA
<213> ORGANISM: Homo sapien

<400> SEQUENCE: 210

```
gacgcttggc cacttgacac tagagtaggg tttggccaac ttttctata aaggaccaga      60
gagtaaatat ttcaggcttt gtgggttgtg cagtctctct tgcaactact cagctctgcc    120
attgtagcat agaaatcagc catagacagg acagaaatga atgggtggta aatggcta      178
```

<210> SEQ ID NO 211
<211> LENGTH: 454
<212> TYPE: DNA
<213> ORGANISM: Homo sapien

<400> SEQUENCE: 211

```
tgggcacctt caatatctat ccagcgcatc taaattcgct tttttcttga ttaaaattt      60
caccacttgc tgttttgct catgtatacc aagtagcagt ggtgtgaggc catgcttgtt    120
ttttgattcg atatcagcac cgtataagag cagtgctttg ccattaatt tatcttcatt    180
gtagacagca tagtgtagag tggtatctcc atactcatct ggaatatttg gatcagtgcc    240
atgttccagc aacattaacg cacattcatc ttcctggcat tgtacggcct ttgtcagagc    300
tgtcctcttt ttgttgtcaa ggacattaag ttgacatcgt ctgtccagca cgagttttac    360
tacttctgaa ttcccattgg cagaggccag atgtagagca gtcctctttt gcttgtccct    420
cttgttcaca tcagtgtccc tgagcataac ggaa                                454
```

<210> SEQ ID NO 212
<211> LENGTH: 337
<212> TYPE: DNA
<213> ORGANISM: Homo sapien

<400> SEQUENCE: 212

```
tccgttatgc cacccagaaa acctactgga gttacttatt aacatcaagg ctggaaccta     60
tttgcctcag tcctatctga ttcatgagca catggttatt actgatcgca ttgaaaacat    120
tgatcacctg ggtttctta tttatcgact gtgtcatgac aaggaaactt acaaactgca    180
acgcagagaa actattaaag gtattcagaa acgtgaagcc agcaattgtt tcgcaattcg    240
gcattttgaa aacaaatttg ccgtggaaac tttaatttgt tcttgaacag tcaagaaaaa    300
cattattgag gaaaattaat atcacagcat aacggaa                             337
```

<210> SEQ ID NO 213
<211> LENGTH: 715
<212> TYPE: DNA
<213> ORGANISM: Homo sapien
<220> FEATURE:
<221> NAME/KEY: misc_feature
<222> LOCATION: (1)...(715)
<223> OTHER INFORMATION: n = A,T,C or G

<400> SEQUENCE: 213

```
tcgggtgatg cctcctcagg catcttccat ccatctcttc aagattagct gtcccaaatg     60
ttttccttc tcttctttac tgataaattt ggactcctt ttgacactga tgacagcttt    120
agtatccttc ttgtcacctt gcagacttta aacataaaaa tactcattgg ttttaaaagg    180
aaaaagtat acattagcac tattaagctt ggccttgaaa cattttctat cttttattaa    240
atgtcggtta gctgaacaga attcatttta caatgcagag tgagaaaaga agggagctat    300
atgcatttga gaatgcaagc attgtcaaat aaacatttta aatgcttct taaagtgagc    360
acatacagaa atacattaag atattagaaa gtgttttgc ttgtgtacta ctaattaggg    420
aagcaccttg tatagttcct cttctaaaat tgaagtagat tttaaaaacc catgtaattt    480
```

```
aattgagctc tcagttcaga tttaggaga atttaacag ggattggtt ttgtctaaat     540 tttgtcaatt tntttagtta atctgtataa tttataaat gtcaaactgt atttagtccg   600 tttcatgct gctatgaaag aaatacccan gacagggtta tttataaang gaaagangtt   660
aatttgactc ccagttcaca ggcctgagga ngnatcnccc gaaatcctta ttgcg       715
```

```
<210> SEQ ID NO 214
<211> LENGTH: 345
<212> TYPE: DNA
<213> ORGANISM: Homo sapien
<220> FEATURE:
<221> NAME/KEY: misc_feature
<222> LOCATION: (1)...(345)
<223> OTHER INFORMATION: n = A,T,C or G

<400> SEQUENCE: 214
```

```
ggtaangngc atacntcggt gctccggccg ccggagtcgg gggattcggg tgatgcctcc    60
tcaggcccac ttgggcctgc tttcccaaa tggcagctcc tctggacatg ccattccttc   120
tcccacctgc ctgattcttc atatgttggg tgtccctgtt ttctggtgc tatttcctga   180 ctgctgttca gctgccactg tcctgcaaag cctgccttt taaatgcctc accattcctt    240
catttgtttc ttaaatatgg gaagtgaaag tgccacctga ggccgggcac agtggctcac    300
gcctgtaatc ccagcacttt gggagcctga ggaggcatca cccga                   345
```

```
<210> SEQ ID NO 215
<211> LENGTH: 429
<212> TYPE: DNA
<213> ORGANISM: Homo sapien

<400> SEQUENCE: 215
```

```
ggtgatgcct cctcaggcga agctcaggga ggacagaaac ctcccgtgga gcagaagggc    60
aaaagctcgc ttgatcttga ttttcagtac gaatacagac cgtgaaagcg gggcctcacg   120
atccttctga cctttgggt tttaagcagg aggtgtcaga aaagttacca cagggataac    180
tggcttgtgg cggccaagcg ttcatagcga cgtcgctttt tgatccttcg atgtcggctc    240
ttcctatcat tgtgaagcag aattcaccaa gcgttggatt gttcacccac taataggaa    300 cgtgagctgg gtttagaccg tcgtgagaca ggttagttt acccctactga tgatgtgtkg    360 ttgccatggt aatcctgctc agtacgagag gaaccgcagg ttcasacatt tggtgtatgt   420
gcttgcctt                                                           429
```

```
<210> SEQ ID NO 216
<211> LENGTH: 593
<212> TYPE: DNA
<213> ORGANISM: Homo sapien
<220> FEATURE:
<221> NAME/KEY: misc_feature
<222> LOCATION: (1)...(593)
<223> OTHER INFORMATION: n = A,T,C or G

<400> SEQUENCE: 216
```

```
tgacacctat gtccngcatc tgttcacagt ttccacaaat agccagcctt tggccacctc    60
tctgtcctga ggtatacaag tatatcagga ggtgtatacc ttctcttctc ttccccacca   120
aagagaacat gcaggctctg gaagctgtct taggagcctt tgggctcaga atttcagagt   180
cttgggtacc ttgatgtgg tctggaagga gaaacattgg ctctggataa ggagtacagc    240
cggaggaggg tcacagagcc ctcagctcaa gcccctgtgc cttagtctaa aagcagcttt    300
```

```
ggatgaggaa gcaggttaag taacatacgt aagcgtacac aggtagaaag tgctgggagt    360
cagaattgca cagtgtgtag gagtagtacc tcaatcaatg agggcaaatc aactgaaaga    420
agaagaccna ttaatgaatt gcttangggg aaggatcaag gctatcatgg agatctttct    480
aggaagatta ttgtttanaa ttatgaaagg antagggcag ggacagggcc agaagtanaa    540
ganaacattg cctatanccc ttgtcttgca cccagatgct ggacaaggtg tca           593
```

<210> SEQ ID NO 217
<211> LENGTH: 335
<212> TYPE: DNA
<213> ORGANISM: Homo sapien

<400> SEQUENCE: 217

```
tgacaccttg tccagcatct gacgtgaaga tgagcagctc agaggaggtg tcctggattt     60
cctggttctg tgggctccgt ggcaatgaat tcttctgtga agtggatgaa gactacatcc    120
aggacaaatt taatcttact ggactcaatg agcaggtccc tcactatcga caagctctag    180
acatgatctt ggacctggag cctgatgaag aactggaaga caaccccaac cagagtgacc    240
tgattgagca ggcagccgag atgctttatg gattgatcca cgcccgctac atccttacca    300
accgtggcat cgcccagatg ctggacaagg tgtca                               335
```

<210> SEQ ID NO 218
<211> LENGTH: 248
<212> TYPE: DNA
<213> ORGANISM: Homo sapien

<400> SEQUENCE: 218

```
tacgtactgg tcttgaaggt cttaggtaga gaaaaaatgt gaatatttaa tcaaagacta     60
tgtatgaaat gggactgtaa gtacagaggg aagggtggcc cttatcgcca gaagttggta    120
gatgcgtccc cgtcatgaaa tgttgtgtca ctgcccgaca tttgccgaat tactgaaatt    180
ccgtagaatt agtgcaaatt ctaacgttgt tcatctaaga ttatggttcc atgtttctag    240
tacttttta                                                            248
```

<210> SEQ ID NO 219
<211> LENGTH: 530
<212> TYPE: DNA
<213> ORGANISM: Homo sapien
<220> FEATURE:
<221> NAME/KEY: misc_feature
<222> LOCATION: (1)...(530)
<223> OTHER INFORMATION: n = A,T,C or G

<400> SEQUENCE: 219

```
tgacgcttgg ccacttgaca caagtagggg ataaggacaa agacccatna ggtggcctgt     60
cagccttttg ttactgttgc ttccctgtca ccacggcccc ctctgtaggg gtgtgctgtg    120
ctctgtggac attggtgcat tttcacacat accattctct ttctgcttca cagcagtcct    180
gaggcgggag cacacaggac taccttgtca gatgangata atgatgtctg gccaactcac    240
cccccaacct tctcactagt tatangaaga gccangccta naaccttcta tcctgnccccc   300 ttgccctatg acctcatccc tgttccatgc cctattctga tttctggtga actttggagc    360
agcctggttt ntcctcctca ctccagcctc tctccatacc atggtangg ggtgctgttc    420 cacncaaang gtcaggtgtg tctggggaat cctnananct gccnggagtt tccnangcat    480
tcttaaaaac cttcttgcct aatcanatng tgtccagtgg ccaaccntcn               530
```

<210> SEQ ID NO 220
<211> LENGTH: 531
<212> TYPE: DNA
<213> ORGANISM: Homo sapien

<400> SEQUENCE: 220

| | | | | | |
|---|---|---|---|---|---|
| tgacgcttgg | ccacttgaca | ctaaatagca | tcttctaaag | gcctgattca | gagttgtgga | 60 |
| aaattctccc | agtgtcaggg | attgtcagga | acagggctgc | tcctgtgctc | actttacctg | 120 |
| ctgtgtttct | gctggaaaag | gagggaagag | gaatggctga | ttttaccta | atgtctccca | 180 |
| gttttttcata | ttcttcttgg | atcctcttct | ctgacaactg | ttccctttg | gtcttcttct | 240 |
| tcttgctcag | agagcaggtc | tctttaaaac | tgagaaggga | gaatgagcaa | atgattaaag | 300 |
| aaaacacact | tctgaggccc | agagatcaaa | tattaggtaa | atactaaacc | gcttgcctgc | 360 |
| tgtggtcact | tttctcctct | ttcacatgct | ctatccctct | atccccacc | tattcatatg | 420 |
| gcttttatct | gccaagttat | ccggcctctc | atcaaccttc | tccctagcc | tactggggga | 480 |
| tatccatctg | gtctgtctc | tggtgtattg | gtgtcaagtg | gccaagcgtc | a | 531 |

<210> SEQ ID NO 221
<211> LENGTH: 530
<212> TYPE: DNA
<213> ORGANISM: Homo sapien

<400> SEQUENCE: 221

| | | | | | |
|---|---|---|---|---|---|
| attgacgctt | ggccacttga | cacccgcctg | cctgcaatac | tggggcaagg | gccttcactg | 60 |
| cttttcctgcc | accagctgcc | actgcacaca | gagatcagaa | atgctaccaa | ccaagactgt | 120 |
| tggtcctcag | cctctctgag | gagaaagagc | agaagcctgg | aagtcagaag | agaagctaga | 180 |
| tcggctacgg | ccttggcagc | cagcttcccc | acctgtggca | ataaagtcgt | gcatggctta | 240 |
| acaatggggg | cacctcctga | gaaacacatt | gttaggcaat | tcggcgtgtg | ttcatcagag | 300 |
| catatttaca | caaacctcga | tagtgcagcc | tactatccac | tattgctcct | acgctgcaaa | 360 |
| cctgaacagc | atgggactgt | actgaatact | ggaagcagct | ggtgatggta | cttatttgtg | 420 |
| tatctaaaca | cagagaaggt | acagtaagaa | tatggtatca | taaacttaca | gggaccgcca | 480 |
| tcctatatgc | agtctgttgt | gaccaaaatg | tgtcaagtgg | ccaagcgtca | | 530 |

<210> SEQ ID NO 222
<211> LENGTH: 578
<212> TYPE: DNA
<213> ORGANISM: Homo sapien
<220> FEATURE:
<221> NAME/KEY: misc_feature
<222> LOCATION: (1)...(578)
<223> OTHER INFORMATION: n = A,T,C or G

<400> SEQUENCE: 222

| | | | | | |
|---|---|---|---|---|---|
| tgtatcgacg | tagtggtctc | cgggctacta | ggccgttgtg | tgctggtagt | acctggttca | 60 |
| ctgaaaggcg | catctccctc | cccgcgtcgc | cctgaagcag | ggggaggact | tcgcccagcc | 120 |
| aaggcagttg | tatgagtttt | agctgcggca | cttcgagacc | tctgagccca | cctccttcag | 180 |
| gagccttccc | cgattaagga | agccagggta | aggattcctt | cctcccccag | acaccacgaa | 240 |
| caaaccacca | ccccccctat | tctggcagcc | catatacatc | agaacgaaac | aaaaataaca | 300 |
| aataaacnaa | aaccaaaaaa | aaaagagaag | gggaaatgta | tatgtctgtc | catcctgttg | 360 |
| cttagcctg | tcagctccta | nagggcaggg | accgtgtctt | ccgaatggtc | tgtgcagcgc | 420 |
| cgactgcggg | aagtatcgga | ggaggaagca | gagtcagcag | aagttgaacg | gtgggcccgg | 480 |

```
cggctcttgg gggctggtgt tgtacttcga gaccgctttc gcttttgtc ttagatttac      540 gtttgctctt tggagtggga naccactacn tcnataca                             578
```

<210> SEQ ID NO 223
<211> LENGTH: 578
<212> TYPE: DNA
<213> ORGANISM: Homo sapien

<400> SEQUENCE: 223

```
tgtatcgacg tagtggtctc ctcttgcaaa ggactggctg gtgaatggtt tccctgaatt       60
atggacttac cctaaacata tcttatcatc attaccagtt gcaaaatatt agaatgtgtt      120
gtcactgttt catttgattc ctagaaggtt agtcttagat atgttacttt aacctgtatg      180
ctgtagtgct ttgaatgcat ttttgtttg cattttgtt tgcccaacct gtcaattata       240
gctgcttagg tctggactgt cctggataaa gctgttaaaa tattcaccag tccagccatc      300
ttacaagcta attaagtcaa ctaaatgctt ccttgttttg ccagacttgt tatgtcaatc      360
ctcaatttct gggttcattt tgggtgccct aaatcttagg gtgtgacttt cttagcatcc      420
tgtaacatcc attcccaagc aagcacaact tcacataata cttccagaa gttcattgct       480 gaagcctttc cttcacccag cggagcaact tgattttcta caacttccct catcagagcc      540
acaagagtat gggatatgga gaccactacg tcgataca                              578
```

<210> SEQ ID NO 224
<211> LENGTH: 345
<212> TYPE: DNA
<213> ORGANISM: Homo sapien
<220> FEATURE:
<221> NAME/KEY: misc_feature
<222> LOCATION: (1)...(345)
<223> OTHER INFORMATION: n = A,T,C or G

<400> SEQUENCE: 224

```
tgtatcgacg tantggtctc ccaaggtgct gggattgcag gcatgagcca ccactcccag       60
gtggatcttt tctttatac ttacttcatt aggtttctgt tattcaagaa gtgtagtggt       120
aaaagtcttt tcaatctaca tggttaaata atgatagcct gggaaataaa tagaaatttt      180
ttctttcatc tttaggttga ataaagaaac agaaaaaata gaacatactg aaaataatct      240
aagttccaac catagaagaa ctgcagaaga aatgaagaaa gtgatgatga tttagatttt      300
gatattgatt tagaagacac aggaggagac cactacgtcg ataca                      345
```

<210> SEQ ID NO 225
<211> LENGTH: 347
<212> TYPE: DNA
<213> ORGANISM: Homo sapien

<400> SEQUENCE: 225

```
tgtatcgacg tagtggtctc caaactgagg tatgtgtgcc actagcacac aaagccttcc       60
aacagggacg caggcacagg cagtttaaag ggaatctgtt tctaaattaa tttccacctt      120
ctctaagtat tctttcctaa aactgatcaa ggtgtgaagc ctgtgctctt tcccaactcc      180
cctttgacaa cagccttcaa ctaacacaag aaaaggcatg tctgacactc ttcctgagtc      240
tgactctgat acgttgttct gatgtctaaa gagctccaga acaccaaagg gacaattcag      300
aatgctggtg tataacagac tccaatggag accactacgt cgataca                    347
```

<210> SEQ ID NO 226
<211> LENGTH: 281

```
<212> TYPE: DNA
<213> ORGANISM: Homo sapien
<220> FEATURE:
<221> NAME/KEY: misc_feature
<222> LOCATION: (1)...(281)
<223> OTHER INFORMATION: n = A,T,C or G

<400> SEQUENCE: 226
aggngnggga ntgtatcgac gtagtggtct cccaacagtc tgtcattcag tctgcaggtg      60
tcagtgtttt ggacaatgag gcaccattgt cacttattga ctcctcagct ctaaatgctg     120
aaattaaatc ttgtcatgac aagtctggaa ttcctgatga ggttttacaa agtattttgg     180
atcaatactc caacaaatca gaaagccaga agaggatcc  tttcaatatt gcagaaccac     240
gagtggattt acacacctca ggagaccact acgtcgatac a                         281

<210> SEQ ID NO 227
<211> LENGTH: 3646
<212> TYPE: DNA
<213> ORGANISM: Homo sapien

<400> SEQUENCE: 227
gggaaacact tcctcccagc cttgtaaggg ttggagccct ctccagtata tgctgcagaa      60 ttttctctc ggtttctcag aggattatgg agtccgcctt aaaaaaggca agctctggac     120
actctgcaaa gtagaatggc caaagtttgg agttgagtgg ccccttgaag ggtcactgaa     180
cctcacaatt gttcaagctg tgtggcgggt tgttactgaa actcccggcc tcctgatca     240 gtttccctac attgatcaat ggctgagttt ggtcaggagc accccttccg tggctccact     300
catgcaccat tcataatttt acctccaagg tcctcctgag ccagaccgtg ttttcgcctc     360
gaccctcagc cggttcggct cgccctgtac tgcctctctc tgaagaagag gagagtctcc     420
ctcacccagt cccaccgcct taaaaccagc ctactccctt agggtcatcc catgtctcct     480
cggctatgtc ccctgtaggc tcatcaccca ttgcctcttg gttgcaaccg tggtgggagg     540
aagtagcccc tctactacca ctgagagagg cacaagtccc tctgggtgat gagtgctcca     600 ccccccttcct ggtttatgtc ccttcttttct acttctgact tgtataattg gaaaacccat     660
aatcctccct tctctgaaaa gccccaggct ttgacctcac tgatggagtc tgtactctgg     720
acacattggc ccacctggga tgactgtcaa cagctccttt tgaccctttt cacctctgaa     780
gagagggaaa gtatccaaag agaggccaaa aagtacaacc tcacatcaac caataggccg     840
gaggaggaag ctagaggaat agtgattaga gacccaattg ggacctaatt gggacccaaa     900
tttctcaagt ggagggagaa cttttgacga ttttccaccgg tatctcctcg tgggtattca     960
gggagctgct cagaaaccta taaacttgtc taaggcgact gaagtcgtcc aggggcatga    1020
tgagtcacca ggagtgtttt tagagcacct ccaggaggct tatcagattt acaccccttt    1080
tgacctggca gcccccgaaa atagccatgc tcttaatttg gcatttgtgg ctcaggcagc    1140
cccagatagt aaaaggaaac tccaaaaact agagggattt tgctggaatg aataccagtc    1200
agcttttaga gatagcctaa aaggttttttg acagtcaaga ggttgaaaaa caaaacaag    1260 cagctcaggc agctgaaaaa agccactgat aaagcatcct ggagtatcag agtttactgt    1320
tagatcagcc tcatttgact tcccctccca catggtgttt aaatccagct acactacttc    1380
ctgactcaaa ctccactatt cctgttcatg actgtcagga actgttggaa actactgaaa    1440
ctggccgacc tgatcttcaa aatgtgcccc taggaaaggt ggatgccacc atgttccacg    1500
acagtagcag cttcctcgag aagggactac gaaaggccgg tgcagctgtt accatggaga    1560
```

-continued

```
cagatgtgtt gtgggctcag gctttaccag caaacacctc agcacaaaag gctgaattga    1620
tcgccctcac tcaggctctc cgatggggta aggatattaa cgttaacact gacagcaggt    1680
acgcctttgc tactgtgcat gtacgtggag ccatctacca ggagcgtggg ctactcacct    1740
cagcaggtgg ctgtaatcca ctgtaaagga catcaaaagg aaaacacggc tgttgcccgt    1800
ggtaaccaga aagctgattc agcagctcaa gatgcagtgt gactttcagt cacgcctcta    1860
aacttgctgc ccacagtctc ctttccacag ccagatctgc ctgacaatcc cgcatactca    1920
acagaagaag aaaactggcc tcagaactca gagccaataa aaatcaggaa ggttggtgga    1980
ttcttcctga ctctagaatc ttcataccc gaactcttgg gaaaacttta atcagtcacc     2040
tacagtctac cacccattta ggaggagcaa agctacctca gctcctccgg agccgtttta   2100
agatccccca tcttcaaagc ctaacagatc aagcagctct ccggtgcaca acctgcgccc   2160
aggtaaatgc caaaaaaggt cctaaaccca gcccaggcca ccgtctccaa gaaaactcac   2220
caggagaaaa gtgggaaatt gactttacag aagtaaaacc acccgggct gggtacaaat    2280 accttctagt actggtagac accttctctg gatggactga agcatttgct accaaaaacg   2340
aaactgtcaa tatggtagtt aagttttac tcaatgaaat catccctcga catgggctgc    2400
ctgtttgcca tagggtctga taatggaccg gccttcgcct tgtctatagt ttagtcagtc   2460
agtaaggcgt taaacattca atggaagctc cattgtgcct atcgacccca gagctctggg   2520
caagtagaac gcatgaactg caccctaaaa aacactctta caaaattaat cttagaaacc   2580
ggtgtaaatt gtgtaagtct ccttcctta gccctactta gagtaaggtg cacccttac    2640 tgggctgggt tcttaccttt tgaaatcatg tatgggaggg tgctgcctat cttgcctaag   2700
ctaagagatg cccaattggc aaaaatatca caaactaatt tattacagta cctacagtct   2760
ccccaacagg tacaagatat catcctgcca cttgttcgag gaacccatcc caatccaatt   2820
cctgaacaga cagggccctg ccattcattc ccgccaggtg acctgttgtt tgttaaaaag   2880
ttccagagag aaggactccc tcctgcttgg aagagacctc acaccgtcat cacgatgcca   2940
acggctctga agtggatgg cattcctgcg tggattcatc actcccgcat caaaaaggcc   3000
aacagagccc aactagaaac atgggtcccc agggctgggt caggcccctt aaaactgcac   3060
ctaagttggg tgaagccatt agattaattc tttttcttaa ttttgtaaaa caatgcatag   3120
cttctgtcaa acttatgtat cttaagactc aatataaccc ccttgttata actgaggaat   3180
caatgatttg attcccccaa aaacacaagt ggggaatgta gtgtccaacc tggttttac    3240 taaccctgtt tttagactct cccttcctt taatcactca gcttgtttcc acctgaattg    3300 actctcccctt agctaagagc gccagatgga ctccatcttg gctctttcac tggcagccgc   3360
ttcctcaagg acttaacttg tgcaagctga ctcccagcac atccaagaat gcaattaact   3420
gataagatac tgtggcaagc tatatccgca gttcccagga attcgtccaa ttgatcacag   3480
cccctctacc cttcagcaac caccaccctg atcagtcagc agccatcagc accgaggcaa   3540
ggccctccac cagcaaaaag attctgactc actgaagact tggatgatca ttagtatttt   3600
tagcagtaaa gttttttttt cttttctt cttttttct cgtgcc                     3646
```

<210> SEQ ID NO 228
<211> LENGTH: 419
<212> TYPE: DNA
<213> ORGANISM: Homo sapien
<220> FEATURE:
<221> NAME/KEY: misc_feature
<222> LOCATION: (1)...(419)
<223> OTHER INFORMATION: n = A,T,C or G

<400> SEQUENCE: 228

```
taagagggta caagatctaa gcacagccgt caatgcagaa cacagaacgt agcctggtaa      60
gtgtgttaag agtgggaatt tttggagtac agagtaaggc acctaaccct agctggggtt    120
tggtgacggt cccagatggc ttacagaaga aagtgtcctg agatgagttt ttaagaatga    180
ataaggatag acacaagtga ggactgactt ggcagtggtg aatggtgggt ggcaaaaaac    240
ttcgcatgta tggaaactgc acgtacagga atgaagaatg agactgtgtg gtgtttaatg    300
agctgcaaat actaatttta tcctgaaagt tttgaagagt taactaaaaa gtatttttta    360
gtaaggaaat aaccctacat ttcagggtta ttgtttgttt anatattgaa ggtgcccaa      419
```

<210> SEQ ID NO 229
<211> LENGTH: 148
<212> TYPE: DNA
<213> ORGANISM: Homo sapien

<400> SEQUENCE: 229

```
aagagggtac ctgtatgtag ccatggtggc aatgagagac tgattactac ctgctggaga     60
ttgtttaagt gagttaatat attaaggata aagggagcca ggttttttga ctgttggaga   120
aggaaattac agatattgaa ggtcccaa                                      148
```

<210> SEQ ID NO 230
<211> LENGTH: 257
<212> TYPE: DNA
<213> ORGANISM: Homo sapien

<400> SEQUENCE: 230

```
taagagggta cmaaaaaaaa aaaatagaac gaatgagtaa gacctactat ttgatagtac     60 aacaggtga ctatagtcaa tgataactta attatacatt taacatagag tgtaattgga    120
ttgtttgtaa ctcgaaggat aaatgcttga gaggatggat accccattct ccatgatgta   180
cttatttcac attacatgcc tgtatcaaag catctcatat accctataaa tatgtacacc   240
tactatgtac cctctta                                                  257
```

<210> SEQ ID NO 231
<211> LENGTH: 260
<212> TYPE: DNA
<213> ORGANISM: Homo sapien

<400> SEQUENCE: 231

```
taagagggta cgggtatttg ctgatgggat tttttttttct ttcttttttct ttggaaaaca    60 aaatgaaagc cagaacaaaa ttattgaaca aaagacaggg actaaatctg gagaaatgaa   120
gtcccctcac ctgactgcca tttcattcta tctgaccttc cagtctaggt taggagaata   180
gggggtggag gggattaatc tgatacaggt atatttaaag caactctgca tgtgtgccag   240
aagtccatgg taccctctta                                               260
```

<210> SEQ ID NO 232
<211> LENGTH: 596
<212> TYPE: DNA
<213> ORGANISM: Homo sapien
<220> FEATURE:
<221> NAME/KEY: misc_feature
<222> LOCATION: (1)...(596)
<223> OTHER INFORMATION: n = A,T,C or G

<400> SEQUENCE: 232

```
tgctcctctt gccttaccaa ccacaaatta gaaccataat gagatgtcac ctcatacctg      60
gtgggattaa cattatttaa aaaatcagaa gtattgacaa ggatgtgaag aaattagaac     120
atctgtgcac tgttggtggg aatgtaaaaa aggtgtggcc actatgggta acagcatgaa     180
ggttcctcaa aaaaatttt ttttaatcta ctctatgatc gatcttgagg ttgtttatgc      240
aaaagaactg aaatcaggat tttgaggaaa tattcacatt cccacatcca tttctgcttt     300
attcataata ctcaagagat ggaaacaacc taaatgtcca tcccgggatg aatggataaa     360
cacagtgtgg tatatgcata caatggaata ttatttagtc tttaaaaaga aaattctat      420 catatactac aacttanatn aaccttgagg acacaatgct nagtgaaata agccacggaa     480
ggacgaatac tgcattattc ccttatatga agtatctaaa gtggtcaaac tcttanagca     540
naaagtaaaa atgggtggtt gccanacagt tggttaggcn agaaganaan cctant         596

<210> SEQ ID NO 233
<211> LENGTH: 96
<212> TYPE: DNA
<213> ORGANISM: Homo sapien

<400> SEQUENCE: 233
tcttctgaag acctttcgcg actcttaagc tcgtggttgg taaggcaaga ggagcgttgg      60
taaggcaaga ggagcgttgg taaggcaaga ggagca                                96

<210> SEQ ID NO 234
<211> LENGTH: 313
<212> TYPE: DNA
<213> ORGANISM: Homo sapien

<400> SEQUENCE: 234
tgtaagtcga gcagtgtgat gataaaactt gaatggatca atagttgctt cttatggatg      60
agcaaagaaa gtagtttctt gtgatggaat ctgctcctgg caaaaatgct gtgaacgttg     120
ttgaaaagac aacaaagagt ttagagtagt acataaattt agaatagtac ataaacttag     180
aatagtacat aaacttagta cataaataat gcacgaagca ggggcagggc ttgagagaat     240
tgacttcaat ttggaaagag tatctactgt aggttagatg ctctcaaaca gcatcacact     300
gctcgactta caa                                                        313

<210> SEQ ID NO 235
<211> LENGTH: 550
<212> TYPE: DNA
<213> ORGANISM: Homo sapien

<400> SEQUENCE: 235
aacgaggaca gatccttaaa aagaatgttg agtgaaaaaa gtagaaaata agataatctc      60
caaagtccag tagcattatt taacattttt taaaaaatac actgataaaa attttgtaca     120
tttcccaaaa atacatatgg aagcacagca gcatgaatgc ctatgggrtt gaggataggg     180
gttgggagta gggatgggga taagggggaa aaataaaacc agagaggagt cttacacatt     240
tcatgaacca aggagtataa ttatttcaac tatttgtacc wgaagtccag aaagagtgga     300
ggcagaaggg ggagaagagg gcgaagaaac gttttttggga gagggtccc asaagagaga     360 ttttcgcgat gtggcgctac atacgttttt ccaggatgcc ttaagctctg caccctattt     420
ttctcatcac taatattaga ttaaacccctt gaagacagc gtctgtggtt tctctacttc     480
agctttccct ccgtgtcttg cacacagtag ctgttttaca agggttgaac tgactgaagt     540
gagattattc                                                           550
```

<210> SEQ ID NO 236
<211> LENGTH: 325
<212> TYPE: DNA
<213> ORGANISM: Homo sapien

<400> SEQUENCE: 236

| tagactgact | catgtcccct | accagagtag | ctagaattaa | tagcacaagc | ctctacaccc | 60 |
| aggaactcac | tattgaatac | ataaatggaa | tttattcagc | cttaaaaagt | ttggaaggaa | 120 |
| attctgacat | atgctaaaac | atggatgaac | cttgaagact | ttatgataag | taaagaagc | 180 |
| cagtcataaa | aggaaaaata | ttgcatgatt | ccacttatat | gaggtaccta | gagtagtcaa | 240 |
| tttcatagaa | acacaaaata | gaatggtgtt | tgccagggct | tttgaggaaa | agggaatgac | 300 |
| aagttagggg | acatgagtca | gtcta | | | | 325 |

<210> SEQ ID NO 237
<211> LENGTH: 373
<212> TYPE: DNA
<213> ORGANISM: Homo sapien
<220> FEATURE:
<221> NAME/KEY: misc_feature
<222> LOCATION: (1)...(373)
<223> OTHER INFORMATION: n = A,T,C or G

<400> SEQUENCE: 237

| tagactgact | catgtcccct | atctactcaa | catttccact | tgaagtctga | taggcatctc | 60 |
| agacttatct | tgtcccaaag | caaactcttt | atttcttttc | atcctagtct | ttatttcttg | 120 |
| tgctgtctta | cccatctcaa | aagagtgcca | aaatccacca | agttgctgaa | acagaaatct | 180 |
| aagaaatatc | cttgattctt | cttttccca | tctacttcac | ttctaattca | ttagtaaata | 240 |
| atctgtttca | gaaaaccaaa | cacctcatgt | tctcactcat | aaggggagt | tgaacaatga | 300 |
| gaacacacag | acacagggag | gggaacatca | cacaccacgg | cccgtcaggg | agtangggac | 360 |
| atgagtcagt | cta | | | | | 373 |

<210> SEQ ID NO 238
<211> LENGTH: 492
<212> TYPE: DNA
<213> ORGANISM: Homo sapien
<220> FEATURE:
<221> NAME/KEY: misc_feature
<222> LOCATION: (1)...(492)
<223> OTHER INFORMATION: n = A,T,C or G

<400> SEQUENCE: 238

| tagactgact | catgtcccct | ataatgctcc | caggcatcag | aaagcatctc | aaactggagc | 60 |
| tgacaccatg | gcagaggttt | caggtaagtc | acaaaggggg | tcctaaagaa | tttgccctca | 120 |
| atatcagagt | gattagaaga | agtggacaga | gctacccaag | ttaaacatat | gcagagataaa | 180 |
| aaaaatatgg | cacttgtgaa | cacacactac | aggaggaaaa | taaggaacat | aatagcatat | 240 |
| tgtgctatta | tgatgatgaa | gaacctctct | anaagaaaac | ataaccaaag | aaacaaagaa | 300 |
| aattcctgcn | aatgtttaat | gctatagaag | aaattaacaa | aacatatat | tcaatgaatt | 360 |
| cagaaaagtt | agcaggtcan | aagaaaacaa | atcaaagacc | agaataatcc | cattttagat | 420 |
| tgtcgagtaa | actanaacag | aaagaatacc | actggaaatt | gaattcctac | gtangggaca | 480 |
| tgantcantc | ta | | | | | 492 |

<210> SEQ ID NO 239

<211> LENGTH: 482
<212> TYPE: DNA
<213> ORGANISM: Homo sapien
<220> FEATURE:
<221> NAME/KEY: misc_feature
<222> LOCATION: (1)...(482)
<223> OTHER INFORMATION: n = A,T,C or G

<400> SEQUENCE: 239

| | | | | | |
|---|---|---|---|---|---|
| tggaaagtat | ttaatgatgg | gcaacttgct | gtttacttcc | tacatatccc | atcatcttct | 60 |
| gtattttttt | aaataacttt | tttttggatt | tttaaagtaa | ccttattctg | agaggtaaca | 120 |
| tggattacat | acttctaagc | cattaggaga | ctctatgtta | aaccaaaagg | aaatgttact | 180 |
| agatcttcat | ttgatcaata | ggatgtgata | atcatcatct | ttctgctcta | atggaaaagt | 240 |
| actanaaaca | tggaaccata | atcttagatg | aacaacgtta | gaatttgcac | taattctacg | 300 |
| gaatttcagt | aattcggcaa | atgtcgggca | gtgacacaac | atttcatgac | ggggacgcat | 360 |
| ctaccaactt | ctggcgataa | gggccaccct | tccctctgta | cttacagtcc | catttcatac | 420 |
| acagtctttg | attaaatatt | cacattttt  | ctctacctaa | agaccttcaa | gaccagtacg | 480 |
| ta | | | | | | 482 |

<210> SEQ ID NO 240
<211> LENGTH: 519
<212> TYPE: DNA
<213> ORGANISM: Homo sapien
<220> FEATURE:
<221> NAME/KEY: misc_feature
<222> LOCATION: (1)...(519)
<223> OTHER INFORMATION: n = A,T,C or G

<400> SEQUENCE: 240

| | | | | | |
|---|---|---|---|---|---|
| tgtatcgacg | tagtggtctc | cccatgtgat | agtctgaaat | atagcctcat | gggatgagag | 60 |
| gctgtgcccc | agcccgacac | ccgtaaaggg | tctgtgctga | ggtggattag | taaaagagga | 120 |
| aagccttgca | gttgagatag | aggaagggca | ctgtctcctg | cctgcccctg | ggaactgaat | 180 |
| gtctcggtat | aaacccgat  | tgtacatttg | ttcaattctg | agataggaga | aaaaccaccc | 240 |
| tatggcggga | ggcgagacat | gttggcagca | atgctgcctt | gttatgcttt | actccacaga | 300 |
| tgtttgggcg | gagggaaaca | taaatctggc | ctacgtgcac | atccaggcat | agtacctccc | 360 |
| tttgaactta | attatgacac | agattccttt | gctcacatgt | ttttttgctg | accttctcct | 420 |
| tattatcacc | ctgctctcct | accgcattcc | ttgtgctgag | ataatgaaaa | taatatcaat | 480 |
| aaaaacttga | nggaactcgg | agaccactac | gtcgataca | | | 519 |

<210> SEQ ID NO 241
<211> LENGTH: 771
<212> TYPE: DNA
<213> ORGANISM: Homo sapien
<220> FEATURE:
<221> NAME/KEY: misc_feature
<222> LOCATION: (1)...(771)
<223> OTHER INFORMATION: n = A,T,C or G

<400> SEQUENCE: 241

| | | | | | |
|---|---|---|---|---|---|
| tgtatcgacg | tagtggtctc | cactcccgcc | ttgacggggc | tgctatctgc | cttccaggcc | 60 |
| actgtcacgg | ctcccgggta | gaagtcactt | atgagacaca | ccagtgtggc | cttgttggct | 120 |
| tgaagctcct | cagaggaggg | tgggaacaga | gtgaccgagg | gggcagcctt | gggctgacct | 180 |
| aggacggtca | gcttggtccc | tccgccaaac | acgagagtgc | tgctgcttgt | atatgagctg | 240 |
| cagtaataat | cagcctcgtc | ctcagcctgg | agcccagaga | tggtcaggga | ggccgtgttg | 300 |

```
ccanacttgg agccagagaa gcgattagaa acccctgagg gccgattacc gacctcataa    360
atcatgaatt tgggggcttt gcctgggtgc tgttggtacc angagacatt attataacca    420
ccaacgtcac tgctggttcc antgcaggga aaatggttga tcnaactgtc caagaaaacc    480
actacgtcca taccaatcca ctaattgccn gccgcctgca ggttcaacca tattggggaa    540
naactccccn ccgccgtttg ggattgncat naacctttga aatttttttcc tattanttgt    600 cccccctaaaa taaaccnttg ggcnttaatc cattgggtcc atancttntt tncccggttt    660
ttaaaanttg tttatcccgc cncccnattt ccccccccaac tttccaaaac ccgaaaccnt    720
tnaaatttnt tnaaaccctg ggggttcccn nnaattnnan ttnaanctnc c              771
```

```
<210> SEQ ID NO 242
<211> LENGTH: 167
<212> TYPE: DNA
<213> ORGANISM: Homo sapien

<400> SEQUENCE: 242
tgggcacctt caatatcggg ctcatcgata acatcacgct gctgatgctg ctgttgctgg     60
tcctctctag gaacctctgg atttttcaaat tctttgagga attcatccaa attatctgcc    120
tctcctcctt tcctccttttt tctaaggtct tctggtacaa gcggtca                  167
```

```
<210> SEQ ID NO 243
<211> LENGTH: 338
<212> TYPE: DNA
<213> ORGANISM: Homo sapien

<400> SEQUENCE: 243
ttgggcacct tcaatatcta ctgatctaaa tagtgtggtt tgaggcctct tgttcctggc     60
taaaaatcct tggcaagagt caatctccac tttacaatag aggtaaaaat cttacaatgg    120
atattcttga caaagctagc atagagacag caattttaca caaggtatttt ttcacctgtt    180 taataacagt ggtttttccta cacccatagg gtgccaccaa gggaggagtg cacagttgca    240
gaaacaaatt aagatactga agacaacact acttaccatt tcccgtatag ctaaccacca    300
gttcaactgt acatgtatgt tcttatgggc aatcaaga                            338
```

```
<210> SEQ ID NO 244
<211> LENGTH: 346
<212> TYPE: DNA
<213> ORGANISM: Homo sapien

<400> SEQUENCE: 244
tttttggctc ccatacagca cactctcatg ggaaatgtct gttctaaggt caacccataa     60
tgcaaaaatc atcaatatac ttgaagatcc ccgtgtaagg tacaatgtat ttaatattat    120
cactgataca attgatccaa taccagtttt agtctggcat tgaatcaaat cactgttttt    180
gttgtataaa aagagaaata tttagcttat atttaagtac catattgtaa gaaaaaagat    240
gcttatcttt acatgctaaa atcatgatct gtacattggt gcagtgaata ttactgtaaa    300
agggaagaag gaatgaagac gagctaagga tattgaaggt gcccaa                   346
```

```
<210> SEQ ID NO 245
<211> LENGTH: 521
<212> TYPE: DNA
<213> ORGANISM: Homo sapien
<220> FEATURE:
<221> NAME/KEY: misc_feature
<222> LOCATION: (1)...(521)
```

<223> OTHER INFORMATION: n = A,T,C or G

<400> SEQUENCE: 245

| accaatccca cacggatact gagggacaag tatatcatcc catttcatcc ctacagcagc | 60 |
| aacttcatga ggcaggagtt attagtccca ttttacagaa gaggaaactg agacttaggg | 120 |
| agatcaagta atttgcccag gtcgcacaat tagtgataga gccagggctt gaagcgacgt | 180 |
| ctgtcttaag ccaatgaccc ctgcagatta ttagagcaac tgttctccac aacagtgtaa | 240 |
| gcctcttgct anaagctcag gtccacaagg gcagagattt ttgtctgttt tgctcattgc | 300 |
| tccttcccca ttgcttagag cagggtctgc cacgaancag gttctcaatg catagttatt | 360 |
| aaatgtatat aagagcaaac atatgttaca gagaactttc tgtatgcttg tcacttacat | 420 |
| gaatcacctg tganatgggt atgcttgttc cccantgttg cagatnaaga tattgaangt | 480 |
| gcccaaatca ctanttgcgg gcgcctgcan gtccancata t | 521 |

<210> SEQ ID NO 246
<211> LENGTH: 482
<212> TYPE: DNA
<213> ORGANISM: Homo sapien
<220> FEATURE:
<221> NAME/KEY: misc_feature
<222> LOCATION: (1)...(482)
<223> OTHER INFORMATION: n = A,T,C or G

<400> SEQUENCE: 246

| tggaaccaat ccaaatacccc atcaatgata gactggataa agaaaatttg gcacatgttc | 60 |
| accatgaaat actatgcagc cataaaaaag gatgagttca tatcctttgc agggacatgg | 120 |
| atgaagctgg agaccatcat tctcagcaaa ctaacaaggg aacagaaaac caaacactgc | 180 |
| atgttctcac tcttaagtgg gagctgaaca atgagaacac atggacacag ggaggggaac | 240 |
| atcacacagt ggggcctgct ggtgggtagg ggtctagggg agggatagca ttaggagaaa | 300 |
| tacctaatgt agatgacggg ttgatgggtg cagcaaacca ccatgacacg tgtataccta | 360 |
| tgtaacaaac ctgcatgttc tgcacatgta ccccagaact taaagtgtta ataaaaaaat | 420 |
| taagaaaaaa gttaagtatg tcatagatac ataaaatatt gtanatattg aaggtgccca | 480 |
| aa | 482 |

<210> SEQ ID NO 247
<211> LENGTH: 474
<212> TYPE: DNA
<213> ORGANISM: Homo sapien
<220> FEATURE:
<221> NAME/KEY: misc_feature
<222> LOCATION: (1)...(474)
<223> OTHER INFORMATION: n = A,T,C or G

<400> SEQUENCE: 247

| ttcgatacag gcacagagta agcagaaaaa tggctgtggt ttaaccaagt gagtacagtt | 60 |
| aagtgagaga ggggcagaga agacaagggc atatgcaggg ggtgattata acaggtggtt | 120 |
| gtgctgggaa gtgagggtac tcggggatga ggaacagtga aaaagtggca aaaagtggta | 180 |
| agatcagtga attgtacttc tccagaattt gatttctggn ggagtcaaat aactatccag | 240 |
| tttggggtat catanggcaa cagttgaggt ataggaggta gaagtcncag tgggataatt | 300 |
| gaggttatga anggtttggt actgactggt actgacaang tctgggttat gaccatggga | 360 |
| atgaatgact gtanaagcgt anaggatgaa actattccac ganaaagggg tccnaaaact | 420 |
| aaaaannnaa gnnnnngggg aatattattt atgtggatat tgaangtgcc caaa | 474 |

<210> SEQ ID NO 248
<211> LENGTH: 355
<212> TYPE: DNA
<213> ORGANISM: Homo sapien
<220> FEATURE:
<221> NAME/KEY: misc_feature
<222> LOCATION: (1)...(355)
<223> OTHER INFORMATION: n = A,T,C or G

<400> SEQUENCE: 248

| | | | | | |
|---|---|---|---|---|---|
| ttcgatacag | gcaaacatga | actgcaggag | ggtggtgacg | atcatgatgt | tgccgatggt | 60 |
| ccggatggnc | acgaagacgc | actggancac | gtgcttacgt | cctttgctc | tgttgatggc | 120 |
| cctgagggga | cgcaggaccc | ttatgaccct | cagaatcttc | acaacgggag | atggcactgg | 180 |
| attgantccc | antgacacca | gagacacccc | aaccaccagn | atatcantat | attgatgtag | 240 |
| ttcctgtaga | nggccccctt | gtggaggaaa | gctccatnag | ttggtcatct | tcaacaggat | 300 |
| ctcaacagtt | tccgatggct | gtgatgggca | tagtcatant | taaccntgtn | tcgaa | 355 |

<210> SEQ ID NO 249
<211> LENGTH: 434
<212> TYPE: DNA
<213> ORGANISM: Homo sapien

<400> SEQUENCE: 249

| | | | | | |
|---|---|---|---|---|---|
| ttggattggt | cctccaggag | aacaagggga | aaaaggtgac | cgagggctcc | ctggaactca | 60 |
| aggatctcca | ggagcaaaag | gggatggggg | aattcctggt | cctgctggtc | ccttaggtcc | 120 |
| acctggtcct | ccaggcttac | caggtcctca | aggcccaaag | ggtaacaaag | gctctactgg | 180 |
| acccgctggc | cagaaaggtg | acagtggtct | tccagggcct | cctgggcctc | caggtccacc | 240 |
| tggtgaagtc | attcagcctt | taccaatctt | gtcctccaaa | aaaacgagaa | gacatactga | 300 |
| aggcatgcaa | gcagatgcag | atgataatat | tcttgattac | tcggatggaa | tggaagaaat | 360 |
| atttggttcc | ctcaattccc | tgaaacaaga | catcgagcat | atgaaatttc | caatgggtac | 420 |
| tcagaccaat | ccaa | | | | | 434 |

<210> SEQ ID NO 250
<211> LENGTH: 430
<212> TYPE: DNA
<213> ORGANISM: Homo sapien
<220> FEATURE:
<221> NAME/KEY: misc_feature
<222> LOCATION: (1)...(430)
<223> OTHER INFORMATION: n = A,T,C or G

<400> SEQUENCE: 250

| | | | | | |
|---|---|---|---|---|---|
| tggattggtc | acatggcaga | gacaggattc | caaggcagtg | agaggaggat | acaatgcttc | 60 |
| tcactagtta | ttattattta | ttttatttt | gagatgaagt | ctcgctttgt | ctcccaggct | 120 |
| ggagagcggt | ggtgcgatct | tggctctctg | caaccccgc | ctcaagcaat | tctcctgtct | 180 |
| tagcctcgcg | ggtagatgga | attacaggcg | cccaccgcca | tgcccaacta | atttttttgt | 240 |
| gtcttcagta | gagacagggt | ttcgccatgt | tgggcaggct | ggtcttgaac | tcctgacctc | 300 |
| nagtgatctg | ccctcctcgg | cctcacaaag | tgctggaatt | acaggcatgg | gctgctgcac | 360 |
| ccagtcaact | tctcactagt | tatggcctta | tcattttcac | cacattctat | tggcccaaaa | 420 |
| aaaaaaaaan | | | | | | 430 |

<210> SEQ ID NO 251

<211> LENGTH: 329
<212> TYPE: DNA
<213> ORGANISM: Homo sapien

<400> SEQUENCE: 251

```
tggtactcca ccatyatggg gtcaaccgcc atcctcgccc tcctcctggc tgttctccaa     60
ggagtctgtg ccgaggtgca gctgrtgcag tctggagcag aggtgaaaaa gtccggggag   120
tctctgaaga tctcctgtaa gggttctgga tacaccttta agatctactg gatcgcctgg   180
gtgcgccagt tgcccgggaa aggcctggag tggatggggc tcatctttcc tgatgactct   240
gataccagat acagcccgtc cttccaaggc caggtcacca tctcagtcga taagtccatc   300
agcaccgcct atctgcagtg gagtaccaa                                     329
```

<210> SEQ ID NO 252
<211> LENGTH: 536
<212> TYPE: DNA
<213> ORGANISM: Homo sapien

<400> SEQUENCE: 252

```
tggtactcca ctcagcccaa ccttaattaa gaattaagag ggaacctatt actattctcc     60
caggctcctc tgctctaacc aggcttctgg gacagtatta gaaaggatgt tctcaacaag   120
tatgtagatc ctgtactggc ctaagaagtt aaactgagaa tagcataaat cagaccaaac   180
ttaatggtcg ttgagacttg tgtcctggag cagctgggat aggaaaactt ttgggcagca   240
agaggaagaa ctgcctggaa gggggcatca tgttaaaaat tacaagggga acccacacca   300
ggcccccttc ccagctctca gcctagagta ttagcatttc tcagctagag actcacaact   360
tccttgctta gaatgtgcca ccggggggag tccctgtggg tgatgaggct ctcaagagtg   420
agagtggcat cctatcttct gtgtgcccac aggagcctgg cccgagactt agcaggtgaa   480
gtttctggtc caggctttgc ccttgactca ctatgtgacc tctggtggag taccaa       536
```

<210> SEQ ID NO 253
<211> LENGTH: 507
<212> TYPE: DNA
<213> ORGANISM: Homo sapien
<220> FEATURE:
<221> NAME/KEY: misc_feature
<222> LOCATION: (1)...(507)
<223> OTHER INFORMATION: n = A,T,C or G

<400> SEQUENCE: 253

```
ntgttgcgat cccagtaact cgggaagctg aggcgggagg atcacctgag ctcaggaggt     60
tgaggccgca gtgagccggg accacgccac tacactccag cctggggcat agagtgagac   120
cctccaagac agaaaagaaa agaaaggaag ggaaagggaa agggaaaagg aaaaggaaaa   180
ggaaaaggaa aaggaaaaga caagacaaaa caagacttga atttggatct cctgacttca   240
attttatgtt ctttctacac cacaattcct ctgcttacta agatgataat ttagaaaccc   300
ctcgttccat tctttacagc aagctggaag tttggtcaag taattacaat aatagtaaca   360
aatttgaata ttatatgcca ggtgtttttc attcctgctc tcacttaatt ctcaccactc   420
tgatataaat acaattgctg ccgggtgtgg tggctcatgc ctgtaatccc ggcactttgg   480
gagaccgagg tgggcggats gcaacaa                                       507
```

<210> SEQ ID NO 254
<211> LENGTH: 222
<212> TYPE: DNA
<213> ORGANISM: Homo sapien

```
<220> FEATURE:
<221> NAME/KEY: misc_feature
<222> LOCATION: (1)...(222)
<223> OTHER INFORMATION: n = A,T,C or G

<400> SEQUENCE: 254
ttggattggt cactgtgagg aagccaaatc ggatccgaga gtctttttct aaaggccagt      60
actggccaca ctttctcctg ccgccttcct caaagctgaa gacacacaga gcaaggcgct     120
tctgttttac tccccaatgg taactccaaa ccatagatgg ttagctnccc tgctcatctt     180
tccacatccc tgctattcag tatagtccgt ggaccaatcc aa                        222

<210> SEQ ID NO 255
<211> LENGTH: 463
<212> TYPE: DNA
<213> ORGANISM: Homo sapien

<400> SEQUENCE: 255
tgttgcgatc cataaatgct gaaatggaaa taaacaacat gatgagggag gattaagttg      60
gggagggagc acattaaggt ggccatgaag tttgttggaa gaagtgactt ttgaacaagg     120
ccttggtgtt aagagctgat gagagtgtcc cagacagagg ggccactggt acaatagacg     180
agatgggaga gggcttggaa ggtgtgcgaa ataggaagga gtttgttctg gtatgagtct     240
agtgaacaca gaggcgagag gccctggtgg gtgcagctgg agagttatgc agaataacat     300
taggccctgt gggggactgt agactgtcag caataatcca cagtttggat tttattctaa     360
gagtgatggg aagccgtgga aaggggggtta agcaaggagt gaaattatca gatttacagt     420
gataaaaata aattggtctg gctactgggg aaaaaaaaaa aaa                       463

<210> SEQ ID NO 256
<211> LENGTH: 262
<212> TYPE: DNA
<213> ORGANISM: Homo sapien

<400> SEQUENCE: 256
ttggattggt caacctgctc aactctacyt ttcctccttc ttcctaaaaa attaatgaat      60
ccaatacatt aatgccaaaa cccttgggtt ttatcaatat ttctgttaaa aagtattatc     120
cagaactgga cataatacta cataataata cataacaacc ccttcatctg gatgcaaaca     180
tctattaata tagcttaaga tcactttcac tttacagaag caacatcctg ttgatgttat     240
tttgatgttt ggaccaatcc aa                                              262

<210> SEQ ID NO 257
<211> LENGTH: 461
<212> TYPE: DNA
<213> ORGANISM: Homo sapien
<220> FEATURE:
<221> NAME/KEY: misc_feature
<222> LOCATION: (1)...(461)
<223> OTHER INFORMATION: n = A,T,C or G

<400> SEQUENCE: 257
gnggnnnnnn nnncaattcg actcngttcc cntggtancc ggtcgacatg ccgcgggat       60 taccgcttgt nnctgggggt gtatgggga ctatgaccgc ttgtagctgg gggtgtatgg     120
gggactatga ccgcttgtag mtggkggtgt atgggggact atgaccgctt gtcgggtggt     180
cggataaacc gacgcaaggg acgtgatcga agctgcgttc ccgctctttc gcatcggtag     240
ggatcatgga cagcaatatc cgcattcgyc tgaaggcgtt cgaccatcgc gtgctcgatc     300
```

-continued

| | | |
|---|---|---|
| aggcgaccgg cgacatcgcc gacaccgcac gccgtaccgg cgcgctcatc cgcggtccga | 360 |
| tcccgcttcc cacgcgcatc gagaagttca cggtcaaccg tggcccgcac gtcgacaaga | 420 |
| agtcgcgcga gcagttcgag gtgcgtacct acaagcggtc a | 461 |

<210> SEQ ID NO 258
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 258

| | | |
|---|---|---|
| tgaccgcttg tagctggggg tgtatggggg actacgaccg cttgtagctg gggtgtatg | 60 |
| ggggactatg accgcttgta gctggggtg tatgggggac tatgaccgct tgtagctggg | 120 |
| ggtgtatggg ggactaggac cgcttgtagc tggggtgta tggggactta tgaccgcttg | 180 |
| tagctggggg tgtatggggg actacgaccg cttgtagctg gggtgtatg ggggactatg | 240 |
| accgcttgta nctgggggtg tatggggac tatgaccgct tgtgctgcct gggggatggg | 300 |
| aggagagttg tggttgggga aaaaaaaaaa aa | 332 |

<210> SEQ ID NO 259
<211> LENGTH: 291
<212> TYPE: DNA
<213> ORGANISM: Homo sapien
<220> FEATURE:
<221> NAME/KEY: misc_feature
<222> LOCATION: (1)...(291)
<223> OTHER INFORMATION: n = A,T,C or G

<400> SEQUENCE: 259

| | | |
|---|---|---|
| taccgcttgt gaccgcttgt gaccgcttgt gaccgcttgt gaccgcttgt gaccgcttgt | 60 |
| gaccgcttgt gaccgcttgt gaccgcttgt gaccgcttgt gaccgcttgt gaccgcttgt | 120 |
| gaccgcttgt gaccgcttgt nacnggggt gtctggggga ctatgannga ntgtnactgg | 180 |
| gggtgtctgg gggnctatga nngantgtna cnggggtgt ctgggggact atganngact | 240 |
| gtgcnncctg ggggatcnga ggagantngn ggntagngat ggttngggan a | 291 |

<210> SEQ ID NO 260
<211> LENGTH: 238
<212> TYPE: DNA
<213> ORGANISM: Homo sapien

<400> SEQUENCE: 260

| | | |
|---|---|---|
| taagagggta ctggttaaaa tacaggaaat ctggggtaat gaggcagaga accaggatac | 60 |
| tttgaggtca gggatgaaaa ctagaatttt tttctttttt tttgcctgag aaacttgctg | 120 |
| ctctgaagag gcccatgtat taattgcttt gatcttcctt ttcttacagc cctttcaagg | 180 |
| gcagagccct ccttatcctg aaggaatctt atccttagct atagtatgta ccctctta | 238 |

<210> SEQ ID NO 261
<211> LENGTH: 746
<212> TYPE: DNA
<213> ORGANISM: Homo sapien
<220> FEATURE:
<221> NAME/KEY: misc_feature
<222> LOCATION: (1)...(746)
<223> OTHER INFORMATION: n = A,T,C or G

<400> SEQUENCE: 261

```
ttgggcacct tcaatatcaa tagctaacat ttattgagtg tttatcgtat cataaaacac    60
tgttctaagc ctttaaacgt actaattcat ttaatgctca taatcacttt agaaggtggg   120
tactagtatt agtctcattt acagatgcaa catgcaggca cagagaggtt aattaacttg   180
cccaaggtaa cacagctaag aaatagaaaa aatattgaat ctggaaagtt gggcttctgg   240
gtaacccaca gagtcttcaa tgagcctggg gcctcactca gtttgctttt acaaagcgaa   300
tgagtaacat cacttaattc agtgagtagg ccaaatggag gtcagctacg agtttctgct   360
gttcttgcag tggactgaca gatgtttaca acgtctggcc atcagtwaat ggactgatta   420
tcattgggaw gtgggtgggc tgaatgttgg ccagtgaagt ttattcawgc catattttta   480
tgtttaggat gacttttggc tggtcctagg gcaagctctg tctgscacgg aacacagaat   540
wacacaggga cccctcaat ttctggtgtg gctagaacca tgaaccactg gttgggggaa    600
caagcggtca aacctaagt gcggccggct ggcagggtcc acccatatgg ggaaaactcc    660
cnacgcgttt ggaatgcctn agctngaatt attctaanag ttgtccncnt aaaattagcc   720
tgggcgttaa tcangggtcn naagcc                                        746
```

<210> SEQ ID NO 262
<211> LENGTH: 588
<212> TYPE: DNA
<213> ORGANISM: Homo sapien
<220> FEATURE:
<221> NAME/KEY: misc_feature
<222> LOCATION: (1)...(588)
<223> OTHER INFORMATION: n = A,T,C or G

<400> SEQUENCE: 262

```
tgaccgcttg tcatctcaca tggggtcctg cacgcttttg cctttgtagg aaacctgaca    60
tttgtctgtt tcttctttct cttttccttc ccatatcctc ctaatttacg tttgacttgt   120
ttgctgagga ggcaggagct agagactgct gtgagctcat agggggtggga agtttatcct   180 tcaagtcccg cccactcatc actgcttctc accttcccct gaccaggctt acaagtgggt   240
tcttgcctgc tttccctttg gacccaacaa gcccctgtaa tgagtgtgca tgactctgac   300
agctgtggac tcagggtcct tggctacagc tgccatgtaa aatatctcat ccagttctcg   360
caaattgtta aaataaccac atttcttaga ttccagtacc caaatcatgt ctttacgaac   420
tgctcctcac acccagaagt ggcacaataa ttcttgggga attattactt ttttttttct   480
ctctnttnnc gnnngnnnng gnnngnccag gaattaccac nttggaagac ctggccngaa   540
tttattatan aggggagccg attnttttc ctaacacaaa gcgggtca                588
```

<210> SEQ ID NO 263
<211> LENGTH: 730
<212> TYPE: DNA
<213> ORGANISM: Homo sapien
<220> FEATURE:
<221> NAME/KEY: misc_feature
<222> LOCATION: (1)...(730)
<223> OTHER INFORMATION: n = A,T,C or G

<400> SEQUENCE: 263

```
tttttttttt tttggcctga gcaactgaaa ttatgaaatt tccatatact caaagagta    60 agactgcaaa aagattaaat gtaaagttg tcttgtatac agtaatgttt aagataccta   120
ttanatttat aaatggaaaa ttagggcatt tggatataca agttgaaaat tcaggagtga   180
ggttgggctg gctgggtata tactgaaaac tgtcagtaca cagatgacat ctaaaaccac   240
```

```
aaatctggtt ttattttagc agtgatatgt gtcactccca caaaagcctt cccaattggc      300
ctcagcatac acaacaagtc acctccccac agccctctac acataaacaa attccttagt      360
ttagttcagg aggaaatgcg ccctttcct tccgctctag gtgaccgcaa ggcccagttc       420
tcgtcaccaa gatgttaagg gaagtctgcc aaagaggcat ctgaaaggaa ataaggggaa      480
tgggagtgac cacaaaggaa agccaaggan aaactttgga gaccgtttct aganccctgg     540
catttcacaa caaaactcng gaacaaacct tgtctcatca atcatttaag cccttcgttt      600
ggannagact ttctgaactg ggcgctgaac ataanccctca ttgaatgtct tcacagtctc    660
ccagctgaag gcacaccttg ggccagaagg ggaatcttcc aggtcctcaa nacagggctc     720 gcccttttgnc                                                            730
```

```
<210> SEQ ID NO 264
<211> LENGTH: 715
<212> TYPE: DNA
<213> ORGANISM: Homo sapien
<220> FEATURE:
<221> NAME/KEY: misc_feature
<222> LOCATION: (1)...(715)
<223> OTHER INFORMATION: n = A,T,C or G

<400> SEQUENCE: 264
tttttttttt tttggccagt atgatagtct ctaccactat attgaagctc ttaggtcatt      60
tacacttaat gtggttatag atgctgttga gcttacttct accaccttgc tatttctccc     120
gtctcttttt tgttcctttt ctcttctttt cctcccttat tttataattg aattttttag    180
gattctattt tatatagatt tatcagctat aacactttgt attctttgt tttgtggttc     240 ttctgtcatt tcaatgtgca tcttaaactc atcacaatct attttcaaat aatatcatat    300
aaccttacat ataatgtaag aatctaccac catatatttc catttctccc ttccatccta    360
tgtntgtcat attttttcct ttatatatgt tttaaagaca taatagtata tgggaggttt    420
ttgcttaaaa tgtgatcaat attccttcaa ngaaacgtaa aaattcaaaa taaatntctg    480
tttattctca aatnnaccta atatttccta ccatntctna tacnttttcaa gaatctgaag   540 gcattggttt tttccggctt aagaacctcc tctaaagcac tctaagcaga attaagtctt    600
ctgggagagg aattctccca agcttgggcc ttnanntgta ctccntnang gttaaanttt    660
ggccgggaaa tagaaattcc aagttaacag gntanttttt nttttttnttn tcncc         715
```

```
<210> SEQ ID NO 265
<211> LENGTH: 152
<212> TYPE: DNA
<213> ORGANISM: Homo sapien

<400> SEQUENCE: 265
tttttttttt tttcccaaca caaagcacca ttatctttcc tcacaatttt caacatagtt     60
tgattcccat gaagaggtta tgatttctaa agaaaacatg gctactatac tatcaatcag   120
ggttaaatct ttttttttttg agacggagtt ta                                  152
```

```
<210> SEQ ID NO 266
<211> LENGTH: 193
<212> TYPE: DNA
<213> ORGANISM: Homo sapien
<220> FEATURE:
<221> NAME/KEY: misc_feature
<222> LOCATION: (1)...(193)
<223> OTHER INFORMATION: n = A,T,C or G

<400> SEQUENCE: 266
```

```
taaactccgt ccccttctta atcaatatgg aggctaccca ctccacatta ccttcttttc      60
aagggactgt ttccgtaact gttgtgggta ttcacgacca ggcttctaaa cctcttaaaa     120
ctccccaatt ctggtgccaa cttggacaac atgcttttt ttttttttt ttttttttn       180 gagacggagt tta                                                        193

<210> SEQ ID NO 267
<211> LENGTH: 460
<212> TYPE: DNA
<213> ORGANISM: Homo sapien

<400> SEQUENCE: 267
tgttgcgatc ccttaagcat gggtgctatt aaaaaaatgg tggagaagaa aatacctgga     60
atttacgtct tatctttaga gattgggaag accctgatgg aggacgtgga gaacagcttc    120
ttcttgaatg tcaattccca agtaacaaca gtgtgtcagg cacttgctaa ggatcctaaa    180
ttgcagcaag gctacaatgc tatgggattc tcccagggag gccaatttct gagggcagtg    240
gctcagagat gcccttcacc tcccatgatc aatctgatct cggttggggg acaacatcaa    300 ggtgttttg gactccctcg atgcccagga gagagctctc acatctgtga cttcatccga    360
aaaacactga atgctggggc gtactccaaa gttgttcagg aacgcctcgt gcaagccgaa    420
tactggcatg acccataaaa ggaggatgtg gatcgcaaca                          460

<210> SEQ ID NO 268
<211> LENGTH: 533
<212> TYPE: DNA
<213> ORGANISM: Homo sapien
<220> FEATURE:
<221> NAME/KEY: misc_feature
<222> LOCATION: (1)...(533)
<223> OTHER INFORMATION: n = A,T,C or G

<400> SEQUENCE: 268
tgttgcgatc cgttgataga atagcgacgt ggtaatgagt gcatggcacg cctccgactt     60
accttcgccc gtggggaccc cgagtacgtc tacggcgtcg tcacttagag taccctctgg    120
acgcccgggc gcgttcgatt taccggaagc gcgagctgca gtgggcttgc gccccggcc    180 aaattctttg gggggtttaa ggccgcgggg aatttgaggt atctctatca gtatgtagcc    240
aagttggaac agtcgccatt cccgaaatcg ctttctttga atccgcaccg cctccagcat    300
tgcctcattc atcaacctga aggcacgcat aagtgacggt tgtgtcttca gcagctccac    360
tccataacta gcgcgctcga cctcgtcttc gtacgcgcca ggtccgtgcg tgcgaattcc    420
caactccggt gagttgcgca tttcaagttn cgaaactgtt cgcctccacn atttggcatg    480
ttcacgcatg acacggaata aactcgtcca gtaccgggaa tgggatcgca aca            533

<210> SEQ ID NO 269
<211> LENGTH: 50
<212> TYPE: DNA
<213> ORGANISM: Homo sapien

<400> SEQUENCE: 269
tttttttttt ttcgcctgaa ttagctacag atcctcctca caagcggtca                50

<210> SEQ ID NO 270
<211> LENGTH: 519
<212> TYPE: DNA
<213> ORGANISM: Homo sapien
```

```
<400> SEQUENCE: 270
tgttgcgatc caaataaccc accagcttct tgcacacttc gcagaagcca ccgtcctttg      60
gctgagtcac gtgaacggtc agtgcaagca gccgcgtgcc agagcagagg tgcagcatgc     120
tgcacaccag ctcagggctg acctcctcca gcaggatgga caggatggag ctgccgtacg     180
tgtccaccac ctcctggcac tcttccgaca gggacttcgg cagcttcgag cacattttgt     240
caaaagcgtc gagtatttct ttctcagtct tgttgttgtc aatcagcttg gtcacctcct     300
tcaccaggaa ttcacacacc tcacagtaaa catcagactt tgctgggacc tcgtgcttct     360
taatgggctc caccagttcc agggcaggga tgacattctt ggaggccact ttggcgggga     420
ccagagtctg catgggcatc tctttcacct catcacagaa cccaaccagc gcacagatct     480
ccttgggttg catgtgcatc atcatctggg atcgcaaca                            519

<210> SEQ ID NO 271
<211> LENGTH: 457
<212> TYPE: DNA
<213> ORGANISM: Homo sapien

<400> SEQUENCE: 271
tttttttttt ttcgggcggc gaccggacgt gcactcctcc agtagcggct gcacgtcgtg      60
ccaatggccc gctatgagga ggtgagcgtg tccggcttcg aggagttcca ccgggccgtg     120
gaacagcaca atgcaagac cattttcgcc tactttacgg gttctaagga cgccgggggg     180
aaaagctggt gccccgactg cgtgcaggct gaaccagtcg tacgagaggg gctgaagcac     240
attagtgaag gatgtgtgtt catctactgc caagtaggag aagagcctta ttggaaagat     300
ccaaataatg acttcagaaa aaacttgaaa gtaacagcag tgcctacact acttaagtat     360
ggaacacctc aaaaactggt agaatctgag tgtcttcagg ccaacctggt ggaaatgttg     420
ttctctgaag attaagattt taggatggca atcaaga                              457

<210> SEQ ID NO 272
<211> LENGTH: 102
<212> TYPE: DNA
<213> ORGANISM: Homo sapien

<400> SEQUENCE: 272
tttttttttt ttgggcaaca acctgaatac ctttttcaagg ctctggcttg ggctcaagcc     60
cgcaggggaa atgcaactgg ccaggtcaca gggcaatcaa ga                        102

<210> SEQ ID NO 273
<211> LENGTH: 455
<212> TYPE: DNA
<213> ORGANISM: Homo sapien
<220> FEATURE:
<221> NAME/KEY: misc_feature
<222> LOCATION: (1)...(455)
<223> OTHER INFORMATION: n = A,T,C or G

<400> SEQUENCE: 273
tttttttttt ttggcaatca acaggtttaa gtcttcggcc gaagttaatc tcgtgttttt      60
ggcaatcaac aggtttaagt cttcggccga agttaatctc gttttttggc aatcaacag     120 gtttaagtct tcggccgaag ttaatctcgt gttttttggca atcaacaggt ttaagtcttc    180
ggccgaagtt aatctcgtgt ttttggcaat caacaggttt aagtcttcgg ccgaagttaa    240
tctcgtgttt ttggcaatca acaggtttaa gtcttcggcc gaagttaatc tcgtgttttt    300
ggcaatcaag aggtttaagt cttcggccga agttaatctc gttttttggg caatcaacag    360
```

```
gtttaagtct tcggccgaan ttaatctcgt gtttttggca atcaacaggt ttaantcttc    420
ggccgaagtt aatctcgtgt ttttggcaat caana                              455

<210> SEQ ID NO 274
<211> LENGTH: 461
<212> TYPE: DNA
<213> ORGANISM: Homo sapien

<400> SEQUENCE: 274 ttttttttt  ttggccaata cccttgatga acatcaatgt gaaaatcctc ggtaaaatac     60
tggcaaacca atccagcag  cacatcaaaa agcttatcca ccatgatcaa gtgggcttca    120
tccctgggat gcaaggctgg ttcaacataa gaaaatcaat aaatgtaatc catcacataa    180
acagaaccaa agacaaaaac cacatgatta tctcaataga tgcagaaaag gccttggaca    240
aattcaacag cccttcatgc taaacactct taataaacta gatattgatg gaatgtatct    300 caaataata  agagctattt atgacaaacc cacagccaat atcatactga atgggcaaag    360
actggaagca ttccctttga aaactggcac aagacaagga tgccctctct caccgctcct    420
attcaacata gtattggaag ttctggccag ggcaatcaag a                       461

<210> SEQ ID NO 275
<211> LENGTH: 729
<212> TYPE: DNA
<213> ORGANISM: Homo sapien
<220> FEATURE:
<221> NAME/KEY: misc_feature
<222> LOCATION: (1)...(729)
<223> OTHER INFORMATION: n = A,T,C or G

<400> SEQUENCE: 275 ttttttttt  ttggccaaca ccaagtcttc cacgtgggag gttttattat gttttacaac     60
catgaaaaca taggaaggtg gctgttacag caaacatttc agatagacga atcggccaag    120
ctccccaaac cccaccttca cagcctcttc cacacgtctc ccanagattg ttgtccttca    180
cttgcaaatt canggatgtt ggaagtngac atttnnagtn gcnggaaccc catcagtgaa    240
ncantaagca gaantacgat gactttgana nacanctgat gaagaacacn ctacngaaaa    300
ccctttctnt cgtgttanga tctcnngtcc ntcactaatg cggcccctg  cnggtccacc    360 atttgggaga actcccccn  cgttggatcc cccttgagt  ntcccattct ngtccccan    420 accngncttg ngngncantn cnncctcnca ccntgtttcc ctgnngtnaa aatnngtttt    480 nccgccncc  naattcccac ccnaatcaca gcgaanccng aaggccttcn naagtgttta    540
angcccngng gtttcctcnt ntanttgcag cctaccctcc cncttnnnnt tncgngttgg    600
tcgcgccctg gncncgcctn gttcctcttt nnggnnacaa cctngntcnn nggcncntcn    660
nnnctnttcc tnnnactagc tngcctntcc ncnccgnggn ncannggcaca ttncncnnac    720 tntgtnncc                                                           729

<210> SEQ ID NO 276
<211> LENGTH: 339
<212> TYPE: DNA
<213> ORGANISM: Homo sapien

<400> SEQUENCE: 276
tgacctgaca tgtagtagat acttaataaa tatttgtgga atgaatggat gaagtggagt     60
tacagagaaa aatagaaaag tacaaattgt tgtcagtgtt ttgaaggaaa attatgatct    120
```

-continued

| | | |
|---|---|---|
| ttcccaaagt tctgacttca ttctaagaca gggttagtat ctccatacat aattttactt | 180 | |
| gcttttgaaa atcaaatgag ataatctatt tagattgata atttatttag actggctata | 240 | |
| aactattaag tgctagcaaa tatacatttt aatctcattt tccacctctt gtgatatagc | 300 | |
| tatgtaggtg ttgactttaa tggatgtcag gtcaatccc | 339 | |

<210> SEQ ID NO 277
<211> LENGTH: 664
<212> TYPE: DNA
<213> ORGANISM: Homo sapien
<220> FEATURE:
<221> NAME/KEY: misc_feature
<222> LOCATION: (1)...(664)
<223> OTHER INFORMATION: n = A,T,C or G

<400> SEQUENCE: 277

| | |
|---|---|
| tgacctgaca tccataacaa aatctttctc cattatattc ttctagggga atttcttgaa | 60 |
| aagcatccaa aggaaacaaa tgatggtaag accgtgccaa gtggggagca gacaccaaag | 120 |
| taagaccaca gattttacat tcaacaggta gctcacagta ctttgcccga cactgtgggc | 180 |
| agaaatagcc tcctaatgta agccctggct cagtattgcc atccaaatgc gccatgctga | 240 |
| aagagggttt tgcatcctgg tcagatnaag aagcaatggt gtgctgagga atcccatac | 300 |
| gaataagtga gcattcagaa cttgagctag caggaggagg actaagatga tgtgtgagca | 360 |
| actctttgta atggctttca tctaaaataa catggtacgt gccaccagtt tcacgagcaa | 420 |
| gtacagtgca aacgcgaact tctgcagaca atccaataac agatactcta atttagctg | 480 |
| cctttagggt cttgattaaa tcataaatat tagatggatc gcaagttgta aggntgctaa | 540 |
| aagatgatta gtacttctcg acttgtatgt ccaggcatgt tgtttttaaan tctgccttag | 600 |
| nccctgctta ggggaattttt taaagaagat ggctctccat gttcanggtc aatcacnaat | 660 |
| tgcc | 664 |

<210> SEQ ID NO 278
<211> LENGTH: 452
<212> TYPE: DNA
<213> ORGANISM: Homo sapien
<220> FEATURE:
<221> NAME/KEY: misc_feature
<222> LOCATION: (1)...(452)
<223> OTHER INFORMATION: n = A,T,C or G

<400> SEQUENCE: 278

| | |
|---|---|
| tgacctgaca ttgaggaaga gcacacacct ctgaaattcc ttaggttcag aagggcattt | 60 |
| gacacagagt gggcctctga taattcatga aatgcattct gaagtcatcc agaatggagg | 120 |
| ctgcaatctg ctgtgctttg ggggttgcct cactgtgctc ctggatatca cacaaaagct | 180 |
| gcaatccttc ttcttcaact aacattttgc agtatttgct gggatttta ctgcagacat | 240 |
| gatacatagc ccatagtgcc cagagctgaa cctctggttg agagaagttg ccaaggagcg | 300 |
| ggaaaaatgt cttgaaagat ctataggtca ccaatgctgt catcttacaa cttgaacttg | 360 |
| gccaattctg tatggttgca tgcagatctt ggagaagagt acgcctctgg aagtcacggg | 420 |
| atatccaaan ctgtctgtca gatgtcaggt ca | 452 |

<210> SEQ ID NO 279
<211> LENGTH: 274
<212> TYPE: DNA
<213> ORGANISM: Homo sapien

<400> SEQUENCE: 279

```
tttttttttt tcggcaagg caaatttact tctgcaaaag ggtgctgctt gcacttttgg      60
ccactgcgag agcacaccaa acaaagtagg gaagggtttt ttatccctaa cgcggttatt    120
ccctggttct gtgtcgtgtc cccattggct ggagtcagac tgcacaatct acactgaccc    180
aactggctac tgtttaaaat tgaatatgaa taattaggta ggaaggggga ggctgtttgt    240
tacggtacaa gacgtgtttg ggcatgtcag gtca                                274

<210> SEQ ID NO 280
<211> LENGTH: 272
<212> TYPE: DNA
<213> ORGANISM: Homo sapien

<400> SEQUENCE: 280
tacctgacat ggagaaataa cttgtagtat tttgcgtgca atggaatact atatgagggt     60
gaaaatgaat gaactagcaa tgcgtgtatc aacatgaata aatccccaaa acataataat    120
gttgaatgga aaggtgagt tcagaagga tatatatgcc ctctaaatcc atttatgtaa      180
acctttaaaa aactacatta tttatggtca taagtccatc cagaaaatat ttaaaaacct    240
acatgggatt gataactact gatgtcaggt ca                                  272

<210> SEQ ID NO 281
<211> LENGTH: 431
<212> TYPE: DNA
<213> ORGANISM: Homo sapien
<220> FEATURE:
<221> NAME/KEY: misc_feature
<222> LOCATION: (1)...(431)
<223> OTHER INFORMATION: n = A,T,C or G

<400> SEQUENCE: 281
tttttttttt ttggccaata gcatgattta aacattggaa aaagtcaaat gagcaatgcg     60 aattttatg ttctcttgaa taatcaaaag agtaggcaac attggttcct cattcttgaa    120
tagcattaat cagaaaatat tgcatagcct ctagcctcct tagagtaggt gtgctctctc    180
aaatatatca tagtcccaca gtttatttca tgtatatttt ctgcctgaat cacatagaca    240
tttgaatttg caacgcctga tgtaaatata taaattctta ccaatcagaa acatagcaag    300
aaattcaggg acttggtcat yatcagggta tgacagcana tccctgtara aacactgata    360
cacactcaca cacgtatgca acgtggagat gtcgcyttww kkktwywcwm rmrycrwcgn    420
aatcacttan n                                                         431

<210> SEQ ID NO 282
<211> LENGTH: 98
<212> TYPE: DNA
<213> ORGANISM: Homo sapien

<400> SEQUENCE: 282
attcgattcg atgcttgagc ccaggagttc aagactgcag tgagccactg cacttcaggc     60
tggacaacag agcgagtccc tgtgccaaaa aaaaaaaa                             98

<210> SEQ ID NO 283
<211> LENGTH: 764
<212> TYPE: DNA
<213> ORGANISM: Homo sapien
<220> FEATURE:
<221> NAME/KEY: misc_feature
<222> LOCATION: (1)...(764)
<223> OTHER INFORMATION: n = A,T,C or G
```

```
<400> SEQUENCE: 283
tttttttttt tcgcaagca cgtgcacttt attgaatgac actgtagaca ggtgtgtggg      60
tataaactgc tgtatctagg ggcaggacca aggggggcagg ggcaacagcc ccagcgtgca    120
gggccascat tgcacagtgg astgcaaagg ttgcaggcta tgggcggcta ctavtaaccc   180
cgtttttcct gtattatctg taacataata tggtagactg tcacagagcc gaatwccart   240
hacasgatga atccaawggt caygaggatg cccasaatca gggcccasat sttcaggcac   300
ttggcggtgg gggcatasgc ctgkgccccg gtcacgtcsc caaccwtcty cctgtcccta   360
cmcttgawtc cncnccttnn nntnccntna tntgcccgcc cncctcctng ngtcaaccng   420
natctgcact anctccctcn cccttntgg antctcntcc ttcaantaan nttatccttn    480
acncccccct cnccttccc ctnccncccn tnatcccngn nccnctatca ntcntnccct    540
cnctntnctn cnnatcgttc cncctnntaa ctacncttn nacnanncct cactnatncc    600
ngnnanttct ttccttccct cccnacgcnn tgcgtgcgcc cgtctngcct nnnctncgna   660
cccnnacttt atttacctt ncaccctagc nctctacttn acccanccnc tcctacctcc   720
nggnccaccc nnccctnatc nctnnctctn tcnnctcntt cccc                    764

<210> SEQ ID NO 284
<211> LENGTH: 157
<212> TYPE: DNA
<213> ORGANISM: Homo sapien

<400> SEQUENCE: 284
caagtgtagg cacagtgatg aaagcctgga gcaaacacaa tctgtgggta attaacgttt      60
atttctcccc ttccaggaac gtcttgcatg gatgatcaaa gatcagctcc tggtcaacat    120
aaataagcta gtttaagata cgttccccta cacttga                              157

<210> SEQ ID NO 285
<211> LENGTH: 150
<212> TYPE: DNA
<213> ORGANISM: Homo sapien

<400> SEQUENCE: 285
attcgattgt actcagacaa caatatgcta agtggaagaa gtcagtcaca aaagaccaca      60
tactgtatga cttcatttac attaagtgtc cagaataggc aaatccgtag agacagaaag    120
tagatgagca gctgcctagg tctgagtaca                                     150

<210> SEQ ID NO 286
<211> LENGTH: 219
<212> TYPE: DNA
<213> ORGANISM: Homo sapien

<400> SEQUENCE: 286
attcgatttt tttttttttg gccatgatga aattcttact ccctcagatt ttttgtctgg      60
ataaatgcaa gtctcaccac cagatgtgaa attacagtaa actttgaagg aatctcctga    120
gcaaccttgg ttaggatcaa tccaatattc accatctggg aagtcaggat ggctgagttg    180
caggtcttta caagttcggg ctggattggt ctgagtaca                           219

<210> SEQ ID NO 287
<211> LENGTH: 196
<212> TYPE: DNA
<213> ORGANISM: Homo sapien

<400> SEQUENCE: 287
```

```
attcgattct tgaggctacc aggagctagg agaagaggca tggaacaaat tttccctcat    60
atccatactc agaaggaacc aaccctgctg acaccttaat ttcagcttct ggcctctaga   120
actgtgagag agtacatttc tcttggttta agccaagaga atctgtcttt tggtacttta   180
tatcatagcc tcaaga                                                   196
```

<210> SEQ ID NO 288
<211> LENGTH: 199
<212> TYPE: DNA
<213> ORGANISM: Homo sapien

<400> SEQUENCE: 288

```
attcgatttc agtccagtcc cagaacccac attgtcaatt actactctgt araagattca    60
tttgttgaaa ttcattgagt aaaacattta tgatccctta atatatgcca attaccatgc   120
taggtactga agattcaagt gaccgagatg ctagcccttg ggttcaagtg atccctctcc   180
cagagtgcac tggactgaa                                                199
```

<210> SEQ ID NO 289
<211> LENGTH: 182
<212> TYPE: DNA
<213> ORGANISM: Homo sapien

<400> SEQUENCE: 289

```
attcgattct tgaggctaca aacctgtaca gtatgttact ctactgaata ctgtaggcaa    60
tagtaataca gaagcaagta tctgtatatg taaacattaa aaaggtacag tgaaacttca   120
gtattataat cttagggacc accattatat atgtggtcca tcattggcca aaaaaaaaaa   180
aa                                                                  182
```

<210> SEQ ID NO 290
<211> LENGTH: 1646
<212> TYPE: DNA
<213> ORGANISM: Homo sapien

<400> SEQUENCE: 290

```
ggcacgagga gaaatgtaat tccatatttt atttgaaact tattccatat tttaattgga    60
tattgagtga ttgggttatc aaacacccac aaactttaat tttgttaaat ttatatggct   120
ttgaaataga agtataagtt gctaccattt tttgataaca ttgaaagata gtattttacc   180
atctttaatc atcttggaaa atacaagtcc tgtgaacaac cactctttca cctagcagca   240
tgaggccaaa agtaaaggct ttaaattata acatatggga ttcttagtag tatgtttttt   300
tcttgaaact cagtggctct atctaacctt actatctcct cactctttct ctaagactaa   360
actctaggct cttaaaaatc tgcccacacc aatcttagaa gctctgaaaa gaatttgtct   420
ttaaatatct tttaatagta acatgtattt tatggaccaa attgacattt tcgactattt   480
tttccaaaaa agtcaggtga atttcagcac actgagttgg gaatttctta tcccagaaga   540
ccaaccaatt tcatatttat ttaagattga ttccatactc cgttttcaag gagaatccct   600
gcagtctcct taaggtaga acaaatactt tctatttttt tttccaccatt gtgggattgg   660 actttaagag gtgactctaa aaaacagag aacaaatatg tctcagttgt attaagcacg   720
gacccatatt atcatattca cttaaaaaaa tgatttcctg tgcacctttt ggcaacttct   780
cttttcaatg tagggaaaaa cttagtcacc ctgaaaaccc acaaaataaa taaaacttgt   840
agatgtgggc agaaggtttg ggggtggaca ttgtatgtgt ttaaattaaa ccctgtatca   900
```

-continued

```
ctgagaagct gttgtatggg tcagagaaaa tgaatgctta gaagctgttc acatcttcaa      960
gagcagaagc aaaccacatg tctcagctat attattattt attttttatg cataaagtga     1020
atcatttctt ctgtattaat ttccaaaggg ttttaccctc tatttaaatg ctttgaaaaa     1080
cagtgcattg acaatgggtt gatattttc tttaaaagaa aaatataatt atgaaagcca      1140
agataatctg aagcctgttt tattttaaaa cttttatgt tctgtggttg atgttgtttg      1200
tttgtttgtt tctattttgt tggttttta ctttgttttt tgttttgttt tgttttgttt     1260
kgcatactac atgcagttct ttaaccaatg tctgtttggc taatgtaatt aaagttgtta     1320
atttatatga gtgcatttca actatgtcaa tggtttctta atatttattg tgtagaagta     1380
ctggtaattt ttttatttac aatatgttta aagagataac agtttgatat gttttcatgt     1440
gtttatagca gaagttattt atttctatgg cattccagcg gatattttgg tgtttgcgag     1500
gcatgcagtc aatattttgt acagttagtg gacagtattc agcaacgcct gatagcttct     1560
ttggccttat gttaaataaa aagacctgtt tgggatgtat tttttatttt taaaaaaaaa     1620
aaaaaaaaaa aaaaaaaaaa aaaaaa                                         1646

<210> SEQ ID NO 291
<211> LENGTH: 1851
<212> TYPE: DNA
<213> ORGANISM: Homo sapien

<400> SEQUENCE: 291
tcatcaccat tgccagcagc ggcaccgtta gtcaggtttt ctgggaatcc cacatgagta       60
cttccgtgtt cttcattctt ttcaatagc cataaatctt ctagctctgg ctggctgttt      120
tcacttcctt taagcctttg tgactcttcc tctgatgtca gctttaagtc ttgttctgga     180
ttgctgtttt cagaagagat ttttaacatc tgttttctt tgtagtcaga aagtaactgg      240
caaattacat gatgatgact agaaacagca tactctctgg ccgtctttcc agatcttgag     300
aagatacatc aacattttgc tcaagtagag ggctgactat acttgctgat ccacaacata     360
cagcaagtat gagagcagtt cttccatatc tatccagcgc atttaaattc gctttttct      420 tgattaaaaa tttcaccact tgctgttttt gctcatgtat accaagtagc agtggtgtga     480
ggccatgctt gttttttgat tcgatatcag caccgtataa gagcagtgct ttggccatta     540
atttatcttc attgtagaca gcatagtgta gagtggtatt tccatactca tctggaatat     600
ttggatcagt gccatgttcc agcaacatta acgcacattc atcttcctgg cattgtacgg     660
cctttgtcag agctgtcctc ttttttgttgt caaggacatt aagttgacat cgtctgtcca     720
gcacgagttt tactacttct gaattcccat tggcagaggc cagatgtaga gcagtcctct     780
tttgcttgtc cctcttgttc acatccgtgt ccctgagcat gacgatgaga tcctttctgg     840
ggactttacc ccaccaggca gctctgtgga gcttgtccag atcttctcca tggacgtggt     900
acctgggatc catgaaggcg ctgtcatcgt agtctcccca agcgaccacg ttgctcttgc     960
cgctcccctg cagcagggga agcagtggca gcaccacttg cacctcttgc tcccaagcgt    1020
cttcacagag gagtcgttgt ggtctccaga agtgcccacg ttgctcttgc cgctccccct    1080
gtccatccag ggaggaagaa atgcaggaaa tgaaagatgc atgcacgatg gtatactcct    1140
cagccatcaa acttctggac agcaggtcac ttccagcaag gtggagaaag ctgtccaccc    1200
acagaggatg agatccagaa accacaatat ccattcacaa acaaacactt ttcagccaga    1260
cacaggtact gaaatcatgt catctgcggc aacatggtgg aacctaccca atcacacatc    1320
aagagatgaa gacactgcag tatatctgca caacgtaata ctcttcatcc ataacaaaat    1380
```

```
aatataattt tcctctggag ccatatggat gaactatgaa ggaagaactc cccgaagaag    1440
ccagtcgcag agaagccaca ctgaagctct gtcctcagcc atcagcgcca cggacaggar    1500
tgtgtttctt ccccagtgat gcagcctcaa gttatcccga agctgccgca gcacacggtg    1560
gctcctgaga acaccccag ctcttccggt ctaacacagg caagtcaata aatgtgataa     1620
tcacataaac agaattaaaa gcaaagtcac ataagcatct caacgacac agaaaaggca     1680 tttgacaaaa tccagcatcc ttgtatttat tgttgcagtt ctcagaggaa atgcttctaa    1740
cttttcccca tttagtatta tgttggctgt gggcttgtca taggtggttt ttattacttt    1800
aaggtatgtc ccttctatgc ctgttttgct gagggtttta attctcgtgc c             1851

<210> SEQ ID NO 292
<211> LENGTH: 1851
<212> TYPE: DNA
<213> ORGANISM: Homo sapien

<400> SEQUENCE: 292
tcatcaccat tgccagcagc ggcaccgtta gtcaggtttt ctgggaatcc cacatgagta      60
cttccgtgtt cttcattctt cttcaatagc cataaatctt ctagctctgg ctggctgttt     120
tcacttcctt taagcctttg tgactcttcc tctgatgtca gctttaagtc ttgttctgga     180
ttgctgtttt cagaagagat ttttaacatc tgttttctt tgtagtcaga aagtaactgg      240
caaattacat gatgatgact agaaacagca tactctctgg ccgtctttcc agatcttgag     300
aagatacatc aacattttgc tcaagtagag ggctgactat acttgctgat ccacaacata    360
cagcaagtat gagagcagtt cttccatatc tatccagcgc atttaaattc gctttttct     420 tgattaaaaa tttcaccact tgctgttttt gctcatgtat accaagtagc agtggtgtga    480
ggccatgctt gttttttgat tcgatatcag caccgtataa gagcagtgct ttggccatta    540
atttatcttc attgtagaca gcatagtgta gagtggtatt tccatactca tctggaatat    600
ttggatcagt gccatgttcc agcaacatta acgcacattc atcttcctgg cattgtacgg    660
cctttgtcag agctgtcctc ttttgttgt caaggacatt aagttgacat cgtctgtcca     720
gcacgagttt tactacttct gaattcccat tggcagaggc cagatgtaga gcagtcctct    780
tttgcttgtc cctcttgttc acatccgtgt ccctgagcat gacgatgaga tcctttctgg    840
ggactttacc ccaccaggca gctctgtgga gcttgtccag atcttctcca tggacgtggt    900
acctgggatc catgaaggcg ctgtcatcgt agtctcccca agcgaccacg ttgctcttgc    960
cgctcccctg cagcaggga agcagtggca gcaccacttg cacctcttgc tcccaagcgt    1020
cttcacagag gagtcgttgt ggtctccaga agtgcccacg ttgctcttgc cgctcccct    1080 gtccatccag ggaggaagaa atgcaggaaa tgaaagatgc atgcacgatg gtatactcct   1140
cagccatcaa acttctggac agcaggtcac ttccagcaag gtggagaaag ctgtccaccc    1200
acagaggatg agatccagaa accacaatat ccattcacaa acaaacactt ttcagccaga    1260
cacaggtact gaaatcatgt catctgcggc aacatggtgg aacctaccca atcacacatc    1320
aagagatgaa gacactgcag tatatctgca caacgtaata ctcttcatcc ataacaaaat    1380
aatataattt tcctctggag ccatatggat gaactatgaa ggaagaactc cccgaagaag    1440
ccagtcgcag agaagccaca ctgaagctct gtcctcagcc atcagcgcca cggacaggar    1500
tgtgtttctt ccccagtgat gcagcctcaa gttatcccga agctgccgca gcacacggtg    1560
gctcctgaga acaccccag ctcttccggt ctaacacagg caagtcaata aatgtgataa     1620
```

-continued

| | |
|---|---|
| tcacataaac agaattaaaa gcaaagtcac ataagcatct caacagacac agaaaaggca | 1680 |
| tttgacaaaa tccagcatcc ttgtatttat tgttgcagtt ctcagaggaa atgcttctaa | 1740 |
| cttttcccca tttagtatta tgttggctgt gggcttgtca taggtggttt ttattacttt | 1800 |
| aaggtatgtc ccttctatgc ctgttttgct gagggtttta attctcgtgc c | 1851 |

<210> SEQ ID NO 293
<211> LENGTH: 668
<212> TYPE: DNA
<213> ORGANISM: Homo sapien

<400> SEQUENCE: 293

| | |
|---|---|
| cttgagcttc caaataygga agactggccc ttacacasgt caatgttaaa atgaatgcat | 60 |
| ttcagtatttt tgaagataaa attrgtagat ctataccttg ttttttgatt cgatatcagc | 120 |
| accrtataag agcagtgctt tggccattaa tttatctttc attrtagaca gcrtagtgya | 180 |
| gagtggtatt tccatactca tctggaatat ttggatcagt gccatgttcc agcaacatta | 240 |
| acgcacattc atcttcctgg cattgtacgg cctgtcagta ttagacccaa aaacaaatta | 300 |
| catatcttag gaattcaaaa taacattcca cagctttcac caactagtta tatttaaagg | 360 |
| agaaaactca tttttatgcc atgtattgaa atcaaaccca cctcatgctg atatagttgg | 420 |
| ctactgcata cctttatcag agctgtcctc tttttgttgt caaggacatt aagttgacat | 480 |
| cgtctgtcca gcaggagttt tactacttct gaattcccat tggcagaggc cagatgtaga | 540 |
| gcagtcctat gagagtgaga agactttta ggaaattgta gtgcactagc tacagccata | 600 |
| gcaatgattc atgtaactgc aaacactgaa tagcctgcta ttactctgcc ttcaaaaaaa | 660 |
| aaaaaaaa | 668 |

<210> SEQ ID NO 294
<211> LENGTH: 1512
<212> TYPE: DNA
<213> ORGANISM: Homo sapien

<400> SEQUENCE: 294

| | |
|---|---|
| gggtcgccca gggggsgcgt gggctttcct cgggtgggtg tgggttttcc ctgggtgggg | 60 |
| tgggctgggc trgaatcccc tgctggggtt ggcaggtttt ggctgggatt gactttttytc | 120 |
| ttcaaacaga ttggaaaccc ggagttacct gctagttggt gaaactggtt ggtagacgcg | 180 |
| atctgttggc tactactggc ttctcctggc tgttaaaagc agatggtggt tgaggttgat | 240 |
| tccatgccgg ctgcttcttc tgtgaagaag ccatttggtc tcaggagcaa gatgggcaag | 300 |
| tggtgctgcc gttgcttccc ctgctgcagg gagagcggca agagcaacgt gggcacttct | 360 |
| ggagaccacg acgactctgc tatgaagaca ctcaggagca agatgggcaa gtggtgccgc | 420 |
| cactgcttcc cctgctgcag ggggagtggc aagagcaacg tgggcgcttc tggagaccac | 480 |
| gacgaytctg ctatgaagac actcaggaac aagatgggca agtggtgctg ccactgcttc | 540 |
| ccctgctgca gggggagcrg caagagcaag gtgggcgctt ggggagacta cgatgacagt | 600 |
| gccttcatgg agcccaggta ccacgtccgt ggagaagatc tggacaagct ccacagagct | 660 |
| gcctggtggg gtaaagtccc cagaaaggat ctcatcgtca tgctcaggga cactgacgtg | 720 |
| aacaagaagg acaagcaaaa gaggactgct ctacatctgg cctctgccaa tgggaattca | 780 |
| gaagtagtaa aactcstgct ggacagacga tgtcaactta atgtccttga caacaaaaag | 840 |
| aggacagctc tgayaaaggc cgtacaatgc caggaagatg aatgtgcgtt aatgttgctg | 900 |
| gaacatggca ctgatccaaa tattccagat gagtatggaa ataccactct rcactaygct | 960 |

```
rtctayaatg aagataaatt aatggccaaa gcactgctct tatayggtgc tgatatcgaa    1020
tcaaaaaaca aggtatagat ctactaattt tatcttcaaa atactgaaat gcattcattt    1080
taacattgac gtgtgtaagg gccagtcttc cgtatttgga agctcaagca taacttgaat    1140
gaaaatattt tgaaatgacc taattatctm agactttatt ttaaatattg ttattttcaa    1200
agaagcatta gagggtacag ttttttttttt ttaaatgcac ttctggtaaa tacttttgtt    1260
gaaaacactg aatttgtaaa aggtaatact tactattttt caattttttcc ctcctaggat    1320 ttttttcccc taatgaatgt aagatggcaa aatttgccct gaaataggtt ttacatgaaa    1380
actccaagaa aagttaaaca tgtttcagtg aatagagatc ctgctccttt ggcaagttcc    1440
taaaaaacag taatagatac gaggtgatgc gcctgtcagt ggcaaggttt aagatatttc    1500
tgatctcgtg cc                                                       1512
```

<210> SEQ ID NO 295
<211> LENGTH: 1853
<212> TYPE: DNA
<213> ORGANISM: Homo sapien

<400> SEQUENCE: 295

```
gggtcgccca gggggsgcgt gggctttcct cgggtgggtg tgggttttcc ctgggtgggg     60
tgggctgggc trgaatcccc tgctggggtt ggcaggtttt ggctgggatt gacttttytc    120
ttcaaacaga ttggaaaccc ggagttacct gctagttggt gaaactggtt ggtagacgcg    180
atctgttggc tactactggc ttctcctggc tgttaaaagc agatggtggt tgaggttgat    240
tccatgccgg ctgcttcttc tgtgaagaag ccatttggtc tcaggagcaa gatgggcaag    300
tggtgctgcc gttgcttccc ctgctgcagg gagagcggca agagcaacgt gggcacttct    360
ggagaccacg acgactctgc tatgaagaca ctcaggagca agatgggcaa gtggtgccgc    420
cactgcttcc cctgctgcag ggggagtggc aagagcaacg tgggcgcttc tggagaccac    480
gacgaytctg ctatgaagac actcaggaac aagatgggca agtggtgctg ccactgcttc    540
ccctgctgca gggggagcrg caagagcaag gtgggcgctt ggggagacta cgatgacagy    600
gccttcatgg akcccaggta ccacgtccrt ggagaagatc tggacaagct ccacagagct    660
gcctggtggg gtaaagtccc cagaaaggat ctcatcgtca tgctcaggga cackgaygtg    720
aacaagargg acaagcaaaa gaggactgct ctacatctgg cctctgccaa tgggaattca    780
gaagtagtaa aactcstgct ggacagacga tgtcaactta atgtccttga caacaaaaag    840
aggacagctc tgayaaaggc cgtacaatgc caggaagatg aatgtgcgtt aatgttgctg    900
gaacatggca ctgatccaaa tattccagat gagtatggaa ataccactct rcactaygct    960
rtctayaatg aagataaatt aatggccaaa gcactgctct tatayggtgc tgatatcgaa   1020
tcaaaaaaca agcatggcct cacaccactg ytacttggtr tacatgagca aaaacagcaa   1080
gtsgtgaaat ttttaatyaa gaaaaagcg aatttaaaat gcrctggata gatatggaag   1140
ractgctctc atacttgctg tatgttgtgg atcagcaagt atagtcagcc ytctacttga   1200
gcaaaatrtt gatgtatctt ctcaagatct ggaaagacgg ccagagagta tgctgtttct   1260
agtcatcatc atgtaatttg ccagttactt tctgactaca aagaaaaaca gatgttaaaa   1320
atctcttctg aaaacagcaa tccagaacaa gacttaaagc tgacatcaga ggaagagtca   1380
caaaggctta aaggaagtga aaacagccag ccagaggcat ggaaactttt aaatttaaac   1440
ttttggttta atgttttttt tttttgcctt aataatatta gatagtccca aatgaaatwa   1500
```

```
cctatgagac taggctttga gaatcaatag attcttttt  taagaatctt ttggctagga    1560
gcggtgtctc acgcctgtaa ttccagcacc ttgagaggct gaggtgggca gatcacgaga    1620
tcaggagatc gagaccatcc tggctaacac ggtgaaaccc catctctact aaaaatacaa    1680
aaacttagct gggtgtggtg gcgggtgcct gtagtcccag ctactcagga rgctgaggca    1740
ggagaatggc atgaacccgg gaggtggagg ttgcagtgag ccgagatccg ccactacact    1800
ccagcctggg tgacagagca agactctgtc tcaaaaaaaa aaaaaaaaaa aaa           1853

<210> SEQ ID NO 296
<211> LENGTH: 2184
<212> TYPE: DNA
<213> ORGANISM: Homo sapien

<400> SEQUENCE: 296
ggcacgagaa ttaaaaccct cagcaaaaca ggcatagaag ggacatacct taaagtaata      60
aaaaccacct atgacaagcc cacagccaac ataatactaa atggggaaaa gttagaagca     120
tttcctctga gaactgcaac aataaataca aggatgctgg attttgtcaa atgccttttc     180
tgtgtctgtt gagatgctta tgtgactttg cttttaattc tgtttatgtg attatcacat     240
ttattgactt gcctgtgtta gaccggaaga gctggggtgt ttctcaggag ccaccgtgtg     300
ctgcggcagc ttcgggataa cttgaggctg catcactggg aagaaacac aytcctgtcc      360 gtggcgctga tggctgagga cagagcttca gtgtggcttc tctgcgactg gcttcttcgg     420
ggagttcttc cttcatagtt catccatatg gctccagagg aaaattatat tattttgtta     480
tggatgaaga gtattacgtt gtgcagatat actgcagtgt cttcatctct tgatgtgtga     540 tgggtaggt tccaccatgt tgccgcagat gacatgattt cagtacctgt gtctggctga      600
aaagtgtttg tttgtgaatg gatattgtgg tttctggatc tcatcctctg tgggtggaca     660
gctttctcca ccttgctgga agtgacctgc tgtccagaag tttgatggct gaggagtata     720
ccatcgtgca tgcatctttc atttcctgca tttcttcctc cctggatgga caggggagc      780 ggcaagagca acgtgggcac ttctggagac cacaacgact cctctgtgaa gacgcttggg     840
agcaagaggt gcaagtggtg ctgccactgc ttcccctgct gcaggggagc ggcaagagca     900
acgtggtcgc ttggggagac tacgatgaca gcgccttcat ggatcccagg taccacgtcc     960
atggagaaga tctggacaag ctccacagag ctgcctggtg gggtaaagtc cccagaaagg    1020
atctcatcgt catgctcagg gacacggatg tgaacaagag ggacaagcaa agaggactg     1080 ctctacatct ggcctctgcc aatgggaatt cagaagtagt aaaactcgtg ctggacagac    1140
gatgtcaact taatgtcctt gacaacaaaa agaggacagc tctgacaaag gccgtacaat    1200
gccaggaaga tgaatgtgcg ttaatgttgc tggaacatgg cactgatcca atattccag     1260 atgagtatgg aaataccact ctacactatg ctgtctacaa tgaagataaa ttaatggcca    1320
aagcactgct cttatacggt gctgatatcg aatcaaaaaa caagcatggc ctcacaccac    1380
tgctacttgg tatacatgag caaaacagc aagtggtgaa attttaatc aagaaaaaag      1440 cgaatttaaa tgcgctggat agatatggaa gaactgctct catacttgct gtatgttgtg    1500
gatcagcaag tatagtcagc cctctacttg agcaaaatgt tgatgtatct tctcaagatc    1560
tggaaagacg gccagagagt atgctgtttc tagtcatcat catgtaattt gccagttact    1620
ttctgactac aaagaaaaac agatgttaaa aatctcttct gaaaacagca atccagaaca    1680
agacttaaag ctgacatcag aggaagagtc acaaaggctt aaaggaagtg aaaacagcca    1740
gccagaggca tggaaacttt taaatttaaa cttttggttt aatgttttt  ttttttgcct    1800
```

```
taataatatt agatagtccc aaatgaaatw acctatgaga ctaggctttg agaatcaata    1860 gattctttt ttaagaatct tttggctagg agcggtgtct cacgcctgta attccagcac    1920
cttgagaggc tgaggtgggc agatcacgag atcaggagat cgagaccatc ctggctaaca    1980
cggtgaaacc ccatctctac taaaaataca aaaacttagc tgggtgtggt ggcgggtgcc    2040
tgtagtccca gctactcagg argctgaggc aggagaatgg catgaacccg ggaggtggag    2100
gttgcagtga gccgagatcc gccactacac tccagcctgg gtgacagagc aagactctgt    2160
ctcaaaaaaa aaaaaaaaaa aaaa                                           2184
```

<210> SEQ ID NO 297
<211> LENGTH: 1855
<212> TYPE: DNA
<213> ORGANISM: Homo sapien
<220> FEATURE:
<221> NAME/KEY: misc_feature
<222> LOCATION: (1)...(1855)
<223> OTHER INFORMATION: n = A,T,C or G

<400> SEQUENCE: 297

```
tgcacgcatc ggccagtgtc tgtgccacgt acactgacgc ccctgagat gtgcacgccg      60 cacgcgcacg ttcacgcgc ggcagcggct tggctggctt gtaacggctt gcacgcgcac     120
gccgcccccg cataaccgtc agactggcct gtaacggctt gcaggcgcac gccgcacgcg     180
cgtaacggct tggctgccct gtaacggctt gcacgtgcat gctgcacgcg cgttaacggc     240
ttggctggca tgtagccgct tggcttggct ttgcattytt tgctkggctk ggcgttgkty     300
tcttggattg acgcttcctc cttggatkga cgtttcctcc ttggatkgac gtttccytyty    360 tcgcgttcct ttgctggact tgacctttty tctgctgggt ttggcattcc tttggggtgg    420
gctgggtgtt ttctccgggg gggktkgccc ttcctggggt gggcgtgggk cgcccccagg    480
gggcgtgggc tttccccggg tgggtgtggg ttttcctggg gtgggggtggg ctgtgctggg    540 atcccctgc tggggttggc agggattgac ttttttcttc aaacagattg gaaacccgga     600
gtaacntgct agttggtgaa actggttggt agacgcgatc tgctggtact actgtttctc     660
ctggctgtta aaagcagatg gtggctgagg ttgattcaat gccggctgct tcttctgtga    720
agaagccatt tggtctcagg agcaagatgg gcaagtggtg cgccactgct tcccctgctg    780 caggggagc ggcaagagca acgtgggcac ttctggagac acaacgact cctctgtgaa      840 gacgcttggg agcaagaggt gcaagtggtg ctgcccactg cttcccctgc tgcaggggag    900
cggcaagagc aacgtggkcg cttggggaga ctacgatgac agcgccttca tggakcccag    960
gtaccacgtc crtggagaag atctggacaa gctccacaga gctgcctggt ggggtaaagt   1020
ccccagaaag gatctcatcg tcatgctcag ggacactgay gtgaacaaga rggacaagca  1080
aaagaggact gctctacatc tggcctctgc caatgggaat tcagaagtag taaaactcgt   1140
gctggacaga cgatgtcaac ttaatgtcct tgcaacaaa agaggacag ctctgacaaa    1200 ggccgtacaa tgccaggaag atgaatgtgc gttaatgttg ctggaacatg gcactgatcc   1260
aaatattcca gatgagtatg gaaataccac tctacactat gctgtctaca atgaagataa   1320
attaatggcc aaagcactgc tcttatacgg tgctgatatc gaatcaaaaa acaaggtata   1380
gatctactaa ttttatcttc aaaatactga aatgcattca ttttaacatt gacgtgtgta   1440
agggccagtc ttccgtattt ggaagctcaa gcataacttg aatgaaaata ttttgaaatg   1500
acctaattat ctaagacttt attttaaata ttgttatttt caaagaagca ttagagggta   1560
```

-continued

```
cagttttttt tttttaaatg cacttctggt aaatactttt gttgaaaaca ctgaatttgt    1620
aaaaggtaat acttactatt tttcaatttt tccctcctag gatttttttc ccctaatgaa    1680
tgtaagatgg caaaatttgc cctgaaatag gttttacatg aaaactccaa gaaaagttaa    1740
acatgtttca gtgaatagag atcctgctcc tttggcaagt tcctaaaaaa cagtaataga    1800
tacgaggtga tgcgcctgtc agtggcaagg tttaagatat ttctgatctc gtgcc         1855
```

<210> SEQ ID NO 298
<211> LENGTH: 1059
<212> TYPE: DNA
<213> ORGANISM: Homo sapien

<400> SEQUENCE: 298

```
gcaacgtggg cacttctgga gaccacaacg actcctctgt gaagacgctt gggagcaaga      60
ggtgcaagtg gtgctgccca ctgcttcccc tgctgcaggg gagcggcaag agcaacgtgg     120
gcgcttgrgg agactmcgat gacagygcct tcatggagcc caggtaccac gtccgtggag     180
aagatctgga caagctccac agagctgccc tggtggggta aagtcccag aaaggatctc     240 atcgtcatgc tcagggacac tgaygtgaac aagarggaca agcaaaagag gactgctcta    300
catctggcct ctgccaatgg gaattcagaa gtagtaaaac tcstgctgga cagacgatgt    360
caacttaatg tccttgacaa caaaaagagg acagctctga yaaaggccgt acaatgccag    420
gaagatgaat gtgcgttaat gttgctggaa catggcactg atccaaatat tccagatgag    480
tatggaaata ccactctrca ctaygctrtc tayaatgaag ataaattaat ggccaaagca    540
ctgctcttat ayggtgctga tatcgaatca aaaaacaagg tatagatcta ctaattttat    600
cttcaaaata ctgaaatgca ttcattttaa cattgacgtg tgtaagggcc agtcttccgt    660
atttggaagc tcaagcataa cttgaatgaa atatttga aatgacctaa ttatctaaga    720
ctttatttta aatattgtta ttttcaaaga agcattagag ggtacagttt ttttttttta    780
aatgcacttc tggtaaatac ttttgttgaa aacactgaat ttgtaaaagg taatacttac    840
tatttttcaa ttttttccctc ctaggatttt tttcccctaa tgaatgtaag atggcaaaat    900
ttgccctgaa ataggtttta catgaaaact ccaagaaaag ttaaacatgt tcagtgaat    960 agagatcctg ctcctttggc aagttcctaa aaaacagtaa tagatacgag gtgatgcgcc   1020
tgtcagtggc aaggtttaag atatttctga tctcgtgcc                          1059
```

<210> SEQ ID NO 299
<211> LENGTH: 329
<212> TYPE: PRT
<213> ORGANISM: Homo sapien

<400> SEQUENCE: 299

```
Met Asp Ile Val Val Ser Gly Ser His Pro Leu Trp Val Asp Ser Phe
  1               5                  10                  15

Leu His Leu Ala Gly Ser Asp Leu Leu Ser Arg Ser Leu Met Ala Glu
                 20                  25                  30

Glu Tyr Thr Ile Val His Ala Ser Phe Ile Ser Cys Ile Ser Ser Ser
             35                  40                  45

Leu Asp Gly Gln Gly Glu Arg Gln Glu Gln Arg Gly His Phe Trp Arg
         50                  55                  60

Pro Gln Arg Leu Leu Cys Glu Asp Ala Trp Glu Gln Glu Val Gln Val
 65                  70                  75                  80

Val Leu Pro Leu Leu Pro Leu Leu Gln Gly Ser Gly Lys Ser Asn Val
                 85                  90                  95
```

```
Val Ala Trp Gly Asp Tyr Asp Asp Ser Ala Phe Met Asp Pro Arg Tyr
            100                 105                 110

His Val His Gly Glu Asp Leu Asp Lys Leu His Arg Ala Ala Trp Trp
            115                 120                 125

Gly Lys Val Pro Arg Lys Asp Leu Ile Val Met Leu Arg Asp Thr Asp
            130                 135                 140

Val Asn Lys Arg Asp Lys Gln Lys Arg Thr Ala Leu His Leu Ala Ser
145                 150                 155                 160

Ala Asn Gly Asn Ser Glu Val Val Lys Leu Val Leu Asp Arg Arg Cys
            165                 170                 175

Gln Leu Asn Val Leu Asp Asn Lys Lys Arg Thr Ala Leu Thr Lys Ala
            180                 185                 190

Val Gln Cys Gln Glu Asp Glu Cys Ala Leu Met Leu Leu Glu His Gly
            195                 200                 205

Thr Asp Pro Asn Ile Pro Asp Glu Tyr Gly Asn Thr Thr Leu His Tyr
            210                 215                 220

Ala Val Tyr Asn Glu Asp Lys Leu Met Ala Lys Ala Leu Leu Leu Tyr
225                 230                 235                 240

Gly Ala Asp Ile Glu Ser Lys Asn Lys His Gly Leu Thr Pro Leu Leu
            245                 250                 255

Leu Gly Ile His Glu Gln Lys Gln Gln Val Val Lys Phe Leu Ile Lys
            260                 265                 270

Lys Lys Ala Asn Leu Asn Ala Leu Asp Arg Tyr Gly Arg Thr Ala Leu
            275                 280                 285

Ile Leu Ala Val Cys Cys Gly Ser Ala Ser Ile Val Ser Pro Leu Leu
            290                 295                 300

Glu Gln Asn Val Asp Val Ser Ser Gln Asp Leu Glu Arg Arg Pro Glu
305                 310                 315                 320

Ser Met Leu Phe Leu Val Ile Ile Met
            325

<210> SEQ ID NO 300
<211> LENGTH: 148
<212> TYPE: PRT
<213> ORGANISM: Homo sapien
<220> FEATURE:
<221> NAME/KEY: VARIANT
<222> LOCATION: (1)...(148)
<223> OTHER INFORMATION: Xaa = Any Amino Acid

<400> SEQUENCE: 300

Met Thr Xaa Pro Ser Trp Ser Pro Gly Thr Thr Ser Val Glu Lys Ile
1               5                   10                  15

Trp Thr Ser Ser Thr Glu Leu Pro Trp Trp Gly Lys Val Pro Arg Lys
            20                  25                  30

Asp Leu Ile Val Met Leu Arg Asp Thr Asp Val Asn Lys Xaa Asp Lys
            35                  40                  45

Gln Lys Arg Thr Ala Leu His Leu Ala Ser Ala Asn Gly Asn Ser Glu
            50                  55                  60

Val Val Lys Leu Xaa Leu Asp Arg Arg Cys Gln Leu Asn Val Leu Asp
65                  70                  75                  80

Asn Lys Lys Arg Thr Ala Leu Xaa Lys Ala Val Gln Cys Gln Glu Asp
            85                  90                  95

Glu Cys Ala Leu Met Leu Leu Glu His Gly Thr Asp Pro Asn Ile Pro
            100                 105                 110
```

-continued

```
Asp Glu Tyr Gly Asn Thr Thr Leu His Tyr Ala Xaa Tyr Asn Glu Asp
            115                 120                 125
Lys Leu Met Ala Lys Ala Leu Leu Leu Tyr Gly Ala Asp Ile Glu Ser
        130                 135                 140
Lys Asn Lys Val
145
```

<210> SEQ ID NO 301
<211> LENGTH: 1155
<212> TYPE: DNA
<213> ORGANISM: Homo sapien

<400> SEQUENCE: 301

| | | | | | |
|---|---|---|---|---|---|
| atggtggttg | aggttgattc | catgccggct | gcctcttctg | tgaagaagcc | atttggtctc | 60 |
| aggagcaaga | tgggcaagtg | gtgctgccgt | tgcttcccct | gctgcaggga | gagcggcaag | 120 |
| agcaacgtgg | gcacttctgg | agaccacgac | gactctgcta | tgaagacact | caggagcaag | 180 |
| atgggcaagt | ggtgccgcca | ctgcttcccc | tgctgcaggg | ggagtggcaa | gagcaacgtg | 240 |
| ggcgcttctg | gagaccacga | cgactctgct | atgaagacac | tcaggaacaa | gatgggcaag | 300 |
| tggtgctgcc | actgcttccc | ctgctgcagg | gggagcggca | agagcaaggt | gggcgcttgg | 360 |
| ggagactacg | atgacagtgc | cttcatggag | cccaggtacc | acgtccgtgg | agaagatctg | 420 |
| gacaagctcc | acagagctgc | ctggtggggt | aaagtcccca | gaaaggatct | catcgtcatg | 480 |
| ctcagggaca | ctgacgtgaa | caagaaggac | aagcaaaaga | ggactgctct | acatctggcc | 540 |
| tctgccaatg | ggaattcaga | agtagtaaaa | ctcctgctgg | acagacgatg | tcaacttaat | 600 |
| gtccttgaca | caaaaagag | gacagctctg | ataaaggccg | tacaatgcca | ggaagatgaa | 660 |
| tgtgcgttaa | tgttgctgga | acatggcact | gatccaaata | ttccagatga | gtatggaaat | 720 |
| accactctgc | actacgctat | ctataatgaa | gataaattaa | tggccaaagc | actgctctta | 780 |
| tatggtgctg | atatcgaatc | aaaaaacaag | catggcctca | caccactgtt | acttggtgta | 840 |
| catgagcaaa | aacagcaagt | cgtgaaattt | ttaatcaaga | aaaaagcgaa | tttaaatgca | 900 |
| ctggatagat | atggaaggac | tgctctcata | cttgctgtat | gttgtggatc | agcaagtata | 960 |
| gtcagccttc | tacttgagca | aaatattgat | gtatcttctc | aagatctatc | tggacagacg | 1020 |
| gccagagagt | atgctgtttc | tagtcatcat | catgtaattt | gccagttact | ttctgactac | 1080 |
| aaagaaaaac | agatgctaaa | aatctcttct | gaaaacagca | atccagaaaa | tgtctcaaga | 1140 |
| accagaaata | aataa | | | | | 1155 |

<210> SEQ ID NO 302
<211> LENGTH: 2000
<212> TYPE: DNA
<213> ORGANISM: Homo sapien

<400> SEQUENCE: 302

| | | | | | |
|---|---|---|---|---|---|
| atggtggttg | aggttgattc | catgccggct | gcctcttctg | tgaagaagcc | atttggtctc | 60 |
| aggagcaaga | tgggcaagtg | gtgctgccgt | tgcttcccct | gctgcaggga | gagcggcaag | 120 |
| agcaacgtgg | gcacttctgg | agaccacgac | gactctgcta | tgaagacact | caggagcaag | 180 |
| atgggcaagt | ggtgccgcca | ctgcttcccc | tgctgcaggg | ggagtggcaa | gagcaacgtg | 240 |
| ggcgcttctg | gagaccacga | cgactctgct | atgaagacac | tcaggaacaa | gatgggcaag | 300 |
| tggtgctgcc | actgcttccc | ctgctgcagg | gggagcggca | agagcaaggt | gggcgcttgg | 360 |
| ggagactacg | atgacagtgc | cttcatggag | cccaggtacc | acgtccgtgg | agaagatctg | 420 |

```
gacaagctcc acagagctgc ctggtggggt aaagtcccca gaaaggatct catcgtcatg      480
ctcagggaca ctgacgtgaa caagaaggac aagcaaaaga ggactgctct acatctggcc      540
tctgccaatg ggaattcaga agtagtaaaa ctcctgctgg acagacgatg tcaacttaat      600
gtccttgaca caaaaagag gacagctctg ataaaggccg tacaatgcca ggaagatgaa       660
tgtgcgttaa tgttgctgga acatggcact gatccaaata ttccagatga gtatggaaat      720
accactctgc actacgctat ctataatgaa gataaattaa tggccaaagc actgctctta      780
tatggtgctg atatcgaatc aaaaaacaag catggcctca caccactgtt acttggtgta      840
catgagcaaa acagcaagt cgtgaaattt ttaatcaaga aaaagcgaa tttaaatgca        900 ctggatagat atggaaggac tgctctcata cttgctgtat gttgtggatc agcaagtata     960
gtcagccttc tacttgagca aaatattgat gtatcttctc aagatctatc tggacagacg    1020
gccagagagt atgctgtttc tagtcatcat catgtaattt gccagttact ttctgactac    1080
aaagaaaaac agatgctaaa atctcttct gaaaacagca atccagaaca agacttaaag     1140 ctgcacatcag aggaagagtc acaaaggttc aaggcagtg aaaatagcca gccagagaaa    1200
atgtctcaag aaccagaaat aaataaggat ggtgatagag aggttgaaga agaaatgaag   1260
aagcatgaaa gtaataatgt gggattacta gaaaacctga ctaatggtgt cactgctggc   1320
aatggtgata atggattaat tcctcaaagg aagagcagaa cacctgaaaa tcagcaattt   1380
cctgacaacg aaagtgaaga gtatcacaga atttgcgaat tagtttctga ctacaaagaa   1440
aaacagatgc caaatactc ttctgaaaac agcaacccag aacaagactt aaagctgaca     1500
tcagaggaag agtcacaaag gcttgagggc agtgaaaatg ccagccaga gctagaaaat   1560 tttatggcta tcgaagaaat gaagaagcac ggaagtactc atgtcggatt cccagaaaac   1620
ctgactaatg gtgccactgc tggcaatggt gatgatggat taattcctcc aaggaagagc   1680
agaacacctg aaagccagca atttcctgac actgagaatg aagagtatca cagtgacgaa   1740
caaaatgata ctcagaagca attttgtgaa gaacagaaca ctggaatatt acacgatgag   1800
attctgattc atgaagaaaa gcagatagaa gtggttgaaa aaatgaattc tgagcttttct   1860 cttagttgta agaaagaaaa agacatcttg catgaaaata gtacgttgcg ggaagaaatt   1920
gccatgctaa gactggagct agacacaatg aaacatcaga gccagctaaa aaaaaaaaa    1980 aaaaaaaaaa aaaaaaaaa                                                 2000
```

<210> SEQ ID NO 303
<211> LENGTH: 2040
<212> TYPE: DNA
<213> ORGANISM: Homo sapien

<400> SEQUENCE: 303

```
atggtggttg aggttgattc catgccggct gcctcttctg tgaagaagcc atttggtctc       60
aggagcaaga tgggcaagtg gtgctgccgt tgcttcccct gctgcaggga gagcggcaag     120
agcaacgtgg gcacttctgg agaccacgac gactctgcta tgaagacact caggagcaag     180
atgggcaagt ggtgccgcca ctgcttcccc tgctgcaggg ggagtggcaa gagcaacgtg     240
ggcgcttctg gagaccacga cgactctgct atgaagacac tcaggaacaa gatgggcaag     300
tggtgctgcc actgcttccc ctgctgcagg ggagcggca agagcaaggt gggcgcttgg     360
ggagactacg atgacagtgc cttcatggag cccaggtacc acgtccgtgg agaagatctg    420
gacaagctcc acagagctgc ctggtggggt aaagtcccca gaaaggatct catcgtcatg    480
ctcagggaca ctgacgtgaa caagaaggac aagcaaaaga ggactgctct acatctggcc    540
```

```
tctgccaatg ggaattcaga agtagtaaaa ctcctgctgg acagacgatg tcaacttaat     600
gtccttgaca acaaaaagag gacagctctg ataaaggccg tacaatgcca ggaagatgaa     660
tgtgcgttaa tgttgctgga acatggcact gatccaaata ttccagatga gtatggaaat     720
accactctgc actacgctat ctataatgaa gataaattaa tggccaaagc actgctctta     780
tatggtgctg atatcgaatc aaaaaacaag catggcctca caccactgtt acttggtgta     840
catgagcaaa aacagcaagt cgtgaaattt ttaatcaaga aaaagcgaa tttaaatgca     900
ctggatagat atggaaggac tgctctcata cttgctgtat gttgtggatc agcaagtata     960
gtcagccttc tacttgagca aaatattgat gtatcttctc aagatctatc tggacagacg    1020
gccagagagt atgctgtttc tagtcatcat catgtaattt gccagttact ttctgactac    1080
aaagaaaaac agatgctaaa aatctcttct gaaacagca atccagaaca agacttaaag    1140
ctgacatcag aggaagagtc acaaaggttc aaggcagtg aaaatagcca gccagagaaa    1200
atgtctcaag aaccagaaat aaataaggat ggtgatagag aggttgaaga agaaatgaag    1260
aagcatgaaa gtaataatgt gggattacta gaaaacctga ctaatggtgt cactgctggc    1320
aatggtgata atggattaat tcctcaaagg aagagcagaa caccctgaaaa tcagcaattt    1380
cctgacaacg aaagtgaaga gtatcacaga atttgcgaat tagtttctga ctacaaagaa    1440
aaacagatgc caaaatactc ttctgaaaac agcaacccag aacaagactt aagctgaca    1500
tcagaggaag agtcacaaag gcttgagggc agtgaaaatg ccagccaga gaaaagatct    1560
caagaaccag aaataaataa ggatggtgat agagagctag aaaatttat ggctatcgaa    1620
gaaatgaaga agcacggaag tactcatgtc ggattcccag aaaacctgac taatggtgcc    1680
actgctggca atggtgatga tggattaatt cctccaagga agagcagaac acctgaaagc    1740
cagcaatttc ctgacactga gaatgaagag tatcacagtg acgaacaaaa tgatactcag    1800
aagcaatttt gtgaagaaca gaacactgga atattacacg atgagattct gattcatgaa    1860
gaaaagcaga tagaagtggt tgaaaaaatg aattctgagc tttctcttag ttgtaagaaa    1920
gaaaaagaca tcttgcatga aaatagtacg ttgcgggaag aaattgccat gctaagactg    1980
gagctagaca caatgaaaca tcagagccag ctaaaaaaaa aaaaaaaaaa aaaaaaaaa    2040
```

<210> SEQ ID NO 304
<211> LENGTH: 384
<212> TYPE: PRT
<213> ORGANISM: Homo sapien

<400> SEQUENCE: 304

```
Met Val Val Glu Val Asp Ser Met Pro Ala Ala Ser Ser Val Lys Lys
  1               5                  10                  15

Pro Phe Gly Leu Arg Ser Lys Met Gly Lys Trp Cys Cys Arg Cys Phe
             20                  25                  30

Pro Cys Cys Arg Glu Ser Gly Lys Ser Asn Val Gly Thr Ser Gly Asp
         35                  40                  45

His Asp Asp Ser Ala Met Lys Thr Leu Arg Ser Lys Met Gly Lys Trp
     50                  55                  60

Cys Arg His Cys Phe Pro Cys Arg Gly Ser Gly Lys Ser Asn Val
 65                  70                  75                  80

Gly Ala Ser Gly Asp His Asp Asp Ser Ala Met Lys Thr Leu Arg Asn
                 85                  90                  95

Lys Met Gly Lys Trp Cys Cys His Cys Phe Pro Cys Cys Arg Gly Ser
            100                 105                 110
```

```
Gly Lys Ser Lys Val Gly Ala Trp Gly Asp Tyr Asp Asp Ser Ala Phe
            115                 120                 125
Met Glu Pro Arg Tyr His Val Arg Gly Glu Asp Leu Asp Lys Leu His
    130                 135                 140
Arg Ala Ala Trp Trp Gly Lys Val Pro Arg Lys Asp Leu Ile Val Met
145                 150                 155                 160
Leu Arg Asp Thr Asp Val Asn Lys Lys Asp Lys Gln Lys Arg Thr Ala
                165                 170                 175
Leu His Leu Ala Ser Ala Asn Gly Asn Ser Glu Val Val Lys Leu Leu
            180                 185                 190
Leu Asp Arg Arg Cys Gln Leu Asn Val Leu Asp Asn Lys Lys Arg Thr
        195                 200                 205
Ala Leu Ile Lys Ala Val Gln Cys Gln Glu Asp Glu Cys Ala Leu Met
    210                 215                 220
Leu Leu Glu His Gly Thr Asp Pro Asn Ile Pro Asp Glu Tyr Gly Asn
225                 230                 235                 240
Thr Thr Leu His Tyr Ala Ile Tyr Asn Glu Asp Lys Leu Met Ala Lys
                245                 250                 255
Ala Leu Leu Leu Tyr Gly Ala Asp Ile Glu Ser Lys Asn Lys His Gly
            260                 265                 270
Leu Thr Pro Leu Leu Leu Gly Val His Glu Gln Lys Gln Gln Val Val
        275                 280                 285
Lys Phe Leu Ile Lys Lys Ala Asn Leu Asn Ala Leu Asp Arg Tyr
    290                 295                 300
Gly Arg Thr Ala Leu Ile Leu Ala Val Cys Cys Gly Ser Ala Ser Ile
305                 310                 315                 320
Val Ser Leu Leu Leu Glu Gln Asn Ile Asp Val Ser Ser Gln Asp Leu
                325                 330                 335
Ser Gly Gln Thr Ala Arg Glu Tyr Ala Val Ser Ser His His Val
            340                 345                 350
Ile Cys Gln Leu Leu Ser Asp Tyr Lys Glu Lys Gln Met Leu Lys Ile
        355                 360                 365
Ser Ser Glu Asn Ser Asn Pro Glu Asn Val Ser Arg Thr Arg Asn Lys
    370                 375                 380

<210> SEQ ID NO 305
<211> LENGTH: 656
<212> TYPE: PRT
<213> ORGANISM: Homo sapien

<400> SEQUENCE: 305

Met Val Val Glu Val Asp Ser Met Pro Ala Ser Ser Val Lys Lys
1               5                   10                  15
Pro Phe Gly Leu Arg Ser Lys Met Gly Lys Trp Cys Cys Arg Cys Phe
            20                  25                  30
Pro Cys Cys Arg Glu Ser Gly Lys Ser Asn Val Gly Thr Ser Gly Asp
        35                  40                  45
His Asp Asp Ser Ala Met Lys Thr Leu Arg Ser Lys Met Gly Lys Trp
    50                  55                  60
Cys Arg His Cys Phe Pro Cys Cys Arg Gly Ser Gly Lys Ser Asn Val
65                  70                  75                  80
Gly Ala Ser Gly Asp His Asp Asp Ser Ala Met Lys Thr Leu Arg Asn
                85                  90                  95
Lys Met Gly Lys Trp Cys Cys His Cys Phe Pro Cys Cys Arg Gly Ser
```

-continued

```
                100                 105                 110
Gly Lys Ser Lys Val Gly Ala Trp Gly Asp Tyr Asp Ser Ala Phe
            115                 120                 125
Met Glu Pro Arg Tyr His Val Arg Gly Glu Asp Leu Asp Lys Leu His
        130                 135                 140
Arg Ala Ala Trp Trp Gly Lys Val Pro Arg Lys Asp Leu Ile Val Met
145                 150                 155                 160
Leu Arg Asp Thr Asp Val Asn Lys Lys Asp Lys Gln Lys Arg Thr Ala
            165                 170                 175
Leu His Leu Ala Ser Ala Asn Gly Asn Ser Glu Val Val Lys Leu Leu
        180                 185                 190
Leu Asp Arg Arg Cys Gln Leu Asn Val Leu Asp Asn Lys Lys Arg Thr
            195                 200                 205
Ala Leu Ile Lys Ala Val Gln Cys Gln Glu Asp Glu Cys Ala Leu Met
        210                 215                 220
Leu Leu Glu His Gly Thr Asp Pro Asn Ile Pro Asp Glu Tyr Gly Asn
225                 230                 235                 240
Thr Thr Leu His Tyr Ala Ile Tyr Asn Glu Asp Lys Leu Met Ala Lys
            245                 250                 255
Ala Leu Leu Leu Tyr Gly Ala Asp Ile Glu Ser Lys Asn Lys His Gly
        260                 265                 270
Leu Thr Pro Leu Leu Leu Gly Val His Glu Gln Lys Gln Gln Val Val
            275                 280                 285
Lys Phe Leu Ile Lys Lys Lys Ala Asn Leu Asn Ala Leu Asp Arg Tyr
        290                 295                 300
Gly Arg Thr Ala Leu Ile Leu Ala Val Cys Cys Gly Ser Ala Ser Ile
305                 310                 315                 320
Val Ser Leu Leu Leu Glu Gln Asn Ile Asp Val Ser Ser Gln Asp Leu
            325                 330                 335
Ser Gly Gln Thr Ala Arg Glu Tyr Ala Val Ser Ser His His His Val
        340                 345                 350
Ile Cys Gln Leu Leu Ser Asp Tyr Lys Glu Lys Gln Met Leu Lys Ile
        355                 360                 365
Ser Ser Glu Asn Ser Asn Pro Glu Gln Asp Leu Lys Leu Thr Ser Glu
        370                 375                 380
Glu Glu Ser Gln Arg Phe Lys Gly Ser Glu Asn Ser Gln Pro Glu Lys
385                 390                 395                 400
Met Ser Gln Glu Pro Glu Ile Asn Lys Asp Gly Asp Arg Glu Val Glu
            405                 410                 415
Glu Glu Met Lys Lys His Glu Ser Asn Asn Val Gly Leu Leu Glu Asn
            420                 425                 430
Leu Thr Asn Gly Val Thr Ala Gly Asn Gly Asp Asn Gly Leu Ile Pro
            435                 440                 445
Gln Arg Lys Ser Arg Thr Pro Glu Asn Gln Gln Phe Pro Asp Asn Glu
        450                 455                 460
Ser Glu Glu Tyr His Arg Ile Cys Glu Leu Val Ser Asp Tyr Lys Glu
465                 470                 475                 480
Lys Gln Met Pro Lys Tyr Ser Ser Glu Asn Ser Asn Pro Glu Gln Asp
            485                 490                 495
Leu Lys Leu Thr Ser Glu Glu Ser Gln Arg Leu Glu Gly Ser Glu
            500                 505                 510
Asn Gly Gln Pro Glu Leu Glu Asn Phe Met Ala Ile Glu Glu Met Lys
        515                 520                 525
```

```
Lys His Gly Ser Thr His Val Gly Phe Pro Glu Asn Leu Thr Asn Gly
            530                 535                 540

Ala Thr Ala Gly Asn Gly Asp Asp Gly Leu Ile Pro Pro Arg Lys Ser
545                 550                 555                 560

Arg Thr Pro Glu Ser Gln Gln Phe Pro Asp Thr Glu Asn Glu Glu Tyr
                565                 570                 575

His Ser Asp Glu Gln Asn Asp Thr Gln Lys Gln Phe Cys Glu Glu Gln
            580                 585                 590

Asn Thr Gly Ile Leu His Asp Glu Ile Leu Ile His Glu Glu Lys Gln
        595                 600                 605

Ile Glu Val Val Glu Lys Met Asn Ser Glu Leu Ser Leu Ser Cys Lys
    610                 615                 620

Lys Glu Lys Asp Ile Leu His Glu Asn Ser Thr Leu Arg Glu Glu Ile
625                 630                 635                 640

Ala Met Leu Arg Leu Glu Leu Asp Thr Met Lys His Gln Ser Gln Leu
                645                 650                 655

<210> SEQ ID NO 306
<211> LENGTH: 671
<212> TYPE: PRT
<213> ORGANISM: Homo sapien

<400> SEQUENCE: 306

Met Val Val Glu Val Asp Ser Met Pro Ala Ala Ser Ser Val Lys Lys
1               5                   10                  15

Pro Phe Gly Leu Arg Ser Lys Met Gly Lys Trp Cys Cys Arg Cys Phe
            20                  25                  30

Pro Cys Cys Arg Glu Ser Gly Lys Ser Asn Val Gly Thr Ser Gly Asp
        35                  40                  45

His Asp Asp Ser Ala Met Lys Thr Leu Arg Ser Lys Met Gly Lys Trp
    50                  55                  60

Cys Arg His Cys Phe Pro Cys Cys Arg Gly Ser Gly Lys Ser Asn Val
65                  70                  75                  80

Gly Ala Ser Gly Asp His Asp Asp Ser Ala Met Lys Thr Leu Arg Asn
            85                  90                  95

Lys Met Gly Lys Trp Cys Cys His Cys Phe Pro Cys Cys Arg Gly Ser
            100                 105                 110

Gly Lys Ser Lys Val Gly Ala Trp Gly Asp Tyr Asp Asp Ser Ala Phe
        115                 120                 125

Met Glu Pro Arg Tyr His Val Arg Gly Glu Asp Leu Asp Lys Leu His
    130                 135                 140

Arg Ala Ala Trp Trp Gly Lys Val Pro Arg Lys Asp Leu Ile Val Met
145                 150                 155                 160

Leu Arg Asp Thr Asp Val Asn Lys Lys Asp Lys Gln Lys Arg Thr Ala
                165                 170                 175

Leu His Leu Ala Ser Ala Asn Gly Asn Ser Glu Val Val Lys Leu Leu
            180                 185                 190

Leu Asp Arg Arg Cys Gln Leu Asn Val Leu Asp Asn Lys Lys Arg Thr
        195                 200                 205

Ala Leu Ile Lys Ala Val Gln Cys Gln Glu Asp Glu Cys Ala Leu Met
    210                 215                 220

Leu Leu Glu His Gly Thr Asp Pro Asn Ile Pro Asp Glu Tyr Gly Asn
225                 230                 235                 240

Thr Thr Leu His Tyr Ala Ile Tyr Asn Glu Asp Lys Leu Met Ala Lys
```

```
                    245                 250                 255
Ala Leu Leu Leu Tyr Gly Ala Asp Ile Glu Ser Lys Asn Lys His Gly
                260                 265                 270

Leu Thr Pro Leu Leu Gly Val His Glu Gln Lys Gln Gln Val Val
            275                 280                 285

Lys Phe Leu Ile Lys Lys Ala Asn Leu Asn Ala Leu Asp Arg Tyr
        290                 295                 300

Gly Arg Thr Ala Leu Ile Leu Ala Val Cys Cys Gly Ser Ala Ser Ile
305                 310                 315                 320

Val Ser Leu Leu Leu Glu Gln Asn Ile Asp Val Ser Ser Gln Asp Leu
                325                 330                 335

Ser Gly Gln Thr Ala Arg Glu Tyr Ala Val Ser Ser His His His Val
                340                 345                 350

Ile Cys Gln Leu Leu Ser Asp Tyr Lys Glu Lys Gln Met Leu Lys Ile
                355                 360                 365

Ser Ser Glu Asn Ser Asn Pro Glu Gln Asp Leu Lys Leu Thr Ser Glu
370                 375                 380

Glu Glu Ser Gln Arg Phe Lys Gly Ser Glu Asn Ser Gln Pro Glu Lys
385                 390                 395                 400

Met Ser Gln Glu Pro Glu Ile Asn Lys Asp Gly Asp Arg Glu Val Glu
                405                 410                 415

Glu Glu Met Lys Lys His Glu Ser Asn Asn Val Gly Leu Leu Glu Asn
                420                 425                 430

Leu Thr Asn Gly Val Thr Ala Gly Asn Gly Asp Asn Gly Leu Ile Pro
                435                 440                 445

Gln Arg Lys Ser Arg Thr Pro Glu Asn Gln Gln Phe Pro Asp Asn Glu
        450                 455                 460

Ser Glu Glu Tyr His Arg Ile Cys Glu Leu Val Ser Asp Tyr Lys Glu
465                 470                 475                 480

Lys Gln Met Pro Lys Tyr Ser Ser Glu Asn Ser Asn Pro Glu Gln Asp
                485                 490                 495

Leu Lys Leu Thr Ser Glu Glu Ser Gln Arg Leu Glu Gly Ser Glu
            500                 505                 510

Asn Gly Gln Pro Glu Lys Arg Ser Gln Glu Pro Glu Ile Asn Lys Asp
        515                 520                 525

Gly Asp Arg Glu Leu Glu Asn Phe Met Ala Ile Glu Glu Met Lys Lys
530                 535                 540

His Gly Ser Thr His Val Gly Phe Pro Glu Asn Leu Thr Asn Gly Ala
545                 550                 555                 560

Thr Ala Gly Asn Gly Asp Asp Gly Leu Ile Pro Pro Arg Lys Ser Arg
                565                 570                 575

Thr Pro Glu Ser Gln Gln Phe Pro Asp Thr Glu Asn Glu Glu Tyr His
            580                 585                 590

Ser Asp Glu Gln Asn Asp Thr Gln Lys Gln Phe Cys Glu Glu Gln Asn
        595                 600                 605

Thr Gly Ile Leu His Asp Glu Ile Leu Ile His Glu Lys Gln Ile
        610                 615                 620

Glu Val Val Glu Lys Met Asn Ser Glu Leu Ser Leu Ser Cys Lys Lys
625                 630                 635                 640

Glu Lys Asp Ile Leu His Glu Asn Ser Thr Leu Arg Glu Glu Ile Ala
                645                 650                 655

Met Leu Arg Leu Glu Leu Asp Thr Met Lys His Gln Ser Gln Leu
                660                 665                 670
```

<210> SEQ ID NO 307
<211> LENGTH: 800
<212> TYPE: DNA
<213> ORGANISM: Homo sapien

<400> SEQUENCE: 307

```
atkagcttcc gcttctgaca acactagaga tccctcccct ccctcagggt atggccctcc      60
acttcatttt tggtacataa catctttata ggacaggggt aaaatcccaa tactaacagg     120
agaatgctta ggactctaac aggttttga gaatgtgttg gtaagggcca ctcaatccaa     180
tttttcttgg tcctccttgt ggtctaggag gacaggcaag ggtgcagatt tcaagaatg     240
catcagtaag ggccactaaa tccgaccttc ctcgttcctc cttgtggtct gggaggaaaa     300
ctagtgtttc tgttgctgtg tcagtgagca caactattcc gatcagcagg gtccagggac     360
cactgcaggt tcttgggcag ggggagaaac aaaacaaacc aaaaccatgg gcrgttttgt     420
ctttcagatg ggaaacactc aggcatcaac aggctcacct ttgaaatgca tcctaagcca     480
atgggacaaa tttgacccac aaaccctgga aaaagaggtg gctcattttt tttgcactat     540
ggcttggccc caacattctc tctctgatgg ggaaaaatgg ccacctgagg gaagtacaga     600
ttacaatact atcctgcagc ttgacctttt ctgtaagagg gaaggcaaat ggagtgaaat     660
accttatgtc caagctttct tttcattgaa ggagaataca ctatgcaaag cttgaaattt     720
acatcccaca ggaggacctc tcagcttacc cccatatcct agcctcccta tagctcccct     780
tcctattagt gataagcctc                                                 800
```

<210> SEQ ID NO 308
<211> LENGTH: 102
<212> TYPE: PRT
<213> ORGANISM: Homo sapien
<220> FEATURE:
<221> NAME/KEY: VARIANT
<222> LOCATION: (1)...(102)
<223> OTHER INFORMATION: Xaa = Any Amino Acid

<400> SEQUENCE: 308

```
Met Gly Xaa Phe Val Phe Gln Met Gly Asn Thr Gln Ala Ser Thr Gly
 1               5                  10                  15

Ser Pro Leu Lys Cys Ile Leu Ser Gln Trp Asp Lys Phe Asp Pro Gln
             20                  25                  30

Thr Leu Glu Lys Glu Val Ala His Phe Phe Cys Thr Met Ala Trp Pro
         35                  40                  45

Gln His Ser Leu Ser Asp Gly Glu Lys Trp Pro Pro Glu Gly Ser Thr
     50                  55                  60

Asp Tyr Asn Thr Ile Leu Gln Leu Asp Leu Phe Cys Lys Arg Glu Gly
 65                  70                  75                  80

Lys Trp Ser Glu Ile Pro Tyr Val Gln Ala Phe Ser Leu Lys Glu
             85                  90                  95

Asn Thr Leu Cys Lys Ala
            100
```

<210> SEQ ID NO 309
<211> LENGTH: 9
<212> TYPE: PRT
<213> ORGANISM: Artificial Sequence
<220> FEATURE:
<223> OTHER INFORMATION: Made in the lab

<400> SEQUENCE: 309

```
Leu Met Ala Glu Glu Tyr Thr Ile Val
  1               5

<210> SEQ ID NO 310
<211> LENGTH: 9
<212> TYPE: PRT
<213> ORGANISM: Artificial Sequence
<220> FEATURE:
<223> OTHER INFORMATION: Made in the lab

<400> SEQUENCE: 310

Lys Leu Met Ala Lys Ala Leu Leu Leu
  1               5

<210> SEQ ID NO 311
<211> LENGTH: 9
<212> TYPE: PRT
<213> ORGANISM: Artificial Sequence
<220> FEATURE:
<223> OTHER INFORMATION: Made in the lab

<400> SEQUENCE: 311

Gly Leu Thr Pro Leu Leu Leu Gly Ile
  1               5

<210> SEQ ID NO 312
<211> LENGTH: 10
<212> TYPE: PRT
<213> ORGANISM: Artificial Sequence
<220> FEATURE:
<223> OTHER INFORMATION: Made in the lab

<400> SEQUENCE: 312

Lys Leu Val Leu Asp Arg Arg Cys Gln Leu
  1               5               10
```